United States Patent
Furue et al.

(10) Patent No.: US 11,844,272 B2
(45) Date of Patent: Dec. 12, 2023

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventors: Ryuhei Furue, Fukuoka (JP); Hirokazu Kuwabara, Fukuoka (JP); Nobutaka Akashi, Fukuoka (JP)

(73) Assignee: Samsung Display Co., Ltd., Yongin-si (KR)

( * ) Notice: Subject to any disclaimer, the term of this patent is extended or adjusted under 35 U.S.C. 154(b) by 534 days.

(21) Appl. No.: 17/074,454

(22) Filed: Oct. 19, 2020

(65) Prior Publication Data

US 2021/0210695 A1 Jul. 8, 2021

(30) Foreign Application Priority Data

Dec. 24, 2019 (KR) .................. 10-2019-0174228

(51) Int. Cl.
| | | |
|---|---|---|
| *C09K 11/06* | (2006.01) | |
| *H10K 85/60* | (2023.01) | |
| *C07D 487/14* | (2006.01) | |
| *H10K 50/11* | (2023.01) | |
| *H10K 101/10* | (2023.01) | |

(52) U.S. Cl.
CPC ......... *H10K 85/654* (2023.02); *C07D 487/14* (2013.01); *C09K 11/06* (2013.01); *H10K 85/6572* (2023.02); *C09K 2211/1007* (2013.01); *C09K 2211/1018* (2013.01); *H10K 50/11* (2023.02); *H10K 2101/10* (2023.02)

(58) Field of Classification Search
CPC ............ H01L 51/0067; H01L 51/0072; H01L 51/5016; C07D 487/14; C09K 2211/1018; C09K 2211/1007; C09K 11/06

USPC ......................................................... 428/690
See application file for complete search history.

(56) References Cited

U.S. PATENT DOCUMENTS

| | | | |
|---|---|---|---|
| 2017/0069848 A1 | 3/2017 | Zeng et al. | |
| 2018/0366653 A1 | 12/2018 | He et al. | |
| 2019/0229276 A1* | 7/2019 | Kwon | ............... H10K 85/6574 |

FOREIGN PATENT DOCUMENTS

| | | |
|---|---|---|
| CN | 106432251 A | 2/2017 |
| DE | 10 2016 115 851 B3 | 7/2017 |
| KR | 10-2018-0083152 A | 7/2018 |
| KR | 10-2019-0089625 A | 7/2019 |
| WO | WO 2018/131877 A1 | 7/2018 |

* cited by examiner

*Primary Examiner* — Hui H Chin
(74) *Attorney, Agent, or Firm* — Lewis Roca Rothgerber Christie LLP

(57) ABSTRACT

An organic electroluminescence device of an embodiment includes a first electrode, a second electrode, and a plurality of functional layers disposed between the first electrode and the second electrode, wherein at least one functional layer of the plurality of functional layers includes a polycyclic compound represented by Formula 1, thereby showing excellent light emitting efficiency in a short wavelength region:

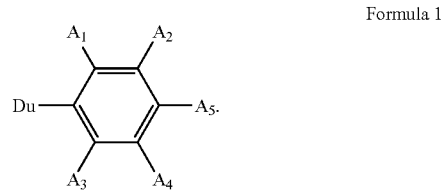

Formula 1

22 Claims, 2 Drawing Sheets

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2019-0174228, filed on Dec. 24, 2019, the entire content of which is hereby incorporated by reference.

BACKGROUND

One or more aspects of embodiments of the present disclosure relate to an organic electroluminescence device and a polycyclic compound used therein, and for example, to a polycyclic compound used as a light-emitting material and an organic electroluminescence device including the same.

Organic electroluminescence displays are recently being developed as image display devices. Different from a liquid crystal display device, an organic electroluminescence display device is a so-called self-luminescent display device, in which holes and electrons respectively injected from a first electrode and a second electrode recombine in an emission layer, and thus a light-emitting material including an organic compound in the emission layer emits light to attain display.

In the application of an organic electroluminescence device to a display device, there is a demand for an organic electroluminescence device having a low driving voltage, increased emission efficiency, and long life span, and there is a demand for new materials capable of stably attaining such characteristics for an organic electroluminescence device.

Recently, in order to accomplish an organic electroluminescence device with high efficiency, materials utilizing triplet state energy phosphorescence emission, delayed fluorescence triplet-triplet annihilation (TTA) (in which singlet excitons are generated by collision of triplet excitons), and/or thermally activated delayed fluorescence (TADF) are being developed.

SUMMARY

One or more aspects of embodiments of the present disclosure are directed toward an organic electroluminescence device showing excellent emission efficiency in a short wavelength region.

One or more aspects of embodiments of the present disclosure are directed toward a polycyclic compound that is a material for an organic electroluminescence device having high color purity and long-life characteristics.

One or more example embodiments of the present disclosure provide a polycyclic compound represented by Formula 1:

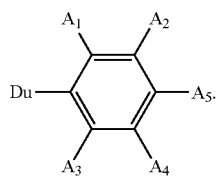

Formula 1

In Formula 1, $A_1$ to $A_5$ may each independently be a hydrogen atom, a deuterium atom, a substituted or unsubstituted oxy group, a substituted or unsubstituted thio group, a substituted or unsubstituted thiocarbonyl group, a substituted or unsubstituted boryl group, a substituted or unsubstituted carbonyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or may be combined with an adjacent group to form a fused heterocycle. At least one of the $A_1$ to $A_5$ or the fused heterocycle may be or include an electron accepting group, "Du" may be represented by Formula 2.

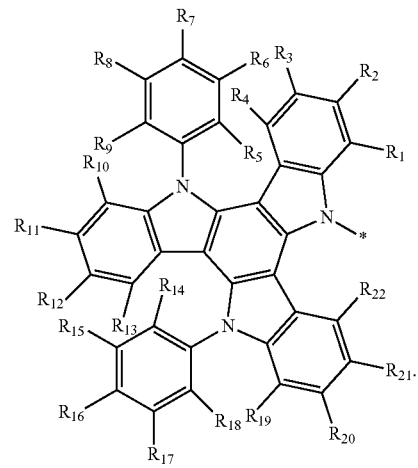

Formula 2

In Formula 2, at least one of $R_1$ to $R_{22}$ may be a cyano group, fluoro group, or trifluoromethyl group, and the remainder may each independently be a hydrogen atom, a deuterium atom, a substituted or unsubstituted oxy group, a substituted or unsubstituted thio group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In an embodiment, Formula 1 may be represented by any one among Formula 1-A to Formula 1-D:

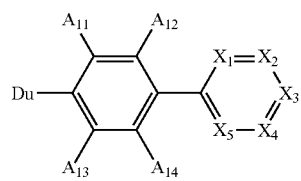

Formula 1-A

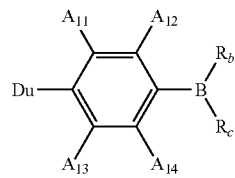

Formula 1-B

Formula 1-C

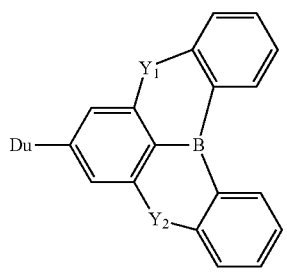

Formula 1-D

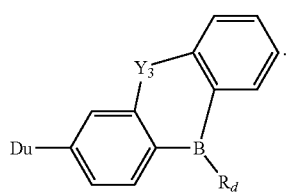

In Formula 1-A, at least one among $X_1$ to $X_5$ may be N, and the remainder may each be $CR_a$; in Formula 1-C and Formula 1-D, $Y_1$ to $Y_3$ may each independently be O, S, $NR_e$, or C(=O). In Formula 1-A and 1-B, $A_{11}$ to $A_{14}$ may each independently be a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. In Formula 1-A to 1-D, $R_a$ to $R_e$ may each independently be a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and "Du" may be the same as defined in Formula 2.

In an embodiment, Formula 1 may be represented by any one among Formula 1-1 to Formula 1-23. In Formula 1-1 to Formula 1-23, "Du" may be the same as defined in Formula 2.

1-1

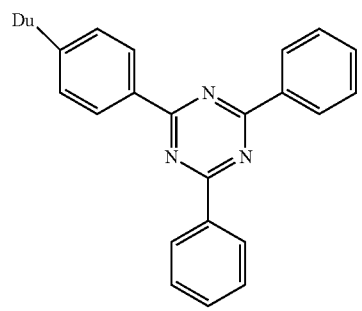

1-2

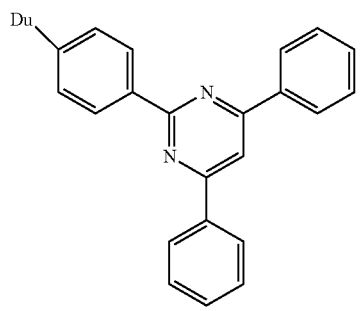

1-3

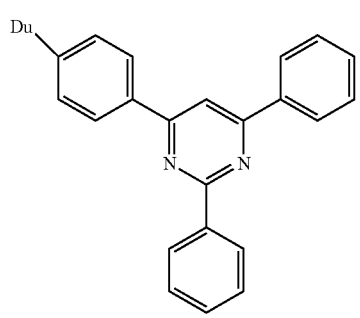

1-4

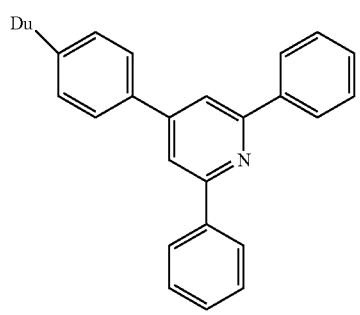

1-5

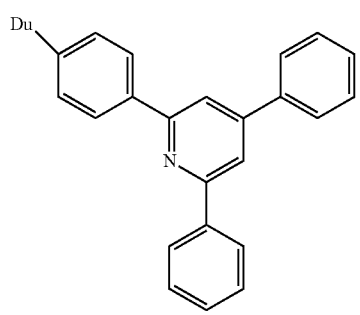

1-6

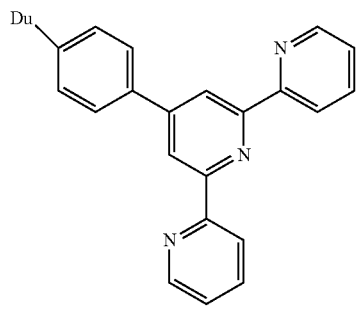

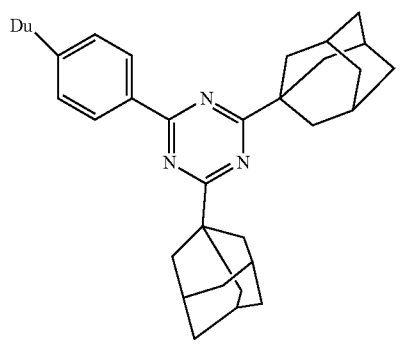
1-7
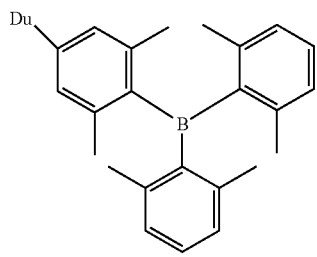
1-13
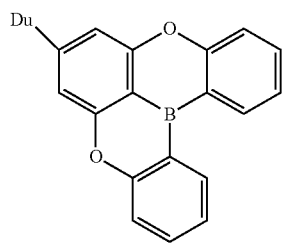
1-14
1-8
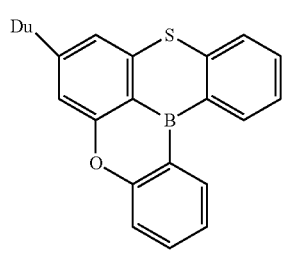
1-15
1-9
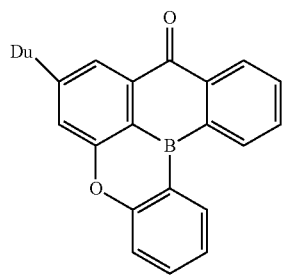
1-16
1-10
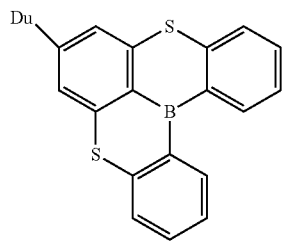
1-17
1-11
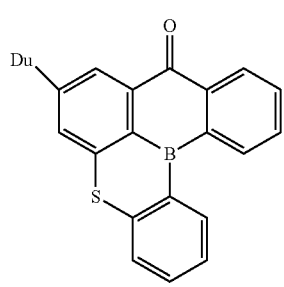
1-18
1-12

-continued 1-19
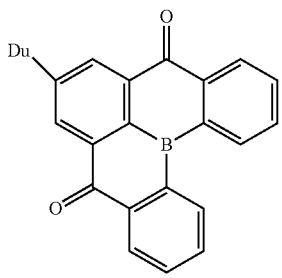

1-20
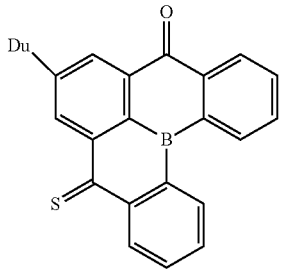

1-21
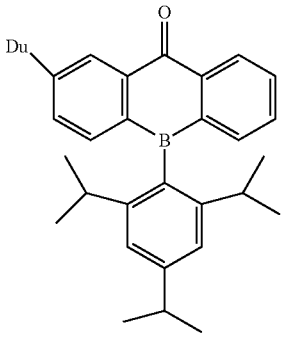

1-22
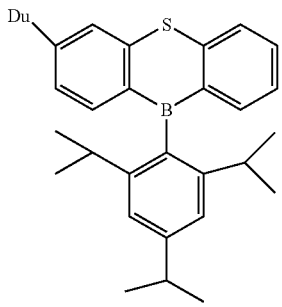

1-23
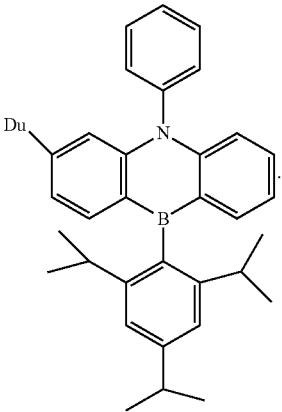

In an embodiment, the electron accepting group may be a substituted or unsubstituted heterocycle having at least one nitrogen atom as a ring forming atom, or a substituted or unsubstituted boryl group.

In an embodiment, the fused heterocycle may be a substituted or unsubstituted heterocycle having a boron atom as a ring forming atom.

In an embodiment, the electron accepting group may include a cyano group, a fluoro group, a carbonyl group, or a sulfonyl group.

In Formula 2, at least one of $R_1$ to $R_{22}$ may be a cyano group, a fluoro group, or a trifluoromethyl group, and the remainder may each be a hydrogen atom.

In Formula 2, at least two or three selected from among $R_1$ to $R_{22}$ may each independently be a cyano group, a fluoro group, or trifluoromethyl group, and the remainder may each be a hydrogen atom.

In an embodiment, the polycyclic compound represented by Formula 1 may be a material to emit thermally activated delayed fluorescence.

In an embodiment, the polycyclic compound represented by Formula 1 may be a material to emit blue light having a central wavelength of about 470 nanometers or less.

One or more example embodiments of the present disclosure provide an organic electroluminescence device including a first electrode; a second electrode on the first electrode; and a plurality of functional layers disposed between the first electrode and the second electrode; wherein at least one functional layer of the plurality of functional layers includes the polycyclic compound. The first electrode and the second electrode may each independently comprise at least one selected from silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), indium (In), tin (Sn), and zinc (Zn), a compound of two or more thereof, a mixture of two or more thereof, or an oxide thereof.

In an embodiment, the plurality of functional layers may include a hole transport region; an emission layer on the hole transport region; and an electron transport region on the emission layer, wherein the emission layer may include the polycyclic compound.

In an embodiment, the emission layer may be to emit delayed fluorescence.

In an embodiment, the emission layer may be to emit light having a maximum emission wavelength of about 470 nanometers or less.

BRIEF DESCRIPTION OF THE FIGURES

The accompanying drawings are included to provide a further understanding of the present disclosure and are incorporated in and constitute a part of this specification. The drawings illustrate example embodiments of the present disclosure and, together with the description, serve to explain principles of the present disclosure. In the drawings.

DETAILED DESCRIPTION

Figure 1:
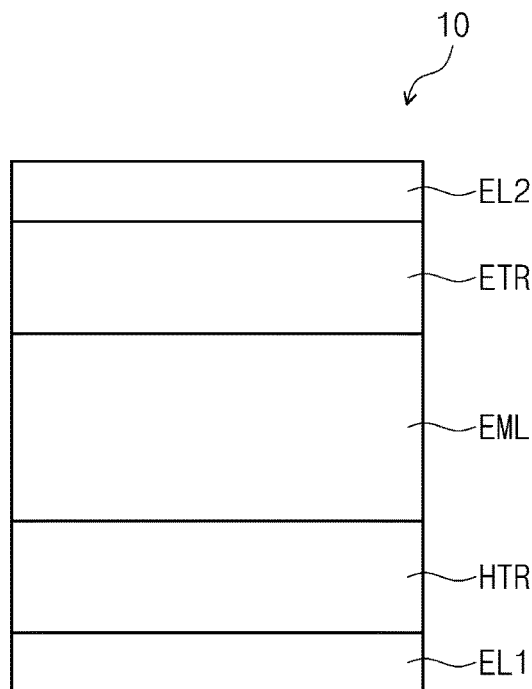
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompanying drawings. The present disclosure may, however, be embodied in different forms and should not be construed as being limited to the embodiments set forth herein. Rather, all modifications, equivalents, and substitutions that are included in the spirit and technical scope of the present disclosure should be included in the present disclosure.

It will be understood that when an element (or region, layer, part, etc.) is referred to as being "on", "connected to" or "coupled to" another element, it can be directly on, connected or coupled to the other element, or intervening elements may be present. When an element is referred to as being "directly on," "directly connected to," or "directly coupled to" another element, there are no intervening elements present.

Like reference numerals refer to like elements throughout, and duplicative descriptions thereof may not be provided. In addition, in the drawings, the thickness, the ratio, and the dimensions of constituent elements may be exaggerated for effective explanation of technical contents.

The term "and/or" includes any and all combinations of one or more of the associated listed items. As used herein, the singular forms "a," "an," and "the" are intended to include the plural forms as well, unless the context clearly indicates otherwise.

As used herein, expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure".

It will be understood that, although the terms "first," "second," etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

In addition, terms such as "below", "beneath", "on" and "above" are used for explaining the relation of elements shown in the drawings. The terms are relative concepts and are used based on the directions shown in the drawing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art unless expressly defined herein, and should not be interpreted in an idealized or overly formal sense.

It will be further understood that the terms "includes," "including," "comprises," "comprising," and/or "have," when used in this specification, specify the presence of stated features, numerals, steps, operations, elements, parts, or the combination thereof, but do not preclude the presence or addition of one or more other features, numerals, steps, operations, elements, parts, or the combination thereof.

Hereinafter, the organic electroluminescence device according to an embodiment of the present disclosure will be explained with reference to the attached drawings.

FIGS. 1 to 4 are cross-sectional views schematically showing organic electroluminescence devices according to an embodiment of the present disclosure. Referring to FIGS. 1 to 4, in an organic electroluminescence device 10 according to an embodiment, a first electrode EL1 and a second electrode EL2 are oppositely disposed, and between the first electrode EL1 and the second electrode EL2, an emission layer EML may be disposed (interposed).

In some embodiments, the organic electroluminescence device 10 of an embodiment may further include a plurality of functional layers between the first electrode EL1 and the second electrode EL2 in addition to the emission layer EML. The plurality of functional layers may include a hole transport region HTR and/or an electron transport region ETR. For example, the organic electroluminescence device 10 of an embodiment may include a first electrode EL1, a hole transport region HTR, an emission layer EML, an electron transport region ETR, and a second electrode EL2, laminated one by one. In some embodiments, the organic electroluminescence device 10 of an embodiment may include a capping layer CPL disposed on the second electrode EL2.

The organic electroluminescence device 10 of an embodiment may include a polycyclic compound of an embodiment, which will be explained later, in the emission layer EML disposed between the first electrode EL1 and the second electrode EL2. However, an embodiment of the present disclosure is not limited thereto, and the organic electroluminescence device 10 of an embodiment may include a polycyclic compound of an embodiment, which will be explained later, in the hole transport region HTR or the electron transport region ETR (which are among the plurality of functional layers disposed between the first electrode EL1 and the second electrode EL2), in addition to the emission layer EML. For example, the organic electroluminescence device 10 of an embodiment may include a polycyclic compound of an embodiment in at least one functional layer among the plurality of functional layers.

Figure 2:
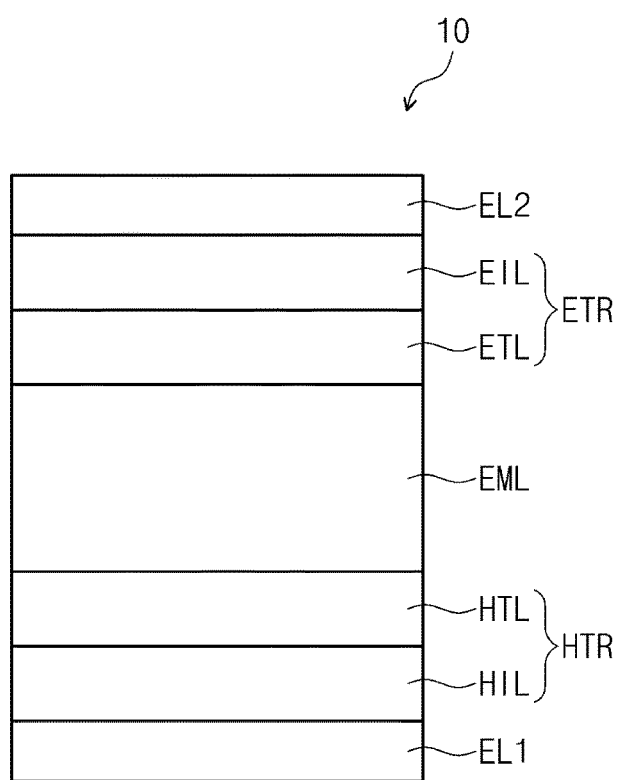
FIG. 2 is a cross-sectional view schematically illustrating an organic electroluminescence device according to an embodiment of the present disclosure.
Figure 3:
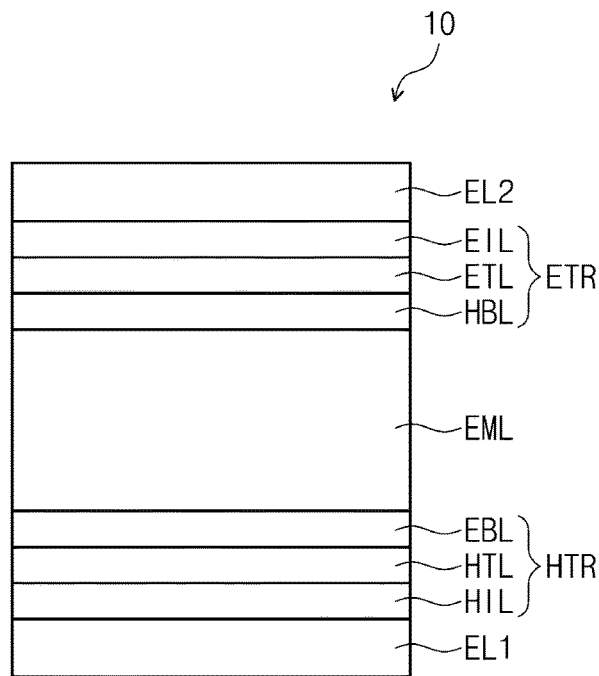
FIG. 3 is a cross-sectional view schematically illustrating an organic electroluminescence device according to an embodiment of the present disclosure.
Figure 4:
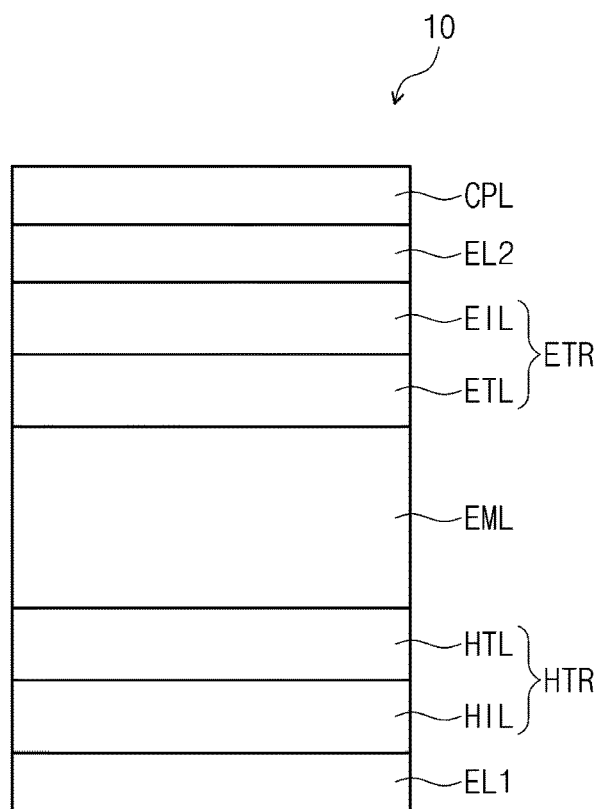
FIG. 4 is a cross-sectional view schematically illustrating an organic electroluminescence device according to an embodiment of the present disclosure.

Compared with FIG. 1, FIG. 2 shows a cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Compared with FIG. 1, FIG. 3 shows the cross-sectional view of an organic electroluminescence device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL. When compared with FIG. 2, FIG. 4 shows the cross-sectional view of an organic electroluminescence device 10 of an embodiment including a capping layer CPL disposed on the second electrode EL2.

The first electrode EL1 may be conductive. The first electrode EL1 may be formed using a metal alloy and/or a conductive compound. The first electrode EL1 may be an anode. The first electrode EL1 may be a pixel electrode. The first electrode EL1 may be a transmissive electrode, a transflective electrode, or a reflective electrode. When the first electrode EL1 is a transmissive electrode, the first electrode EL1 may be formed using a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers including a reflective layer or a transflective layer formed using the above-described materials, and a transmissive conductive layer formed using ITO, IZO, ZnO, and/or ITZO. For example, the first electrode EL1 may include a three-layer structure of ITO/Ag/ITO. However, an embodiment of the present disclosure is not limited thereto. The thickness of the first electrode EL1 may be about 1,000 Å to about 10,000 Å, for example, about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be about 50 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material (e.g., together). In some embodiments, the hole transport region HTR may have a structure of a single layer formed using a plurality of different materials, or a structure in which a hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL are laminated on the first electrode EL1, without limitation.

The hole transport region HTR may be formed using any suitable method(s) (such as a vacuum deposition method, a spin coating method, a cast method, a Langmuir-Blodgett (LB) method, an inkjet printing method, a laser printing method, and/or a laser induced thermal imaging (LITI) method).

The hole injection layer HIL may include, for example, a phthalocyanine compound (such as copper phthalocyanine, N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino]triphenylamine (m-MTDATA), 4,4', 4"-tris(N,N-diphenylamino)triphenylamine (TDATA), 4,4', 4"-tris{N,-2-naphthyl)-N-phenylamino}-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(1-naphthalene-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], and/or dipyrazino[2,3-f:2',3'-h]quinoxaline-2,3,6,7,10,11-hexacarbonitrile (HAT-CN)).

The hole transport layer HTL may further include, for example, carbazole derivatives (such as N-phenyl carbazole and/or polyvinyl carbazole), fluorene-based derivatives, N,N'-bis(3-methylphenyl)-N,N'-diphenyl-[1,1-biphenyl]-4, 4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be about 50 Å to about 10,000 Å, for example, about 100 Å to about 5,000 Å. The thickness of the hole injection layer HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be a quinone derivative, metal oxide, or cyano group-containing compound, without limitation. Non-limiting examples of the p-dopant include quinone derivatives (such as tetracyanoquinodimethane (TCNQ) and/or 2,3,5,6-tetrafluoro-7,7,8,8-tetracyanoquinodimethane (F4-TCNQ)), and metal oxides (such as tungsten oxide and/or molybdenum oxide).

As described above, the hole transport region HTR may further include at least one of a hole buffer layer or an electron blocking layer EBL in addition to the hole injection layer HIL and the hole transport layer HTL. The hole buffer may compensate for an optical resonance distance of the wavelength of light emitted from an emission layer EML, and may thereby increase the light emission efficiency of the device. Materials that may be included in a hole transport region HTR may also be included in the hole buffer layer. The electron blocking layer EBL may prevent or reduce electron injection from the electron transport region ETR to the hole transport region HTR.

The emission layer EML may be provided on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multilayer structure having a plurality of layers formed using a plurality of different materials.

In the organic electroluminescence device 10 of an embodiment, the emission layer EML may include the polycyclic compound of an embodiment.

The polycyclic compound according to an embodiment may be represented by Formula 1, "Du" in Formula 1 may be represented by Formula 2. In the polycyclic compound according to an embodiment represented by Formula 1, "Du" corresponds to an electron donor, and the remaining portion

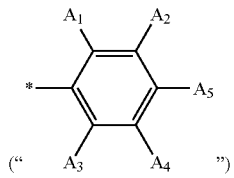

including the $A_1$ to $A_5$ substituents in Formula 1 may include an electron acceptor.

Formula 1

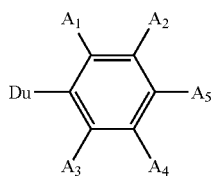

Formula 2

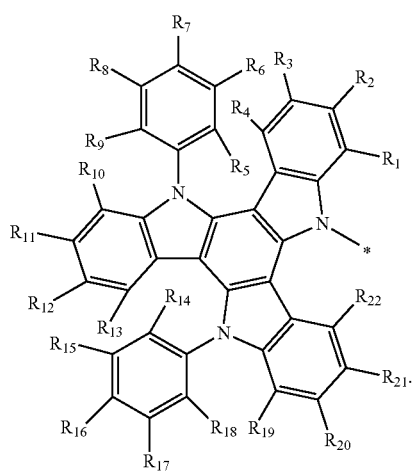

In Formula 1, $A_1$ to $A_5$ may each independently be a hydrogen atom, a deuterium atom, a substituted or unsubstituted oxy group, a substituted or unsubstituted thio group, a substituted or unsubstituted thiocarbonyl group, a substituted or unsubstituted boryl group, a substituted or unsubstituted carbonyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or may be combined with an adjacent group to form a fused heterocycle.

At least one of $A_1$ to $A_5$, or a fused heterocycle formed by combining one or more of $A_1$ to $A_5$ with adjacent groups may be an electron acceptor. At least one of $A_1$ to $A_5$ or a fused heterocycle formed by combining one or more of $A_1$ to $A_5$ with adjacent groups may include an electron accepting group.

For example, at least one of $A_1$ to $A_5$ may include a cyano group, a fluoro group, a carbonyl group, or a sulfonyl group as a substituent. In some embodiments, the fused heterocycle formed by combining at least one of $A_1$ to $A_5$ with adjacent groups may include a cyano group, a fluoro group, a carbonyl group, or a sulfonyl group as a substituent. In an embodiment, the cyano group, fluoro group, carbonyl group, or sulfonyl group may be an electron accepting group.

At least one of $A_1$ to $A_5$ may be a substituted or unsubstituted heterocycle including at least one nitrogen atom as a ring forming atom, or a substituted or unsubstituted boryl group. For example, at least one of $A_1$ to $A_5$ may be a substituted or unsubstituted pyridine group, a substituted or unsubstituted pyrimidine group, or a substituted or unsubstituted triazine group. In some embodiments, at least one of $A_1$ to $A_5$ may be a boryl group substituted with a substituted or unsubstituted phenyl group. In some embodiments, the substituted or unsubstituted heterocycle including at least one nitrogen atom as a ring forming atom, and/or the substituted or unsubstituted boryl group may each be an electron accepting group.

In addition, the fused heterocycle formed by combining at least one of $A_1$ to $A_5$ with adjacent groups may be a substituted or unsubstituted heterocycle including a boron atom as a ring-forming atom, and in an embodiment, the fused heterocycle may be or include an electron accepting group.

In the description, the term "substituted or unsubstituted" refers to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boryl group, a phosphine oxide group, a phosphine sulfide group, an alkyl group, an alkenyl group, an alkynyl group, an alkoxy group, a hydrocarbon ring group, an aryl group, and a heterocyclic group. Each of the above substituents may be unsubstituted or further substituted. For example, a biphenyl group may be interpreted as an aryl group or as a phenyl group substituted with a phenyl group.

In the description, the term "forming a ring via combination with an adjacent group" may refer to formation of a substituted or unsubstituted hydrocarbon ring, or a substituted or unsubstituted heterocycle. The hydrocarbon ring may be or include an aliphatic hydrocarbon ring or an aromatic hydrocarbon ring. The heterocycle may be or include an aliphatic heterocycle or an aromatic heterocycle. The ring formed by combination with an adjacent group may be a monocyclic ring or a polycyclic ring. In addition, the ring formed via combination with an adjacent group may be combined with another ring to form a spiro structure.

In the description, the term "adjacent group" may refer to a substituent on the same atom or point, a substituent on an atom that is directly connected to the base atom or point, or a substituent sterically positioned (e.g., within intramolecular bonding distance) to the corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the alkyl group may be a linear, branched or cyclic alkyl group. The carbon number of the alkyl may be 1 to 50, 1 to 30, 1 to 20, 1 to 10, or 1 to 6. Non-limiting examples of the alkyl include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the term "hydrocarbon ring group" may refer to an optional functional group or substituent derived from an aliphatic hydrocarbon ring. The hydrocarbon ring group may be a saturated hydrocarbon ring group of 5 to 20 carbon atoms for forming a ring.

In the description, the term "aryl group" may refer to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the description, the heterocyclic group may include one or more among boron (B), oxygen (O), nitrogen (N), phosphorus (P), silicon (Si), and sulfur (S) as heteroatoms. When the heterocyclic group includes two or more heteroatoms, the two or more heteroatoms may be the same or different. The heterocyclic group may be a monocyclic heterocyclic group or a polycyclic heterocyclic group, and in some embodiments may be a heteroaryl group. The carbon number for forming a ring of the heteroaryl group may be 2 to 30, 2 to 20, or 2 to 10.

In the description, the heteroaryl group may include one or more among B, O, N, P, Si and S as heteroatoms. When the heteroaryl group includes two or more heteroatoms, the two or more heteroatoms may be the same or different. The heteroaryl group may be a monocyclic heteroaryl group or a polycyclic heteroaryl group. The carbon number for forming a ring of the heteroaryl group may be 2 to 30, 2 to 20, or 2 to 10. Non-limiting examples of the heteroaryl group include thiophene, furan, pyrrole, imidazole, triazole, pyridine, bipyridine, pyrimidine, triazine, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc.

In the description, the oxy group may be an alkoxy group or an aryl oxy group. The alkoxy group may include a linear, branched or cyclic alkyl chain. The carbon number of the alkoxy group is not specifically limited but may be, for example, 1 to 20 or 1 to 10. The carbon number for forming a ring of the aryl oxy group is not specifically limited, but for example, may be 6 to 30, 6 to 20, or 6 to 15. Non-limiting examples of the oxy group include methoxy, ethoxy, n-propoxy, isopropoxy, butoxy, pentyloxy, hexyloxy, octyloxy, nonyloxy, decyloxy, benzyloxy, etc. However, an embodiment of the present disclosure is not limited thereto.

In the description, the thio group may be an alkylthio group or an arylthio group. The carbon number of the alkylthio group is not specifically limited but may be, for example, 1 to 20 or 1 to 10. The carbon number of the arylthio group is not specifically limited, but for example, may be 6 to 30, 6 to 20, or 6 to 15. For example, the alkyl group in the alkylthio group may be the same as the above-described alkyl groups, and the aryl group in the arylthio group may be the same as the above-described aryl groups.

In the description, the boryl group may be an alkyl boryl group or an aryl boryl group. Non-limiting examples of the boryl group include a trimethylboryl group, a triethylboryl group, a t-butyldimethylboryl group, a triphenylboryl group, a diphenylboryl group, a phenylboryl group, etc. For example, the alkyl group in the alkyl boryl group may be the same as the above-described alkyl groups, and the aryl group in the aryl boryl group may be the same as the above-described aryl groups.

In the description, "-•" means a connected position.

In the polycyclic compound according to an embodiment, Formula 1 may be represented by anyone among Formula 1-A to Formula 1-D:

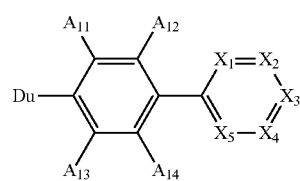

Formula 1-A

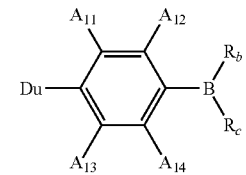

Formula 1-B

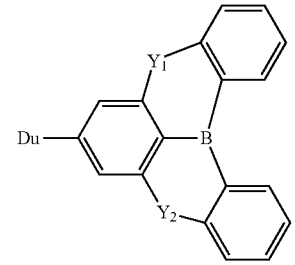

Formula 1-C

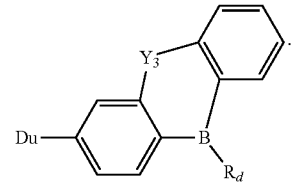

Formula 1-D

In Formula 1-A, at least one among $X_1$ to $X_5$ may be N, and the remainder may each be $CR_a$. For example, one selected from $X_1$ to $X_5$ in the compound represented by Formula 1-A may be N and the others may be $CR_a$. In some embodiments, two or three selected from $X_1$ to $X_5$ in the compound represented by Formula 1-A may be N, and the others may be $CR_a$.

In Formula 1-A, $R_a$ may be a hydrogen atom, a deuterium atom, a substituted or unsubstituted alkyl group having 1 to 20 carbon atoms, a substituted or unsubstituted aliphatic ring group having 6 to 30 carbon atoms for forming a ring, a substituted or unsubstituted aryl group of 6 to 30 carbon atoms for forming a ring, or a substituted or unsubstituted heteroaryl group of 2 to 30 carbon atoms for forming a ring. For example, $R_a$ may be a hydrogen atom, a methyl group, a t-butyl group, a cyclohexyl group, an adamantly group, a phenyl group, or a pyridine group. However, an embodiment of the present disclosure is not limited thereto.

In Formula 1-B, $R_b$ and $R_c$ may each independently be a hydrogen atom, a deuterium atom, a substituted or unsubstituted alkyl group of 1 to 20 carbon atoms, a substituted or unsubstituted aliphatic ring group having 6 to 30 carbon atoms for forming a ring, a substituted or unsubstituted aryl group of 6 to 30 carbon atoms for forming a ring, or a substituted or unsubstituted heteroaryl group of 2 to 30 carbon atoms for forming a ring. For example, $R_b$ and $R_c$ may each independently be an unsubstituted phenyl group, or a phenyl group substituted with alkyl group. However, an embodiment of the present disclosure is not limited thereto.

In Formula 1-A and 1-B, $A_{11}$ to $A_{14}$ may each independently be a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. $A_{11}$ to $A_{14}$ may each independently be a hydrogen atom, or a methyl group. However, an embodiment of the present disclosure is not limited thereto.

In Formula 1-C and Formula 1-D, $Y_1$ to $Y_3$ may each independently be O, S, $NR_e$, or C(=O). In Formula 1-C, $Y_1$ and $Y_2$ may be the same or different. $R_a$ may be a hydrogen atom, a deuterium atom, a substituted or unsubstituted alkyl group having 1 to 20 carbon atoms, a substituted or unsubstituted aliphatic ring group having 6 to 30 carbon atoms for forming a ring, a substituted or unsubstituted aryl group of 6 to 30 carbon atoms for forming a ring, or a substituted or unsubstituted heteroaryl group of 2 to 30 carbon atoms for forming a ring. For example, $R_a$ may be a substituted or unsubstituted phenyl group. However, an embodiment of the present disclosure is not limited thereto.

In addition, in Formula 1-D, Rd may be a hydrogen atom, a deuterium atom, a substituted or unsubstituted alkyl group having 1 to 20 carbon atoms, a substituted or unsubstituted aliphatic ring group having 6 to 30 carbon atoms for forming a ring, a substituted or unsubstituted aryl group of 6 to 30 carbon atoms for forming a ring, or a substituted or unsubstituted heteroaryl group of 2 to 30 carbon atoms for forming a ring. For example, Rd may be a substituted or unsubstituted phenyl group. However, an embodiment of the present disclosure is not limited thereto.

In the polycyclic compound according to an embodiment, "Du" may be represented by Formula 2. In Formula 2, at least one of $R_1$ to $R_{22}$ may be a cyano group, a fluoro group, or a trifluoromethyl group, and the remainder may each independently be a hydrogen atom, a deuterium atom, a substituted or unsubstituted oxy group, a substituted or unsubstituted thio group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 2, any one selected from $R_1$ to $R_{22}$ may be a cyano group, a fluoro group, or a trifluoromethyl group, and the remainder may each independently be a hydrogen atom, a deuterium atom, a substituted or unsubstituted oxy group, a substituted or unsubstituted thio group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, any one selected from $R_1$ to $R_{22}$ may be a cyano group, a fluoro group, or a trifluoromethyl group, and the remainder may each be a hydrogen atom.

In some embodiments, in Formula 2, two selected from $R_1$ to $R_{22}$ may each independently be a cyano group, a fluoro group, or a trifluoromethyl group, and the remainder may each independently be a hydrogen atom, a deuterium atom, a substituted or unsubstituted oxy group, a substituted or unsubstituted thio group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, two selected from $R_1$ to $R_{22}$ may each independently be a cyano group, a fluoro group, or a trifluoromethyl group, and the remainder may each be a hydrogen atom. In some embodiments, two selected from $R_1$ to $R_{22}$ may be identical and selected from a cyano group, a fluoro group, and a trifluoromethyl group, and in some embodiments, two selected from $R_1$ to $R_{22}$ may be different from each other and selected from a cyano group, a fluoro group, and a trifluoromethyl group.

In some embodiments, in Formula 2, three selected from $R_1$ to $R_{22}$ may each independently be a cyano group, a fluoro group, or a trifluoromethyl group, and the remainder may each independently be a hydrogen atom, a deuterium atom, a substituted or unsubstituted oxy group, a substituted or unsubstituted thio group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, three selected from $R_1$ to $R_{22}$ may each independently be a cyano group, a fluoro group, or a trifluoromethyl group, and the remainder may each be a hydrogen atom. In some embodiments, three selected from $R_1$ to $R_{22}$ may be identical and selected from a cyano group, a fluoro group, and a trifluoromethyl group. In some embodiments, at least one of the three may be different from the other two, and may be selected from a cyano group, a fluoro group, and a trifluoromethyl group.

Formula 2 may be represented by any one among Compound (A)-1 to Compound (A)-18. Compounds (A)-1 to (A)-18 correspond to examples of compounds in which one selected from $R_1$ to $R_7$, $R_{10}$ to $R_{16}$, and $R_{19}$ to $R_{22}$ is a cyano group, and the others are each a hydrogen atom. For example, Compound (A)-1 corresponds to the case in which $R_1$ is a cyano group and $R_2$ to $R_{22}$ are each a hydrogen atom, in Formula 2. The compounds represented by the case in which $R_5$ is substituted with one cyano group is the same as the case in which R is substituted with one cyano group (e.g., due to molecular symmetry). Similarly, the case in which $R_6$ is substituted with a cyano group is the same as the case in which R is substituted with a cyano group; the case in which $R_{15}$ is substituted with a cyano group is the same as the case in which $R_{17}$ is substituted with a cyano group; and the case in which $R_{14}$ is substituted with a cyano group is the same as the case in which $R_{18}$ is substituted with a cyano group. Therefore, these cases are not separately described as additional compounds.

| (A)-9 | (A)-8 | (A)-7 | (A)-6 | (A)-5 | (A)-4 | (A)-3 | (A)-2 | (A)-1 | Compound Number |
|---|---|---|---|---|---|---|---|---|---|
| H | H | H | H | H | H | H | H | CN | $R_1$ |
| H | H | H | H | H | H | H | CN | H | $R_2$ |
| H | H | H | H | H | H | CN | H | H | $R_3$ |
| H | H | H | H | H | CN | H | H | H | $R_4$ |
| H | H | H | H | CN | H | H | H | H | $R_5$ |
| H | H | H | CN | H | H | H | H | H | $R_6$ |
| H | H | CN | H | H | H | H | H | H | $R_7$ |
| H | H | H | H | H | H | H | H | H | $R_8$ |
| H | H | H | H | H | H | H | H | H | $R_9$ |
| H | CN | H | H | H | H | H | H | H | $R_{10}$ |
| CN | H | H | H | H | H | H | H | H | $R_{11}$ |
| H | H | H | H | H | H | H | H | H | $R_{12}$ |
| H | H | H | H | H | H | H | H | H | $R_{13}$ |
| H | H | H | H | H | H | H | H | H | $R_{14}$ |
| H | H | H | H | H | H | H | H | H | $R_{15}$ |
| H | H | H | H | H | H | H | H | H | $R_{16}$ |
| H | H | H | H | H | H | H | H | H | $R_{17}$ |
| H | H | H | H | H | H | H | H | H | $R_{18}$ |
| H | H | H | H | H | H | H | H | H | $R_{19}$ |
| H | H | H | H | H | H | H | H | H | $R_{20}$ |
| H | H | H | H | H | H | H | H | H | $R_{21}$ |
| H | H | H | H | H | H | H | H | H | $R_{22}$ |

| (A)-18 | (A)-17 | (A)-16 | (A)-15 | (A)-14 | (A)-13 | (A)-12 | (A)-11 | (A)-10 | Compound Number |
|---|---|---|---|---|---|---|---|---|---|
| H | H | H | H | H | H | H | H | H | $R_1$ |
| H | H | H | H | H | H | H | H | H | $R_2$ |
| H | H | H | H | H | H | H | H | H | $R_3$ |
| H | H | H | H | H | H | H | H | H | $R_4$ |
| H | H | H | H | H | H | H | H | H | $R_5$ |
| H | H | H | H | H | H | H | H | H | $R_6$ |
| H | H | H | H | H | H | H | H | H | $R_7$ |
| H | H | H | H | H | H | H | H | H | $R_8$ |
| H | H | H | H | H | H | H | H | H | $R_9$ |
| H | H | H | H | H | H | H | H | H | $R_{10}$ |
| H | H | H | H | H | H | H | H | H | $R_{11}$ |
| H | H | H | H | H | H | H | H | CN | $R_{12}$ |
| H | H | H | H | H | H | H | CN | H | $R_{13}$ |
| H | H | H | H | H | H | CN | H | H | $R_{14}$ |
| H | H | H | H | H | CN | H | H | H | $R_{15}$ |
| H | H | H | H | CN | H | H | H | H | $R_{16}$ |
| H | H | H | H | H | H | H | H | H | $R_{17}$ |
| H | H | H | H | H | H | H | H | H | $R_{18}$ |
| H | H | H | CN | H | H | H | H | H | $R_{19}$ |
| H | H | CN | H | H | H | H | H | H | $R_{20}$ |
| H | CN | H | H | H | H | H | H | H | $R_{21}$ |
| CN | H | H | H | H | H | H | H | H | $R_{22}$ |

Formula 2 may be represented by any one among Compound (B)-1 to Compound (B)-18. Compounds (B)-1 to (B)-18 correspond to examples of compounds in which one selected from $R_1$ to $R_7$, $R_{10}$ to $R_{16}$, and $R_{19}$ to $R_{22}$ is a fluoro group, and the others are each a hydrogen atom. For example, Compound (B)-1 corresponds to the case in which $R_1$ is a fluoro group and $R_2$ to $R_{22}$ are each a hydrogen atom, in Formula 2. As described in the description of the example compounds containing cyano group substituents, the compounds represented by the case in which $R_5$ is substituted with one fluoro group is the same as the case in which $R_9$ is substituted with one fluoro group, etc. Because $R_6$ and $R_8$, $R_{15}$ and $R_{17}$, $R_{14}$ and $R_{18}$ are also equivalent by symmetry as described above, they are not separately described as additional compounds.

| (B)-9 | (B)-8 | (B)-7 | (B)-6 | (B)-5 | (B)-4 | (B)-3 | (B)-2 | (B)-1 | Compound Number |
|---|---|---|---|---|---|---|---|---|---|
| H | H | H | H | H | H | H | H | F | $R_1$ |
| H | H | H | H | H | H | H | F | H | $R_2$ |
| H | H | F | H | H | H | H | H | H | $R_3$ |
| H | H | H | H | H | F | H | H | H | $R_4$ |
| H | H | H | H | F | H | H | H | H | $R_5$ |
| H | H | H | F | H | H | H | H | H | $R_6$ |
| H | H | F | H | H | H | H | H | H | $R_7$ |
| H | H | H | H | H | H | H | H | H | $R_8$ |
| H | H | H | H | H | H | H | H | H | $R_9$ |
| H | F | H | H | H | H | H | H | H | $R_{10}$ |
| F | H | H | H | H | H | H | H | H | $R_{11}$ |
| H | H | H | H | H | H | H | H | H | $R_{12}$ |
| H | H | H | H | H | H | H | H | H | $R_{13}$ |
| H | H | H | H | H | H | H | H | H | $R_{14}$ |
| H | H | H | H | H | H | H | H | H | $R_{15}$ |
| H | H | H | H | H | H | H | H | H | $R_{16}$ |
| H | H | H | H | H | H | H | H | H | $R_{17}$ |
| H | H | H | H | H | H | H | H | H | $R_{18}$ |
| H | H | H | H | H | H | H | H | H | $R_{19}$ |
| H | H | H | H | H | H | H | H | H | $R_{20}$ |
| H | H | H | H | H | H | H | H | H | $R_{21}$ |
| H | H | H | H | H | H | H | H | H | $R_{22}$ |

-continued

| | (B)-18 | (B)-17 | (B)-16 | (B)-15 | (B)-14 | (B)-13 | (B)-12 | (B)-11 | (B)-10 | Compound Number |
|---|---|---|---|---|---|---|---|---|---|---|
| | H | H | H | H | H | H | H | H | H | $R_1$ |
| | H | H | H | H | H | H | H | H | H | $R_2$ |
| | H | H | H | H | H | H | H | H | H | $R_3$ |
| | H | H | H | H | H | H | H | H | H | $R_4$ |
| | H | H | H | H | H | H | H | H | H | $R_5$ |
| | H | H | H | H | H | H | H | H | H | $R_6$ |
| | H | H | H | H | H | H | H | H | H | $R_7$ |
| | H | H | H | H | H | H | H | H | H | $R_8$ |
| | H | H | H | H | H | H | H | H | H | $R_9$ |
| | H | H | H | H | H | H | H | H | H | $R_{10}$ |
| | H | H | H | H | H | H | H | H | H | $R_{11}$ |
| | H | H | H | H | H | H | H | H | F | $R_{12}$ |
| | H | H | H | H | H | H | H | F | H | $R_{13}$ |
| | H | H | H | H | H | H | F | H | H | $R_{14}$ |
| | H | H | H | H | H | F | H | H | H | $R_{15}$ |
| | H | H | H | H | F | H | H | H | H | $R_{16}$ |
| | H | H | H | F | H | H | H | H | H | $R_{17}$ |
| | H | H | F | H | H | H | H | H | H | $R_{18}$ |
| | H | H | H | F | H | H | H | H | H | $R_{19}$ |
| | H | H | F | H | H | H | H | H | H | $R_{20}$ |
| | H | F | H | H | H | H | H | H | H | $R_{21}$ |
| | F | H | F | H | H | H | H | H | H | $R_{22}$ |

Formula 2 may be represented by any one among Compound (C)-1 to Compound (C)-18. Compounds (C)-1 to (C)-18 correspond to examples of compounds in which one selected from $R_1$ to $R_7$, $R_{10}$ to $R_{16}$, and $R_{19}$ to $R_{22}$ is a trifluoromethyl group, and the others are hydrogen atoms. For example, Compound (C)-1 corresponds to the case in which $R_1$ is a trifluoromethyl group and $R_2$ to $R_{22}$ are each a hydrogen atom, in Formula 2. As described in the description of the example compounds containing cyano group substituents, the compounds represented by the case in which $R_5$ is substituted with one trifluoromethyl group is the same as the case in which $R_9$ is substituted with one trifluoromethyl group. Because $R_6$ and $R_8$, $R_{15}$ and $R_{17}$, $R_{14}$ and $R_{18}$ are also equivalent by symmetry as described above, they are not separately described as additional compounds.

| Compound Number | (C)-1 | (C)-2 | (C)-3 | (C)-4 | (C)-5 | (C)-6 | (C)-7 | (C)-8 | (C)-9 |
|---|---|---|---|---|---|---|---|---|---|
| $R_1$ | $CF_3$ | H | H | H | H | H | H | H | H |
| $R_2$ | H | $CF_3$ | H | H | H | H | H | H | H |
| $R_3$ | H | H | $CF_3$ | H | H | H | H | H | H |
| $R_4$ | H | H | H | $CF_3$ | H | H | H | H | H |
| $R_5$ | H | H | H | H | $CF_3$ | H | H | H | H |
| $R_6$ | H | H | H | H | H | CF | H | H | H |
| $R_7$ | H | H | H | H | H | H | $CF_3$ | H | H |
| $R_8$ | H | H | H | H | H | H | H | H | H |
| $R_9$ | H | H | H | H | H | H | H | H | H |
| $R_{10}$ | H | H | H | H | H | H | H | $CF_3$ | H |
| $R_{11}$ | H | H | H | H | H | H | H | H | $CF_3$ |
| $R_{12}$ | H | H | H | H | H | H | H | H | H |
| $R_{13}$ | H | H | H | H | H | H | H | H | H |
| $R_{14}$ | H | H | H | H | H | H | H | H | H |
| $R_{15}$ | H | H | H | H | H | H | H | H | H |
| $R_{16}$ | H | H | H | H | H | H | H | H | H |
| $R_{17}$ | H | H | H | H | H | H | H | H | H |
| $R_{18}$ | H | H | H | H | H | H | H | H | H |
| $R_{19}$ | H | H | H | H | H | H | H | H | H |
| $R_{20}$ | H | H | H | H | H | H | H | H | H |
| $R_{21}$ | H | H | H | H | H | H | H | H | H |
| $R_{22}$ | H | H | H | H | H | H | H | H | H |

| Compound Number | (C)-10 | (C)-11 | (C)-12 | (C)-13 | (C)-14 | (C)-15 | (C)-16 | (C)-17 | (C)-18 |
|---|---|---|---|---|---|---|---|---|---|
| $R_1$ | H | H | H | H | H | H | H | H | H |
| $R_2$ | H | H | H | H | H | H | H | H | H |
| $R_3$ | H | H | H | H | H | H | H | H | H |
| $R_4$ | H | H | H | H | H | H | H | H | H |
| $R_5$ | H | H | H | H | H | H | H | H | H |
| $R_6$ | H | H | H | H | H | H | H | H | H |
| $R_7$ | H | H | H | H | H | H | H | H | H |
| $R_8$ | H | H | H | H | H | H | H | H | H |
| $R_9$ | H | H | H | H | H | H | H | H | H |
| $R_{10}$ | H | H | H | H | H | H | H | H | H |
| $R_{11}$ | H | H | H | H | H | H | H | H | H |
| $R_{12}$ | $CF_3$ | H | H | H | H | H | H | H | H |
| $R_{13}$ | H | $CF_3$ | H | H | H | H | H | H | H |
| $R_{14}$ | H | H | $CF_3$ | H | H | H | H | H | H |
| $R_{15}$ | H | H | H | $CF_3$ | H | H | H | H | H |
| $R_{16}$ | H | H | H | H | $CF_3$ | H | H | H | H |
| $R_{17}$ | H | H | H | H | H | H | H | H | H |
| $R_{18}$ | H | H | H | H | H | H | H | H | H |
| $R_{19}$ | H | H | H | H | H | $CF_3$ | H | H | H |
| $R_{20}$ | H | H | H | H | H | H | $CF_3$ | H | H |
| $R_{21}$ | H | H | H | H | H | H | H | $CF_3$ | H |
| $R_{22}$ | H | H | H | H | H | H | H | H | $CF_3$ |

Formula 2 may be represented by any one among Compound (D)-1 to Compound (D)-152. Compounds (D)-1 to (D)-152 correspond to examples of compounds in which two or three selected from $R_1$ to $R_7$, $R_{10}$ to $R_{16}$, and $R_{19}$ to $R_{22}$ are cyano groups, and the others are each a hydrogen atom. For example, Compound (D)-1 corresponds to the case in which $R_1$ and $R_2$ are cyano groups and $R_3$ to $R_{22}$ are each a hydrogen atom, in Formula 2. In addition, Compound (D)-44 corresponds to the case in which $R_3$, $R_{16}$, and $R_{19}$ are cyano groups, and $R_1$, $R_2$ to $R_{15}$, $R_{17}$, $R_{18}$, and $R_{20}$ to $R_{22}$ are each a hydrogen atom.

| Compound Number | (D)-1 | (D)-2 | (D)-3 | (D)-4 | (D)-5 | (D)-6 | (D)-7 | (D)-8 | (D)-9 | (D)-10 | (D)-11 | (D)-12 | (D)-13 |
|---|---|---|---|---|---|---|---|---|---|---|---|---|---|
| $R_1$ | CN | CN | CN | CN | CN | CN | CN | CN | CN | CN | CN | CN | CN |
| $R_2$ | CN | H | H | H | H | H | H | H | H | H | H | H | H |
| $R_3$ | H | CN | H | H | H | H | H | H | H | H | H | H | F |
| $R_4$ | H | H | CN | H | H | H | H | H | H | H | H | H | H |
| $R_5$ | H | H | H | CN | H | H | H | H | H | H | H | H | H |
| $R_6$ | H | H | H | H | CN | H | H | H | H | H | H | H | H |
| $R_7$ | H | H | H | H | H | CN | H | H | H | H | H | H | H |
| $R_8$ | H | H | H | H | H | H | H | H | H | H | H | H | H |
| $R_9$ | H | H | H | H | H | H | H | H | H | H | H | H | H |
| $R_{10}$ | H | H | H | H | H | H | CN | H | H | H | H | H | H |
| $R_{11}$ | H | H | H | H | H | H | H | CN | H | H | H | H | H |
| $R_{12}$ | H | H | H | H | H | H | H | H | CN | H | H | H | H |
| $R_{13}$ | H | H | H | H | H | H | H | H | H | CN | H | H | H |
| $R_{14}$ | H | H | H | H | H | H | H | H | H | H | CN | H | H |
| $R_{15}$ | H | H | H | H | H | H | H | H | H | H | H | CN | H |
| $R_{16}$ | H | H | H | H | H | H | H | H | H | H | H | H | CN |
| $R_{17}$ | H | H | H | H | H | H | H | H | H | H | H | H | H |
| $R_{18}$ | H | H | H | H | H | H | H | H | H | H | H | H | H |
| $R_{19}$ | H | H | H | H | H | H | H | H | H | H | H | H | H |
| $R_{20}$ | H | H | H | H | H | H | H | H | H | H | H | H | H |
| $R_{21}$ | H | H | H | H | H | H | H | H | H | H | H | H | H |
| $R_{22}$ | H | H | H | H | H | H | H | H | H | H | H | H | H |

| Compound Number | (D)-14 | (D)-15 | (D)-16 | (D)-17 | (D)-18 | (D)-19 | (D)-20 | (D)-21 | (D)-22 | (D)-23 | (D)-24 | (D)-25 | (D)-26 |
|---|---|---|---|---|---|---|---|---|---|---|---|---|---|
| $R_1$ | CN | CN | CN | CN | H | H | H | H | H | H | H | H | H |
| $R_2$ | H | H | H | H | CN | CN | CN | CN | CN | CN | CN | CN | CN |
| $R_3$ | H | H | H | H | CN | H | H | H | H | H | H | H | H |
| $R_4$ | H | H | H | H | H | CN | H | H | H | H | H | H | H |
| $R_5$ | H | H | H | H | H | H | CN | H | H | H | H | H | H |
| $R_6$ | H | H | H | H | H | H | H | CN | H | H | H | H | H |
| $R_7$ | H | H | H | H | H | H | H | H | CN | H | H | H | H |
| $R_8$ | H | H | H | H | H | H | H | H | H | H | H | H | H |
| $R_9$ | H | H | H | H | H | H | H | H | H | H | H | H | H |
| $R_{10}$ | H | H | H | H | H | H | H | H | H | CN | H | H | H |
| $R_{11}$ | H | H | H | H | H | H | H | H | H | H | H | H | H |
| $R_{12}$ | H | H | H | H | H | H | H | H | H | H | H | CN | H |
| $R_{13}$ | H | H | H | H | H | H | H | H | H | H | H | H | CN |
| $R_{14}$ | H | H | H | H | H | H | H | H | H | H | H | H | H |
| $R_{15}$ | H | E | H | H | H | H | H | H | H | H | H | H | H |
| $R_{16}$ | H | H | H | H | H | H | H | H | H | H | H | H | H |
| $R_{17}$ | H | H | H | H | H | H | H | H | H | H | H | H | H |
| $R_{18}$ | H | H | H | H | H | H | H | H | H | H | H | H | H |
| $R_{19}$ | CN | H | H | H | H | H | H | H | H | H | H | H | H |
| $R_{20}$ | H | CN | H | H | H | H | H | H | H | H | H | H | H |
| $R_{21}$ | H | H | CN | H | H | H | H | H | H | H | H | H | H |
| $R_{22}$ | H | H | H | CN | H | H | H | H | H | H | H | H | H |

| Compound Number | (D)-27 | (D)-28 | (D)-29 | (D)-30 | (D)-31 | (D)-32 | (D)-33 | (D)-34 | (D)-35 | (D)-36 | (D)-37 | (D)-38 | (D)-39 |
|---|---|---|---|---|---|---|---|---|---|---|---|---|---|
| $R_1$ | H | H | H | H | H | H | H | H | H | H | H | H | H |
| $R_2$ | CN | CN | CN | CN | CN | CN | CN | H | H | H | H | H | H |
| $R_3$ | H | H | H | H | H | H | H | CN | CN | CN | CN | CN | CN |
| $R_4$ | H | H | H | H | H | H | H | H | CN | H | H | H | H |
| $R_5$ | H | H | H | H | H | H | H | H | H | CN | H | H | H |
| $R_6$ | H | H | H | H | H | H | H | H | H | H | CN | H | H |
| $R_7$ | H | H | H | H | H | H | H | H | H | H | H | CN | H |
| $R_8$ | H | H | H | H | H | H | H | H | H | H | H | H | H |
| $R_9$ | H | H | H | H | H | H | H | H | H | H | H | H | H |
| $R_{10}$ | H | H | H | H | H | H | H | H | H | H | H | H | CN |
| $R_{11}$ | H | H | H | H | H | H | H | H | H | H | H | H | H |
| $R_{12}$ | H | H | H | H | H | H | H | H | H | H | H | H | H |

-continued

| | | | | | | | | | | | | | |
|---|---|---|---|---|---|---|---|---|---|---|---|---|---|
| H | H | H | H | H | H | H | H | H | H | H | H | H | R$_{13}$ |
| H | H | H | H | H | H | H | H | H | H | H | H | CN | R$_{14}$ |
| H | H | H | H | H | H | H | H | H | H | H | CN | H | R$_{15}$ |
| H | H | H | H | H | H | H | H | H | H | CN | H | H | R$_{16}$ |
| H | H | H | H | H | H | H | H | H | H | H | H | H | R$_{17}$ |
| H | H | H | H | H | H | H | H | H | H | H | H | H | R$_{18}$ |
| H | H | H | H | H | H | H | H | H | CN | H | H | H | R$_{19}$ |
| H | H | H | H | H | H | H | H | CN | H | H | H | H | R$_{20}$ |
| H | H | H | H | H | H | H | CN | H | H | H | H | H | R$_{21}$ |
| H | H | H | H | H | H | CN | H | H | H | H | H | H | R$_{22}$ |

| (D)-52 | (D)-51 | (D)-50 | (D)-49 | (D)-48 | (D)-47 | (D)-46 | (D)-45 | (D)-44 | (D)-43 | (D)-42 | (D)-41 | (D)-40 | Compound Number |
|---|---|---|---|---|---|---|---|---|---|---|---|---|---|
| H | H | H | H | H | H | H | H | H | H | H | H | H | R$_{1}$ |
| H | H | H | H | H | H | H | H | H | H | H | H | H | R$_{2}$ |
| H | H | H | H | CN | CN | CN | CN | CN | CN | CN | CN | CN | R$_{3}$ |
| CN | CN | CN | CN | CN | H | H | H | H | H | H | H | H | R$_{4}$ |
| H | H | H | H | CN | H | H | H | H | H | H | H | H | R$_{5}$ |
| H | H | H | CN | H | H | H | H | H | H | H | H | H | R$_{6}$ |
| H | H | CN | H | H | H | H | H | H | H | H | H | H | R$_{7}$ |
| H | H | H | H | H | H | H | H | H | H | H | H | H | R$_{8}$ |
| H | H | H | H | H | H | H | H | H | H | H | H | H | R$_{9}$ |
| H | CN | H | H | H | H | H | H | H | H | H | H | H | R$_{10}$ |
| CN | H | H | H | H | H | H | H | H | H | H | H | H | R$_{11}$ |
| H | H | H | H | H | H | H | H | H | H | H | H | CN | R$_{12}$ |
| H | H | H | H | H | H | H | H | H | H | H | CN | H | R$_{13}$ |
| H | H | H | H | H | H | H | H | H | H | CN | H | H | R$_{14}$ |
| H | H | H | H | H | H | H | H | H | CN | H | H | H | R$_{15}$ |
| H | H | H | H | H | H | H | H | CN | H | H | H | H | R$_{16}$ |
| H | H | H | H | H | H | H | H | H | H | H | H | H | R$_{17}$ |
| H | H | H | H | H | H | H | H | H | H | H | H | H | R$_{18}$ |
| H | H | H | H | H | H | H | CN | H | H | H | H | H | R$_{19}$ |
| H | H | H | H | H | H | CN | H | H | H | H | H | H | R$_{20}$ |
| H | H | H | H | H | CN | H | H | H | H | H | H | H | R$_{21}$ |
| H | H | H | H | CN | H | H | H | H | H | H | H | H | R$_{22}$ |

| (D)-65 | (D)-64 | (D)-63 | (D)-62 | (D)-61 | (D)-60 | (D)-59 | (D)-58 | (D)-57 | (D)-56 | (D)-55 | (D)-54 | (D)-53 | Compound Number |
|---|---|---|---|---|---|---|---|---|---|---|---|---|---|
| H | H | H | H | H | H | H | H | H | H | H | H | H | R$_{1}$ |
| H | H | H | H | H | H | H | H | H | H | H | H | H | R$_{2}$ |
| H | H | H | H | H | H | H | H | H | H | H | H | H | R$_{3}$ |
| H | H | H | H | CN | CN | CN | CN | CN | CN | CN | CN | CH | R$_{4}$ |
| CN | CN | CN | CN | H | H | H | H | H | H | H | H | H | R$_{5}$ |
| H | H | H | CN | H | H | H | H | H | H | H | H | H | R$_{6}$ |
| H | H | CN | H | H | H | H | H | H | H | H | H | H | R$_{7}$ |
| H | H | H | H | H | H | H | H | H | H | H | H | H | R$_{8}$ |
| H | H | H | H | H | H | H | H | H | H | H | H | H | R$_{9}$ |
| H | CN | H | H | H | H | H | H | H | H | H | H | H | R$_{10}$ |
| CN | H | H | H | H | H | H | H | H | H | H | H | H | R$_{11}$ |
| H | H | H | H | H | H | H | H | H | H | H | H | CN | R$_{12}$ |
| H | H | H | H | H | H | H | H | H | H | H | CN | H | R$_{13}$ |
| H | H | H | H | H | H | H | H | H | H | CN | H | H | R$_{14}$ |
| H | H | H | H | H | H | H | H | H | CN | H | H | H | R$_{15}$ |
| H | H | H | H | H | H | H | H | CN | H | H | H | H | R$_{16}$ |
| H | H | H | H | H | H | H | H | H | H | H | H | H | R$_{17}$ |
| H | H | H | H | H | H | H | H | H | H | H | H | H | R$_{18}$ |
| H | H | H | H | H | H | H | CN | H | H | H | H | H | R$_{19}$ |
| H | H | H | H | H | H | CN | H | H | H | H | H | H | R$_{20}$ |
| H | H | H | H | H | CN | H | H | H | H | H | H | H | R$_{21}$ |
| H | H | H | H | CN | H | H | H | H | H | H | H | H | R$_{22}$ |

| (D)-78 | (D)-77 | (D)-76 | (D)-75 | (D)-74 | (D)-73 | (D)-72 | (D)-71 | (D)-70 | (D)-69 | (D)-68 | (D)-67 | (D)-66 | Compound Number |
|---|---|---|---|---|---|---|---|---|---|---|---|---|---|
| H | H | H | H | H | H | H | H | H | H | H | H | H | R$_{1}$ |
| H | H | H | H | H | H | H | H | H | H | H | H | H | R$_{2}$ |
| H | H | H | H | H | H | H | H | H | H | H | H | H | R$_{3}$ |
| H | H | H | H | H | H | H | H | H | H | H | H | H | R$_{4}$ |
| H | H | H | H | CN | CN | CN | CN | CN | CN | CN | CN | CN | R$_{5}$ |
| CN | CN | CN | CN | H | H | H | H | H | H | H | H | H | R$_{6}$ |
| H | H | H | CN | H | H | H | H | H | H | H | H | H | R$_{7}$ |
| H | H | H | H | H | H | H | H | H | H | H | H | H | R$_{8}$ |
| H | H | H | H | H | H | H | H | H | H | H | H | H | R$_{9}$ |
| H | H | CN | H | H | H | H | H | H | H | H | H | H | R$_{10}$ |
| H | CN | H | H | H | H | H | H | H | H | H | H | H | R$_{11}$ |
| CN | H | H | H | H | H | H | H | H | H | H | H | CN | R$_{12}$ |
| H | H | H | H | H | H | H | H | H | H | H | CN | H | R$_{13}$ |

-continued

| | | | | | | | | | | | | | |
|---|---|---|---|---|---|---|---|---|---|---|---|---|---|
| H | H | H | H | H | H | H | H | H | H | CN | H | H | R₁₄ |
| H | H | H | H | H | H | H | H | H | CN | H | H | H | R₁₅ |
| H | H | H | H | H | H | H | H | CN | H | H | H | H | R₁₆ |
| H | H | H | H | H | H | H | H | H | H | H | H | H | R₁₇ |
| H | H | H | H | H | H | H | H | H | H | H | H | H | R₁₈ |
| H | H | H | H | H | H | H | CN | H | H | H | H | H | R₁₉ |
| H | H | H | H | H | H | CN | H | H | H | H | H | H | R₂₀ |
| H | H | H | H | H | CN | H | H | H | H | H | H | H | R₂₁ |
| H | H | H | H | CN | H | H | H | H | H | H | H | H | R₂₂ |

| (D)-91 | (D)-90 | (D)-89 | (D)-88 | (D)-87 | (D)-86 | (D)-85 | (D)-84 | (D)-83 | (D)-82 | (D)-81 | (D)-80 | (D)-79 | Compound Number |
|---|---|---|---|---|---|---|---|---|---|---|---|---|---|
| H | H | H | H | H | H | H | H | H | H | H | H | H | R₁ |
| H | H | H | H | H | H | H | H | H | H | H | H | H | R₂ |
| H | H | H | H | H | H | H | H | H | H | H | H | H | R₃ |
| H | H | H | H | H | H | H | H | H | H | H | H | H | R₄ |
| H | H | H | H | H | H | H | H | H | H | H | H | H | R₅ |
| H | H | H | H | H | CN | CN | CN | CN | CN | CN | CN | CN | R₆ |
| CN | CN | CN | CN | CN | H | H | H | H | H | H | H | H | R₇ |
| H | H | H | H | H | H | H | H | H | H | H | H | H | R₈ |
| H | H | H | H | H | H | H | H | H | H | H | H | H | R₉ |
| H | H | H | H | CN | H | H | H | H | H | H | H | H | R₁₀ |
| H | H | H | CN | H | H | H | H | H | H | H | H | H | R₁₁ |
| H | H | CN | H | H | H | H | H | H | H | H | H | H | R₁₂ |
| H | CN | H | H | H | H | H | H | H | H | H | H | CN | R₁₃ |
| CN | H | H | H | H | H | H | H | H | H | H | CN | H | R₁₄ |
| H | H | H | H | H | H | H | H | H | H | CN | H | H | R₁₅ |
| H | H | H | H | H | H | H | H | H | CN | H | H | H | R₁₆ |
| H | H | H | H | H | H | H | H | H | H | H | H | H | R₁₇ |
| H | H | H | H | H | H | H | H | H | H | H | H | H | R₁₈ |
| H | H | H | H | H | H | H | H | CN | H | H | H | H | R₁₉ |
| H | H | H | H | H | H | H | CN | H | H | H | H | H | R₂₀ |
| H | H | H | H | H | H | CN | H | H | H | H | H | H | R₂₁ |
| H | H | H | H | H | CN | H | H | H | H | H | H | H | R₂₂ |

| (D)-104 | (D)-103 | (D)-102 | (D)-101 | (D)-100 | (D)-99 | (D)-98 | (D)-97 | (D)-96 | (D)-95 | (D)-94 | (D)-93 | (D)-92 | Compound Number |
|---|---|---|---|---|---|---|---|---|---|---|---|---|---|
| H | H | H | H | H | H | H | H | H | H | H | H | H | R₁ |
| H | H | H | H | H | H | H | H | H | H | H | H | H | R₂ |
| H | H | H | H | H | H | H | H | H | H | H | H | H | R₃ |
| H | H | H | H | H | H | H | H | H | H | H | H | H | R₄ |
| H | H | H | H | H | H | H | H | H | H | H | H | H | R₅ |
| H | H | H | H | H | H | H | H | H | H | H | H | H | R₆ |
| H | H | H | H | H | H | H | CN | CN | CN | CN | CN | CN | R₇ |
| H | H | H | H | H | H | H | H | H | H | H | H | H | R₈ |
| H | H | H | H | H | H | H | H | H | H | H | H | H | R₉ |
| CN | CN | CN | CN | CN | CN | CN | H | H | H | H | H | H | R₁₀ |
| H | H | H | H | H | H | CN | H | H | H | H | H | H | R₁₁ |
| H | H | H | H | H | CN | H | H | H | H | H | H | H | R₁₂ |
| H | H | H | H | CN | H | H | H | H | H | H | H | H | R₁₃ |
| H | H | H | CN | H | H | H | H | H | H | H | H | H | R₁₄ |
| H | H | CN | H | H | H | H | H | H | H | H | H | CN | R₁₅ |
| H | CN | H | H | H | H | H | H | H | H | H | CN | H | R₁₆ |
| H | H | H | H | H | H | H | H | H | H | H | H | H | R₁₇ |
| H | H | H | H | H | H | H | H | H | H | H | H | H | R₁₈ |
| CN | H | H | H | H | H | H | H | H | H | CN | H | H | R₁₉ |
| H | H | H | H | H | H | H | H | H | CN | H | H | H | R₂₀ |
| H | H | H | H | H | H | H | H | CN | H | H | H | H | R₂₁ |
| H | H | H | H | H | H | H | CN | H | H | H | H | H | R₂₂ |

| (D)-117 | (D)-116 | (D)-115 | (D)-114 | (D)-113 | (D)-112 | (D)-111 | (D)-110 | (D)-109 | (D)-108 | (D)-107 | (D)-106 | (D)-105 | Compound Number |
|---|---|---|---|---|---|---|---|---|---|---|---|---|---|
| H | H | H | H | H | H | H | H | H | H | H | H | H | R₁ |
| H | H | H | H | H | H | H | H | H | H | H | H | H | R₂ |
| H | H | H | H | H | H | H | H | H | H | H | H | H | R₃ |
| H | H | H | H | H | H | H | H | H | H | H | H | H | R₄ |
| H | H | H | H | H | H | H | H | H | H | H | H | H | R₅ |
| H | H | H | H | H | H | H | H | H | H | H | H | H | R₆ |
| H | H | H | H | H | H | H | H | H | H | H | H | H | R₇ |
| H | H | H | H | H | H | H | H | H | H | H | H | H | R₈ |
| H | H | H | H | H | H | H | H | H | H | H | H | H | R₉ |
| H | H | H | H | H | H | H | H | H | H | CN | CN | CN | R₁₀ |
| H | CN | CN | CN | CN | CN | CN | CN | CN | CN | H | H | H | R₁₁ |
| CN | H | H | H | H | H | H | H | H | CN | H | H | H | R₁₂ |
| CN | H | H | H | H | H | H | H | CN | H | H | H | H | R₁₃ |
| H | H | H | H | H | H | H | CN | H | H | H | H | H | R₁₄ |

| R15 | H | H | H | H | H | H | CN | H | H | H | H | H | H |
|---|---|---|---|---|---|---|---|---|---|---|---|---|---|
| R16 | H | H | H | H | H | CN | H | H | H | H | H | H | H |
| R17 | H | H | H | H | H | H | H | H | H | H | H | H | H |
| R18 | H | H | H | H | H | H | H | H | H | H | H | H | H |
| R19 | H | H | H | H | CN | H | H | H | H | H | H | H | H |
| R20 | H | H | H | CN | H | H | H | H | H | H | H | H | CN |
| R21 | H | H | CN | H | H | H | H | H | H | H | CN | H | H |
| R22 | H | CN | H | H | H | H | H | H | H | CN | H | H | H |

| Compound Number | (D)-118 | (D)-119 | (D)-120 | (D)-121 | (D)-122 | (D)-123 | (D)-124 | (D)-125 | (D)-126 | (D)-127 | (D)-128 | (D)-129 | (D)-130 |
|---|---|---|---|---|---|---|---|---|---|---|---|---|---|
| $R_1$ | H | H | H | H | H | H | H | H | H | H | H | H | H |
| $R_2$ | H | H | H | H | H | H | H | H | H | H | H | H | H |
| $R_3$ | H | H | H | H | H | H | H | H | H | H | H | H | H |
| $R_4$ | H | H | H | H | H | H | H | H | H | H | H | H | H |
| $R_5$ | H | H | H | H | H | H | H | H | H | H | H | H | H |
| $R_6$ | H | H | H | H | H | H | H | H | H | H | H | H | H |
| $R_7$ | H | H | H | H | H | H | H | H | H | H | H | H | H |
| $R_8$ | H | H | H | H | H | H | H | H | H | H | H | H | H |
| $R_9$ | H | H | H | H | H | H | H | H | H | H | H | H | H |
| $R_{10}$ | H | H | H | H | H | H | H | H | H | H | H | H | H |
| $R_{11}$ | H | H | H | H | H | H | H | H | H | H | H | H | H |
| $R_{12}$ | CN | CN | CN | CN | CN | CN | CN | H | H | H | H | H | H |
| $R_{13}$ | H | H | H | H | H | H | H | CN | CN | CN | CN | CN | CN |
| $R_{14}$ | CN | H | H | H | H | H | H | CN | H | H | H | H | H |
| $R_{15}$ | H | CN | H | H | H | H | H | H | CN | H | H | H | H |
| $R_{16}$ | H | H | CN | H | H | H | H | H | H | CN | H | H | H |
| $R_{17}$ | H | H | H | H | H | H | H | H | H | H | H | H | H |
| $R_{18}$ | H | H | H | H | H | H | H | H | H | H | H | H | H |
| $R_{19}$ | H | H | H | H | H | CN | H | H | H | H | H | H | H |
| $R_{20}$ | H | H | H | H | CN | H | H | H | H | H | H | CN | H |
| $R_{21}$ | H | H | H | CN | H | H | H | H | H | H | H | H | CN |
| $R_{22}$ | H | H | H | H | H | H | CN | H | H | H | H | H | H |

| Compound Number | (D)-131 | (D)-132 | (D)-133 | (D)-134 | (D)-135 | (D)-136 | (D)-137 | (D)-138 | (D)-139 | (D)-140 | (D)-141 | (D)-142 | (D)-143 |
|---|---|---|---|---|---|---|---|---|---|---|---|---|---|
| $R_1$ | H | H | H | H | H | H | H | H | H | H | H | H | H |
| $R_2$ | H | H | H | H | H | H | H | H | H | H | H | H | H |
| $R_3$ | H | H | H | H | H | H | H | H | H | H | H | H | H |
| $R_4$ | H | H | H | H | H | H | H | H | H | H | H | H | H |
| $R_5$ | H | H | H | H | H | H | H | H | H | H | H | H | H |
| $R_6$ | H | H | H | H | H | H | H | H | H | H | H | H | H |
| $R_7$ | H | H | H | H | H | H | H | H | H | H | H | H | H |
| $R_8$ | H | H | H | H | H | H | H | H | H | H | H | H | H |
| $R_9$ | H | H | H | H | H | H | H | H | H | H | H | H | H |
| $R_{10}$ | H | H | H | H | H | H | H | H | H | H | H | H | H |
| $R_{11}$ | H | H | H | H | H | H | H | H | H | H | H | H | H |
| $R_{12}$ | H | H | H | H | H | H | H | H | H | H | H | H | H |
| $R_{13}$ | CN | H | H | H | H | H | H | H | H | H | H | H | H |
| $R_{14}$ | H | CN | CN | CN | CN | CN | CN | H | H | H | H | H | H |
| $R_{15}$ | H | CN | H | H | H | H | H | CN | CN | CN | CN | CN | H |
| $R_{16}$ | H | H | CN | H | H | H | H | CN | H | H | H | H | CN |
| $R_{17}$ | H | H | H | H | H | H | H | H | H | H | H | H | H |
| $R_{18}$ | H | H | H | H | H | H | H | H | H | H | H | H | H |
| $R_{19}$ | H | H | H | CN | H | H | H | H | CN | H | H | H | CN |
| $R_{20}$ | H | H | H | H | CN | H | H | H | H | CN | H | H | H |
| $R_{21}$ | H | H | H | H | H | CN | H | H | H | H | CN | H | H |
| $R_{22}$ | CN | H | H | H | H | H | CN | H | H | H | H | CN | H |

| Compound Number | (D)-144 | (D)-145 | (D)-146 | (D)-147 | (D)-148 | (D)-149 | (D)-150 | (D)-151 | (D)-152 |
|---|---|---|---|---|---|---|---|---|---|
| $R_1$ | H | H | H | H | H | H | H | H | H |
| $R_2$ | H | H | H | H | H | H | H | H | H |
| $R_3$ | H | H | H | H | H | H | H | H | H |
| $R_4$ | H | H | H | H | H | H | H | H | H |
| $R_5$ | H | H | H | H | H | H | H | H | H |
| $R_6$ | H | H | H | H | H | H | H | H | H |
| $R_7$ | H | H | H | H | H | H | H | H | H |
| $R_8$ | H | H | H | H | H | H | H | H | H |
| $R_9$ | H | H | H | H | H | H | H | H | H |
| $R_{10}$ | H | H | H | H | H | H | H | H | H |
| $R_{11}$ | H | H | H | H | H | H | H | H | H |
| $R_{12}$ | H | H | H | H | H | H | H | H | H |
| $R_{13}$ | H | H | H | H | H | H | H | H | H |
| $R_{14}$ | H | H | H | H | H | H | H | H | H |
| $R_{15}$ | H | H | H | H | H | H | H | H | H |

-continued

| | | | | | | | | | |
|---|---|---|---|---|---|---|---|---|---|
| H | H | H | H | H | H | CN | CN | CN | $R_{16}$ |
| H | H | H | H | H | H | H | H | H | $R_{17}$ |
| H | H | H | H | H | H | H | H | H | $R_{18}$ |
| H | H | H | CN | CN | CN | H | H | H | $R_{19}$ |
| H | CN | CN | H | H | CN | H | H | CN | $R_{20}$ |
| CN | H | CN | H | CN | H | H | CN | H | $R_{21}$ |
| CN | CN | H | CN | H | H | CN | H | H | $R_{22}$ |

Formula 2 may be represented by any one among Compound (E)-1 to Compound (E)-152. Compounds (E)-1 to (E)-152 correspond to examples of compounds in which two or three selected from $R_1$ to $R_7$, $R_{10}$ to $R_{16}$, and $R_{19}$ to $R_{22}$ are fluoro groups, and the others are hydrogen atoms. For example, Compound (E)-1 corresponds to the case in which $R_1$ and $R_2$ are fluoro groups and $R_3$ to $R_{22}$ are each a hydrogen atom, in Formula 2. In addition, Compound (E)-44 corresponds to the case in which $R_3$, $R_{16}$ and $R_{19}$ are fluoro groups, and $R_1$, $R_2$ to $R_{15}$, $R_{17}$, $R_{18}$, and $R_{20}$ to $R_{22}$ are each a hydrogen atom.

| (E)-10 | (E)-9 | (E)-8 | (E)-7 | (E)-6 | (E)-5 | (E)-4 | (E)-3 | (E)-2 | (E)-1 | Compound Number |
|---|---|---|---|---|---|---|---|---|---|---|
| F | F | F | F | F | F | F | F | F | F | $R_1$ |
| H | H | H | H | H | H | H | H | H | F | $R_2$ |
| H | H | H | H | H | H | H | H | F | H | $R_3$ |
| H | H | H | H | H | H | H | F | H | H | $R_4$ |
| H | H | H | H | H | H | F | H | H | H | $R_5$ |
| H | H | H | H | H | F | H | H | H | H | $R_6$ |
| H | H | H | H | F | H | H | H | H | H | $R_7$ |
| H | H | H | H | H | H | H | H | H | H | $R_8$ |
| H | H | H | H | H | H | H | H | H | H | $R_9$ |
| H | H | H | F | H | H | H | H | H | H | $R_{10}$ |
| H | H | F | H | H | H | H | H | H | H | $R_{11}$ |
| H | F | H | H | H | H | H | H | H | H | $R_{12}$ |
| F | H | H | H | H | H | H | H | H | H | $R_{13}$ |
| H | H | H | H | H | H | H | H | H | H | $R_{14}$ |
| H | H | H | H | H | H | H | H | H | H | $R_{15}$ |
| H | H | H | H | H | H | H | H | H | H | $R_{16}$ |
| H | H | H | H | H | H | H | H | H | H | $R_{17}$ |
| H | H | H | H | H | H | H | H | H | H | $R_{18}$ |
| H | H | H | H | H | H | H | H | H | H | $R_{19}$ |
| H | H | H | H | H | H | H | H | H | H | $R_{20}$ |
| H | H | H | H | H | H | H | H | H | H | $R_{21}$ |
| H | H | H | H | H | H | H | H | H | H | $R_{22}$ |

| (E)-21 | (E)-20 | (E)-19 | (E)-18 | (E)-17 | (E)-16 | (E)-15 | (E)-14 | (E)-13 | (E)-12 | (E)-11 | Compound Number |
|---|---|---|---|---|---|---|---|---|---|---|---|
| H | H | H | H | F | F | F | F | F | F | F | $R_1$ |
| F | F | F | F | H | H | H | H | H | H | H | $R_2$ |
| H | H | H | F | H | H | H | H | H | H | H | $R_3$ |
| H | H | F | H | H | H | H | H | H | H | H | $R_4$ |
| H | F | H | H | H | H | H | H | H | H | H | $R_5$ |
| F | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | F | $R_{14}$ |
| H | H | H | H | H | H | H | H | H | F | H | $R_{15}$ |
| H | H | H | H | H | H | H | H | F | H | H | $R_{16}$ |
| H | H | H | H | H | H | H | F | H | H | H | $R_{17}$ |
| H | H | H | H | H | H | F | H | H | H | H | $R_{18}$ |
| H | H | H | H | H | F | H | H | H | H | H | $R_{19}$ |
| H | H | H | H | F | H | H | H | H | H | H | $R_{20}$ |
| H | H | H | F | H | H | H | H | H | H | H | $R_{21}$ |
| H | H | F | H | H | H | H | H | H | H | H | $R_{22}$ |

-continued

| Compound Number | (E)-22 | (E)-23 | (E)-24 | (E)-25 | (E)-26 | (E)-27 | (E)-28 | (E)-29 | (E)-30 | (E)-31 | (E)-32 |
|---|---|---|---|---|---|---|---|---|---|---|---|
| $R_1$ | H | H | H | H | H | H | H | H | H | H | H |
| $R_2$ | F | F | F | F | F | F | F | F | F | F | F |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | F | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | F | H | H | H | H | H | H | H | H | H |
| $R_{11}$ | H | H | F | H | H | H | H | H | H | H | H |
| $R_{12}$ | H | H | H | F | H | H | H | H | H | H | H |
| $R_{13}$ | H | H | H | H | F | H | H | H | H | H | H |
| $R_{14}$ | H | H | H | H | H | F | H | H | H | H | H |
| $R_{15}$ | H | H | H | H | H | H | F | H | H | H | H |
| $R_{16}$ | H | H | H | H | H | H | H | F | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | H | F | H | H |
| $R_{20}$ | H | H | H | H | H | H | H | H | H | F | H |
| $R_{21}$ | H | H | H | H | H | H | H | H | H | H | F |
| $R_{22}$ | H | H | H | H | H | H | H | H | H | H | H |

| Compound Number | (E)-33 | (E)-34 | (E)-35 | (E)-36 | (E)-37 | (E)-38 | (E)-39 | (E)-40 | (E)-41 | (E)-42 | (E)-43 |
|---|---|---|---|---|---|---|---|---|---|---|---|
| $R_1$ | H | H | H | H | H | H | H | H | H | H | H |
| $R_2$ | F | H | H | H | H | H | H | H | H | H | H |
| $R_3$ | H | F | F | F | F | F | F | F | F | F | F |
| $R_4$ | H | F | H | H | H | H | H | H | H | H | H |
| $R_5$ | H | H | F | H | H | H | H | H | H | H | H |
| $R_6$ | H | H | H | F | H | H | H | H | H | H | H |
| $R_7$ | H | H | H | H | F | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | F | H | H | H | H |
| $R_{11}$ | H | H | H | H | H | F | H | H | H | H | H |
| $R_{12}$ | H | H | H | H | H | H | H | F | H | H | H |
| $R_{13}$ | H | H | H | H | H | H | H | H | F | H | H |
| $R_{14}$ | H | H | H | H | H | H | H | H | H | F | H |
| $R_{15}$ | H | H | H | H | H | H | H | H | H | H | F |
| $R_{16}$ | H | H | H | H | H | H | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | H | H | H | H |
| $R_{20}$ | H | H | H | H | H | H | H | H | H | H | H |
| $R_{21}$ | H | H | H | H | H | H | H | H | H | H | H |
| $R_{22}$ | F | H | H | H | H | H | H | H | H | H | H |

| Compound Number | (E)-44 | (E)-45 | (E)-46 | (E)-47 | (E)-48 | (E)-49 | (E)-50 | (E)-51 | (E)-52 | (E)-53 | (E)-54 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | F | F | F | F | H | H | H | H | H | H | H |
| $R_4$ | H | H | H | H | F | F | F | F | F | F | F |
| $R_5$ | H | H | H | H | F | H | H | H | H | H | H |
| $R_6$ | H | H | H | F | H | H | H | H | H | H | H |
| $R_7$ | H | H | H | H | H | H | F | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | F | H | H | H |
| $R_{11}$ | H | H | H | H | H | H | H | H | F | H | H |
| $R_{12}$ | H | H | H | H | H | H | H | H | H | F | H |
| $R_{13}$ | H | H | H | H | H | H | H | H | H | H | F |
| $R_{14}$ | H | H | H | H | H | H | H | H | H | H | H |
| $R_{15}$ | H | H | H | H | H | H | H | H | H | H | H |
| $R_{16}$ | F | H | H | H | H | H | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | H | H | H | H |
| $R_{20}$ | H | F | H | H | H | H | H | H | H | H | H |
| $R_{21}$ | H | H | F | H | H | H | H | H | H | H | H |
| $R_{22}$ | H | H | H | F | H | H | H | H | H | H | H |

| Compound Number | (E)-55 | (E)-56 | (E)-57 | (E)-58 | (E)-59 | (E)-60 | (E)-61 | (E)-62 | (E)-63 | (E)-64 | (E)-65 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | F | F | F | F | F | F | F | H | H | H | H |
| $R_5$ | H | H | H | H | H | H | H | F | F | F | F |
| $R_6$ | H | H | H | H | H | H | H | F | H | H | H |
| $R_7$ | H | H | H | H | H | H | H | H | F | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | F | H |
| $R_{11}$ | H | H | H | H | H | H | H | H | H | H | F |
| $R_{12}$ | H | H | H | H | H | H | H | H | H | H | H |
| $R_{13}$ | H | H | H | H | H | H | H | H | H | H | H |
| $R_{14}$ | F | H | H | H | H | H | H | H | H | H | H |
| $R_{15}$ | H | F | H | H | H | H | H | H | H | H | H |
| $R_{16}$ | H | H | F | H | H | H | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | F | H | H | H | H | H | H | H |
| $R_{20}$ | H | H | H | H | F | H | H | H | H | H | H |
| $R_{21}$ | H | H | H | H | H | F | H | H | H | H | H |
| $R_{22}$ | H | H | H | H | H | H | F | H | H | H | H |

| Compound Number | (E)-66 | (E)-67 | (E)-68 | (E)-69 | (E)-70 | (E)-71 | (E)-72 | (E)-73 | (E)-74 | (E)-75 | (E)-76 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | F | F | F | F | F | F | F | F | F | H | H |
| $R_6$ | H | H | H | H | H | H | H | H | H | F | F |
| $R_7$ | H | H | H | H | H | H | H | H | H | F | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | F |
| $R_{11}$ | H | H | H | H | H | H | H | H | H | H | H |
| $R_{12}$ | F | H | H | H | H | H | H | H | H | H | H |
| $R_{13}$ | H | F | H | H | H | H | H | H | H | H | H |
| $R_{14}$ | H | H | F | H | H | H | H | H | H | H | H |
| $R_{15}$ | H | H | H | F | H | H | H | H | H | H | H |
| $R_{16}$ | H | H | H | H | F | H | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | F | H | H | H | H | H |
| $R_{20}$ | H | H | H | H | H | H | F | H | H | H | H |
| $R_{21}$ | H | H | H | H | H | H | H | F | H | H | H |
| $R_{22}$ | H | H | H | H | H | H | H | H | F | H | H |

| Compound Number | (E)-77 | (E)-78 | (E)-79 | (E)-80 | (E)-81 | (E)-82 | (E)-83 | (E)-84 | (E)-85 | (E)-86 | (E)-87 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | F | F | F | F | F | F | F | F | F | F | H |
| $R_7$ | H | H | H | H | H | H | H | H | H | H | F |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | F |
| $R_{11}$ | F | H | H | H | H | H | H | H | H | H | H |
| $R_{12}$ | H | F | H | H | H | H | H | H | H | H | H |
| $R_{13}$ | H | H | F | H | H | H | H | H | H | H | H |
| $R_{14}$ | H | H | H | F | H | H | H | H | H | H | H |
| $R_{15}$ | H | H | H | H | F | H | H | H | H | H | H |
| $R_{16}$ | H | H | H | H | H | F | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | F | H | H | H | H |
| $R_{20}$ | H | H | H | H | H | H | H | F | H | H | H |
| $R_{21}$ | H | H | H | H | H | H | H | H | F | H | H |
| $R_{22}$ | H | H | H | H | H | H | H | H | H | F | H |

-continued

| (E)-98 | (E)-97 | (E)-96 | (E)-95 | (E)-94 | (E)-93 | (E)-92 | (E)-91 | (E)-90 | (E)-89 | (E)-88 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | F | F | F | F | F | F | F | F | F | F | $R_7$ |
| H | H | H | H | H | H | H | H | H | H | H | $R_8$ |
| H | H | H | H | H | H | H | H | H | H | H | $R_9$ |
| F | H | H | H | H | H | H | H | H | H | H | $R_{10}$ |
| H | H | H | H | H | H | H | H | H | H | F | $R_{11}$ |
| H | H | H | H | H | H | H | H | H | F | H | $R_{12}$ |
| H | H | H | H | H | H | H | H | F | H | H | $R_{13}$ |
| H | H | H | H | H | H | H | F | H | H | H | $R_{14}$ |
| H | H | H | H | H | H | F | H | H | H | H | $R_{15}$ |
| H | H | H | H | H | F | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | F | H | H | H | H | H | H | H | $R_{19}$ |
| H | H | F | H | H | H | H | H | H | H | H | $R_{20}$ |
| H | H | H | H | H | H | H | H | H | H | H | $R_{21}$ |
| H | F | H | H | H | H | H | H | H | H | H | $R_{22}$ |

| (E)-109 | (E)-108 | (E)-107 | (E)-106 | (E)-105 | (E)-104 | (E)-103 | (E)-102 | (E)-101 | (E)-100 | (E)-99 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | F | F | F | F | F | F | F | F | F | $R_{10}$ |
| F | F | H | H | H | H | H | H | H | H | H | $R_{11}$ |
| H | F | H | H | H | H | H | H | H | H | F | $R_{12}$ |
| F | H | H | H | H | H | H | H | H | H | H | $R_{13}$ |
| H | H | H | H | H | H | H | F | H | H | H | $R_{14}$ |
| H | H | H | H | H | H | F | H | H | H | H | $R_{15}$ |
| H | H | H | H | H | F | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | F | H | H | H | H | H | H | $R_{19}$ |
| H | H | H | F | H | H | H | H | H | H | H | $R_{20}$ |
| H | H | F | H | H | H | H | H | H | H | H | $R_{21}$ |
| H | H | F | H | H | H | H | H | H | H | H | $R_{22}$ |

| (E)-120 | (E)-119 | (E)-118 | (E)-117 | (E)-116 | (E)-115 | (E)-114 | (E)-113 | (E)-112 | (E)-111 | (E)-110 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | F | F | F | F | F | F | F | $R_{11}$ |
| F | F | F | F | H | H | H | H | H | H | H | $R_{12}$ |
| H | H | H | F | H | H | H | H | H | H | H | $R_{13}$ |
| H | H | F | H | H | H | H | H | H | H | F | $R_{14}$ |
| H | F | H | H | H | H | H | H | H | F | H | $R_{15}$ |
| F | H | H | H | H | H | H | F | H | H | H | $R_{16}$ |
| H | H | H | H | H | H | H | H | H | H | H | $R_{17}$ |
| H | H | H | H | H | H | F | H | H | H | H | $R_{18}$ |
| H | H | H | H | H | F | H | H | H | H | H | $R_{19}$ |
| H | H | H | H | F | H | H | H | H | H | H | $R_{20}$ |
| H | H | H | F | H | H | H | H | H | H | H | $R_{21}$ |
| H | H | H | F | H | H | H | H | H | H | H | $R_{22}$ |

-continued

| Compound Number | (E)-121 | (E)-122 | (E)-123 | (E)-124 | (E)-125 | (E)-126 | (E)-127 | (E)-128 | (E)-129 | (E)-130 | (E)-131 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | F | F | F | F | H | H | H | H | H | H | H |
| $R_{13}$ | H | H | H | H | F | F | F | F | F | F | F |
| $R_{14}$ | H | H | H | H | F | H | H | H | H | H | H |
| $R_{15}$ | H | H | H | H | H | F | H | H | H | H | H |
| $R_{16}$ | H | H | H | H | H | H | F | H | H | H | H |
| $R_{17}$ | H | H | H | H | H | H | H | H | H | H | H |
| $R_{18}$ | H | H | H | H | H | H | H | H | H | H | H |
| $R_{19}$ | F | H | H | H | H | H | H | F | H | H | H |
| $R_{20}$ | H | H | F | H | H | H | H | H | F | H | H |
| $R_{21}$ | H | F | H | H | H | H | H | H | H | F | H |
| $R_{22}$ | H | H | H | F | H | H | H | H | H | H | F |

| Compound Number | (E)-132 | (E)-133 | (E)-134 | (E)-135 | (E)-136 | (E)-137 | (E)-138 | (E)-139 | (E)-140 | (E)-141 | (E)-142 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | H | H | H | H | H | H | H | H | H | H | H |
| $R_{13}$ | H | H | H | H | H | H | H | H | H | H | H |
| $R_{14}$ | F | F | F | F | F | F | H | H | H | H | H |
| $R_{15}$ | F | H | H | H | H | H | F | F | F | F | F |
| $R_{16}$ | H | F | H | H | H | H | F | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | F | H | H | H | H | F | H | H | H |
| $R_{20}$ | H | H | H | F | H | H | H | H | F | H | H |
| $R_{21}$ | H | H | H | H | F | H | H | H | H | F | H |
| $R_{22}$ | H | H | H | H | H | F | H | H | H | H | F |

| Compound Number | (E)-143 | (E)-144 | (E)-145 | (E)-146 | (E)-147 | (E)-148 | (E)-149 | (E)-150 | (E)-151 | (E)-152 |
|---|---|---|---|---|---|---|---|---|---|---|
| $R_1$ | H | H | H | H | H | H | H | H | H | H |
| $R_2$ | H | H | H | H | H | H | H | H | H | H |
| $R_3$ | H | H | H | H | H | H | H | H | H | H |
| $R_4$ | H | H | H | H | H | H | H | H | H | H |
| $R_5$ | H | H | H | H | H | H | H | H | H | H |
| $R_6$ | H | H | H | H | H | H | H | H | H | H |
| $R_7$ | H | H | H | H | H | H | H | H | H | H |
| $R_8$ | H | H | H | H | H | H | H | H | H | H |
| $R_9$ | H | H | H | H | H | H | H | H | H | H |
| $R_{10}$ | H | H | H | H | H | H | H | H | H | H |
| $R_{11}$ | H | H | H | H | H | H | H | H | H | H |
| $R_{12}$ | H | H | H | H | H | H | H | H | H | H |
| $R_{13}$ | H | H | H | H | H | H | H | H | H | H |
| $R_{14}$ | H | H | H | H | H | H | H | H | H | H |
| $R_{15}$ | H | H | H | H | H | H | H | H | H | H |
| $R_{16}$ | F | F | F | F | H | H | H | H | H | H |
| $R_{17}$ | H | H | H | H | H | H | H | H | H | H |
| $R_{18}$ | H | H | H | H | H | H | H | H | H | H |
| $R_{19}$ | F | H | H | H | F | F | F | H | H | H |
| $R_{20}$ | H | F | H | H | H | F | H | H | F | H |
| $R_{21}$ | H | H | H | H | F | H | F | H | F | H |
| $R_{22}$ | H | H | H | F | H | H | F | H | F | F |

Formula 2 may be represented by any one among Compound (F)-1 to Compound (F)-302. Compounds (F)-1 to (F)-302 correspond to examples of compounds in which two or three selected from $R_1$ to $R_7$, $R_{10}$ to $R_{16}$, and $R_{19}$ to $R_{22}$ are each independently a cyano group or a fluoro group. For example, one of two selected from $R_1$ to $R_7$, $R_{10}$ to $R_{16}$, and $R_{19}$ to $R_{22}$ may be a cyano group, the other may be a fluoro group, and the remaining substituents may be hydrogen atoms. In some embodiments, one of three selected from $R_1$ to $R_7$, $R_{10}$ to $R_{16}$, and $R_{19}$ to $R_{22}$ may be a cyano group, the other two may be fluoro groups, and the remaining substituents may be hydrogen atoms. In some embodiments, any one of three selected from $R_1$ to $R_7$, $R_{10}$ to $R_{16}$, and $R_{19}$ to $R_{22}$ may be a fluoro group, the other two may be cyano groups, and the remaining substituents may be hydrogen atoms. The compounds represented by the case in which $R_5$ is substituted with one cyano group or one fluoro group is the same as the case in which $R_9$ is substituted with one cyano group or one fluoro group. Because $R_6$ and $R_8$, $R_{15}$ and $R_{17}$, $R_{14}$ and $R_{18}$ may be the same as described above, they are not separately described as separate compounds.

| Compound Number | (F)-1 | (F)-2 | (F)-3 | (F)-4 |
|---|---|---|---|---|
| $R_1$ | CN | CN | CN | CN |
| $R_2$ | F | H | H | H |
| $R_3$ | H | F | H | H |
| $R_4$ | H | H | F | H |
| $R_5$ | H | H | H | F |
| $R_6$ | H | H | H | H |
| $R_7$ | H | H | H | H |
| $R_8$ | H | H | H | H |
| $R_9$ | H | H | H | H |
| $R_{10}$ | H | H | H | H |
| $R_{11}$ | H | H | H | H |
| $R_{12}$ | H | H | H | H |
| $R_{13}$ | H | H | H | H |
| $R_{14}$ | H | H | H | H |
| $R_{15}$ | H | H | H | H |
| $R_{16}$ | H | H | H | H |
| $R_{17}$ | H | H | H | H |
| $R_{18}$ | H | H | H | H |
| $R_{19}$ | H | H | H | H |
| $R_{20}$ | H | H | H | H |
| $R_{21}$ | H | H | H | H |
| $R_{22}$ | H | H | H | H |

| Compound Number | (F)-5 | (F)-6 | (F)-7 | (F)-8 | (F)-9 | (F)-10 | (F)-11 | (F)-12 | (F)-13 | (F)-14 | (F)-15 |
|---|---|---|---|---|---|---|---|---|---|---|---|
| $R_1$ | CN | CN | CN | CN | CN | CN | CN | CN | CN | CN | CN |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | F | H | H | H | H | H | H | H | H | H | H |
| $R_7$ | H | F | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | F | H | H | H | H | H | H | H | H |
| $R_{11}$ | H | H | H | F | H | H | H | H | H | H | H |
| $R_{12}$ | H | H | H | H | F | H | H | H | H | H | H |
| $R_{13}$ | H | H | H | H | H | F | H | H | H | H | H |
| $R_{14}$ | H | H | H | H | H | H | F | H | H | H | H |
| $R_{15}$ | H | H | H | H | H | H | H | F | H | H | H |
| $R_{16}$ | H | H | H | H | H | H | H | H | F | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | H | H | H | H |
| $R_{20}$ | H | H | H | H | H | H | H | H | H | F | H |
| $R_{21}$ | H | H | H | H | H | H | H | H | H | H | F |
| $R_{22}$ | H | H | H | H | H | H | H | H | H | H | H |

| Compound Number | (F)-16 | (F)-17 | (F)-18 | (F)-19 | (F)-20 | (F)-21 | (F)-22 | (F)-23 | (F)-24 | (F)-25 | (F)-26 |
|---|---|---|---|---|---|---|---|---|---|---|---|
| $R_1$ | CN | CN | H | H | H | H | H | H | H | H | H |
| $R_2$ | H | H | CN | CN | CN | CN | CN | CN | CN | CN | CN |
| $R_3$ | H | H | H | F | H | H | H | H | H | H | H |
| $R_4$ | H | H | H | H | F | H | H | H | H | H | H |
| $R_5$ | H | H | H | H | H | F | H | H | H | H | H |
| $R_6$ | H | H | H | H | H | H | F | H | H | H | H |
| $R_7$ | H | H | H | H | H | H | H | F | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | F | H | H |
| $R_{12}$ | H | H | H | H | H | H | H | H | H | F | H |

-continued

| | | | | | | | | | | | |
|---|---|---|---|---|---|---|---|---|---|---|---|
| F | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | F | $R_{21}$ |
| H | H | H | H | H | H | H | H | H | H | H | $R_{22}$ |

| (F)-37 | (F)-36 | (F)-35 | (F)-34 | (F)-33 | (F)-32 | (F)-31 | (F)-30 | (F)-29 | (F)-28 | (F)-27 | Compound Number |
|---|---|---|---|---|---|---|---|---|---|---|---|
| H | H | H | H | H | H | H | H | H | H | H | $R_1$ |
| H | H | H | H | CN | CN | CN | CN | CN | CN | CN | $R_2$ |
| CN | CN | CN | CN | H | H | H | H | H | H | H | $R_3$ |
| H | H | H | F | H | H | H | H | H | H | H | $R_4$ |
| H | H | F | H | H | H | H | H | H | H | H | $R_5$ |
| H | F | H | H | H | H | H | H | H | H | H | $R_6$ |
| F | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | F | $R_{14}$ |
| H | H | H | H | H | H | H | H | H | F | H | $R_{15}$ |
| H | H | H | H | H | H | H | H | F | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | F | H | H | H | $R_{19}$ |
| H | H | H | H | H | H | F | H | H | H | H | $R_{20}$ |
| H | H | H | H | H | F | H | H | H | H | H | $R_{21}$ |
| H | H | H | H | F | H | H | H | H | H | H | $R_{22}$ |

| (F)-48 | (F)-47 | (F)-46 | (F)-45 | (F)-44 | (F)-43 | (F)-42 | (F)-41 | (F)-40 | (F)-39 | (F)-38 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | CN | CN | CN | CN | CN | CN | CN | CN | CN | CN | $R_3$ |
| CN | H | H | H | H | H | H | H | H | H | H | $R_4$ |
| F | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | F | $R_{10}$ |
| H | H | H | H | H | H | H | H | H | F | H | $R_{11}$ |
| H | H | H | H | H | H | H | H | F | H | H | $R_{12}$ |
| H | H | H | H | H | H | H | F | H | H | H | $R_{13}$ |
| H | H | H | H | H | H | F | H | H | H | H | $R_{14}$ |
| H | H | H | H | H | F | H | H | H | H | H | $R_{15}$ |
| H | H | H | H | F | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | F | H | H | H | H | H | H | H | $R_{19}$ |
| H | H | F | H | H | H | H | H | H | H | H | $R_{20}$ |
| H | F | H | H | H | H | H | H | H | H | H | $R_{21}$ |
| H | H | H | H | H | H | H | H | H | H | H | $R_{22}$ |

| (F)-59 | (F)-58 | (F)-57 | (F)-56 | (F)-55 | (F)-54 | (F)-53 | (F)-52 | (F)-51 | (F)-50 | (F)-49 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| CN | CN | CN | CN | CN | CN | CN | CN | CN | CN | CN | $R_4$ |
| H | H | H | H | H | H | H | H | H | H | H | $R_5$ |
| H | H | H | H | H | H | H | H | H | H | F | $R_6$ |
| H | H | H | H | H | H | H | H | H | F | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | F | H | H | $R_{10}$ |
| H | H | H | H | H | H | H | F | H | H | H | $R_{11}$ |
| H | H | H | H | H | H | F | H | H | H | H | $R_{12}$ |
| H | H | H | H | H | F | H | H | H | H | H | $R_{13}$ |

-continued

| | | | | | | | | | | | |
|---|---|---|---|---|---|---|---|---|---|---|---|
| H | H | H | H | F | H | H | H | H | H | H | $R_{14}$ |
| H | H | H | F | H | H | H | H | H | H | H | $R_{15}$ |
| H | H | F | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | F | H | H | H | H | H | H | H | H | H | $R_{19}$ |
| F | H | H | H | H | H | H | H | H | H | H | $R_{20}$ |
| H | H | H | H | H | H | H | H | H | H | H | $R_{21}$ |
| H | H | H | H | H | H | H | H | H | H | H | $R_{22}$ |

| (F)-70 | (F)-69 | (F)-68 | (F)-67 | (F)-66 | (F)-65 | (F)-64 | (F)-63 | (F)-62 | (F)-61 | (F)-60 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | CN | CN | $R_4$ |
| CN | CN | CN | CN | CN | CN | CN | CN | CN | H | H | $R_5$ |
| H | H | H | H | H | H | H | H | F | H | H | $R_6$ |
| H | H | H | H | H | H | H | F | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | F | H | H | H | H | $R_{10}$ |
| H | H | H | H | H | F | H | H | H | H | H | $R_{11}$ |
| H | H | H | H | F | H | H | H | H | H | H | $R_{12}$ |
| H | H | H | F | H | H | H | H | H | H | H | $R_{13}$ |
| H | H | F | H | H | H | H | H | H | H | H | $R_{14}$ |
| H | F | H | H | H | H | H | H | H | H | H | $R_{15}$ |
| F | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | F | $R_{21}$ |
| H | H | H | H | H | H | H | H | H | F | H | $R_{22}$ |

| (F)-81 | (F)-80 | (F)-79 | (F)-78 | (F)-77 | (F)-76 | (F)-75 | (F)-74 | (F)-73 | (F)-72 | (F)-71 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | CN | CN | CN | CN | $R_5$ |
| CN | CN | CN | CN | CN | CN | CN | H | H | H | H | $R_6$ |
| H | H | H | H | H | H | F | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | F | H | H | H | H | H | $R_{10}$ |
| H | H | H | H | F | H | H | H | H | H | H | $R_{11}$ |
| H | H | H | F | H | H | H | H | H | H | H | $R_{12}$ |
| H | H | F | H | H | H | H | H | H | H | H | $R_{13}$ |
| H | F | H | H | H | H | H | H | H | H | H | $R_{14}$ |
| F | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | F | $R_{18}$ |
| H | H | H | H | H | H | H | H | H | F | H | $R_{19}$ |
| H | H | H | H | H | H | H | H | F | H | H | $R_{20}$ |
| H | H | H | H | H | H | F | H | H | H | H | $R_{21}$ |
| H | H | H | H | H | H | H | H | H | H | H | $R_{22}$ |

| (F)-92 | (F)-91 | (F)-90 | (F)-89 | (F)-88 | (F)-87 | (F)-86 | (F)-85 | (F)-84 | (F)-83 | (F)-82 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | CN | CN | CN | CN | $R_6$ |
| CN | CN | CN | CN | CN | CN | CN | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | F | H | H | H | H | $R_{10}$ |
| H | H | H | H | H | F | H | H | H | H | H | $R_{11}$ |
| H | H | H | H | F | H | H | H | H | H | H | $R_{12}$ |
| H | H | H | F | H | H | H | H | H | H | H | $R_{13}$ |
| H | H | F | H | H | H | H | H | H | H | H | $R_{14}$ |

-continued

| (F)-103 | (F)-102 | (F)-101 | (F)-100 | (F)-99 | (F)-98 | (F)-97 | (F)-96 | (F)-95 | (F)-94 | (F)-93 | Compound Number |
|---|---|---|---|---|---|---|---|---|---|---|---|
| H | F | H | H | H | H | H | H | H | H | H | $R_{15}$ |
| F | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | F | $R_{19}$ |
| H | H | H | H | H | H | H | H | H | F | H | $R_{20}$ |
| H | H | H | H | H | H | H | H | F | H | H | $R_{21}$ |
| H | H | H | H | H | H | H | F | H | H | H | $R_{22}$ |

| (F)-103 | (F)-102 | (F)-101 | (F)-100 | (F)-99 | (F)-98 | (F)-97 | (F)-96 | (F)-95 | (F)-94 | (F)-93 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | CN | CN | CN | CN | $R_7$ |
| H | H | H | H | H | H | H | H | H | H | H | $R_8$ |
| H | H | H | H | H | H | H | H | H | H | H | $R_9$ |
| CN | CN | CN | CN | CN | CN | CN | H | H | H | H | $R_{10}$ |
| H | H | H | H | H | H | F | H | H | H | H | $R_{11}$ |
| H | H | H | H | H | F | H | H | H | H | H | $R_{12}$ |
| H | H | H | H | F | H | H | H | H | H | H | $R_{13}$ |
| H | H | H | F | H | H | H | H | H | H | H | $R_{14}$ |
| H | H | F | H | H | H | H | H | H | H | H | $R_{15}$ |
| H | F | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| F | H | H | H | H | H | H | H | H | H | F | $R_{19}$ |
| H | H | H | H | H | H | H | H | H | F | H | $R_{20}$ |
| H | H | H | H | H | H | H | H | F | H | H | $R_{21}$ |
| H | H | H | H | H | H | F | H | H | H | H | $R_{22}$ |

| (F)-114 | (F)-113 | (F)-112 | (F)-111 | (F)-110 | (F)-109 | (F)-108 | (F)-107 | (F)-106 | (F)-105 | (F)-104 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | CN | CN | CN | $R_{10}$ |
| CN | CN | CN | CN | CN | CN | CN | CN | H | H | H | $R_{11}$ |
| H | H | H | H | H | H | H | F | H | H | H | $R_{12}$ |
| H | H | H | H | H | H | F | H | H | H | H | $R_{13}$ |
| H | H | H | H | H | F | H | H | H | H | H | $R_{14}$ |
| H | H | H | H | F | H | H | H | H | H | H | $R_{15}$ |
| H | H | H | F | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | F | H | H | H | H | H | H | H | H | $R_{19}$ |
| H | F | H | H | H | H | H | H | H | H | F | $R_{20}$ |
| F | H | H | H | H | H | H | H | H | F | H | $R_{21}$ |
| H | H | H | H | H | H | H | H | F | H | H | $R_{22}$ |

| (F)-125 | (F)-124 | (F)-123 | (F)-122 | (F)-121 | (F)-120 | (F)-119 | (F)-118 | (F)-117 | (F)-116 | (F)-115 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | CN | $R_{11}$ |
| H | H | CN | CN | CN | CN | CN | CN | CN | CN | H | $R_{12}$ |
| CN | CN | H | H | H | H | H | H | H | F | H | $R_{13}$ |
| H | F | H | H | H | H | H | H | F | H | H | $R_{14}$ |
| F | H | H | H | H | H | H | F | H | H | H | $R_{15}$ |

| | | | | | | | | | | | |
|---|---|---|---|---|---|---|---|---|---|---|---|
| H | H | H | H | H | H | F | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | F | H | H | H | H | H | $R_{19}$ |
| H | H | H | H | F | H | H | H | H | H | H | $R_{20}$ |
| H | H | H | F | H | H | H | H | H | H | H | $R_{21}$ |
| H | H | F | H | H | H | H | H | H | H | F | $R_{22}$ |

| (F)-136 | (F)-135 | (F)-134 | (F)-133 | (F)-132 | (F)-131 | (F)-130 | (F)-129 | (F)-128 | (F)-127 | (F)-126 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | CN | CN | CN | CN | CN | $R_{13}$ |
| CN | CN | CN | CN | CN | CN | H | H | H | H | H | $R_{14}$ |
| H | H | H | H | H | F | H | H | H | H | H | $R_{15}$ |
| H | H | H | H | H | H | H | H | H | H | F | $R_{16}$ |
| H | H | H | H | H | H | H | H | H | H | H | $R_{17}$ |
| H | H | H | H | H | H | H | H | H | H | H | $R_{18}$ |
| H | H | H | F | H | H | H | H | F | H | H | $R_{19}$ |
| H | H | F | H | H | H | H | F | H | H | H | $R_{20}$ |
| H | F | H | H | H | H | F | H | H | H | H | $R_{21}$ |
| F | H | H | H | H | F | H | H | H | H | H | $R_{22}$ |

| (F)-147 | (F)-146 | (F)-145 | (F)-144 | (F)-143 | (F)-142 | (F)-141 | (F)-140 | (F)-139 | (F)-138 | (F)-137 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | CN | CN | CN | CN | $R_{15}$ |
| H | H | CN | CN | CN | CN | H | H | H | H | F | $R_{16}$ |
| H | H | H | H | H | H | H | H | H | H | H | $R_{17}$ |
| H | H | H | H | H | H | H | H | H | H | H | $R_{18}$ |
| CN | CN | H | H | H | F | H | H | H | F | H | $R_{19}$ |
| H | F | H | H | F | H | H | H | F | H | H | $R_{20}$ |
| F | H | H | F | H | H | H | F | H | H | H | $R_{21}$ |
| H | H | F | H | H | H | F | H | H | H | H | $R_{22}$ |

| (F)-158 | (F)-157 | (F)-156 | (F)-155 | (F)-154 | (F)-153 | (F)-152 | (F)-151 | (F)-150 | (F)-149 | (F)-148 | Compound Number |
|---|---|---|---|---|---|---|---|---|---|---|---|
| F | F | F | F | F | F | F | H | H | H | H | $R_1$ |
| H | H | H | H | H | H | CN | H | H | H | H | $R_2$ |
| H | H | H | H | H | CN | H | H | H | H | H | $R_3$ |
| H | H | H | H | CN | H | H | H | H | H | H | $R_4$ |
| H | H | H | CN | H | H | H | H | H | H | H | $R_5$ |
| H | H | CN | H | H | H | H | H | H | H | H | $R_6$ |
| H | CN | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| CN | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |

-continued

| | | | | | | | | | | | |
|---|---|---|---|---|---|---|---|---|---|---|---|
| H | H | H | H | H | H | H | H | H | H | H | $R_{17}$ |
| H | H | H | H | H | H | H | H | H | H | H | $R_{18}$ |
| H | H | H | H | H | H | H | H | H | H | CN | $R_{19}$ |
| H | H | H | H | H | H | H | H | CN | CN | H | $R_{20}$ |
| H | H | H | H | H | H | H | CN | H | F | H | $R_{21}$ |
| H | H | H | H | H | H | F | F | H | F | H | $R_{22}$ |

| (F)-169 | (F)-168 | (F)-167 | (F)-166 | (F)-165 | (F)-164 | (F)-163 | (F)-162 | (F)-161 | (F)-160 | (F)-159 | Compound Number |
|---|---|---|---|---|---|---|---|---|---|---|---|
| H | F | F | F | F | F | F | F | F | F | F | $R_1$ |
| F | H | H | H | H | H | H | H | H | H | H | $R_2$ |
| CN | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | CN | $R_{11}$ |
| H | H | H | H | H | H | H | H | H | CN | H | $R_{12}$ |
| H | H | H | H | H | H | H | H | CN | H | H | $R_{13}$ |
| H | H | H | H | H | H | H | CN | H | H | H | $R_{14}$ |
| H | H | H | H | H | H | CN | H | H | H | H | $R_{15}$ |
| H | H | H | H | H | CN | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | CN | H | H | H | H | H | H | $R_{19}$ |
| H | H | H | CN | H | H | H | H | H | H | H | $R_{20}$ |
| H | H | CN | H | H | H | H | H | H | H | H | $R_{21}$ |
| H | CN | H | H | H | H | H | H | H | H | H | $R_{22}$ |

| (F)-180 | (F)-179 | (F)-179 | (F)-177 | (F)-176 | (F)-175 | (F)-174 | (F)-173 | (F)-172 | (F)-171 | (F)-170 | Compound Number |
|---|---|---|---|---|---|---|---|---|---|---|---|
| H | H | H | H | H | H | H | H | H | H | H | $R_1$ |
| F | F | F | F | F | F | F | F | F | F | F | $R_2$ |
| H | H | H | H | H | H | H | H | H | H | H | $R_3$ |
| H | H | H | H | H | H | H | H | H | H | CN | $R_4$ |
| H | H | H | H | H | H | H | H | H | CN | H | $R_5$ |
| H | H | H | H | H | H | H | H | CN | H | H | $R_6$ |
| H | H | H | H | H | H | H | CN | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | CN | H | H | H | H | $R_{10}$ |
| H | H | H | H | H | CN | H | H | H | H | H | $R_{11}$ |
| H | H | H | H | CN | H | H | H | H | H | H | $R_{12}$ |
| H | H | H | CN | H | H | H | H | H | H | H | $R_{13}$ |
| H | H | CN | H | H | H | H | H | H | H | H | $R_{14}$ |
| H | CN | H | H | H | H | H | H | H | H | H | $R_{15}$ |
| CN | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | H | $R_{22}$ |

| (F)-191 | (F)-190 | (F)-189 | (F)-188 | (F)-189 | (F)-186 | (F)-185 | (F)-184 | (F)-183 | (F)-182 | (F)-181 | Compound Number |
|---|---|---|---|---|---|---|---|---|---|---|---|
| H | H | H | H | H | H | H | F | F | H | F | $R_1$ |
| H | H | H | H | H | H | H | H | H | F | H | $R_2$ |
| F | F | F | F | F | F | F | H | H | H | H | $R_3$ |
| H | H | H | H | H | H | CN | H | H | H | H | $R_4$ |
| H | H | H | H | H | CN | H | H | H | H | H | $R_5$ |
| H | H | H | H | CN | H | H | H | H | H | H | $R_6$ |
| H | H | H | CN | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | CN | H | H | H | H | H | H | H | H | $R_{10}$ |
| H | CN | H | H | H | H | H | H | H | H | H | $R_{11}$ |
| CN | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |

-continued

|   |   |   |   |   |   |   |   |   |   |   |     |
|---|---|---|---|---|---|---|---|---|---|---|-----|
| H | H | H | H | H | H | H | H | H | H | H | R$_{18}$ |
| H | H | H | H | H | H | H | H | H | H | CN | R$_{19}$ |
| H | H | H | H | H | H | H | H | H | CN | H | R$_{20}$ |
| H | H | H | H | H | H | H | H | CN | H | H | R$_{21}$ |
| H | H | H | H | H | H | H | CN | H | H | H | R$_{22}$ |

| (F)-202 | (F)-201 | (F)-200 | (F)-199 | (F)-198 | (F)-197 | (F)-196 | (F)-195 | (F)-194 | (F)-193 | (F)-192 | Compound Number |
|---|---|---|---|---|---|---|---|---|---|---|---|
| H | H | H | H | H | H | H | H | H | H | H | R$_{1}$ |
| H | H | H | H | H | H | H | H | H | H | H | R$_{2}$ |
| H | H | H | H | F | F | F | F | F | F | F | R$_{3}$ |
| F | F | F | F | H | H | H | H | H | H | H | R$_{4}$ |
| H | H | H | CN | H | H | H | H | H | H | H | R$_{5}$ |
| H | H | CN | H | H | H | H | H | H | H | H | R$_{6}$ |
| H | CN | H | H | H | H | H | H | H | H | H | R$_{7}$ |
| H | H | H | H | H | H | H | H | H | H | H | R$_{8}$ |
| H | H | H | H | H | H | H | H | H | H | H | R$_{9}$ |
| CN | H | H | H | H | H | H | H | H | H | H | R$_{10}$ |
| H | H | H | H | H | H | H | H | H | H | H | R$_{11}$ |
| H | H | H | H | H | H | H | H | H | H | H | R$_{12}$ |
| H | H | H | H | H | H | H | H | H | H | CN | R$_{13}$ |
| H | H | H | H | H | H | H | H | H | CN | H | R$_{14}$ |
| H | H | H | H | H | H | H | H | CN | H | H | R$_{15}$ |
| H | H | H | H | H | H | H | CN | H | H | H | R$_{16}$ |
| H | H | H | H | H | H | H | H | H | H | H | R$_{17}$ |
| H | H | H | H | H | H | H | H | H | H | H | R$_{18}$ |
| H | H | H | H | H | H | H | CN | H | H | H | R$_{19}$ |
| H | H | H | H | H | H | CN | H | H | H | H | R$_{20}$ |
| H | H | H | H | H | CN | H | H | H | H | H | R$_{21}$ |
| H | H | H | H | CN | H | H | H | H | H | H | R$_{22}$ |

| (F)-213 | (F)-212 | (F)-211 | (F)-210 | (F)-209 | (F)-208 | (F)-207 | (F)-206 | (F)-205 | (F)-204 | (F)-203 | Compound Number |
|---|---|---|---|---|---|---|---|---|---|---|---|
| H | H | H | H | H | H | H | H | H | H | H | R$_{1}$ |
| H | H | H | H | H | H | H | H | H | H | H | R$_{2}$ |
| H | H | H | H | H | H | H | H | H | H | H | R$_{3}$ |
| H | F | F | F | F | F | F | F | F | F | F | R$_{4}$ |
| F | H | H | H | H | H | H | H | H | H | H | R$_{5}$ |
| CN | H | H | H | H | H | H | H | H | H | H | R$_{6}$ |
| H | H | H | H | H | H | H | H | H | H | H | R$_{7}$ |
| H | H | H | H | H | H | H | H | H | H | H | R$_{8}$ |
| H | H | H | H | H | H | H | H | H | H | H | R$_{9}$ |
| H | H | H | H | H | H | H | H | H | H | H | R$_{10}$ |
| H | H | H | H | H | H | H | H | H | H | CN | R$_{11}$ |
| H | H | H | H | H | H | H | H | H | CN | H | R$_{12}$ |
| H | H | H | H | H | H | H | H | CN | H | H | R$_{13}$ |
| H | H | H | H | H | H | H | CN | H | H | H | R$_{14}$ |
| H | H | H | H | H | H | CN | H | H | H | H | R$_{15}$ |
| H | H | H | H | H | CN | H | H | H | H | H | R$_{16}$ |
| H | H | H | H | H | H | H | H | H | H | H | R$_{17}$ |
| H | H | H | H | H | H | H | H | H | H | H | R$_{18}$ |
| H | H | H | H | CN | H | H | H | H | H | H | R$_{19}$ |
| H | H | H | CN | H | H | H | H | H | H | H | R$_{20}$ |
| H | H | CN | H | H | H | H | H | H | H | H | R$_{21}$ |
| H | CN | H | H | H | H | H | H | H | H | H | R$_{22}$ |

| (F)-224 | (F)-223 | (F)-222 | (F)-221 | (F)-220 | (F)-219 | (F)-218 | (F)-217 | (F)-216 | (F)-215 | (F)-214 | Compound Number |
|---|---|---|---|---|---|---|---|---|---|---|---|
| H | H | H | H | H | H | H | H | H | H | H | R$_{1}$ |
| H | H | H | H | H | H | H | H | H | H | H | R$_{2}$ |
| H | H | H | H | H | H | H | H | H | H | H | R$_{3}$ |
| H | H | H | H | H | H | H | H | H | H | H | R$_{4}$ |
| F | F | F | F | F | F | F | F | F | F | F | R$_{5}$ |
| H | H | H | H | H | H | H | H | H | H | H | R$_{6}$ |
| H | H | H | H | H | H | H | H | H | H | CN | R$_{7}$ |
| H | H | H | H | H | H | H | H | H | H | H | R$_{8}$ |
| H | H | H | H | H | H | H | H | H | H | H | R$_{9}$ |
| H | H | H | H | H | H | H | H | H | CN | H | R$_{10}$ |
| H | H | H | H | H | H | H | H | CN | H | H | R$_{11}$ |
| H | H | H | H | H | H | H | CN | H | H | H | R$_{12}$ |
| H | H | H | H | H | H | CN | H | H | H | H | R$_{13}$ |
| H | H | H | H | H | CN | H | H | H | H | H | R$_{14}$ |
| H | H | H | H | CN | H | H | H | H | H | H | R$_{15}$ |
| H | H | H | CN | H | H | H | H | H | H | H | R$_{16}$ |
| H | H | H | H | H | H | H | H | H | H | H | R$_{17}$ |
| H | H | H | H | H | H | H | H | H | H | H | R$_{18}$ |

-continued

| (F)-235 | (F)-234 | (F)-233 | (F)-232 | (F)-231 | (F)-230 | (F)-229 | (F)-228 | (F)-227 | (F)-226 | (F)-225 | Compound Number |
|---|---|---|---|---|---|---|---|---|---|---|---|
| H | H | CN | H | H | H | H | H | H | H | H | $R_{19}$ |
| H | CN | H | H | H | H | H | H | H | H | H | $R_{20}$ |
| CN | H | H | H | H | H | H | H | H | H | H | $R_{21}$ |
| H | H | H | H | H | H | H | H | H | H | H | $R_{22}$ |

| (F)-235 | (F)-234 | (F)-233 | (F)-232 | (F)-231 | (F)-230 | (F)-229 | (F)-228 | (F)-227 | (F)-226 | (F)-225 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | F | $R_5$ |
| F | F | F | F | F | F | F | F | F | F | H | $R_6$ |
| H | H | H | H | H | H | H | H | H | CN | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | CN | H | $R_{10}$ |
| H | H | H | H | H | H | H | H | CN | H | H | $R_{11}$ |
| H | H | H | H | H | H | H | CN | H | H | H | $R_{12}$ |
| H | H | H | H | H | H | CN | H | H | H | H | $R_{13}$ |
| H | H | H | H | H | CN | H | H | H | H | H | $R_{14}$ |
| H | H | H | H | CN | H | H | H | H | H | H | $R_{15}$ |
| H | H | H | CN | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | CN | H | H | H | H | H | H | H | H | $R_{19}$ |
| H | CN | H | H | H | H | H | H | H | H | H | $R_{20}$ |
| CN | H | H | H | H | H | H | H | H | H | H | $R_{21}$ |
| H | H | H | H | H | H | H | H | H | H | CN | $R_{22}$ |

| (F)-246 | (F)-245 | (F)-244 | (F)-243 | (F)-242 | (F)-241 | (F)-240 | (F)-239 | (F)-238 | (F)-237 | (F)-236 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | F | $R_6$ |
| F | F | F | F | F | F | F | F | F | F | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | CN | H | $R_{10}$ |
| H | H | H | H | H | H | H | H | CN | H | H | $R_{11}$ |
| H | H | H | H | H | H | H | CN | H | H | H | $R_{12}$ |
| H | H | H | H | H | H | CN | H | H | H | H | $R_{13}$ |
| H | H | H | H | H | CN | H | H | H | H | H | $R_{14}$ |
| H | H | H | H | CN | H | H | H | H | H | H | $R_{15}$ |
| H | H | H | CN | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | CN | H | H | H | H | H | H | H | H | $R_{19}$ |
| H | CN | H | H | H | H | H | H | H | H | H | $R_{20}$ |
| CN | H | H | H | H | H | H | H | H | H | H | $R_{21}$ |
| H | H | H | H | H | H | H | H | H | H | CN | $R_{22}$ |

| (F)-257 | (F)-256 | (F)-255 | (F)-254 | (F)-253 | (F)-252 | (F)-251 | (F)-250 | (F)-249 | (F)-248 | (F)-247 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | F | $R_7$ |
| H | H | H | H | H | H | H | H | H | H | H | $R_8$ |
| H | H | H | H | H | H | H | H | H | H | H | $R_9$ |
| F | F | F | F | F | F | F | F | F | F | H | $R_{10}$ |
| H | H | H | H | H | H | H | H | H | CN | H | $R_{11}$ |
| H | H | H | H | H | H | H | H | CN | H | H | $R_{12}$ |
| H | H | H | H | H | H | H | CN | H | H | H | $R_{13}$ |
| H | H | H | H | H | H | CN | H | H | H | H | $R_{14}$ |
| H | H | H | H | H | CN | H | H | H | H | H | $R_{15}$ |
| H | H | H | H | CN | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | CN | H | H | H | H | H | H | H | $R_{19}$ |

-continued

| | | | | | | | | | | | |
|---|---|---|---|---|---|---|---|---|---|---|---|
| H | H | CN | H | H | H | H | H | H | H | H | $R_{20}$ |
| H | CN | H | H | H | H | H | H | H | H | H | $R_{21}$ |
| CN | H | H | H | H | H | H | H | H | H | CN | $R_{22}$ |

| (F)-268 | (F)-267 | (F)-266 | (F)-265 | (F)-264 | (F)-263 | (F)-262 | (F)-261 | (F)-260 | (F)-259 | (F)-258 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | F | F | F | F | F | F | F | F | F | $R_{11}$ |
| F | F | H | H | H | H | H | H | H | H | CN | $R_{12}$ |
| H | CN | H | H | H | H | H | H | H | CN | H | $R_{13}$ |
| CN | H | H | H | H | H | H | H | CN | H | H | $R_{14}$ |
| H | H | H | H | H | H | H | CN | H | H | H | $R_{15}$ |
| H | H | H | H | H | H | CN | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | CN | H | H | H | H | H | $R_{19}$ |
| H | H | H | H | CN | H | H | H | H | H | H | $R_{20}$ |
| H | H | H | CN | H | H | H | H | H | H | H | $R_{21}$ |
| H | H | CN | H | H | H | H | H | H | H | H | $R_{22}$ |

| (F)-279 | (F)-278 | (F)-277 | (F)-276 | (F)-275 | (F)-274 | (F)-273 | (F)-272 | (F)-271 | (F)-270 | (F)-269 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | F | F | F | F | F | F | $R_{12}$ |
| F | F | F | F | F | H | H | H | H | H | H | $R_{13}$ |
| H | H | H | H | CN | H | H | H | H | H | H | $R_{14}$ |
| H | H | H | CN | H | H | H | H | H | H | CN | $R_{15}$ |
| H | H | CN | H | H | H | H | H | H | CN | H | $R_{16}$ |
| H | H | H | H | H | H | H | H | H | H | H | $R_{17}$ |
| H | H | H | H | H | H | H | H | H | H | H | $R_{18}$ |
| H | CN | H | H | H | H | H | H | CN | H | H | $R_{19}$ |
| CN | H | H | H | H | H | H | CN | H | H | H | $R_{20}$ |
| H | H | H | H | H | H | CN | H | H | H | H | $R_{21}$ |
| H | H | H | H | H | CN | H | H | H | H | H | $R_{22}$ |

| (F)-290 | (F)-289 | (F)-288 | (F)-287 | (F)-286 | (F)-285 | (F)-284 | (F)-283 | (F)-282 | (F)-281 | (F)-280 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | F | F | $R_{12}$ |
| H | H | H | H | H | H | H | H | F | H | H | $R_{13}$ |
| F | F | F | H | H | H | H | H | CN | H | H | $R_{14}$ |
| H | H | CN | H | H | H | H | CN | H | H | H | $R_{15}$ |
| H | H | H | H | H | H | H | H | H | H | H | $R_{16}$ |
| H | H | H | H | H | H | H | H | H | H | H | $R_{17}$ |
| H | CN | H | H | H | H | CN | H | H | H | H | $R_{18}$ |
| CN | H | H | H | H | CN | H | H | H | H | H | $R_{19}$ |
| | | | | | | | | | | | $R_{20}$ |

-continued

| | | | | | | | | | | | |
|---|---|---|---|---|---|---|---|---|---|---|---|
| H | H | H | H | CN | H | H | H | H | H | CN | $R_{21}$ |
| H | H | H | CN | H | H | H | H | H | CN | H | $R_{22}$ |

| (F)-301 | (F)-300 | (F)-299 | (F)-298 | (F)-297 | (F)-296 | (F)-295 | (F)-294 | (F)-293 | (F)-292 | (F)-291 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | F | F | $R_{15}$ |
| H | H | H | H | H | F | F | F | F | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | CN | H | H | $R_{19}$ |
| F | F | H | H | CN | H | H | CN | H | H | H | $R_{20}$ |
| H | CN | H | CN | H | H | CN | H | H | H | CN | $R_{21}$ |
| CN | H | CN | H | H | CN | H | H | H | CN | H | $R_{22}$ |

| (F)-302 | Compound Number |
|---|---|
| H | $R_1$ |
| H | $R_2$ |
| H | $R_3$ |
| H | $R_4$ |
| H | $R_5$ |
| H | $R_6$ |
| H | $R_7$ |
| H | $R_8$ |
| H | $R_9$ |
| H | $R_{10}$ |
| H | $R_{11}$ |
| H | $R_{12}$ |
| H | $R_{13}$ |
| H | $R_{14}$ |
| H | $R_{15}$ |
| H | $R_{16}$ |
| H | $R_{17}$ |
| H | $R_{18}$ |
| H | $R_{19}$ |
| H | $R_{20}$ |
| F | $R_{21}$ |
| CN | $R_{22}$ |

Formula 2 may be represented by any one among Compound (G)-1 to Compound (G)-302. Compounds (G)-1 to (G)-302 correspond to examples of compounds in which two or three selected from $R_1$ to $R_7$, $R_{10}$ to $R_{16}$, and $R_{19}$ to $R_{22}$ are each independently a cyano group or a trifluoromethyl group. For example, one of two selected from $R_1$ to $R_7$, $R_{10}$ to $R_{16}$, and $R_{19}$ to $R_{22}$ may be a cyano group, the other may be a trifluoromethyl group, and the remaining substituents may be hydrogen atoms. In some embodiments, any one of three selected from $R_1$ to $R_7$, $R_{10}$ to $R_{16}$, and $R_{19}$ to $R_{22}$ may be a cyano group, the other two may be trifluoromethyl groups, and the remaining substituents may be hydrogen atoms. In some embodiments, any one of three selected from $R_1$ to $R_7$, $R_{10}$ to $R_{16}$, and $R_{19}$ to $R_{22}$ may be a trifluoromethyl group, the other two may be cyano groups, and the remaining substituents may be hydrogen atoms. The compounds represented by the case in which $R_5$ is substituted with one cyano group or one trifluoromethyl group is the same as the case in which $R_9$ is substituted with one cyano group or one trifluoromethyl group. Because $R_6$ and $R_8$, $R_{15}$ and $R_{17}$, $R_{14}$ and $R_{18}$ are also equivalent by symmetry as described above, they are not separately described as additional compounds.

| (G)-10 | (G)-9 | (G)-8 | (G)-7 | (G)-6 | (G)-5 | (G)-4 | (G)-3 | (G)-2 | (G)-1 | Compound Number |
|---|---|---|---|---|---|---|---|---|---|---|
| CN | CN | CN | CN | CN | CN | CN | CN | CN | CN | $R_1$ |
| H | H | H | H | H | H | H | H | H | $CF_3$ | $R_2$ |
| H | H | H | H | H | H | H | H | $CF_3$ | H | $R_3$ |
| H | H | H | H | H | H | H | $CF_3$ | H | H | $R_4$ |

-continued

| | | | | | | | | | | |
|---|---|---|---|---|---|---|---|---|---|---|
| H | H | H | H | H | H | CF$_3$ | H | H | H | R$_5$ |
| H | H | H | H | H | CF$_3$ | H | H | H | H | R$_6$ |
| H | H | H | H | CF$_3$ | H | H | H | H | H | R$_7$ |
| H | H | H | H | H | H | H | H | H | H | R$_8$ |
| H | H | H | H | H | H | H | H | H | H | R$_9$ |
| H | H | H | CF$_3$ | H | H | H | H | H | H | R$_{10}$ |
| H | H | CF$_3$ | H | H | H | H | H | H | H | R$_{11}$ |
| H | CF$_3$ | H | H | H | H | H | H | H | H | R$_{12}$ |
| CF$_3$ | H | H | H | H | H | H | H | H | H | R$_{13}$ |
| H | H | H | H | H | H | H | H | H | H | R$_{14}$ |
| H | H | H | H | H | H | H | H | H | H | R$_{15}$ |
| H | H | H | H | H | H | H | H | H | H | R$_{16}$ |
| H | H | H | H | H | H | H | H | H | H | R$_{17}$ |
| H | H | H | H | H | H | H | H | H | H | R$_{18}$ |
| H | H | H | H | H | H | H | H | H | H | R$_{19}$ |
| H | H | H | H | H | H | H | H | H | H | R$_{20}$ |
| H | H | H | H | H | H | H | H | H | H | R$_{21}$ |
| H | H | H | H | H | H | H | H | H | H | R$_{22}$ |

| (G)-21 | (G)-20 | (G)-19 | (G)-18 | (G)-17 | (G)-16 | (G)-15 | (G)-14 | (G)-13 | (G)-12 | (G)-11 | Compound Number |
|---|---|---|---|---|---|---|---|---|---|---|---|
| H | H | H | H | CN | CN | CN | CN | CN | CN | CN | R$_1$ |
| CN | CN | CN | CN | H | H | H | H | H | H | H | R$_2$ |
| H | H | H | CF$_3$ | H | H | H | H | H | H | H | R$_3$ |
| H | H | CF$_3$ | H | H | H | H | H | H | H | H | R$_4$ |
| H | CF$_3$ | H | H | H | H | H | H | H | H | H | R$_5$ |
| CF$_3$ | H | H | H | H | H | H | H | H | H | H | R$_6$ |
| H | H | H | H | H | H | H | H | H | H | H | R$_7$ |
| H | H | H | H | H | H | H | H | H | H | H | R$_8$ |
| H | H | H | H | H | H | H | H | H | H | H | R$_9$ |
| H | H | H | H | H | H | H | H | H | H | H | R$_{10}$ |
| H | H | H | H | H | H | H | H | H | H | H | R$_{11}$ |
| H | H | H | H | H | H | H | H | H | H | H | R$_{12}$ |
| H | H | H | H | H | H | H | H | H | H | H | R$_{13}$ |
| H | H | H | H | H | H | H | H | H | H | CF$_3$ | R$_{14}$ |
| H | H | H | H | H | H | H | H | H | CF$_3$ | H | R$_{15}$ |
| H | H | H | H | H | H | H | H | CF$_3$ | H | H | R$_{16}$ |
| H | H | H | H | H | H | H | H | H | H | H | R$_{17}$ |
| H | H | H | H | H | H | H | H | H | H | H | R$_{18}$ |
| H | H | H | H | H | H | H | CF$_3$ | H | H | H | R$_{19}$ |
| H | H | H | H | H | H | CF$_3$ | H | H | H | H | R$_{20}$ |
| H | H | H | H | H | CF$_3$ | H | H | H | H | H | R$_{21}$ |
| H | H | H | H | CF$_3$ | H | H | H | H | H | H | R$_{22}$ |

| (G)-32 | (G)-31 | (G)-30 | (G)-29 | (G)-28 | (G)-27 | (G)-26 | (G)-25 | (G)-24 | (G)-23 | (G)-22 | Compound Number |
|---|---|---|---|---|---|---|---|---|---|---|---|
| H | H | H | H | H | H | H | H | H | H | H | R$_1$ |
| CN | CN | CN | CN | CN | CN | CN | CN | CN | CN | CN | R$_2$ |
| H | H | H | H | H | H | H | H | H | H | H | R$_3$ |
| H | H | H | H | H | H | H | H | H | H | H | R$_4$ |
| H | H | H | H | H | H | H | H | H | H | H | R$_5$ |
| H | H | H | H | H | H | H | H | H | H | H | R$_6$ |
| H | H | H | H | H | H | H | H | H | H | CF$_3$ | R$_7$ |
| H | H | H | H | H | H | H | H | H | H | H | R$_8$ |
| H | H | H | H | H | H | H | H | H | H | H | R$_9$ |
| H | H | H | H | H | H | H | H | CF$_3$ | H | H | R$_{10}$ |
| H | H | H | H | H | H | H | CF$_3$ | H | H | H | R$_{11}$ |
| H | H | H | H | H | H | CF$_3$ | H | H | H | H | R$_{12}$ |
| H | H | H | H | H | CF$_3$ | H | H | H | H | H | R$_{13}$ |
| H | H | H | H | CF$_3$ | H | H | H | H | H | H | R$_{14}$ |
| H | H | H | CF$_3$ | H | H | H | H | H | H | H | R$_{15}$ |
| H | H | CF$_3$ | H | H | H | H | H | H | H | H | R$_{16}$ |
| H | H | H | H | H | H | H | H | H | H | H | R$_{17}$ |
| H | H | H | H | H | H | H | H | H | H | H | R$_{18}$ |
| H | H | CF$_3$ | H | H | H | H | H | H | H | H | R$_{19}$ |
| H | CF$_3$ | H | H | H | H | H | H | H | H | H | R$_{20}$ |
| CF$_3$ | H | H | H | H | H | H | H | H | H | H | R$_{21}$ |
| H | H | H | H | H | H | H | H | H | H | H | R$_{22}$ |

| (G)-43 | (G)-42 | (G)-41 | (G)-40 | (G)-39 | (G)-38 | (G)-37 | (G)-36 | (G)-35 | (G)-34 | (G)-33 | Compound Number |
|---|---|---|---|---|---|---|---|---|---|---|---|
| H | H | H | H | H | H | H | H | H | H | H | R$_1$ |
| H | H | H | H | H | H | H | H | H | H | CN | R$_2$ |
| CN | CN | CN | CN | CN | CN | CN | CN | CN | CN | H | R$_3$ |
| H | H | H | H | H | H | H | H | H | CF$_3$ | H | R$_4$ |
| H | H | H | H | H | H | H | H | CF$_3$ | H | H | R$_5$ |

-continued

| | (G)-44 | (G)-45 | (G)-46 | (G)-47 | (G)-48 | (G)-49 | (G)-50 | (G)-51 | (G)-52 | (G)-53 | (G)-54 | |
|---|---|---|---|---|---|---|---|---|---|---|---|---|
| | H | H | H | H | CF$_3$ | H | H | H | H | H | H | R$_6$ |
| | H | H | H | CF$_3$ | H | H | H | H | H | H | H | R$_7$ |
| | H | H | H | H | H | H | H | H | H | H | H | R$_8$ |
| | H | H | H | H | H | H | H | H | H | H | H | R$_9$ |
| | H | H | H | H | H | CF$_3$ | H | H | H | H | H | R$_{10}$ |
| | H | H | H | H | H | H | CF$_3$ | H | H | H | H | R$_{11}$ |
| | H | H | H | H | H | H | H | CF$_3$ | H | H | H | R$_{12}$ |
| | H | H | H | H | H | H | H | H | CF$_3$ | H | H | R$_{13}$ |
| | H | H | H | H | H | H | H | H | H | CF$_3$ | H | R$_{14}$ |
| | H | H | H | H | H | H | H | H | H | H | CF$_3$ | R$_{15}$ |
| | H | H | H | H | H | H | H | H | H | H | H | R$_{16}$ |
| | H | H | H | H | H | H | H | H | H | H | H | R$_{17}$ |
| | H | H | H | H | H | H | H | H | H | H | H | R$_{18}$ |
| | H | H | H | H | H | H | H | H | H | H | H | R$_{19}$ |
| | H | H | H | H | H | H | H | H | H | H | H | R$_{20}$ |
| | H | H | H | H | H | H | H | H | H | H | H | R$_{21}$ |
| | CF$_3$ | H | H | H | H | H | H | H | H | H | H | R$_{22}$ |

| Compound Number | (G)-44 | (G)-45 | (G)-46 | (G)-47 | (G)-48 | (G)-49 | (G)-50 | (G)-51 | (G)-52 | (G)-53 | (G)-54 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | CN | CN | CN | CN | H | H | H | H | H | H | H |
| R$_4$ | H | H | H | H | CN | CN | CN | CN | CN | CN | CN |
| R$_5$ | H | H | H | CF$_3$ | H | H | H | H | H | H | H |
| R$_6$ | H | H | H | H | CF$_3$ | H | H | H | H | H | H |
| R$_7$ | H | H | H | H | H | CF$_3$ | H | H | H | H | H |
| R$_8$ | H | H | H | H | H | H | H | H | H | H | H |
| R$_9$ | H | H | H | H | H | H | H | H | H | H | H |
| R$_{10}$ | H | H | H | H | H | H | H | CF$_3$ | H | H | H |
| R$_{11}$ | H | H | H | H | H | H | H | H | CF$_3$ | H | H |
| R$_{12}$ | H | H | H | H | H | H | H | H | H | CF$_3$ | H |
| R$_{13}$ | H | H | H | H | H | H | H | H | H | H | CF$_3$ |
| R$_{14}$ | H | H | H | H | H | H | H | H | H | H | H |
| R$_{15}$ | H | H | H | H | H | H | H | H | H | H | H |
| R$_{16}$ | CF$_3$ | H | H | H | H | H | H | H | H | H | H |
| R$_{17}$ | H | H | H | H | H | H | H | H | H | H | H |
| R$_{18}$ | H | H | H | H | H | H | H | H | H | H | H |
| R$_{19}$ | CF$_3$ | H | H | H | H | H | H | H | H | H | H |
| R$_{20}$ | H | CF$_3$ | H | H | H | H | H | H | H | H | H |
| R$_{21}$ | H | H | CF$_3$ | H | H | H | H | H | H | H | H |
| R$_{22}$ | H | H | H | CF$_3$ | H | H | H | H | H | H | H |

| Compound Number | (G)-55 | (G)-56 | (G)-57 | (G)-58 | (G)-59 | (G)-60 | (G)-61 | (G)-62 | (G)-63 | (G)-64 | (G)-65 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | H | H | H | H | H | H | H | H | H | H | H |
| R$_4$ | CN | CN | CN | CN | CN | CN | CN | H | H | H | H |
| R$_5$ | H | H | H | H | H | H | H | CN | CN | CN | CN |
| R$_6$ | H | H | H | H | H | H | H | CF$_3$ | H | H | H |
| R$_7$ | H | H | H | H | H | H | H | H | CF$_3$ | H | H |
| R$_8$ | H | H | H | H | H | H | H | H | H | H | H |
| R$_9$ | H | H | H | H | H | H | H | H | H | H | H |
| R$_{10}$ | H | H | H | H | H | H | H | H | H | CF$_3$ | H |
| R$_{11}$ | H | H | H | H | H | H | H | H | H | H | CF$_3$ |
| R$_{12}$ | H | H | H | H | H | H | H | H | H | H | H |
| R$_{13}$ | H | H | H | H | H | H | H | H | H | H | H |
| R$_{14}$ | CF$_3$ | H | H | H | H | H | H | H | H | H | H |
| R$_{15}$ | H | CF$_3$ | H | H | H | H | H | H | H | H | H |
| R$_{16}$ | H | H | CF$_3$ | H | H | H | H | H | H | H | H |
| R$_{17}$ | H | H | H | H | H | H | H | H | H | H | H |
| R$_{18}$ | H | H | H | H | H | H | H | H | H | H | H |
| R$_{19}$ | H | H | H | CF$_3$ | H | H | H | H | H | H | H |
| R$_{20}$ | H | H | H | H | CF$_3$ | H | H | H | H | H | H |
| R$_{21}$ | H | H | H | H | H | CF$_3$ | H | H | H | H | H |
| R$_{22}$ | H | H | H | H | H | H | CF$_3$ | H | H | H | H |

| Compound Number | (G)-66 | (G)-67 | (G)-68 | (G)-69 | (G)-70 | (G)-71 | (G)-72 | (G)-73 | (G)-74 | (G)-75 | (G)-76 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | H | H | H | H | H | H | H | H | H | H | H |
| R$_4$ | H | H | H | H | H | H | H | H | H | H | H |
| R$_5$ | CN | CN | CN | CN | CN | CN | CN | CN | CN | H | H |
| R$_6$ | H | H | H | H | H | H | H | H | H | CN | CN |

-continued

| | | | | | | | | | | | Compound Number |
|---|---|---|---|---|---|---|---|---|---|---|---|
| H | CF₃ | H | H | H | H | H | H | H | H | H | R₇ |
| H | H | H | H | H | H | H | H | H | H | H | R₈ |
| H | H | H | H | H | H | H | H | H | H | H | R₉ |
| H | CF₃ | H | H | H | H | H | H | H | H | H | R₁₀ |
| CF₃ | H | H | H | H | H | H | H | H | H | H | R₁₁ |
| H | H | H | H | H | H | H | H | H | H | CF₃ | R₁₂ |
| H | H | H | H | H | H | H | H | H | CF₃ | H | R₁₃ |
| H | H | H | H | H | H | H | H | CF₃ | H | H | R₁₄ |
| H | H | H | H | H | H | H | CF₃ | H | H | H | R₁₅ |
| H | H | H | H | H | H | CF₃ | H | H | H | H | R₁₆ |
| H | H | H | H | H | CF₃ | H | H | H | H | H | R₁₇ |
| H | H | H | H | H | H | H | H | H | H | H | R₁₈ |
| H | H | H | H | H | CF₃ | H | H | H | H | H | R₁₉ |
| H | H | H | H | CF₃ | H | H | H | H | H | H | R₂₀ |
| H | H | H | CF₃ | H | H | H | H | H | H | H | R₂₁ |
| H | H | CF₃ | H | H | H | H | H | H | H | H | R₂₂ |

| (G)-87 | (G)-86 | (G)-85 | (G)-84 | (G)-83 | (G)-82 | (G)-81 | (G)-80 | (G)-79 | (G)-78 | (G)-77 | Compound Number |
|---|---|---|---|---|---|---|---|---|---|---|---|
| H | H | H | H | H | H | H | H | H | H | H | R₁ |
| H | H | H | H | H | H | H | H | H | H | H | R₂ |
| H | H | H | H | H | H | H | H | H | H | H | R₃ |
| H | H | H | H | H | H | H | H | H | H | H | R₄ |
| H | H | H | H | H | H | H | H | H | H | H | R₅ |
| H | H | CN | CN | CN | CN | CN | CN | CN | CN | CN | R₆ |
| CN | CN | H | H | H | H | H | H | H | H | H | R₇ |
| H | H | H | H | H | H | H | H | H | H | H | R₈ |
| H | H | H | H | H | H | H | H | H | H | H | R₉ |
| H | CF₃ | H | H | H | H | H | H | H | H | H | R₁₀ |
| CF₃ | H | H | H | H | H | H | H | H | H | H | R₁₁ |
| H | H | H | H | H | H | H | H | H | H | CF₃ | R₁₂ |
| H | H | H | H | H | H | H | H | H | CF₃ | H | R₁₃ |
| H | H | H | H | H | H | H | H | CF₃ | H | H | R₁₄ |
| H | H | H | H | H | H | H | CF₃ | H | H | H | R₁₅ |
| H | H | H | H | H | H | CF₃ | H | H | H | H | R₁₆ |
| H | H | H | H | H | CF₃ | H | H | H | H | H | R₁₇ |
| H | H | H | H | H | H | H | H | H | H | H | R₁₈ |
| H | H | H | H | H | CF₃ | H | H | H | H | H | R₁₉ |
| H | H | H | H | CF₃ | H | H | H | H | H | H | R₂₀ |
| H | H | H | CF₃ | H | H | H | H | H | H | H | R₂₁ |
| H | H | CF₃ | H | H | H | H | H | H | H | H | R₂₂ |

| (G)-98 | (G)-97 | (G)-96 | (G)-95 | (G)-94 | (G)-93 | (G)-92 | (G)-91 | (G)-90 | (G)-89 | (G)-88 | Compound Number |
|---|---|---|---|---|---|---|---|---|---|---|---|
| H | H | H | H | H | H | H | H | H | H | H | R₁ |
| H | H | H | H | H | H | H | H | H | H | H | R₂ |
| H | H | H | H | H | H | H | H | H | H | H | R₃ |
| H | H | H | H | H | H | H | H | H | H | H | R₄ |
| H | H | H | H | H | H | H | H | H | H | H | R₅ |
| H | H | H | H | H | H | H | H | H | H | H | R₆ |
| H | H | CN | CN | CN | CN | CN | CN | CN | CN | CN | R₇ |
| H | H | H | H | H | H | H | H | H | H | H | R₈ |
| H | H | H | H | H | H | H | H | H | H | H | R₉ |
| CN | CN | H | H | H | H | H | H | H | H | H | R₁₀ |
| H | CF₃ | H | H | H | H | H | H | H | H | H | R₁₁ |
| CF₃ | H | H | H | H | H | H | H | H | H | CF₃ | R₁₂ |
| H | H | H | H | H | H | H | H | H | CF₃ | H | R₁₃ |
| H | H | H | H | H | H | H | H | CF₃ | H | H | R₁₄ |
| H | H | H | H | H | H | H | CF₃ | H | H | H | R₁₅ |
| H | H | H | H | H | H | CF₃ | H | H | H | H | R₁₆ |
| H | H | H | H | H | CF₃ | H | H | H | H | H | R₁₇ |
| H | H | H | H | H | H | H | H | H | H | H | R₁₈ |
| H | H | H | H | H | CF₃ | H | H | H | H | H | R₁₉ |
| H | H | H | H | CF₃ | H | H | H | H | H | H | R₂₀ |
| H | H | H | CF₃ | H | H | H | H | H | H | H | R₂₁ |
| H | H | CF₃ | H | H | H | H | H | H | H | H | R₂₂ |

| (G)-109 | (G)-108 | (G)-107 | (G)-106 | (G)-105 | (G)-104 | (G)-103 | (G)-102 | (G)-101 | (G)-100 | (G)-99 | Compound Number |
|---|---|---|---|---|---|---|---|---|---|---|---|
| H | H | H | H | H | H | H | H | H | H | H | R₁ |
| H | H | H | H | H | H | H | H | H | H | H | R₂ |
| H | H | H | H | H | H | H | H | H | H | H | R₃ |
| H | H | H | H | H | H | H | H | H | H | H | R₄ |
| H | H | H | H | H | H | H | H | H | H | H | R₅ |
| H | H | H | H | H | H | H | H | H | H | H | R₆ |
| H | H | H | H | H | H | H | H | H | H | H | R₇ |

-continued

| | | | | | | | | | | |
|---|---|---|---|---|---|---|---|---|---|---|
| H | H | H | H | H | H | H | H | H | H | $R_8$ |
| H | H | H | H | H | H | H | H | H | H | $R_9$ |
| H | H | H | CN | CN | CN | CN | CN | CN | CN | $R_{10}$ |
| CN | CN | CN | H | H | H | H | H | H | H | $R_{11}$ |
| H | H | $CF_3$ | H | H | H | H | H | H | H | $R_{12}$ |
| H | $CF_3$ | H | H | H | H | H | H | H | $CF_3$ | $R_{13}$ |
| $CF_3$ | H | H | H | H | H | H | H | $CF_3$ | H | $R_{14}$ |
| H | H | H | H | H | H | H | $CF_3$ | H | H | $R_{15}$ |
| H | H | H | H | H | H | $CF_3$ | H | H | H | $R_{16}$ |
| H | H | H | H | H | H | H | H | H | H | $R_{17}$ |
| H | H | H | H | H | H | H | H | H | H | $R_{18}$ |
| H | H | H | H | H | $CF_3$ | H | H | H | H | $R_{19}$ |
| H | H | H | H | $CF_3$ | H | H | H | H | H | $R_{20}$ |
| H | H | H | $CF_3$ | H | H | H | H | H | H | $R_{21}$ |
| H | H | H | $CF_3$ | H | H | H | H | H | H | $R_{22}$ |

| (G)-120 | (G)-119 | (G)-118 | (G)-117 | (G)-116 | (G)-115 | (G)-114 | (G)-113 | (G)-112 | (G)-111 | (G)-110 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | CN | CN | CN | CN | CN | CN | $R_{11}$ |
| CN | CN | CN | CN | CN | H | H | H | H | H | H | $R_{12}$ |
| H | H | H | H | $CF_3$ | H | H | H | H | H | H | $R_{13}$ |
| H | H | H | $CF_3$ | H | H | H | H | H | H | H | $R_{14}$ |
| H | H | $CF_3$ | H | H | H | H | H | H | H | $CF_3$ | $R_{15}$ |
| H | $CF_3$ | H | H | H | H | H | H | H | $CF_3$ | H | $R_{16}$ |
| $CF_3$ | H | H | H | H | H | H | H | H | H | H | $R_{17}$ |
| H | H | H | H | H | H | H | H | H | H | H | $R_{18}$ |
| $CF_3$ | H | H | H | H | H | H | H | $CF_3$ | H | H | $R_{19}$ |
| H | H | H | H | H | H | H | $CF_3$ | H | H | H | $R_{20}$ |
| H | H | H | H | H | H | $CF_3$ | H | H | H | H | $R_{21}$ |
| H | H | H | H | H | $CF_3$ | H | H | H | H | H | $R_{22}$ |

| (G)-131 | (G)-130 | (G)-129 | (G)-128 | (G)-127 | (G)-126 | (G)-125 | (G)-124 | (G)-123 | (G)-122 | (G)-121 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | CN | CN | CN | $R_{12}$ |
| H | CN | CN | CN | CN | CN | CN | CN | H | H | H | $R_{13}$ |
| CN | H | H | H | H | H | H | $CF_3$ | H | H | H | $R_{14}$ |
| $CF_3$ | H | H | H | H | H | $CF_3$ | H | H | H | H | $R_{15}$ |
| H | H | H | H | H | $CF_3$ | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | $CF_3$ | H | H | H | H | H | H | $R_{19}$ |
| H | H | H | $CF_3$ | H | H | H | H | H | H | $CF_3$ | $R_{20}$ |
| H | H | $CF_3$ | H | H | H | H | H | H | $CF_3$ | H | $R_{21}$ |
| H | $CF_3$ | H | H | H | H | H | $CF_3$ | H | H | H | $R_{22}$ |

| (G)-142 | (G)-141 | (G)-140 | (G)-139 | (G)-138 | (G)-137 | (G)-136 | (G)-135 | (G)-134 | (G)-133 | (G)-132 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |

-continued

| (G)-153 | (G)-152 | (G)-151 | (G)-150 | (G)-149 | (G)-148 | (G)-147 | (G)-146 | (G)-145 | (G)-144 | (G)-143 | Compound Number |
|---|---|---|---|---|---|---|---|---|---|---|---|
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | CN | CN | CN | CN | CN | $R_{14}$ |
| H | CN | CN | CN | CN | CN | H | H | H | H | H | $R_{15}$ |
| CN | H | H | H | H | CF$_3$ | H | H | H | H | CF$_3$ | $R_{16}$ |
| H | H | H | H | H | H | H | H | H | H | H | $R_{17}$ |
| H | H | H | H | H | H | H | H | H | H | H | $R_{18}$ |
| CF$_3$ | H | H | H | CF$_3$ | H | H | H | H | CF$_3$ | H | $R_{19}$ |
| H | H | H | CF$_3$ | H | H | H | H | CF$_3$ | H | H | $R_{20}$ |
| H | H | CF$_3$ | H | H | H | H | CF$_3$ | H | H | H | $R_{21}$ |
| H | CF$_3$ | H | H | H | H | CF$_3$ | H | H | H | H | $R_{22}$ |

| (G)-153 | (G)-152 | (G)-151 | (G)-150 | (G)-149 | (G)-148 | (G)-147 | (G)-146 | (G)-145 | (G)-144 | (G)-143 | Compound Number |
|---|---|---|---|---|---|---|---|---|---|---|---|
| CF$_3$ | CF$_3$ | H | H | H | H | H | H | H | H | H | $R_1$ |
| H | CN | H | H | H | H | H | H | H | H | H | $R_2$ |
| CN | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | CN | CN | CN | $R_{16}$ |
| H | H | H | H | H | H | H | H | H | H | H | $R_{17}$ |
| H | H | H | H | H | H | H | H | H | H | H | $R_{18}$ |
| H | H | H | H | H | CN | CN | CN | H | H | H | $R_{19}$ |
| H | H | H | CN | CN | H | H | CF$_3$ | H | H | CF$_3$ | $R_{20}$ |
| H | H | CN | H | CF$_3$ | H | CF$_3$ | H | CF$_3$ | H | H | $R_{21}$ |
| H | H | CF$_3$ | CF$_3$ | H | CF$_3$ | H | CF$_3$ | H | CF$_3$ | H | $R_{22}$ |

| (G)-164 | (G)-163 | (G)-162 | (G)-161 | (G)-160 | (G)-159 | (G)-158 | (G)-157 | (G)-156 | (G)-155 | (G)-154 | Compound Number |
|---|---|---|---|---|---|---|---|---|---|---|---|
| CF$_3$ | CF$_3$ | CF$_3$ | CF$_3$ | CF$_3$ | CF$_3$ | CF$_3$ | CF$_3$ | CF$_3$ | CF$_3$ | CF$_3$ | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | CN | $R_4$ |
| H | H | H | H | H | H | H | H | H | CN | H | $R_5$ |
| H | H | H | H | H | H | H | H | CN | H | H | $R_6$ |
| H | H | H | H | H | H | H | CN | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | CN | H | H | H | H | $R_{10}$ |
| H | H | H | H | H | CN | H | H | H | H | H | $R_{11}$ |
| H | H | H | H | CN | H | H | H | H | H | H | $R_{12}$ |
| H | H | H | CN | H | H | H | H | H | H | H | $R_{13}$ |
| H | H | CN | H | H | H | H | H | H | H | H | $R_{14}$ |
| H | CN | H | H | H | H | H | H | H | H | H | $R_{15}$ |
| CN | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | H | $R_{22}$ |

| (G)-175 | (G)-174 | (G)-173 | (G)-172 | (G)-171 | (G)-170 | (G)-169 | (G)-168 | (G)-167 | (G)-166 | (G)-165 | Compound Number |
|---|---|---|---|---|---|---|---|---|---|---|---|
| H | H | H | H | H | H | H | CF$_3$ | CF$_3$ | CF$_3$ | CF$_3$ | $R_1$ |
| CF$_3$ | CF$_3$ | CF$_3$ | CF$_3$ | CF$_3$ | CF$_3$ | CF$_3$ | H | H | H | H | $R_2$ |
| H | H | H | H | H | H | CN | H | H | H | H | $R_3$ |
| H | H | H | H | H | CN | H | H | H | H | H | $R_4$ |
| H | H | H | H | CN | H | H | H | H | H | H | $R_5$ |
| H | H | H | CN | H | H | H | H | H | H | H | $R_6$ |
| H | H | CN | H | H | H | H | H | H | H | H | $R_7$ |
| H | H | H | H | H | H | H | H | H | H | H | $R_8$ |
| H | H | H | H | H | H | H | H | H | H | H | $R_9$ |

-continued

| | | | | | | | | | | | |
|---|---|---|---|---|---|---|---|---|---|---|---|
| H | CN | H | H | H | H | H | H | H | H | H | $R_{10}$ |
| CN | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | CN | $R_{19}$ |
| H | H | H | H | H | H | H | H | H | CN | H | $R_{20}$ |
| H | H | H | H | H | H | H | H | CN | H | H | $R_{21}$ |
| H | H | H | H | H | H | H | H | H | H | H | $R_{22}$ |

| (G)-186 | (G)-185 | (G)-184 | (G)-183 | (G)-182 | (G)-181 | (G)-180 | (G)-179 | (G)-178 | (G)-177 | (G)-176 | Compound Number |
|---|---|---|---|---|---|---|---|---|---|---|---|
| H | H | H | H | H | H | H | H | H | H | H | $R_1$ |
| H | H | $CF_3$ | $CF_3$ | $CF_3$ | $CF_3$ | $CF_3$ | $CF_3$ | $CF_3$ | $CF_3$ | $CF_3$ | $R_2$ |
| $CF_3$ | $CF_3$ | H | H | H | H | H | H | H | H | H | $R_3$ |
| H | CN | H | H | H | H | H | H | H | H | H | $R_4$ |
| CN | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | CN | $R_{12}$ |
| H | H | H | H | H | H | H | H | H | CN | H | $R_{13}$ |
| H | H | H | H | H | H | H | H | CN | H | H | $R_{14}$ |
| H | H | H | H | H | H | H | CN | H | H | H | $R_{15}$ |
| H | H | H | H | H | H | CN | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | CN | H | H | H | H | H | $R_{19}$ |
| H | H | H | H | CN | H | H | H | H | H | H | $R_{20}$ |
| H | H | H | CN | H | H | H | H | H | H | H | $R_{21}$ |
| H | H | CN | H | H | H | H | H | H | H | H | $R_{22}$ |

| (G)-197 | (G)-196 | (G)-195 | (G)-194 | (G)-193 | (G)-192 | (G)-191 | (G)-190 | (G)-189 | (G)-188 | (G)-187 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| $CF_3$ | $CF_3$ | $CF_3$ | $CF_3$ | $CF_3$ | $CF_3$ | $CF_3$ | $CF_3$ | $CF_3$ | $CF_3$ | $CF_3$ | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | CN | $R_6$ |
| H | H | H | H | H | H | H | H | H | CN | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | CN | H | H | $R_{10}$ |
| H | H | H | H | H | H | H | CN | H | H | H | $R_{11}$ |
| H | H | H | H | H | H | CN | H | H | H | H | $R_{12}$ |
| H | H | H | H | H | CN | H | H | H | H | H | $R_{13}$ |
| H | H | H | H | CN | H | H | H | H | H | H | $R_{14}$ |
| H | H | H | CN | H | H | H | H | H | H | H | $R_{15}$ |
| H | H | CN | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | CN | H | H | H | H | H | H | H | H | H | $R_{19}$ |
| CN | H | H | H | H | H | H | H | H | H | H | $R_{20}$ |
| H | H | H | H | H | H | H | H | H | H | H | $R_{21}$ |
| H | H | H | H | H | H | H | H | H | H | H | $R_{22}$ |

| (G)-208 | (G)-207 | (G)-206 | (G)-205 | (G)-204 | (G)-203 | (G)-202 | (G)-201 | (G)-200 | (G)-199 | (G)-198 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | $CF_3$ | $R_3$ |
| $CF_3$ | $CF_3$ | $CF_3$ | $CF_3$ | $CF_3$ | $CF_3$ | $CF_3$ | $CF_3$ | $CF_3$ | $CF_3$ | H | $R_4$ |
| H | H | H | H | H | H | H | H | H | CN | H | $R_5$ |
| H | H | H | H | H | H | H | H | CN | H | H | $R_6$ |
| H | H | H | H | H | H | H | CN | H | H | H | $R_7$ |
| H | H | H | H | H | H | H | H | H | H | H | $R_8$ |
| H | H | H | H | H | H | H | H | H | H | H | $R_9$ |
| H | H | H | H | H | CN | H | H | H | H | H | $R_{10}$ |

-continued

| | | | | | | | | | | | |
|---|---|---|---|---|---|---|---|---|---|---|---|
| H | H | H | H | H | CN | H | H | H | H | H | $R_{11}$ |
| H | H | H | H | CN | H | H | H | H | H | H | $R_{12}$ |
| H | H | H | CN | H | H | H | H | H | H | H | $R_{13}$ |
| H | H | CN | H | H | H | H | H | H | H | H | $R_{14}$ |
| H | CN | H | H | H | H | H | H | H | H | H | $R_{15}$ |
| CN | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | CN | $R_{22}$ |

| (G)-219 | (G)-218 | (G)-217 | (G)-216 | (G)-215 | (G)-214 | (G)-213 | (G)-212 | (G)-211 | (G)-210 | (G)-209 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | $CF_3$ | $CF_3$ | $CF_3$ | $CF_3$ | $R_4$ |
| $CF_3$ | $CF_3$ | $CF_3$ | $CF_3$ | $CF_3$ | $CF_3$ | $CF_3$ | H | H | H | H | $R_5$ |
| H | H | H | H | H | H | CN | H | H | H | H | $R_6$ |
| H | H | H | H | H | CN | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | CN | H | H | H | H | H | H | $R_{10}$ |
| H | H | H | CN | H | H | H | H | H | H | H | $R_{11}$ |
| H | H | CN | H | H | H | H | H | H | H | H | $R_{12}$ |
| H | CN | H | H | H | H | H | H | H | H | H | $R_{13}$ |
| CN | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | CN | $R_{19}$ |
| H | H | H | H | H | H | H | H | H | CN | H | $R_{20}$ |
| H | H | H | H | H | H | H | H | CN | H | H | $R_{21}$ |
| H | H | H | H | H | H | H | CN | H | H | H | $R_{22}$ |

| (G)-230 | (G)-229 | (G)-228 | (G)-227 | (G)-226 | (G)-225 | (G)-224 | (G)-223 | (G)-222 | (G)-221 | (G)-220 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | $CF_3$ | $CF_3$ | $CF_3$ | $CF_3$ | $CF_3$ | $CF_3$ | $R_5$ |
| $CF_3$ | $CF_3$ | $CF_3$ | $CF_3$ | $CF_3$ | H | H | H | H | H | H | $R_6$ |
| H | H | H | H | CN | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | CN | H | H | H | H | H | H | H | $R_{11}$ |
| H | H | CN | H | H | H | H | H | H | H | H | $R_{12}$ |
| H | CN | H | H | H | H | H | H | H | H | H | $R_{13}$ |
| CN | H | H | H | H | H | H | H | H | H | H | $R_{14}$ |
| H | H | H | H | H | H | H | H | H | H | CN | $R_{15}$ |
| H | H | H | H | H | H | H | H | H | CN | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | CN | H | H | $R_{19}$ |
| H | H | H | H | H | H | H | CN | H | H | H | $R_{20}$ |
| H | H | H | H | H | H | CN | H | H | H | H | $R_{21}$ |
| H | H | H | H | H | CN | H | H | H | H | H | $R_{22}$ |

| (G)-241 | (G)-240 | (G)-239 | (G)-238 | (G)-237 | (G)-236 | (G)-235 | (G)-234 | (G)-233 | (G)-232 | (G)-231 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | $CF_3$ | $CF_3$ | $CF_3$ | $CF_3$ | $CF_3$ | $CF_3$ | $R_6$ |
| $CF_3$ | $CF_3$ | $CF_3$ | $CF_3$ | $CF_3$ | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | CN | H | H | H | H | H | H | $R_{10}$ |
| H | H | H | CN | H | H | H | H | H | H | H | $R_{11}$ |

-continued

| | | | | | | | | | | |
|---|---|---|---|---|---|---|---|---|---|---|
| H | H | CN | H | H | H | H | H | H | H | H | R$_{12}$ |
| H | CN | H | H | H | H | H | H | H | H | H | R$_{13}$ |
| CN | H | H | H | H | H | H | H | H | H | H | R$_{14}$ |
| H | H | H | H | H | H | H | H | H | H | CN | R$_{15}$ |
| H | H | H | H | H | H | H | H | H | CN | H | R$_{16}$ |
| H | H | H | H | H | H | H | H | H | H | H | R$_{17}$ |
| H | H | H | H | H | H | H | H | H | H | H | R$_{18}$ |
| H | H | H | H | H | H | H | H | CN | H | H | R$_{19}$ |
| H | H | H | H | H | H | H | CN | H | H | H | R$_{20}$ |
| H | H | H | H | H | H | CN | H | H | H | H | R$_{21}$ |
| H | H | H | H | H | CN | H | H | H | H | H | R$_{22}$ |

| (G)-252 | (G)-251 | (G)-250 | (G)-249 | (G)-248 | (G)-247 | (G)-246 | (G)-245 | (G)-244 | (G)-243 | (G)-242 | Compound Number |
|---|---|---|---|---|---|---|---|---|---|---|---|
| H | H | H | H | H | H | H | H | H | H | H | R$_1$ |
| H | H | H | H | H | H | H | H | H | H | H | R$_2$ |
| H | H | H | H | H | H | H | H | H | H | H | R$_3$ |
| H | H | H | H | H | H | H | H | H | H | H | R$_4$ |
| H | H | H | H | H | H | H | H | H | H | H | R$_5$ |
| H | H | H | H | H | H | H | H | H | H | H | R$_6$ |
| H | H | H | H | H | CF$_3$ | CF$_3$ | CF$_3$ | CF$_3$ | CF$_3$ | CF$_3$ | R$_7$ |
| H | H | H | H | H | H | H | H | H | H | H | R$_8$ |
| H | H | H | H | H | H | H | H | H | H | H | R$_9$ |
| CF$_3$ | CF$_3$ | CF$_3$ | CF$_3$ | CF$_3$ | H | H | H | H | H | H | R$_{10}$ |
| H | H | H | H | CN | H | H | H | H | H | H | R$_{11}$ |
| H | H | H | CN | H | H | H | H | H | H | H | R$_{12}$ |
| H | H | CN | H | H | H | H | H | H | H | H | R$_{13}$ |
| H | CN | H | H | H | H | H | H | H | H | H | R$_{14}$ |
| CN | H | H | H | H | H | H | H | H | H | CN | R$_{15}$ |
| H | H | H | H | H | H | H | H | H | CN | H | R$_{16}$ |
| H | H | H | H | H | H | H | H | H | H | H | R$_{17}$ |
| H | H | H | H | H | H | H | H | H | H | H | R$_{18}$ |
| H | H | H | H | H | H | H | H | CN | H | H | R$_{19}$ |
| H | H | H | H | H | H | H | CN | H | H | H | R$_{20}$ |
| H | H | H | H | H | H | CN | H | H | H | H | R$_{21}$ |
| H | H | H | H | H | CN | H | H | H | H | H | R$_{22}$ |

| (G)-263 | (G)-262 | (G)-261 | (G)-260 | (G)-259 | (G)-258 | (G)-257 | (G)-256 | (G)-255 | (G)-254 | (G)-253 | Compound Number |
|---|---|---|---|---|---|---|---|---|---|---|---|
| H | H | H | H | H | H | H | H | H | H | H | R$_1$ |
| H | H | H | H | H | H | H | H | H | H | H | R$_2$ |
| H | H | H | H | H | H | H | H | H | H | H | R$_3$ |
| H | H | H | H | H | H | H | H | H | H | H | R$_4$ |
| H | H | H | H | H | H | H | H | H | H | H | R$_5$ |
| H | H | H | H | H | H | H | H | H | H | H | R$_6$ |
| H | H | H | H | H | H | H | H | H | H | H | R$_7$ |
| H | H | H | H | H | H | H | H | H | H | H | R$_8$ |
| H | H | H | H | H | H | H | H | H | H | H | R$_9$ |
| H | H | H | H | H | H | CF$_3$ | CF$_3$ | CF$_3$ | CF$_3$ | CF$_3$ | R$_{10}$ |
| CF$_3$ | CF$_3$ | CF$_3$ | CF$_3$ | CF$_3$ | CF$_3$ | H | H | H | H | H | R$_{11}$ |
| H | H | H | H | H | CN | H | H | H | H | H | R$_{12}$ |
| H | H | H | H | CN | H | H | H | H | H | H | R$_{13}$ |
| H | H | H | CN | H | H | H | H | H | H | H | R$_{14}$ |
| H | H | CN | H | H | H | H | H | H | H | H | R$_{15}$ |
| H | CN | H | H | H | H | H | H | H | H | CN | R$_{16}$ |
| H | H | H | H | H | H | H | H | H | CN | H | R$_{17}$ |
| H | H | H | H | H | H | H | H | CN | H | H | R$_{18}$ |
| CN | H | H | H | H | H | H | H | H | H | H | R$_{19}$ |
| H | H | H | H | H | H | H | CN | H | H | H | R$_{20}$ |
| H | H | H | H | H | H | CN | H | H | H | H | R$_{21}$ |
| H | H | H | H | H | H | H | H | H | H | H | R$_{22}$ |

| (G)-274 | (G)-273 | (G)-272 | (G)-271 | (G)-270 | (G)-269 | (G)-268 | (G)-267 | (G)-266 | (G)-265 | (G)-264 | Compound Number |
|---|---|---|---|---|---|---|---|---|---|---|---|
| H | H | H | H | H | H | H | H | H | H | H | R$_1$ |
| H | H | H | H | H | H | H | H | H | H | H | R$_2$ |
| H | H | H | H | H | H | H | H | H | H | H | R$_3$ |
| H | H | H | H | H | H | H | H | H | H | H | R$_4$ |
| H | H | H | H | H | H | H | H | H | H | H | R$_5$ |
| H | H | H | H | H | H | H | H | H | H | H | R$_6$ |
| H | H | H | H | H | H | H | H | H | H | H | R$_7$ |
| H | H | H | H | H | H | H | H | H | H | H | R$_8$ |
| H | H | H | H | H | H | H | H | H | H | H | R$_9$ |
| H | H | H | H | H | H | H | H | H | H | H | R$_{10}$ |
| H | H | H | H | H | H | H | H | CF$_3$ | CF$_3$ | CF$_3$ | R$_{11}$ |
| CF$_3$ | CF$_3$ | CF$_3$ | CF$_3$ | CF$_3$ | CF$_3$ | CF$_3$ | CF$_3$ | H | H | H | R$_{12}$ |

| | | | | | | | | | | | |
|---|---|---|---|---|---|---|---|---|---|---|---|
| H | H | H | H | H | H | H | CN | H | H | H | $R_{13}$ |
| H | H | H | H | H | H | CN | H | H | H | H | $R_{14}$ |
| H | H | H | H | H | CN | H | H | H | H | H | $R_{15}$ |
| H | H | H | H | CN | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | CN | H | H | H | H | H | H | H | $R_{19}$ |
| H | H | CN | H | H | H | H | H | H | H | CN | $R_{20}$ |
| H | CN | H | H | H | H | H | H | H | CN | H | $R_{21}$ |
| CN | H | H | H | H | H | H | CN | H | H | H | $R_{22}$ |

| (G)-285 | (G)-284 | (G)-283 | (G)-282 | (G)-281 | (G)-280 | (G)-279 | (G)-278 | (G)-277 | (G)-276 | (G)-275 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | $CF_3$ | $CF_3$ | $CF_3$ | $CF_3$ | $CF_3$ | $CF_3$ | $CF_3$ | $R_{13}$ |
| $CF_3$ | $CF_3$ | $CF_3$ | $CF_3$ | H | H | H | H | H | H | CN | $R_{14}$ |
| H | H | H | CN | H | H | H | H | H | CN | H | $R_{15}$ |
| H | H | CN | H | H | H | H | H | CN | H | H | $R_{16}$ |
| H | H | H | H | H | H | H | H | H | H | H | $R_{17}$ |
| H | H | H | H | H | H | H | H | H | H | H | $R_{18}$ |
| H | CN | H | H | H | H | H | CN | H | H | H | $R_{19}$ |
| CN | H | H | H | H | H | CN | H | H | H | H | $R_{20}$ |
| H | H | H | H | H | CN | H | H | H | H | H | $R_{21}$ |
| H | H | H | H | CN | H | H | H | H | H | H | $R_{22}$ |

| (G)-296 | (G)-295 | (G)-294 | (G)-293 | (G)-292 | (G)-291 | (G)-290 | (G)-289 | (G)-288 | (G)-287 | (G)-286 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | $CF_3$ | $CF_3$ | $R_{14}$ |
| H | H | H | H | $CF_3$ | $CF_3$ | $CF_3$ | $CF_3$ | $CF_3$ | H | H | $R_{15}$ |
| $CF_3$ | $CF_3$ | $CF_3$ | $CF_3$ | H | H | H | H | CN | H | H | $R_{16}$ |
| H | H | H | H | H | H | H | H | H | H | H | $R_{17}$ |
| H | H | H | H | H | H | H | H | H | H | H | $R_{18}$ |
| H | H | H | CN | H | H | H | CN | H | H | H | $R_{19}$ |
| H | H | CN | H | H | H | CN | H | H | H | H | $R_{20}$ |
| H | CN | H | H | H | CN | H | H | H | CN | H | $R_{21}$ |
| CN | H | H | H | CN | H | H | H | CN | H | H | $R_{22}$ |

| (G)-302 | (G)-301 | (G)-300 | (G)-299 | (G)-298 | (G)-297 | Compound Number |
|---|---|---|---|---|---|---|
| H | H | H | H | H | H | $R_1$ |
| H | H | H | H | H | H | $R_2$ |
| H | H | H | H | H | H | $R_3$ |
| H | H | H | H | H | H | $R_4$ |
| H | H | H | H | H | H | $R_5$ |
| H | H | H | H | H | H | $R_6$ |
| H | H | H | H | H | H | $R_7$ |
| H | H | H | H | H | H | $R_8$ |
| H | H | H | H | H | H | $R_9$ |
| H | H | H | H | H | H | $R_{10}$ |
| H | H | H | H | H | H | $R_{11}$ |
| H | H | H | H | H | H | $R_{12}$ |
| H | H | H | H | H | H | $R_{13}$ |

-continued

| | | | | | | |
|---|---|---|---|---|---|---|
| H | H | H | H | H | H | R$_{14}$ |
| H | H | H | H | H | H | R$_{15}$ |
| H | H | H | H | H | H | R$_{16}$ |
| H | H | H | H | H | H | R$_{17}$ |
| H | H | H | H | H | H | R$_{18}$ |
| H | H | H | CF$_3$ | CF$_3$ | CF$_3$ | R$_{19}$ |
| H | CF$_3$ | CF$_3$ | H | H | CN | R$_{20}$ |
| CF$_3$ | H | CN | H | CN | H | R$_{21}$ |
| CN | CN | H | CN | H | H | R$_{22}$ |

Formula 2 may be represented by any one among Compound (H)-1 to Compound (H)-302. Compounds (H)-1 to (H)-302 correspond to examples of compounds in which two or three selected from R$_1$ to R$_7$, R$_{10}$ to R$_{16}$, and R$_{19}$ to R$_{22}$ are each independently a fluoro group or a trifluoromethyl group. For example, one of two selected from R$_1$ to R$_7$, R$_{10}$ to R$_{16}$, and R$_{19}$ to R$_{22}$ may be a fluoro group, the other may be a trifluoromethyl group, and the remaining substituents may be hydrogen atoms. In some embodiments, one of three selected from R$_1$ to R$_7$, R$_{10}$ to R$_{16}$, and R$_{19}$ to R$_{22}$ may be a fluoro group, the other two may be trifluoromethyl groups, and the remaining substituents may be hydrogen atoms. In some embodiments, any one of three selected from R$_1$ to R$_7$, R$_{10}$ to R$_{16}$, and R$_{19}$ to R$_{22}$ may be a trifluoromethyl group, the other two may be fluoro groups, and the remaining substituents may be hydrogen atoms. The compounds represented by the case in which R$_5$ is substituted with one fluoro group or one trifluoromethyl group is the same as the case in which R$_9$ is substituted with one fluoro group or one trifluoromethyl group. Because R$_6$ and R$_8$, R$_{15}$ and R$_{17}$, R$_{14}$ and R$_{18}$ are also equivalent by symmetry as described above, they are not separately described as additional compounds.

| (H)-10 | (H)-9 | (H)-8 | (H)-7 | (H)-6 | (H)-5 | (H)-4 | (H)-3 | (H)-2 | (H)-1 | Compound Number |
|---|---|---|---|---|---|---|---|---|---|---|
| F | F | F | F | F | F | F | F | F | F | R$_1$ |
| H | H | H | H | H | H | H | H | H | CF$_3$ | R$_2$ |
| H | H | H | H | H | H | H | H | CF$_3$ | H | R$_3$ |
| H | H | H | H | H | H | H | CF$_3$ | H | H | R$_4$ |
| H | H | H | H | H | H | CF$_3$ | H | H | H | R$_5$ |
| H | H | H | H | H | CF$_3$ | H | H | H | H | R$_6$ |
| H | H | H | H | CF$_3$ | H | H | H | H | H | R$_7$ |
| H | H | H | H | H | H | H | H | H | H | R$_8$ |
| H | H | H | H | H | H | H | H | H | H | R$_9$ |
| H | H | H | CF$_3$ | H | H | H | H | H | H | R$_{10}$ |
| H | H | CF$_3$ | H | H | H | H | H | H | H | R$_{11}$ |
| H | CF$_3$ | H | H | H | H | H | H | H | H | R$_{12}$ |
| CF$_3$ | H | H | H | H | H | H | H | H | H | R$_{13}$ |
| H | H | H | H | H | H | H | H | H | H | R$_{14}$ |
| H | H | H | H | H | H | H | H | H | H | R$_{15}$ |
| H | H | H | H | H | H | H | H | H | H | R$_{16}$ |
| H | H | H | H | H | H | H | H | H | H | R$_{17}$ |
| H | H | H | H | H | H | H | H | H | H | R$_{18}$ |
| H | H | H | H | H | H | H | H | H | H | R$_{19}$ |
| H | H | H | H | H | H | H | H | H | H | R$_{20}$ |
| H | H | H | H | H | H | H | H | H | H | R$_{21}$ |
| H | H | H | H | H | H | H | H | H | H | R$_{22}$ |

| (H)-21 | (H)-20 | (H)-19 | (H)-18 | (H)-17 | (H)-16 | (H)-15 | (H)-14 | (H)-13 | (H)-12 | (H)-11 | Compound Number |
|---|---|---|---|---|---|---|---|---|---|---|---|
| H | H | H | H | F | F | F | F | F | F | F | R$_1$ |
| F | F | F | F | H | H | H | H | H | H | H | R$_2$ |
| H | H | H | CF$_3$ | H | H | H | H | H | H | H | R$_3$ |
| H | H | CF$_3$ | H | H | H | H | H | H | H | H | R$_4$ |
| H | CF$_3$ | H | H | H | H | H | H | H | H | H | R$_5$ |
| CF$_3$ | H | H | H | H | H | H | H | H | H | H | R$_6$ |
| H | H | H | H | H | H | H | H | H | H | H | R$_7$ |
| H | H | H | H | H | H | H | H | H | H | H | R$_8$ |
| H | H | H | H | H | H | H | H | H | H | H | R$_9$ |
| H | H | H | H | H | H | H | H | H | H | H | R$_{10}$ |
| H | H | H | H | H | H | H | H | H | H | H | R$_{11}$ |
| H | H | H | H | H | H | H | H | H | H | H | R$_{12}$ |
| H | H | H | H | H | H | H | H | H | H | H | R$_{13}$ |
| H | H | H | H | H | H | H | H | H | H | CF$_3$ | R$_{14}$ |
| H | H | H | H | H | H | H | H | H | CF$_3$ | H | R$_{15}$ |
| H | H | H | H | H | H | H | H | CF$_3$ | H | H | R$_{16}$ |
| H | H | H | H | H | H | H | H | H | H | H | R$_{17}$ |
| H | H | H | H | H | H | H | H | H | H | H | R$_{18}$ |
| H | H | H | H | H | H | H | CF$_3$ | H | H | H | R$_{19}$ |
| H | H | H | H | H | H | CF$_3$ | H | H | H | H | R$_{20}$ |
| H | H | H | H | H | CF$_3$ | H | H | H | H | H | R$_{21}$ |
| H | H | H | CF$_3$ | H | H | H | H | H | H | H | R$_{22}$ |

| (H)-32 | (H)-31 | (H)-30 | (H)-29 | (H)-28 | (H)-27 | (H)-26 | (H)-25 | (H)-24 | (H)-23 | (H)-22 | Compound Number |
|---|---|---|---|---|---|---|---|---|---|---|---|
| H | H | H | H | H | H | H | H | H | H | H | $R_1$ |
| F | F | F | F | F | F | F | F | F | F | F | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | $CF_3$ | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | $CF_3$ | H | $R_{10}$ |
| H | H | H | H | H | H | H | H | $CF_3$ | H | H | $R_{11}$ |
| H | H | H | H | H | H | H | $CF_3$ | H | H | H | $R_{12}$ |
| H | H | H | H | H | H | $CF_3$ | H | H | H | H | $R_{13}$ |
| H | H | H | H | H | $CF_3$ | H | H | H | H | H | $R_{14}$ |
| H | H | H | H | $CF_3$ | H | H | H | H | H | H | $R_{15}$ |
| H | H | H | $CF_3$ | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | $CF_3$ | H | H | H | H | H | H | H | H | $R_{19}$ |
| H | $CF_3$ | H | H | H | H | H | H | H | H | H | $R_{20}$ |
| $CF_3$ | H | H | H | H | H | H | H | H | H | H | $R_{21}$ |
| H | H | H | H | H | H | H | H | H | H | H | $R_{22}$ |

| (H)-43 | (H)-42 | (H)-41 | (H)-40 | (H)-39 | (H)-38 | (H)-37 | (H)-36 | (H)-35 | (H)-34 | (H)-33 | Compound Number |
|---|---|---|---|---|---|---|---|---|---|---|---|
| H | H | H | H | H | H | H | H | H | H | H | $R_1$ |
| H | H | H | H | H | H | H | H | H | H | F | $R_2$ |
| F | F | F | F | F | F | F | F | F | F | H | $R_3$ |
| H | H | H | H | H | H | H | H | H | $CF_3$ | H | $R_4$ |
| H | H | H | H | H | H | H | H | $CF_3$ | H | H | $R_5$ |
| H | H | H | H | H | H | H | $CF_3$ | H | H | H | $R_6$ |
| H | H | H | H | H | H | $CF_3$ | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | $CF_3$ | H | H | H | H | H | $R_{10}$ |
| H | H | H | H | $CF_3$ | H | H | H | H | H | H | $R_{11}$ |
| H | H | H | $CF_3$ | H | H | H | H | H | H | H | $R_{12}$ |
| H | H | $CF_3$ | H | H | H | H | H | H | H | H | $R_{13}$ |
| H | $CF_3$ | H | H | H | H | H | H | H | H | H | $R_{14}$ |
| $CF_3$ | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | $CF_3$ | $R_{22}$ |

| (H)-54 | (H)-53 | (H)-52 | (H)-51 | (H)-50 | (H)-49 | (H)-48 | (H)-47 | (H)-46 | (H)-45 | (H)-44 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | F | F | F | F | $R_3$ |
| F | F | F | F | F | F | F | H | H | H | H | $R_4$ |
| H | H | H | H | H | H | $CF_3$ | H | H | H | H | $R_5$ |
| H | H | H | H | H | $CF_3$ | H | H | H | H | H | $R_6$ |
| H | H | H | H | $CF_3$ | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | $CF_3$ | H | H | H | H | H | H | H | $R_{10}$ |
| H | H | $CF_3$ | H | H | H | H | H | H | H | H | $R_{11}$ |
| H | $CF_3$ | H | H | H | H | H | H | H | H | H | $R_{12}$ |
| $CF_3$ | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | $CF_3$ | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | $CF_3$ | $R_{19}$ |
| H | H | H | H | H | H | H | H | H | $CF_3$ | H | $R_{20}$ |
| H | H | H | H | H | H | H | H | $CF_3$ | H | H | $R_{21}$ |
| H | H | H | H | H | H | H | $CF_3$ | H | H | H | $R_{22}$ |

| (H)-65 | (H)-64 | (H)-63 | (H)-62 | (H)-61 | (H)-60 | (H)-59 | (H)-58 | (H)-57 | (H)-56 | (H)-55 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | F | F | F | F | F | F | F | $R_4$ |
| F | F | F | F | H | H | H | H | H | H | H | $R_5$ |
| H | H | H | $CF_3$ | H | H | H | H | H | H | H | $R_6$ |
| H | H | $CF_3$ | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | $CF_3$ | H | H | H | H | H | H | H | H | H | $R_{10}$ |
| $CF_3$ | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | $CF_3$ | $R_{14}$ |
| H | H | H | H | H | H | H | H | H | $CF_3$ | H | $R_{15}$ |
| H | H | H | H | H | H | H | H | $CF_3$ | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | $CF_3$ | H | H | H | $R_{19}$ |
| H | H | H | H | H | H | $CF_3$ | H | H | H | H | $R_{20}$ |
| H | H | H | H | H | $CF_3$ | H | H | H | H | H | $R_{21}$ |
| H | H | H | H | $CF_3$ | H | H | H | H | H | H | $R_{22}$ |

| (H)-76 | (H)-75 | (H)-74 | (H)-73 | (H)-72 | (H)-71 | (H)-70 | (H)-69 | (H)-68 | (H)-67 | (H)-66 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | F | F | F | F | F | F | F | F | F | $R_5$ |
| F | F | H | H | H | H | H | H | H | H | H | $R_6$ |
| H | $CF_3$ | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | $CF_3$ | H | H | H | H | H | H | H | H | H | $R_{10}$ |
| $CF_3$ | H | H | H | H | H | H | H | H | H | H | $R_{11}$ |
| H | H | H | H | H | H | H | H | H | H | $CF_3$ | $R_{12}$ |
| H | H | H | H | H | H | H | H | H | $CF_3$ | H | $R_{13}$ |
| H | H | H | H | H | H | H | H | $CF_3$ | H | H | $R_{14}$ |
| H | H | H | H | H | H | H | $CF_3$ | H | H | H | $R_{15}$ |
| H | H | H | H | H | H | $CF_3$ | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | $CF_3$ | H | H | H | H | H | $R_{19}$ |
| H | H | H | H | $CF_3$ | H | H | H | H | H | H | $R_{20}$ |
| H | H | H | $CF_3$ | H | H | H | H | H | H | H | $R_{21}$ |
| H | H | $CF_3$ | H | H | H | H | H | H | H | H | $R_{22}$ |

| (H)-87 | (H)-86 | (H)-85 | (H)-84 | (H)-83 | (H)-82 | (H)-81 | (H)-80 | (H)-79 | (H)-78 | (H)-77 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | F | F | F | F | F | F | F | F | F | $R_6$ |
| F | F | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | $CF_3$ | H | H | H | H | H | H | H | H | H | $R_{10}$ |
| $CF_3$ | H | H | H | H | H | H | H | H | H | H | $R_{11}$ |
| H | H | H | H | H | H | H | H | H | H | $CF_3$ | $R_{12}$ |
| H | H | H | H | H | H | H | H | H | $CF_3$ | H | $R_{13}$ |
| H | H | H | H | H | H | H | H | $CF_3$ | H | H | $R_{14}$ |
| H | H | H | H | H | H | H | $CF_3$ | H | H | H | $R_{15}$ |
| H | H | H | H | H | H | $CF_3$ | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | $CF_3$ | H | H | H | H | H | $R_{19}$ |
| H | H | H | H | $CF_3$ | H | H | H | H | H | H | $R_{20}$ |
| H | H | H | $CF_3$ | H | H | H | H | H | H | H | $R_{21}$ |
| H | H | $CF_3$ | H | H | H | H | H | H | H | H | $R_{22}$ |

-continued

| | (H)-88 | (H)-89 | (H)-90 | (H)-91 | (H)-92 | (H)-93 | (H)-94 | (H)-95 | (H)-96 | (H)-97 | (H)-98 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | H | H | H | H | H | H | H | H | H | H | H |
| R$_4$ | H | H | H | H | H | H | H | H | H | H | H |
| R$_5$ | H | H | H | H | H | H | H | H | H | H | H |
| R$_6$ | H | H | H | H | H | H | H | H | H | H | H |
| R$_7$ | F | F | F | F | F | F | F | F | F | H | H |
| R$_8$ | H | H | H | H | H | H | H | H | H | H | H |
| R$_9$ | H | H | H | H | H | H | H | H | H | H | H |
| R$_{10}$ | H | H | H | H | H | H | H | H | H | H | F |
| R$_{11}$ | H | H | H | H | H | H | H | H | H | CF$_3$ | H |
| R$_{12}$ | CF$_3$ | H | H | H | H | H | H | H | H | H | CF$_3$ |
| R$_{13}$ | H | CF$_3$ | H | H | H | H | H | H | H | H | H |
| R$_{14}$ | H | H | CF$_3$ | H | H | H | H | H | H | H | H |
| R$_{15}$ | H | H | H | CF$_3$ | H | H | H | H | H | H | H |
| R$_{16}$ | H | H | H | H | CF$_3$ | H | H | H | H | H | H |
| R$_{17}$ | H | H | H | H | H | H | H | H | H | H | H |
| R$_{18}$ | H | H | H | H | H | H | H | H | H | H | H |
| R$_{19}$ | H | H | H | H | H | H | CF$_3$ | H | H | H | H |
| R$_{20}$ | H | H | H | H | H | H | H | CF$_3$ | H | H | H |
| R$_{21}$ | H | H | H | H | H | H | H | H | CF$_3$ | H | H |
| R$_{22}$ | H | H | H | H | H | H | H | H | H | H | H |

| | (H)-99 | (H)-100 | (H)-101 | (H)-102 | (H)-103 | (H)-104 | (H)-105 | (H)-106 | (H)-107 | (H)-108 | (H)-109 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | H | H | H | H | H | H | H | H | H | H | H |
| R$_4$ | H | H | H | H | H | H | H | H | H | H | H |
| R$_5$ | H | H | H | H | H | H | H | H | H | H | H |
| R$_6$ | H | H | H | H | H | H | H | H | H | H | H |
| R$_7$ | H | H | H | H | H | H | H | H | H | H | H |
| R$_8$ | H | H | H | H | H | H | H | H | H | H | H |
| R$_9$ | H | H | H | H | H | H | H | H | H | H | H |
| R$_{10}$ | F | F | F | F | F | F | F | H | H | H | H |
| R$_{11}$ | H | H | H | H | H | H | H | F | F | F | F |
| R$_{12}$ | H | H | H | H | H | H | H | CF$_3$ | H | H | H |
| R$_{13}$ | CF$_3$ | H | H | H | H | H | H | H | H | CF$_3$ | H |
| R$_{14}$ | H | CF$_3$ | H | H | H | H | H | H | H | H | CF$_3$ |
| R$_{15}$ | H | H | CF$_3$ | H | H | H | H | H | H | H | H |
| R$_{16}$ | H | H | H | CF$_3$ | H | H | H | H | H | H | H |
| R$_{17}$ | H | H | H | H | H | H | H | H | H | H | H |
| R$_{18}$ | H | H | H | H | H | H | H | H | H | H | H |
| R$_{19}$ | H | H | H | H | CF$_3$ | H | H | H | H | H | H |
| R$_{20}$ | H | H | H | H | H | CF$_3$ | H | H | H | H | H |
| R$_{21}$ | H | H | H | H | H | H | CF$_3$ | H | H | H | H |
| R$_{22}$ | H | H | H | H | H | H | H | CF$_3$ | H | H | H |

| | (H)-110 | (H)-111 | (H)-112 | (H)-113 | (H)-114 | (H)-115 | (H)-116 | (H)-117 | (H)-118 | (H)-119 | (H)-120 |
|---|---|---|---|---|---|---|---|---|---|---|---|
| R$_1$ | H | H | H | H | H | H | H | H | H | H | H |
| R$_2$ | H | H | H | H | H | H | H | H | H | H | H |
| R$_3$ | H | H | H | H | H | H | H | H | H | H | H |
| R$_4$ | H | H | H | H | H | H | H | H | H | H | H |
| R$_5$ | H | H | H | H | H | H | H | H | H | H | H |
| R$_6$ | H | H | H | H | H | H | H | H | H | H | H |
| R$_7$ | H | H | H | H | H | H | H | H | H | H | H |
| R$_8$ | H | H | H | H | H | H | H | H | H | H | H |
| R$_9$ | H | H | H | H | H | H | H | H | H | H | H |
| R$_{10}$ | H | H | H | H | H | H | H | H | H | H | H |
| R$_{11}$ | F | F | F | F | F | F | H | H | H | H | H |
| R$_{12}$ | H | H | H | H | H | H | F | F | F | F | F |
| R$_{13}$ | H | H | H | H | H | H | H | CF$_3$ | H | H | H |
| R$_{14}$ | H | H | H | H | H | H | CF$_3$ | H | H | H | H |
| R$_{15}$ | CF$_3$ | H | H | H | H | H | H | H | CF$_3$ | H | H |
| R$_{16}$ | H | CF$_3$ | H | H | H | H | H | H | H | CF$_3$ | H |
| R$_{17}$ | H | H | H | H | H | H | H | H | H | H | H |
| R$_{18}$ | H | H | H | H | H | H | H | H | H | H | H |
| R$_{19}$ | H | H | CF$_3$ | H | H | H | H | H | H | H | CF$_3$ |
| R$_{20}$ | H | H | H | CF$_3$ | H | H | H | H | H | H | H |
| R$_{21}$ | H | H | H | H | CF$_3$ | H | H | H | H | H | H |
| R$_{22}$ | H | H | H | H | H | CF$_3$ | H | H | H | H | H |

-continued

| Compound Number | (H)-121 | (H)-122 | (H)-123 | (H)-124 | (H)-125 | (H)-126 | (H)-127 | (H)-128 | (H)-129 | (H)-130 | (H)-131 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | F | F | F | H | H | H | H | H | H | H | H |
| $R_{13}$ | H | H | H | F | F | F | F | F | F | F | H |
| $R_{14}$ | H | H | H | $CF_3$ | H | H | H | H | H | H | F |
| $R_{15}$ | H | H | H | H | $CF_3$ | H | H | H | H | H | $CF_3$ |
| $R_{16}$ | H | H | H | H | H | $CF_3$ | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | $CF_3$ | H | H | H |
| $R_{20}$ | $CF_3$ | H | H | H | H | H | H | H | H | H | H |
| $R_{21}$ | H | $CF_3$ | H | H | H | H | H | H | $CF_3$ | H | H |
| $R_{22}$ | H | H | $CF_3$ | H | H | H | H | H | H | $CF_3$ | H |

| Compound Number | (H)-132 | (H)-133 | (H)-134 | (H)-135 | (H)-136 | (H)-137 | (H)-138 | (H)-139 | (H)-140 | (H)-141 | (H)-142 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | H | H | H | H | H | H | H | H | H | H | H |
| $R_{13}$ | H | H | H | H | H | H | H | H | H | H | H |
| $R_{14}$ | F | F | F | F | F | H | H | H | H | H | H |
| $R_{15}$ | H | H | H | H | H | F | F | F | F | F | H |
| $R_{16}$ | H | $CF_3$ | H | H | H | $CF_3$ | H | H | H | H | F |
| $R_{17}$ | H | H | H | H | H | H | H | H | H | H | H |
| $R_{18}$ | H | H | H | H | H | H | H | H | H | H | H |
| $R_{19}$ | H | $CF_3$ | H | H | H | H | $CF_3$ | H | H | H | $CF_3$ |
| $R_{20}$ | H | H | $CF_3$ | H | H | H | H | $CF_3$ | H | H | H |
| $R_{21}$ | H | H | H | $CF_3$ | H | H | H | H | $CF_3$ | H | H |
| $R_{22}$ | H | H | H | H | $CF_3$ | H | H | H | H | $CF_3$ | H |

| Compound Number | (H)-143 | (H)-144 | (H)-145 | (H)-146 | (H)-147 | (H)-148 | (H)-149 | (H)-150 | (H)-151 | (H)-152 | (H)-153 |
|---|---|---|---|---|---|---|---|---|---|---|---|
| $R_1$ | H | H | H | H | H | H | H | H | H | $CF_3$ | $CF_3$ |
| $R_2$ | H | H | H | H | H | H | H | H | H | F | H |
| $R_3$ | H | H | H | H | H | H | H | H | H | H | F |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | H | H | H | H | H | H | H | H | H | H | H |
| $R_{13}$ | H | H | H | H | H | H | H | H | H | H | H |
| $R_{14}$ | H | H | H | H | H | H | H | H | H | H | H |
| $R_{15}$ | H | H | H | H | H | H | H | H | H | H | H |
| $R_{16}$ | F | F | F | H | H | H | H | H | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | F | F | F | H | H | H | H | H |
| $R_{20}$ | $CF_3$ | H | $CF_3$ | H | H | H | F | F | H | H | H |
| $R_{21}$ | H | $CF_3$ | H | $CF_3$ | H | $CF_3$ | H | $CF_3$ | F | H | H |
| $R_{22}$ | H | H | $CF_3$ | H | $CF_3$ | H | $CF_3$ | H | $CF_3$ | H | H |

-continued

| (H)-164 | (H)-163 | (H)-162 | (H)-161 | (H)-160 | (H)-159 | (H)-158 | (H)-157 | (H)-156 | (H)-155 | (H)-154 | Compound Number |
|---|---|---|---|---|---|---|---|---|---|---|---|
| $CF_3$ | $CF_3$ | $CF_3$ | $CF_3$ | $CF_3$ | $CF_3$ | $CF_3$ | $CF_3$ | $CF_3$ | $CF_3$ | $CF_3$ | $R_1$ |
| H | H | H | H | H | H | H | H | H | H | H | $R_2$ |
| H | H | H | H | H | H | H | H | H | H | F | $R_3$ |
| H | H | H | H | H | H | H | H | H | F | H | $R_4$ |
| H | H | H | H | H | H | H | H | F | H | H | $R_5$ |
| H | H | H | H | H | H | H | F | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | F | H | H | H | H | H | $R_{10}$ |
| H | H | H | H | H | H | H | H | H | H | H | $R_{11}$ |
| H | H | H | H | F | H | H | H | H | H | H | $R_{12}$ |
| H | H | H | F | H | H | H | H | H | H | H | $R_{13}$ |
| H | H | F | H | H | H | H | H | H | H | H | $R_{14}$ |
| H | F | H | H | H | H | H | H | H | H | H | $R_{15}$ |
| F | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | H | $R_{22}$ |

| (H)-175 | (H)-174 | (H)-173 | (H)-172 | (H)-171 | (H)-170 | (H)-169 | (H)-168 | (H)-167 | (H)-166 | (H)-165 | Compound Number |
|---|---|---|---|---|---|---|---|---|---|---|---|
| H | H | H | H | H | H | H | $CF_3$ | $CF_3$ | $CF_3$ | $CF_3$ | $R_1$ |
| $CF_3$ | $CF_3$ | $CF_3$ | $CF_3$ | $CF_3$ | $CF_3$ | $CF_3$ | H | H | H | H | $R_2$ |
| H | H | H | H | H | H | F | H | H | H | H | $R_3$ |
| H | H | H | H | H | F | H | H | H | H | H | $R_4$ |
| H | H | H | H | F | H | H | H | H | H | H | $R_5$ |
| H | H | H | F | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | F | H | H | H | H | H | H | H | H | H | $R_{10}$ |
| F | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | F | $R_{19}$ |
| H | H | H | H | H | H | H | H | H | F | H | $R_{20}$ |
| H | H | H | H | H | H | H | H | F | H | H | $R_{21}$ |
| H | H | H | H | H | H | H | H | H | H | H | $R_{22}$ |

| (H)-186 | (H)-185 | (H)-184 | (H)-183 | (H)-182 | (H)-181 | (H)-180 | (H)-179 | (H)-178 | (H)-177 | (H)-176 | Compound Number |
|---|---|---|---|---|---|---|---|---|---|---|---|
| H | H | H | H | H | H | H | H | H | H | H | $R_1$ |
| H | H | $CF_3$ | $CF_3$ | $CF_3$ | $CF_3$ | $CF_3$ | $CF_3$ | $CF_3$ | $CF_3$ | $CF_3$ | $R_2$ |
| $CF_3$ | $CF_3$ | H | H | H | H | H | H | H | H | H | $R_3$ |
| H | F | H | H | H | H | H | H | H | H | H | $R_4$ |
| F | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | F | $R_{12}$ |
| H | H | H | H | H | H | H | H | H | F | H | $R_{13}$ |
| H | H | H | H | H | H | H | H | F | H | H | $R_{14}$ |
| H | H | H | H | H | H | H | F | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | F | H | H | H | H | H | H | $R_{20}$ |
| H | H | H | F | H | H | H | H | H | H | H | $R_{21}$ |
| H | H | F | H | H | H | H | H | H | H | H | $R_{22}$ |

-continued

| (H)-197 | (H)-196 | (H)-195 | (H)-194 | (H)-193 | (H)-192 | (H)-191 | (H)-190 | (H)-189 | (H)-188 | (H)-187 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| $CF_3$ | $CF_3$ | $CF_3$ | $CF_3$ | $CF_3$ | $CF_3$ | $CF_3$ | $CF_3$ | $CF_3$ | $CF_3$ | $CF_3$ | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | F | $R_6$ |
| H | H | H | H | H | H | H | H | H | F | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | F | H | H | $R_{10}$ |
| H | H | H | H | H | H | H | F | H | H | H | $R_{11}$ |
| H | H | H | H | H | H | F | H | H | H | H | $R_{12}$ |
| H | H | H | H | H | F | H | H | H | H | H | $R_{13}$ |
| H | H | H | H | F | H | H | H | H | H | H | $R_{14}$ |
| H | H | H | F | H | H | H | H | H | H | H | $R_{15}$ |
| H | H | F | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | F | H | H | H | H | H | H | H | H | H | $R_{19}$ |
| H | H | H | H | H | H | H | H | H | H | H | $R_{20}$ |
| F | H | H | H | H | H | H | H | H | H | H | $R_{21}$ |
| H | H | H | H | H | H | H | H | H | H | H | $R_{22}$ |

| (H)-208 | (H)-207 | (H)-206 | (H)-205 | (H)-204 | (H)-203 | (H)-202 | (H)-201 | (H)-200 | (H)-199 | (H)-198 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | $CF_3$ | $R_3$ |
| $CF_3$ | $CF_3$ | $CF_3$ | $CF_3$ | $CF_3$ | $CF_3$ | $CF_3$ | $CF_3$ | $CF_3$ | $CF_3$ | H | $R_4$ |
| H | H | H | H | H | H | H | H | H | F | H | $R_5$ |
| H | H | H | H | H | H | H | H | H | H | H | $R_6$ |
| H | H | H | H | H | H | H | F | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | F | H | H | H | H | $R_{10}$ |
| H | H | H | H | H | F | H | H | H | H | H | $R_{11}$ |
| H | H | H | H | F | H | H | H | H | H | H | $R_{12}$ |
| H | H | H | F | H | H | H | H | H | H | H | $R_{13}$ |
| H | H | F | H | H | H | H | H | H | H | H | $R_{14}$ |
| H | F | H | H | H | H | H | H | H | H | H | $R_{15}$ |
| F | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | H | $R_{19}$ |
| H | H | H | H | H | H | H | H | H | H | H | $R_{20}$ |
| H | H | H | H | H | H | H | H | H | H | H | $R_{21}$ |
| H | H | H | H | H | H | H | H | H | H | F | $R_{22}$ |

| (H)-219 | (H)-218 | (H)-217 | (H)-216 | (H)-215 | (H)-214 | (H)-213 | (H)-212 | (H)-211 | (H)-210 | (H)-209 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | $CF_3$ | $CF_3$ | $CF_3$ | $CF_3$ | $R_4$ |
| $CF_3$ | $CF_3$ | $CF_3$ | $CF_3$ | $CF_3$ | $CF_3$ | $CF_3$ | H | H | H | H | $R_5$ |
| H | H | H | H | H | H | F | H | H | H | H | $R_6$ |
| H | H | H | H | H | F | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | F | H | H | H | H | H | H | $R_{10}$ |
| H | H | H | F | H | H | H | H | H | H | H | $R_{11}$ |
| H | H | F | H | H | H | H | H | H | H | H | $R_{12}$ |
| H | F | H | H | H | H | H | H | H | H | H | $R_{13}$ |
| F | H | H | H | H | H | H | H | H | H | H | $R_{14}$ |
| H | H | H | H | H | H | H | H | H | H | H | $R_{15}$ |
| H | H | H | H | H | H | H | H | H | H | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | H | H | H | F | $R_{19}$ |
| H | H | H | H | H | H | H | H | H | F | H | $R_{20}$ |
| H | H | H | H | H | H | H | H | F | H | H | $R_{21}$ |
| H | H | H | H | H | H | H | F | H | H | H | $R_{22}$ |

-continued

| (H)-230 | (H)-229 | (H)-228 | (H)-227 | (H)-226 | (H)-225 | (H)-224 | (H)-223 | (H)-222 | (H)-221 | (H)-220 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | $CF_3$ | $CF_3$ | $CF_3$ | $CF_3$ | $CF_3$ | $CF_3$ | $R_5$ |
| $CF_3$ | $CF_3$ | $CF_3$ | $CF_3$ | $CF_3$ | H | H | H | H | H | H | $R_6$ |
| H | H | H | H | F | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | F | H | H | H | H | H | H | $R_{10}$ |
| H | H | H | F | H | H | H | H | H | H | H | $R_{11}$ |
| H | H | F | H | H | H | H | H | H | H | H | $R_{12}$ |
| H | F | H | H | H | H | H | H | H | H | H | $R_{13}$ |
| F | H | H | H | H | H | H | H | H | H | H | $R_{14}$ |
| H | H | H | H | H | H | H | H | H | H | F | $R_{15}$ |
| H | H | H | H | H | H | H | H | H | F | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | F | H | H | H | $R_{19}$ |
| H | H | H | H | H | H | F | H | H | H | H | $R_{20}$ |
| H | H | H | H | H | F | H | H | H | H | H | $R_{21}$ |
| H | H | H | H | H | F | H | H | H | H | H | $R_{22}$ |

| (H)-241 | (H)-240 | (H)-239 | (H)-238 | (H)-237 | (H)-236 | (H)-235 | (H)-234 | (H)-233 | (H)-232 | (H)-231 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | $CF_3$ | $CF_3$ | $CF_3$ | $CF_3$ | $CF_3$ | $CF_3$ | $R_6$ |
| $CF_3$ | $CF_3$ | $CF_3$ | $CF_3$ | $CF_3$ | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | F | H | H | H | H | H | H | $R_{10}$ |
| H | H | H | F | H | H | H | H | H | H | H | $R_{11}$ |
| H | H | F | H | H | H | H | H | H | H | H | $R_{12}$ |
| H | F | H | H | H | H | H | H | H | H | H | $R_{13}$ |
| F | H | H | H | H | H | H | H | H | H | H | $R_{14}$ |
| H | H | H | H | H | H | H | H | H | H | F | $R_{15}$ |
| H | H | H | H | H | H | H | H | H | F | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | F | H | H | H | $R_{19}$ |
| H | H | H | H | H | H | F | H | H | H | H | $R_{20}$ |
| H | H | H | H | H | F | H | H | H | H | H | $R_{21}$ |
| H | H | H | H | H | F | H | H | H | H | H | $R_{22}$ |

| (H)-252 | (H)-251 | (H)-250 | (H)-249 | (H)-248 | (H)-247 | (H)-246 | (H)-245 | (H)-244 | (H)-243 | (H)-242 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | $CF_3$ | $CF_3$ | $CF_3$ | $CF_3$ | $CF_3$ | $CF_3$ | $R_7$ |
| H | H | H | H | H | H | H | H | H | H | H | $R_8$ |
| H | H | H | H | H | H | H | H | H | H | H | $R_9$ |
| $CF_3$ | $CF_3$ | $CF_3$ | $CF_3$ | $CF_3$ | H | H | H | H | H | H | $R_{10}$ |
| H | H | H | H | F | H | H | H | H | H | H | $R_{11}$ |
| H | H | H | F | H | H | H | H | H | H | H | $R_{12}$ |
| H | H | F | H | H | H | H | H | H | H | H | $R_{13}$ |
| H | F | H | H | H | H | H | H | H | H | H | $R_{14}$ |
| F | H | H | H | H | H | H | H | H | H | F | $R_{15}$ |
| H | H | H | H | H | H | H | H | H | F | H | $R_{16}$ |
| H | H | H | H | H | H | H | H | H | H | H | $R_{17}$ |
| H | H | H | H | H | H | H | H | H | H | H | $R_{18}$ |
| H | H | H | H | H | H | H | F | H | H | H | $R_{19}$ |
| H | H | H | H | H | H | F | H | H | H | H | $R_{20}$ |
| H | H | H | H | H | F | H | H | H | H | H | $R_{21}$ |
| H | H | H | H | H | F | H | H | H | H | H | $R_{22}$ |

| Compound Number | (H)-253 | (H)-254 | (H)-255 | (H)-256 | (H)-257 | (H)-258 | (H)-259 | (H)-260 | (H)-261 | (H)-262 | (H)-263 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | $CF_3$ | $CF_3$ | $CF_3$ | $CF_3$ | $CF_3$ | H | H | H | H | H | H |
| $R_{11}$ | H | H | H | H | H | $CF_3$ | $CF_3$ | $CF_3$ | $CF_3$ | $CF_3$ | $CF_3$ |
| $R_{12}$ | H | H | H | H | H | F | H | H | H | H | H |
| $R_{13}$ | H | H | H | H | H | H | F | H | H | H | H |
| $R_{14}$ | H | H | H | H | H | H | H | F | H | H | H |
| $R_{15}$ | H | H | H | H | H | H | H | H | F | H | H |
| $R_{16}$ | F | H | H | H | H | H | H | H | H | F | H |
| $R_{17}$ | H | H | H | H | H | H | H | H | H | H | H |
| $R_{18}$ | H | H | H | H | H | H | H | H | H | H | H |
| $R_{19}$ | H | F | H | H | H | H | H | H | H | H | F |
| $R_{20}$ | H | H | F | H | H | H | H | H | H | H | H |
| $R_{21}$ | H | H | H | F | H | H | H | H | H | H | H |
| $R_{22}$ | H | H | H | H | F | H | H | H | H | H | H |

| Compound Number | (H)-264 | (H)-265 | (H)-266 | (H)-267 | (H)-268 | (H)-269 | (H)-270 | (H)-271 | (H)-272 | (H)-273 | (H)-274 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | $CF_3$ | $CF_3$ | $CF_3$ | H | H | H | H | H | H | H | H |
| $R_{12}$ | H | H | H | $CF_3$ | $CF_3$ | $CF_3$ | $CF_3$ | $CF_3$ | $CF_3$ | $CF_3$ | $CF_3$ |
| $R_{13}$ | H | H | F | H | H | H | H | H | H | H | H |
| $R_{14}$ | H | H | H | H | F | H | H | H | H | H | H |
| $R_{15}$ | H | H | H | H | H | H | F | H | H | H | H |
| $R_{16}$ | H | H | H | H | H | H | H | F | H | H | H |
| $R_{17}$ | H | H | H | H | H | H | H | H | H | H | H |
| $R_{18}$ | H | H | H | H | H | H | H | H | H | H | H |
| $R_{19}$ | H | H | H | H | H | H | H | F | H | H | H |
| $R_{20}$ | F | H | H | H | H | H | H | H | F | H | H |
| $R_{21}$ | H | F | H | H | H | H | H | H | H | F | H |
| $R_{22}$ | H | H | F | H | H | H | H | H | H | H | F |

| Compound Number | (H)-275 | (H)-276 | (H)-277 | (H)-278 | (H)-279 | (H)-280 | (H)-281 | (H)-282 | (H)-283 | (H)-284 | (H)-285 |
|---|---|---|---|---|---|---|---|---|---|---|---|
| $R_1$ | H | H | H | H | H | H | H | H | H | H | H |
| $R_2$ | H | H | H | H | H | H | H | H | H | H | H |
| $R_3$ | H | H | H | H | H | H | H | H | H | H | H |
| $R_4$ | H | H | H | H | H | H | H | H | H | H | H |
| $R_5$ | H | H | H | H | H | H | H | H | H | H | H |
| $R_6$ | H | H | H | H | H | H | H | H | H | H | H |
| $R_7$ | H | H | H | H | H | H | H | H | H | H | H |
| $R_8$ | H | H | H | H | H | H | H | H | H | H | H |
| $R_9$ | H | H | H | H | H | H | H | H | H | H | H |
| $R_{10}$ | H | H | H | H | H | H | H | H | H | H | H |
| $R_{11}$ | H | H | H | H | H | H | H | H | H | H | H |
| $R_{12}$ | H | H | H | H | H | H | H | H | H | H | H |
| $R_{13}$ | $CF_3$ | $CF_3$ | $CF_3$ | $CF_3$ | $CF_3$ | $CF_3$ | $CF_3$ | H | H | H | H |
| $R_{14}$ | F | H | H | H | H | H | H | $CF_3$ | $CF_3$ | $CF_3$ | $CF_3$ |
| $R_{15}$ | H | F | H | H | H | H | H | F | H | H | H |
| $R_{16}$ | H | H | F | H | H | H | H | H | F | H | H |
| $R_{17}$ | H | H | H | H | H | H | H | H | H | H | H |
| $R_{18}$ | H | H | H | H | H | H | H | H | H | H | H |
| $R_{19}$ | H | H | H | F | H | H | H | H | H | F | H |
| $R_{20}$ | H | H | H | H | F | H | H | H | H | H | F |
| $R_{21}$ | H | H | H | H | H | F | H | H | H | H | H |
| $R_{22}$ | H | H | H | H | H | H | F | H | H | H | H |

| (H)-296 | (H)-295 | (H)-294 | (H)-293 | (H)-292 | (H)-291 | (H)-290 | (H)-289 | (H)-288 | (H)-287 | (H)-286 | Compound Number |
|---|---|---|---|---|---|---|---|---|---|---|---|
| H | H | H | H | H | H | H | H | H | H | H | $R_1$ |
| H | H | H | H | H | H | H | H | H | H | H | $R_2$ |
| H | H | H | H | H | H | H | H | H | H | H | $R_3$ |
| H | H | H | H | H | H | H | H | H | H | H | $R_4$ |
| H | H | H | H | H | H | H | H | H | H | H | $R_5$ |
| H | H | H | H | H | H | H | H | H | H | H | $R_6$ |
| H | H | H | H | H | H | H | H | H | H | H | $R_7$ |
| H | H | H | H | H | H | H | H | H | H | H | $R_8$ |
| H | H | H | H | H | H | H | H | H | H | H | $R_9$ |
| H | H | H | H | H | H | H | H | H | H | H | $R_{10}$ |
| H | H | H | H | H | H | H | H | H | H | H | $R_{11}$ |
| H | H | H | H | H | H | H | H | H | H | H | $R_{12}$ |
| H | H | H | H | H | H | H | H | H | H | H | $R_{13}$ |
| H | H | H | H | H | H | H | H | H | $CF_3$ | $CF_3$ | $R_{14}$ |
| H | H | H | H | $CF_3$ | $CF_3$ | $CF_3$ | $CF_3$ | $CF_3$ | H | H | $R_{15}$ |
| $CF_3$ | $CF_3$ | $CF_3$ | $CF_3$ | H | H | H | H | F | H | H | $R_{16}$ |
| H | H | H | H | H | H | H | H | H | H | H | $R_{17}$ |
| H | H | H | H | H | H | H | H | H | H | H | $R_{18}$ |
| H | H | H | F | H | H | H | F | H | H | H | $R_{19}$ |
| H | H | F | H | H | H | F | H | H | H | H | $R_{20}$ |
| H | F | H | H | H | F | H | H | H | H | F | $R_{21}$ |
| F | H | H | H | F | H | H | H | H | F | H | $R_{22}$ |

| (H)-302 | (H)-301 | (H)-300 | (H)-299 | (H)-298 | (H)-297 | Compound Number |
|---|---|---|---|---|---|---|
| H | H | H | H | H | H | $R_1$ |
| H | H | H | H | H | H | $R_2$ |
| H | H | H | H | H | H | $R_3$ |
| H | H | H | H | H | H | $R_4$ |
| H | H | H | H | H | H | $R_5$ |
| H | H | H | H | H | H | $R_6$ |
| H | H | H | H | H | H | $R_7$ |
| H | H | H | H | H | H | $R_8$ |
| H | H | H | H | H | H | $R_9$ |
| H | H | H | H | H | H | $R_{10}$ |
| H | H | H | H | H | H | $R_{11}$ |
| H | H | H | H | H | H | $R_{12}$ |
| H | H | H | H | H | H | $R_{13}$ |
| H | H | H | H | H | H | $R_{14}$ |
| H | H | H | H | H | H | $R_{15}$ |
| H | H | H | H | H | H | $R_{16}$ |
| H | H | H | H | H | H | $R_{17}$ |
| H | H | H | H | H | H | $R_{18}$ |
| H | H | H | $CF_3$ | $CF_3$ | $CF_3$ | $R_{19}$ |
| H | $CF_3$ | $CF_3$ | H | H | F | $R_{20}$ |
| $CF_3$ | H | F | H | F | H | $R_{21}$ |
| F | F | H | F | H | H | $R_{22}$ |

The electron donor of the polycyclic compound represented by Formula 2, "Du", may be represented by any one among the compounds (A)-1 to (A)-18, (B)-1 to (B)-18, (C)-1 to (C)-18, (D)-1 to (D)-152, (E)-1 to (E)-152, (F)-1 to (F)-302, (G)-1 to (G)-302, and (H)-1 to (H)-302.

In the polycyclic compound of an embodiment, the electron donor indicated by "Du" includes at least one electron accepting group as a substituent, and the electron donor is weakened compared to the case in which the electron accepting group is not included, so that the polycyclic compound in an embodiment may be to emit light at a relatively short wavelength region. For example, an electron donor "Du" of the polycyclic compound of an embodiment includes a diindeno carbazole (in which three carbazole groups are condensed), and includes at least one electron accepting group (such as a cyano group, a fluoro group, and/or a trifluoromethyl group). Therefore, the polycyclic compound of an embodiment may be to emit light in a wavelength region of 470 nm or less and exhibit excellent luminous efficiency characteristics.

Formula 1 may be represented by any one among Formula 1-1 to Formula 1-23. In Formula 1-1 to Formula 1-23, "Du" is represented by Formula 2. In addition, in Formula 1-1 to Formula 1-23, "Du" may be represented by any one among (A)-1 to (A)-18, (B)-1 to (B)-18, (C)-1 to (C)-18, (D)-1 to (D)-152, (E)-1 to (E)-152, (F)-1 to (F)-302, (G)-1 to (G)-302, and (H)-1 to (H)-302.

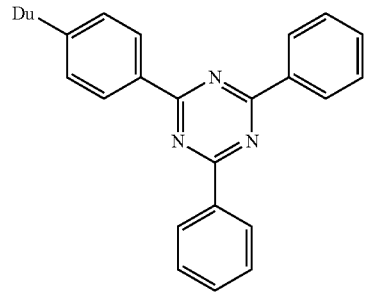

1-1

-continued
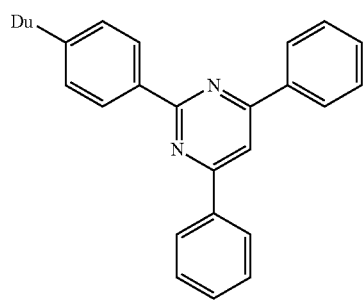
1-2
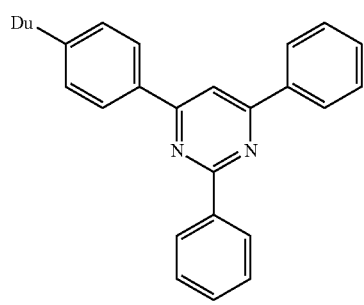
1-3
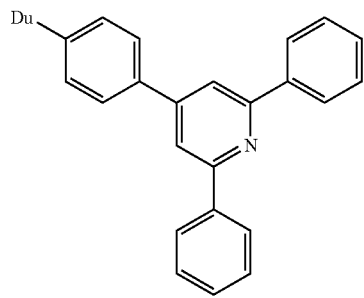
1-4
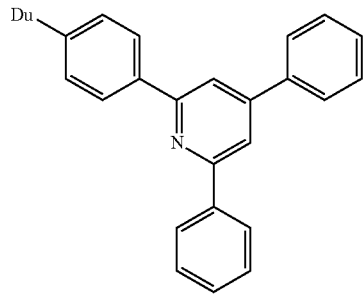
1-5
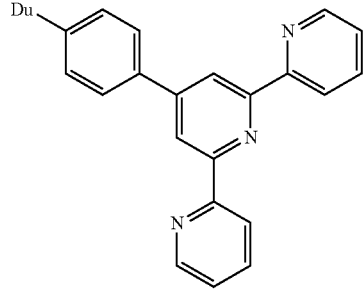
1-6
-continued
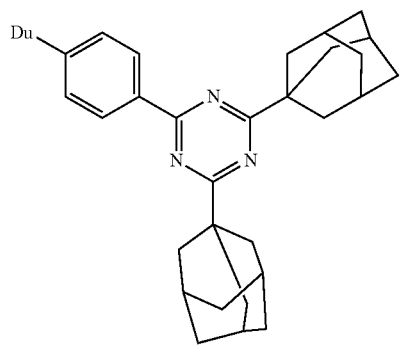
1-7
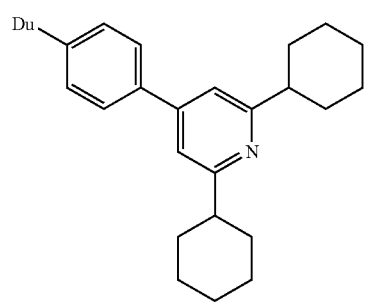
1-8
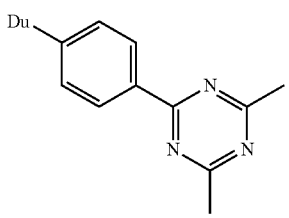
1-9
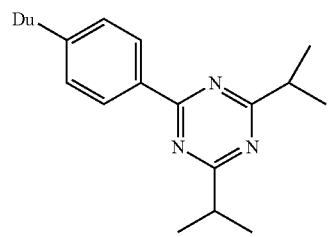
1-10
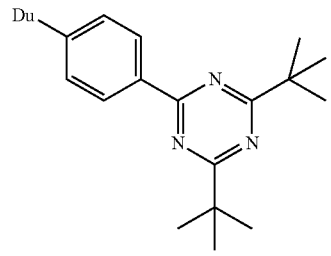
1-11
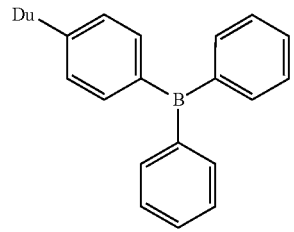
1-12

1-13 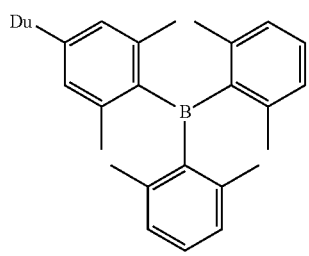
1-14 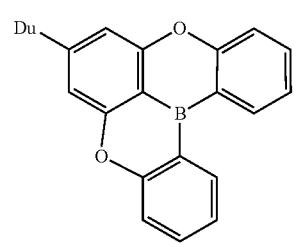
1-15 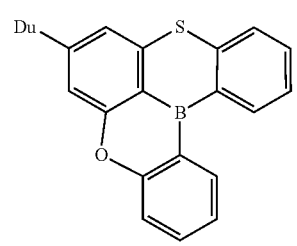
1-16 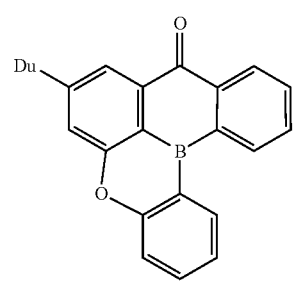
1-17 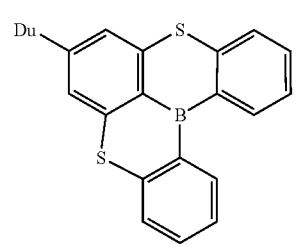
1-18 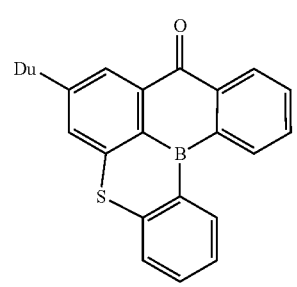
1-19 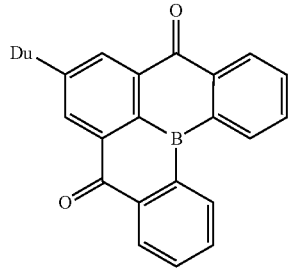
1-20 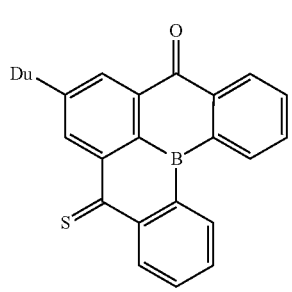
1-21 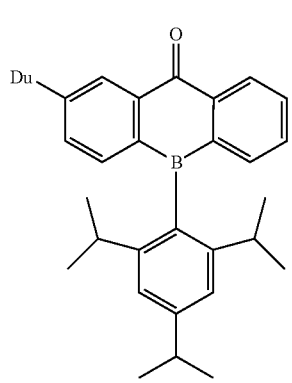
1-22 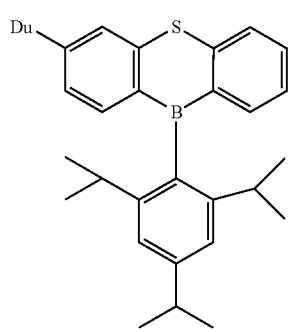

-continued

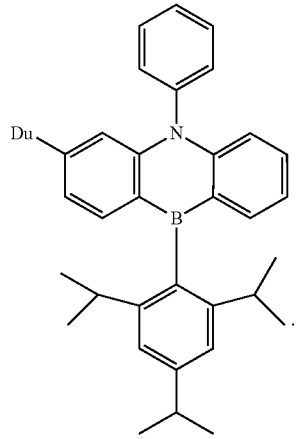

1-23

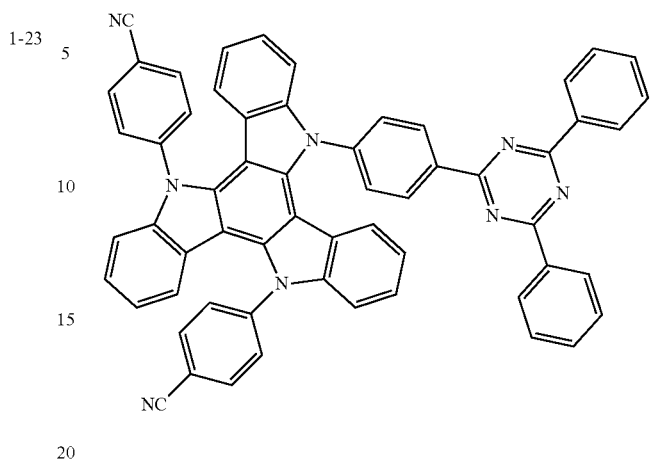

2

The polycyclic compound of an embodiment has a D (Donor)-A (Acceptor) molecular structure. The polycyclic compound of an embodiment may be used as a thermally activated delayed fluorescence (TADF) material due to having a large twist angle between the diindenocarbazole electron donor and the electron acceptor. In addition, the polycyclic compound of an embodiment may be used as a light emitting material to emit light in the blue wavelength region, due to a relatively low degree of electron donation because of the introduction of an electron accepting group substituent on the electron donor.

The polycyclic compound of an embodiment may be any one among the compounds represented in Compound Group 1. The organic electroluminescence device 10 of an embodiment may include at least one polycyclic compound among the polycyclic compounds represented in Compound Group 1 in an emission layer EML.

Compound Group 1

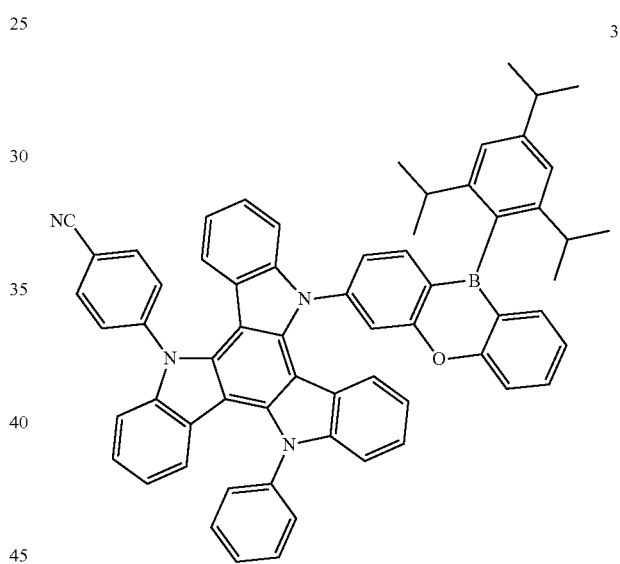

3

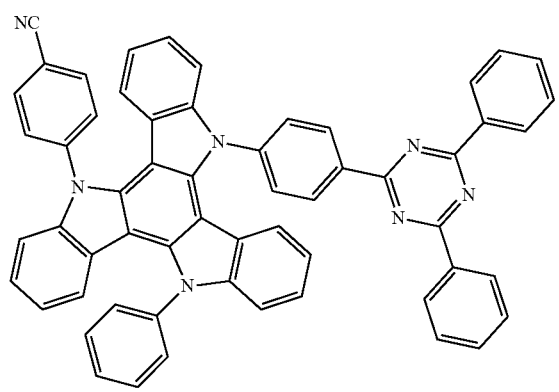

1

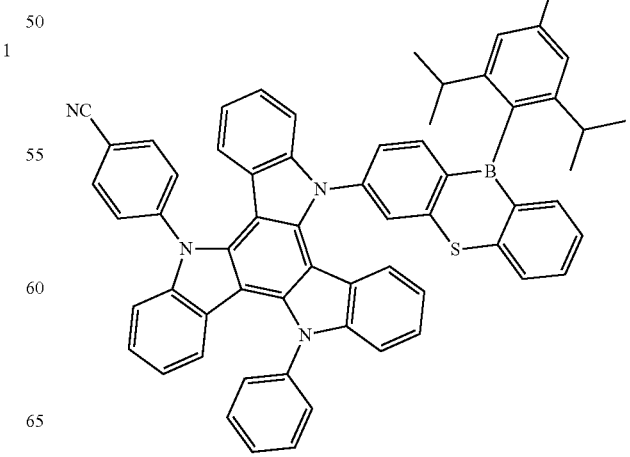

4

105
-continued
5
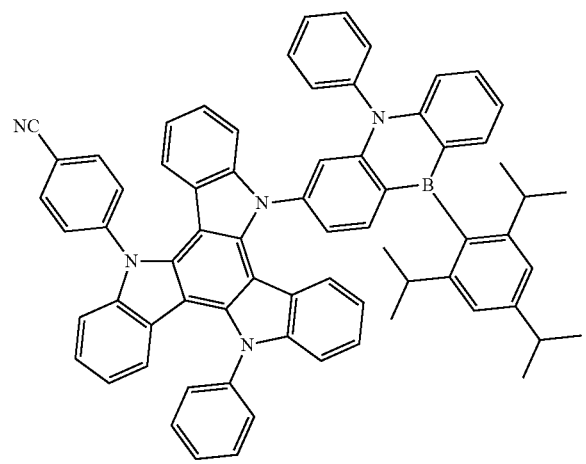
6
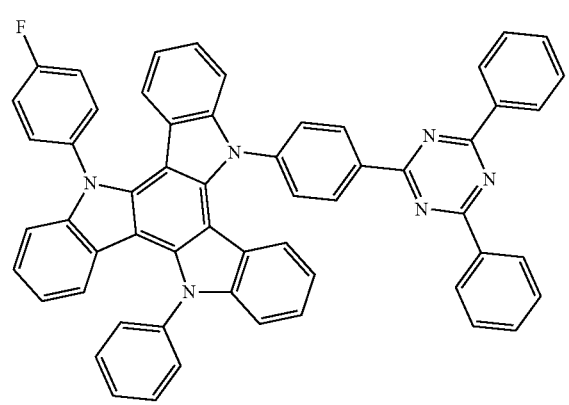
7
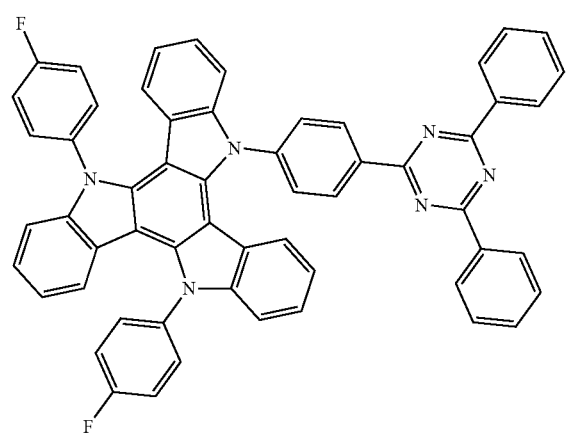
106
-continued
8
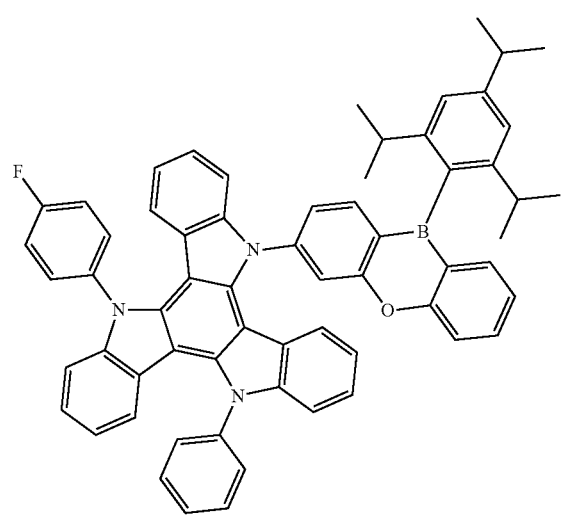
9
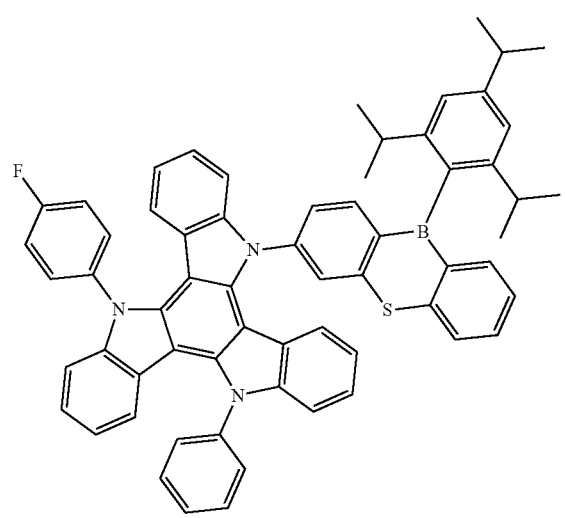
10
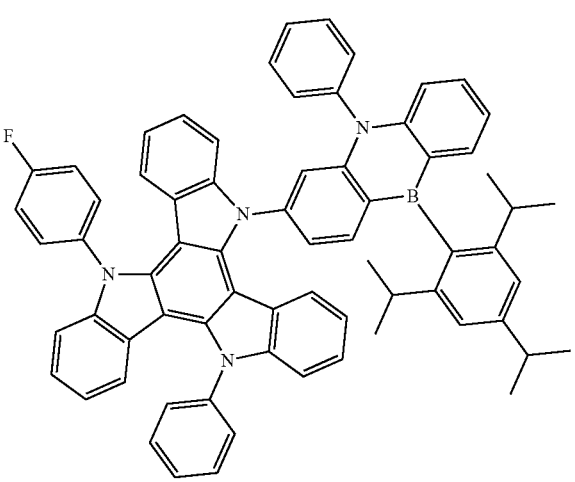

11
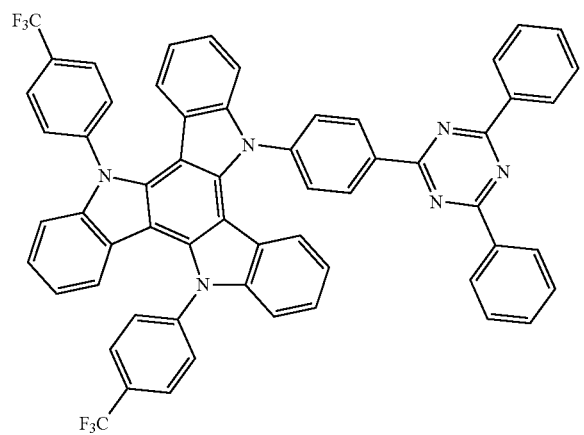
12
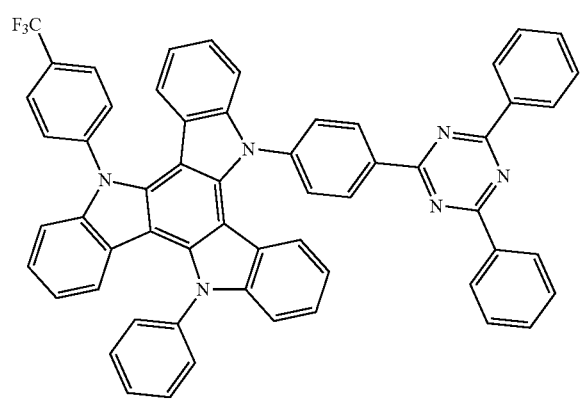
13
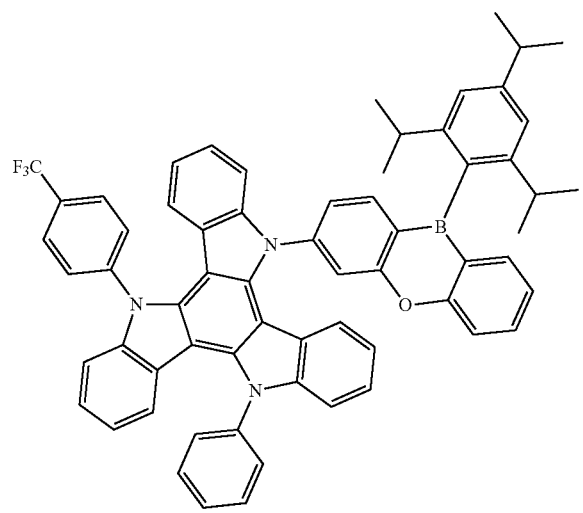
14
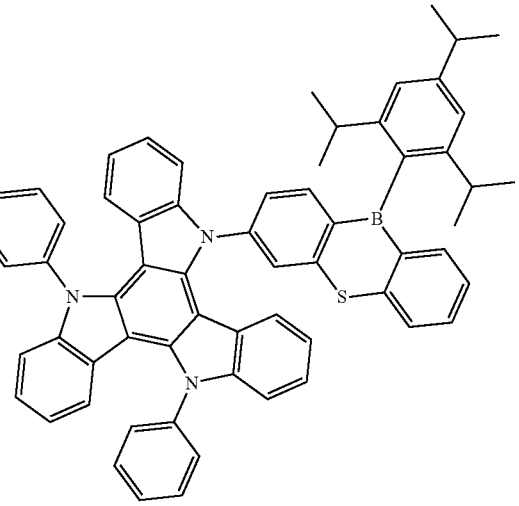
15
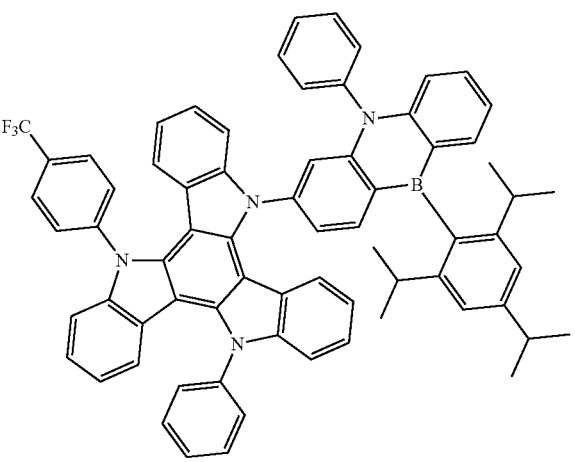
16
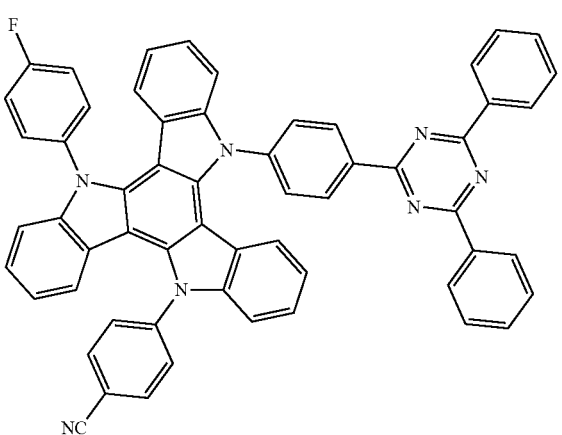

17
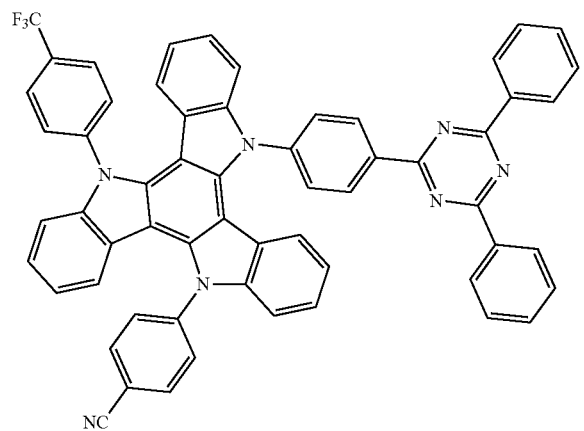
18
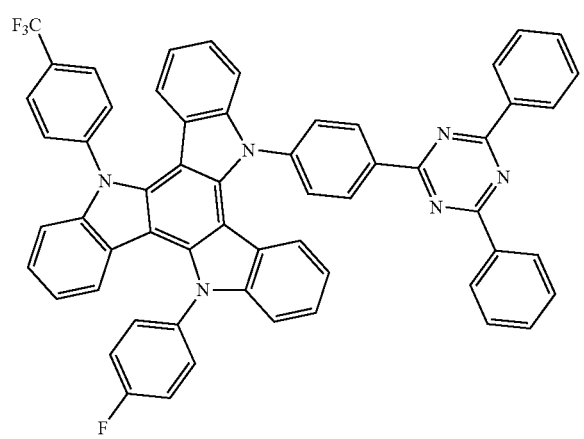
19
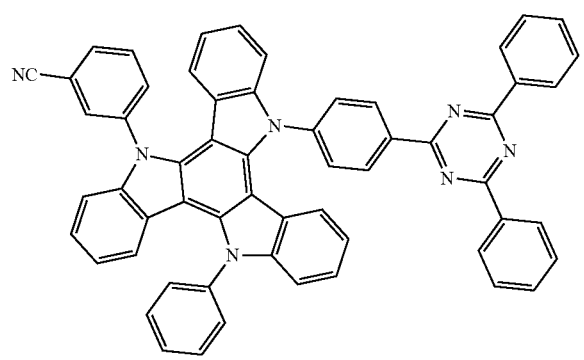
20
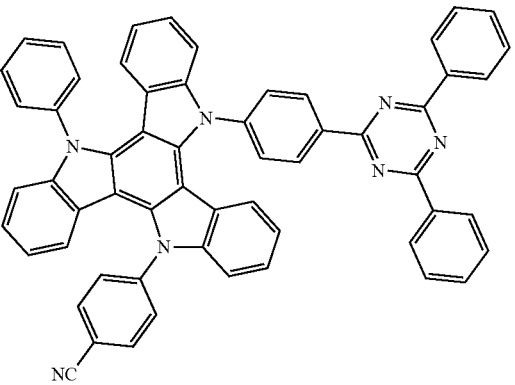
21
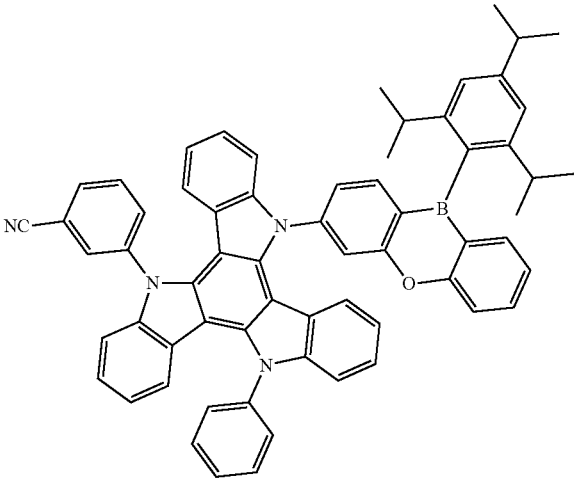
22
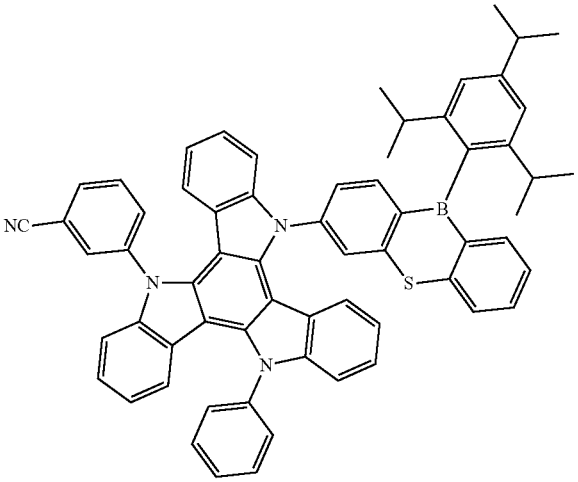

23
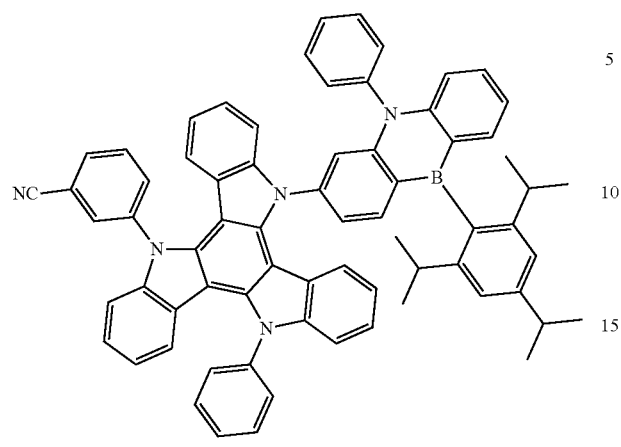
24
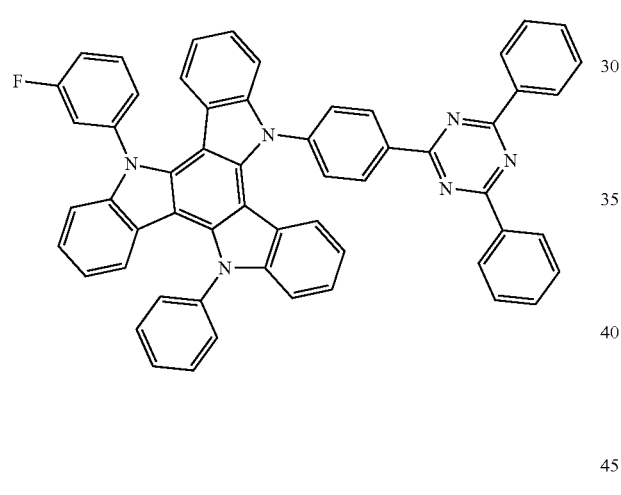
25
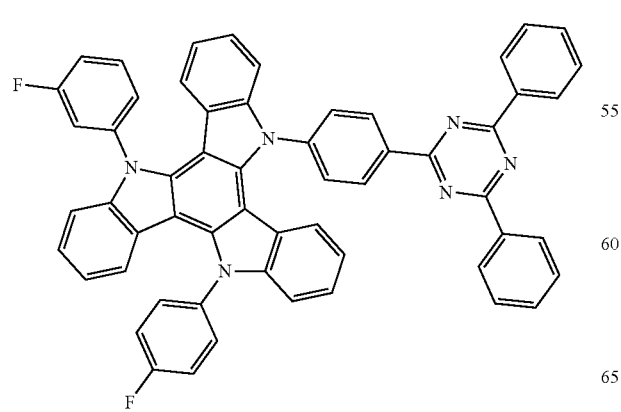
26
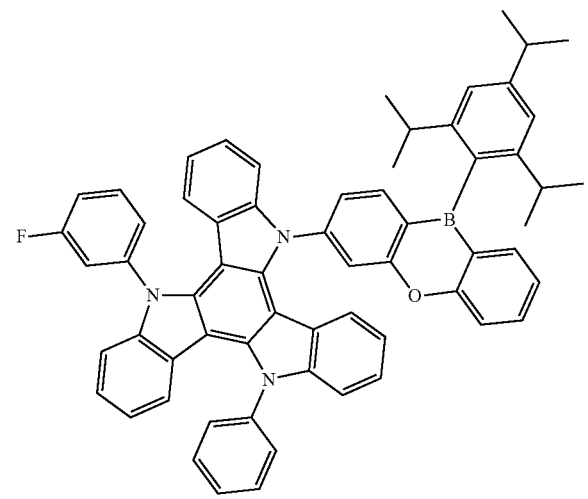
27
28

29
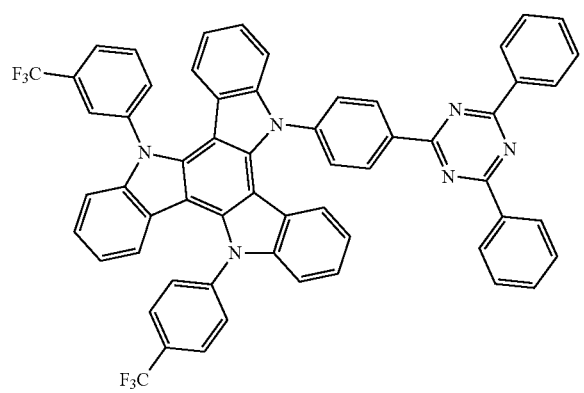
30
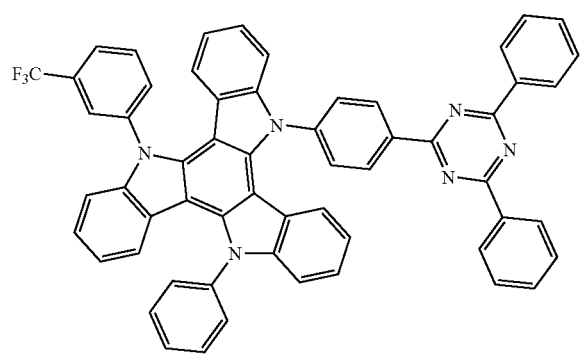
31
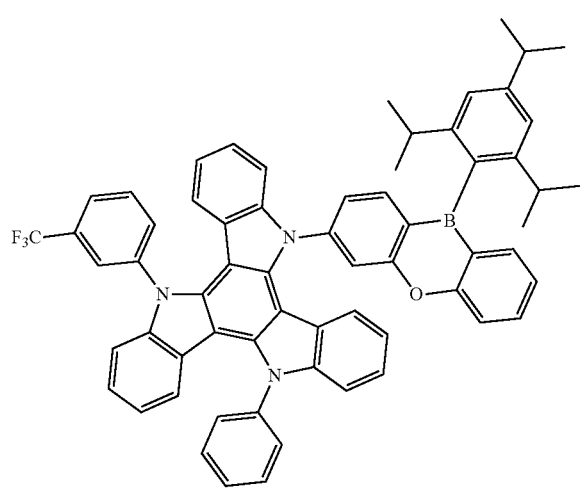
32
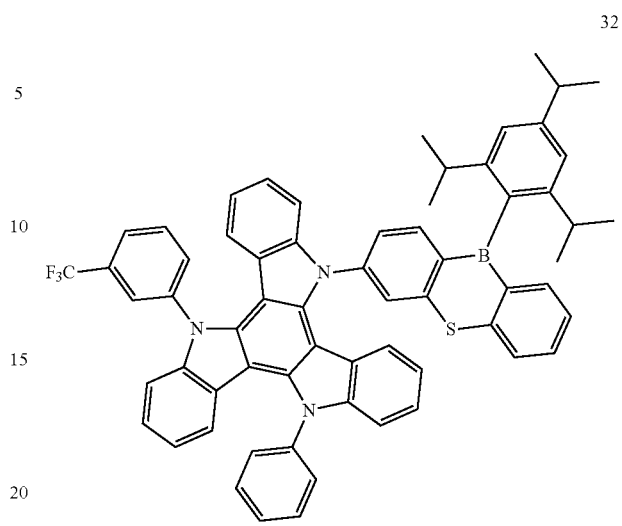
33
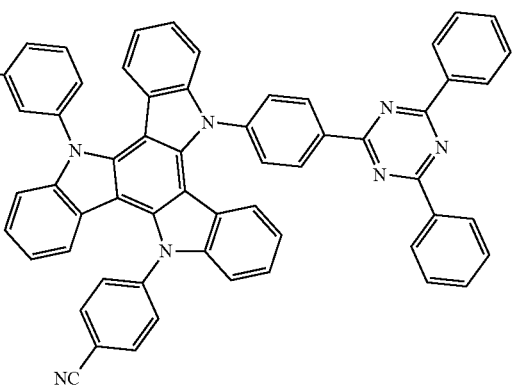
34

115
-continued
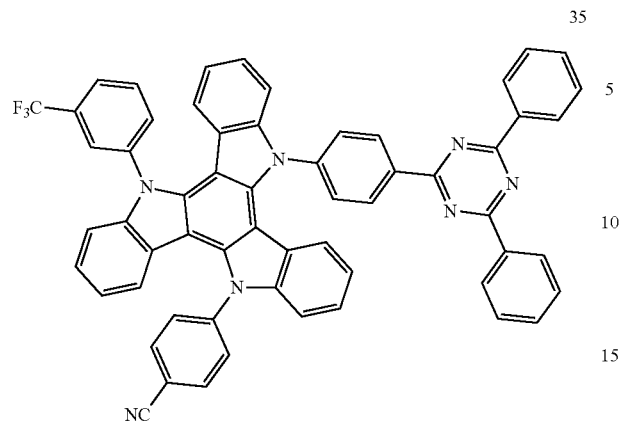
35
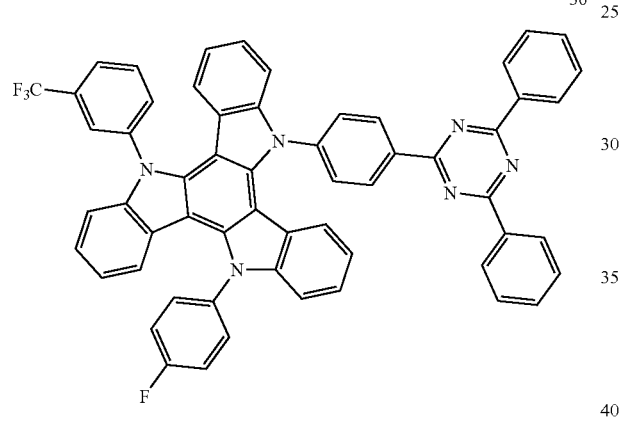
36
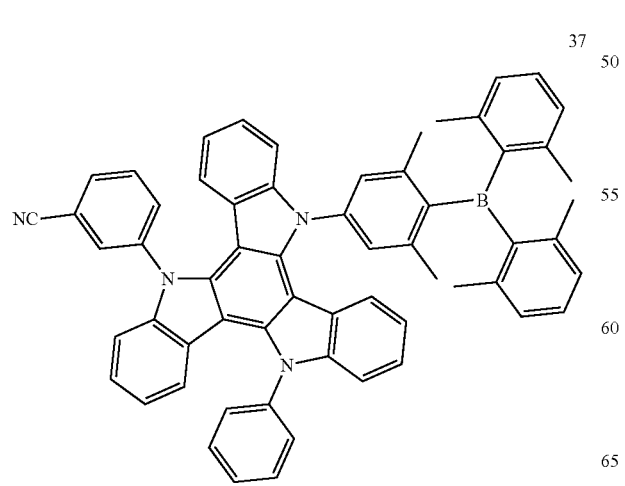
37
116
-continued
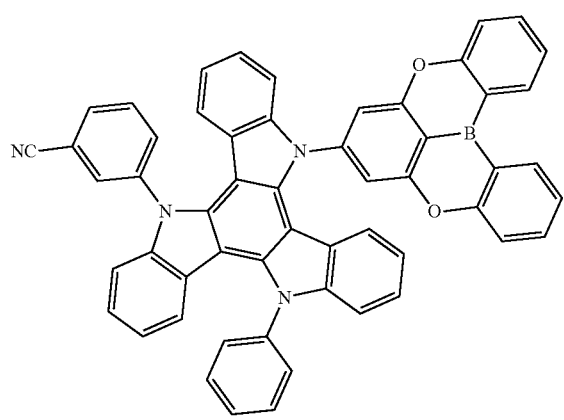
38
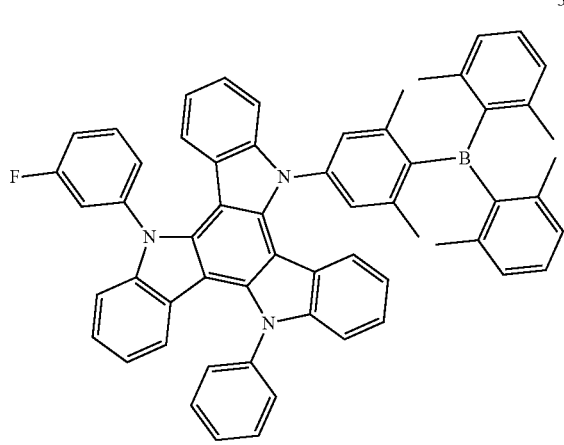
39
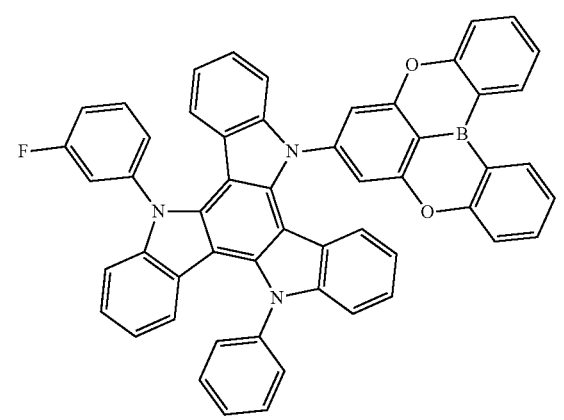
40

41

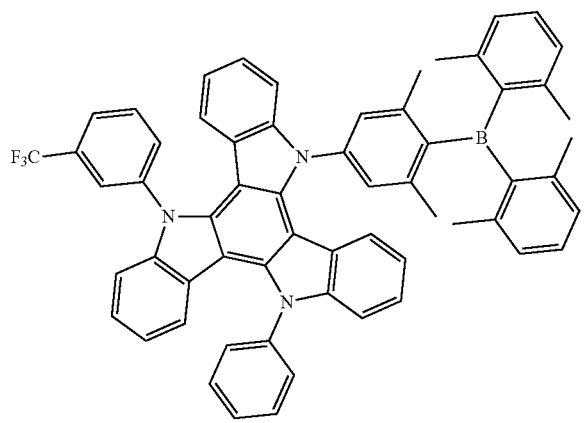

42

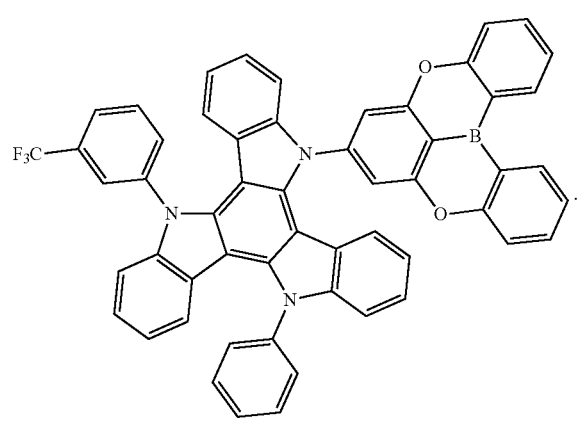

The polycyclic compound of an embodiment may be used as a blue emission material. For example, the polycyclic compound according to an embodiment may be used as a light-emitting material to emit blue light having a light-emitting central wavelength (λmax) in a wavelength region of about 470 nm or less. For example, the polycyclic compound of an embodiment may be a light-emitting material having a light-emitting central wavelength in a wavelength region of about 430 nm to about 470 nm. The polycyclic compound of an embodiment, represented by Formula 1 may be a blue thermally activated delayed fluorescence dopant. However, an embodiment of the present disclosure is not limited thereto.

In the organic electroluminescence device 10 of an embodiment, the emission layer EML may be to emit delayed fluorescence when the emission layer EML includes the polycyclic compound of an embodiment. For example, the emission layer EML may be to emit thermally activated delayed fluorescence (TADF).

In some embodiments, the organic electroluminescence device 10 of an embodiment may include a plurality of emission layers. The plurality of emission layers may be laminated one by one and provided. For example, the organic electroluminescence device 10 including a plurality of emission layers may be to emit white light. The organic electroluminescence device including the plurality of emission layers may be an organic electroluminescence device having a tandem structure. When the organic electroluminescence device 10 includes a plurality of emission layers, at least one emission layer EML may include the polycyclic compound of an embodiment.

In an embodiment, the emission layer EML includes a host and a dopant and may include the polycyclic compound of an embodiment as a dopant. For example, in the organic electroluminescence device 10 of an embodiment, the emission layer EML may include a host to emit delayed fluorescence and a dopant to emit delayed fluorescence and may include the polycyclic compound as a dopant to emit delayed fluorescence. The emission layer EML may include at least one among the polycyclic compounds represented in the Compound Group 1 as a thermally activated delayed fluorescence dopant.

In some embodiments, the emission layer EML may further include any suitable host material(s) and the above-described polycyclic compound.

For example, in an embodiment, the emission layer EML may include as a host material, tris(8-hydroxyquinolino) aluminum (Alq$_3$), 4,4'-bis(N-carbazolyl)-1,1'-biphenyl (CBP), poly(N-vinyl carbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2''-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzo[b,d]furan (PPF), 3,3'-bis(N-carbazolyl)-1,1'-biphenyl (mCBP), 1,3-bis(N-carbazolyl)benzene (mCP), etc. However, an embodiment of the present disclosure is not limited thereto. Any suitable host material(s) to emit delayed fluorescence other than the above host materials may be included.

In the organic electroluminescence device 10 of an embodiment, the emission layer EML may further include any suitable dopant material(s). In an embodiment, the emission layer EML may include as a dopant, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBP)), pyrene and derivatives thereof (for example, 1,1-dipyrene, 1,4-dipyrenylbenzene, 1,4-bis(N,N-diphenylamino)pyrene), etc.

In the organic electroluminescence device 10 of an embodiment, as shown in FIGS. 1 to 4, the electron transport region ETR is provided on the emission layer EML. The electron transport region ETR may include at least one of an hole blocking layer HBL, an electron transport layer ETL, or an electron injection layer EIL. However, an embodiment of the present disclosure is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL, without limitation. The thickness of the electron transport region ETR may be, for example, about 1,000 Å to about 1,500 Å.

The electron transport region ETR may be formed using one or more suitable methods (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazolyl-1-ylphenyl)-9,10-dinaphthylanthracene, 1,3,5-tri(1-phenyl-1H-benz[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate (Bebq2), 9,10-di(naphthalene-2-yl)anthracene (ADN), 1,3-bis[3,5-di(pyridine-3-yl)phenyl]benzene (BmPyPhB), or a mixture thereof, without limitation. The thickness of the electron transport layer ETL may be about 100 Å to about 1,000 Å and may be, for example, about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include a metal halide (such as LiF, NaCl, CsF, RbCl and/or RbI), a lanthanide metal (such as ytterbium (Yb), a metal oxide (such as $Li_2O$ and/or BaO), or 8-hydroxyquinolinato-lithium (LiQ). However, an embodiment of the present disclosure is not limited thereto. The electron injection layer EIL may be formed using a mixture material of an electron transport material and an insulating organo metal salt. The organo metal salt may be a material having an energy band gap of about 4 eV or more. The organo metal salt may include, for example, one or more metal acetates, metal benzoates, metal acetoacetates, metal acetylacetonates, and/or metal stearates. The thickness of the electron injection layer EIL may be about 1 Å to about 100 Å, or about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the present disclosure is not limited thereto.

The second electrode EL2 is provided on the electron transport region ETR. The second electrode EL2 may be a common electrode and/or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

On the second electrode EL2 of the organic electroluminescence device 10 of an embodiment, a capping layer CPL may be further disposed. The capping layer CPL may include, for example, α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol-9-yl) triphenylamine (TCTA), etc.

The organic electroluminescence device 10 according to an embodiment of the present disclosure may include the polycyclic compound of an embodiment in at least one functional layer disposed between the first electrode EL1 and the second electrode EL2. For example, the organic electroluminescence device 10 according to an embodiment of the present disclosure includes the polycyclic compound of an embodiment in the emission layer EML, thereby showing excellent emission efficiency in a light-emitting wavelength region of blue light. In some embodiments, the polycyclic compound according to an embodiment may be used as a thermally activated delayed fluorescence emitting material, and the emission layer EML may show high emission efficiency properties via thermally activated delayed fluorescence emission by including the polycyclic compound of an embodiment.

In some embodiments, the polycyclic compound of an embodiment may be included in an organic layer other than the emission layer EML as a material for the organic electroluminescence device 10. For example, the organic electroluminescence device 10 according to an embodiment of the present disclosure may include the polycyclic compound in at least one functional layer disposed between the first electrode EL1 and the second electrode EL2, or in the capping layer (CPL) disposed on the second electrode EL2.

Hereinafter, the polycyclic compound according to an embodiment and the organic electroluminescence device of an embodiment of the present disclosure will be explained in more detail with reference to embodiments and comparative embodiments. The following embodiments are only illustrations to assist the understanding of the present disclosure, and the scope of the present disclosure is not limited thereto.

EXAMPLES

1. Synthesis of Polycyclic Compound of an Embodiment

Synthesis of Compounds 1, 3, 4, and 5

Reaction 1-1

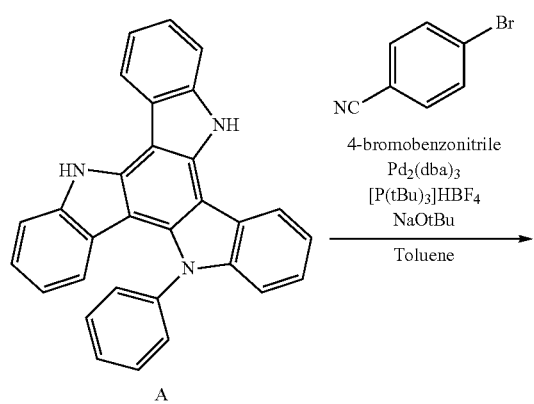

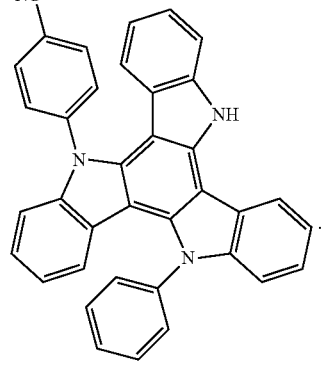

Intermediate 1

Compound A (synthesized by the method for Sub 1-1 described in patent document WO2018131877, the entire content of which is hereby incorporated by reference) (20.0 g, 47.5 mmol), 4-bromobenzonitrile (9.50 g, 52.2 mmol), bis (dibenzylidene acetone) palladium(0) (Pd(dba)$_2$, 0.87 g, 0.95 mmol), tri-tert-butyl phosphonium tetrafluoroborate (P(t-Bu)$_3$HBF$_4$), 1.10 g, 3.80 mmol), and sodium tert-butoxide (NaOt-Bu, 6.85 g, 71.3 mmol) were added to toluene (1.2 L), and the mixture was heated and stirred at 80° C. for 2 hours. Then, water was added, the mixture was separated by filtration through Celite, and then the organic layer was concentrated. The product was purified by silica gel column chromatography to obtain Intermediate Compound 1 (21.0 g, yield 85%). The molecular weight measured by FAB-MS is m/z=523 (M$^+$+1).

Reaction 1-2

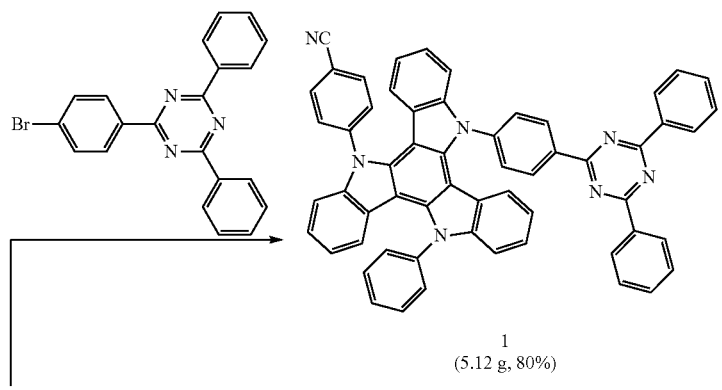

1
(5.12 g, 80%)

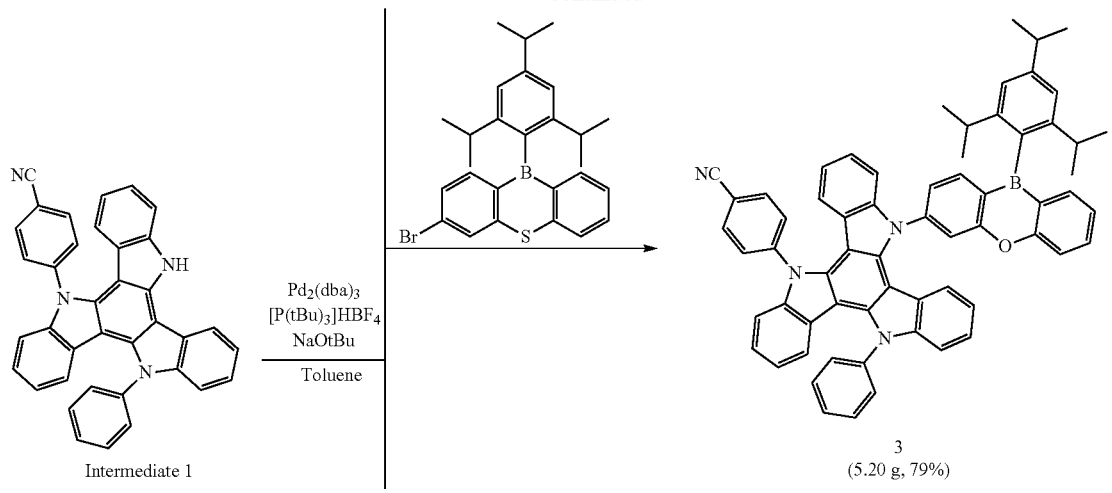
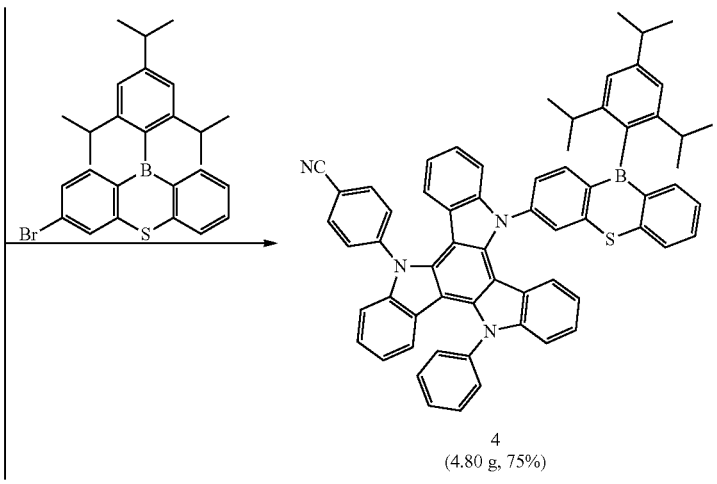
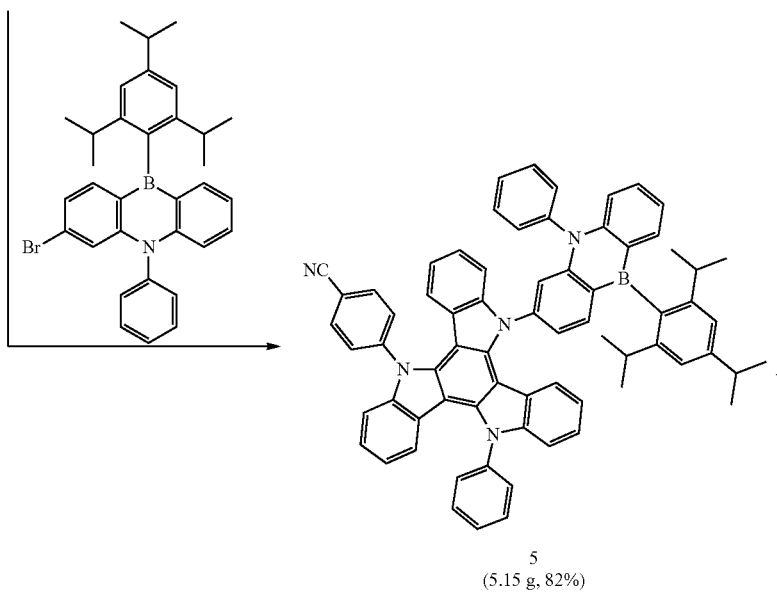

Additional reactions using Intermediate Compound 1 were carried out under substantially the same conditions as described above, and Compounds 1, 3, 4, and 5 were synthesized. The yields and weights of the synthesized compounds are described in the synthetic scheme disclosed in Reaction 1-2 above.

Synthesis of Compound 2

Reaction 2-1

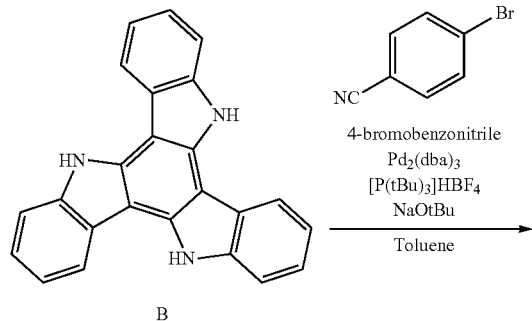

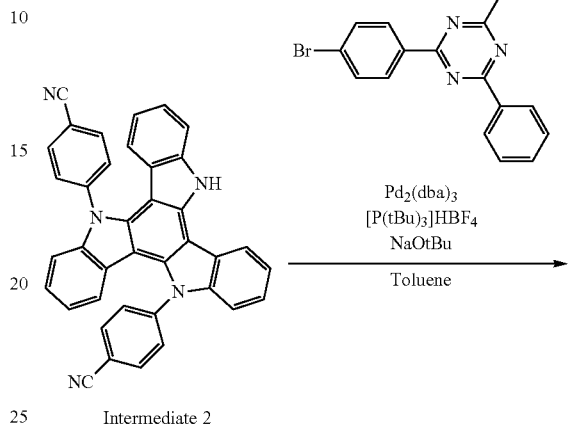

Intermediate 2

Reaction 2-2

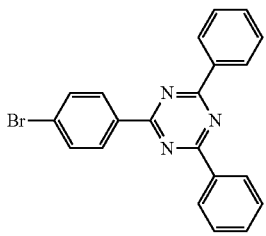

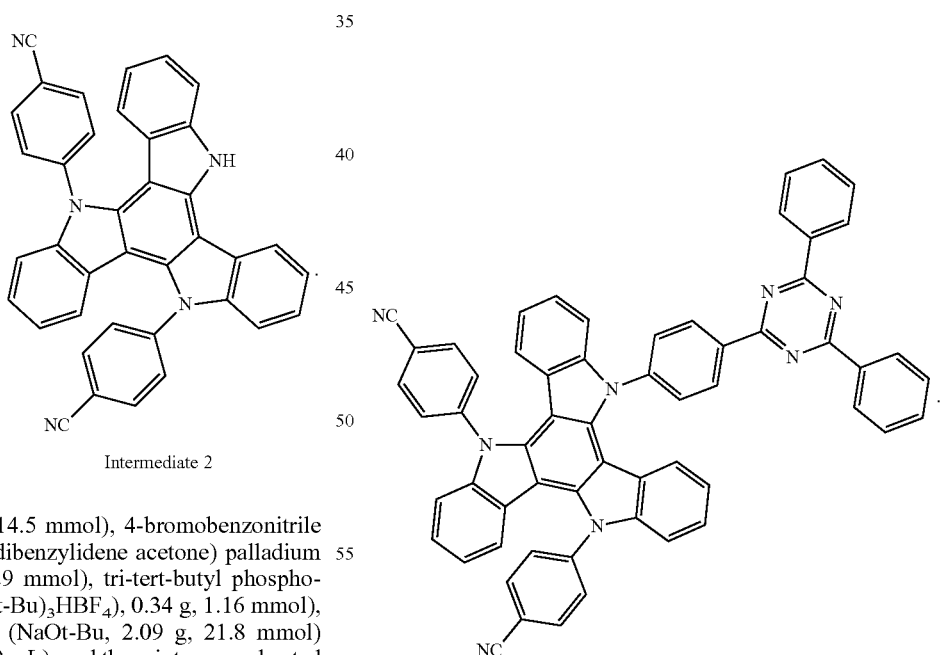

2

Compound B (5.00 g, 14.5 mmol), 4-bromobenzonitrile (5.81 g, 31.9 mmol), bis(dibenzylidene acetone) palladium (0) (Pd(dba)$_2$, 0.27 g, 0.29 mmol), tri-tert-butyl phosphonium tetrafluoroborate (P(t-Bu)$_3$HBF$_4$), 0.34 g, 1.16 mmol), and sodium tert-butoxide (NaOt-Bu, 2.09 g, 21.8 mmol) were added to toluene (200 mL), and the mixture was heated and stirred at 80° C. for 2 hours. Then, water was added, the mixture was separated by filtration through Celite, and then the organic layer was concentrated. Purified by silica gel column chromatography to obtain Intermediate Compound 2 (5.56 g, yield 70%). The molecular weight measured by FAB-MS is m/z=548 (M$^+$+1). Compound B was purchased from Tokyo Chemical Industry Co., Ltd. and used for synthesis.

Another reaction was carried out under substantially the same conditions as described above to provide Compound 2 (5.11 g, yield 89%). The molecular weight measured by FAB-MS is m/z=855 (M$^+$+1).

Synthesis of Compounds 6, 8, 9, and 10

Reaction 3-1

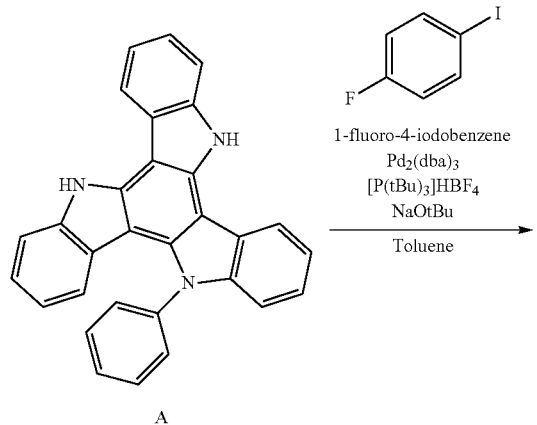

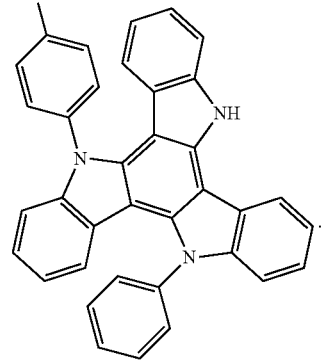

Intermediate 3

Compound A (20.0 g, 47.5 mmol), 1-fluoro-4-iodobenzene (11.6 g, 52.2 mmol), bis(dibenzylidene acetone) palladium(0) (Pd(dba)$_2$, 0.87 g, 0.95 mmol), tri-tert-butyl phosphonium tetrafluoroborate (P(t-Bu)$_3$HBF$_4$), 1.10 g, 3.80 mmol), and sodium tert-butoxide (NaOt-Bu, 6.85 g, 71.3 mmol) were added to toluene (1.2 L), and the mixture was heated and stirred at 80° C. for 2 hours. Then, water was added, the mixture was separated by filtration through Celite, and the organic layer was concentrated and purified by silica gel column chromatography to obtain Intermediate Compound 3 (20.1 g, yield 82%). The molecular weight measured by FAB-MS is m/z=517 (M$^+$+1).

Reaction 3-2

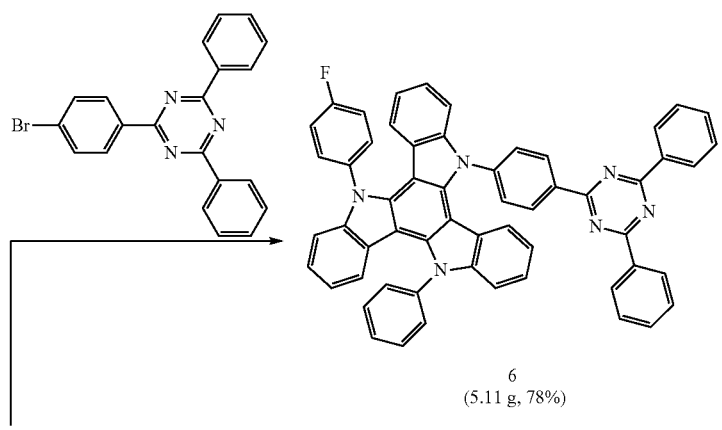

6
(5.11 g, 78%)

-continued
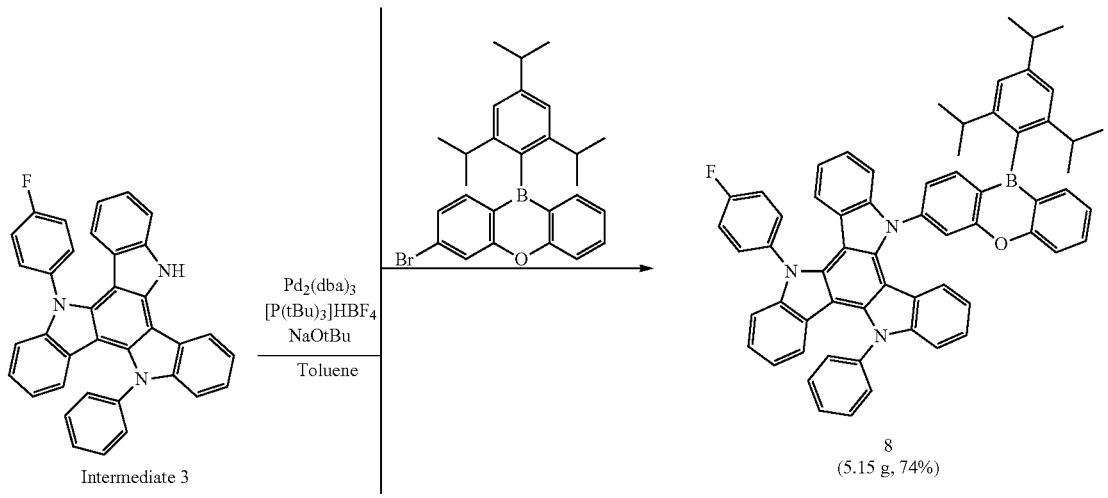
8
(5.15 g, 74%)
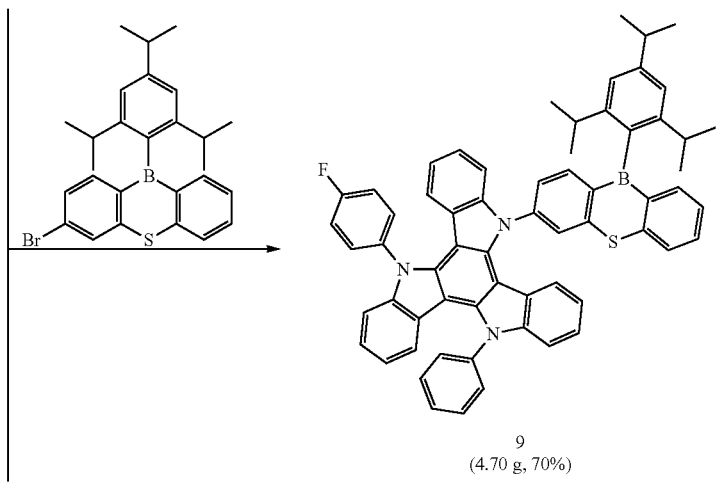
9
(4.70 g, 70%)
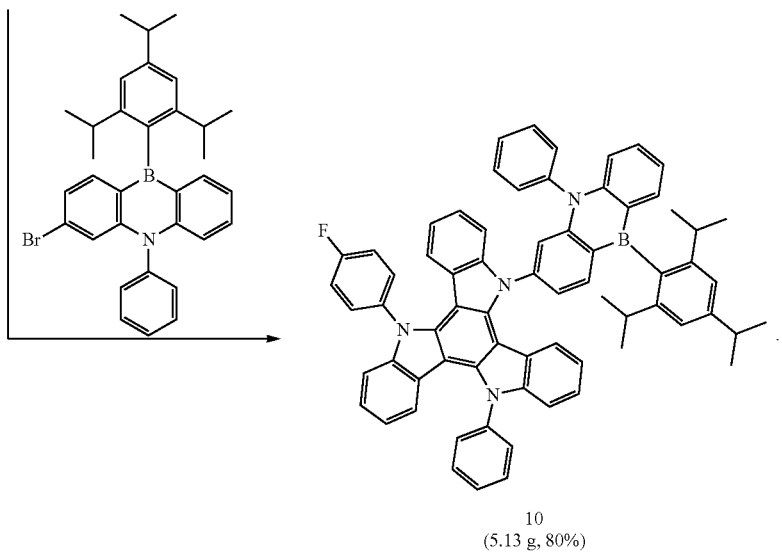
10
(5.13 g, 80%)

The reactions were carried out under substantially the same conditions as described above to provide Compounds 6, 8, 9, and 10. The yields and weights of the synthesized compounds are described in the synthetic scheme disclosed in Reaction 3-2.

Synthesis of Compound 7

Reaction 4-1

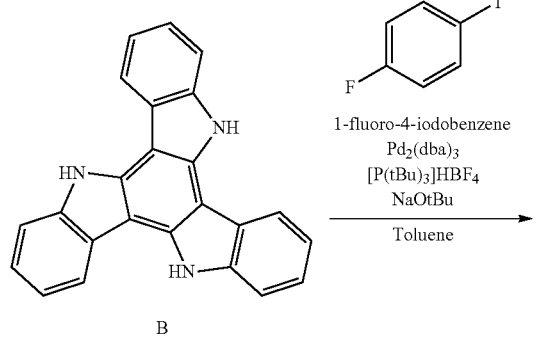

B

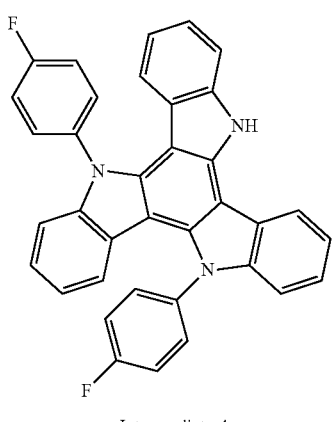

Intermediate 4

Compound B (5.00 g, 14.5 mmol), 1-fluoro-4-iodobenzene (7.08 g, 31.9 mmol), bis(dibenzylidene acetone) palladium(0) (Pd(dba)$_2$, 0.87 g, 0.95 mmol), tri-tert-butyl phosphonium tetrafluoroborate (P(t-Bu)$_3$HBF$_4$), 1.10 g, 3.80 mmol), and sodium tert-butoxide (NaOt-Bu, 6.85 g, 71.3 mmol) were added to toluene (1.2 L), and the mixture was heated and stirred at 80° C. for 2 hours. Then, water was added, the mixture was separated by filtration through Celite, and then the organic layer was concentrated and purified by silica gel column chromatography to obtain Intermediate Compound 4 (6.18 g, yield 80%). The molecular weight measured by FAB-MS is m/z=534 (M$^+$+1).

Reaction 4-2

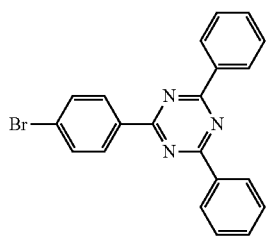

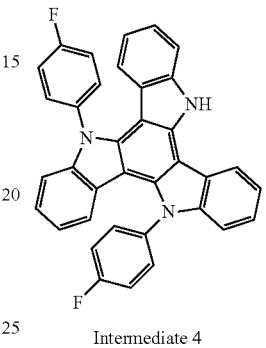

Intermediate 4

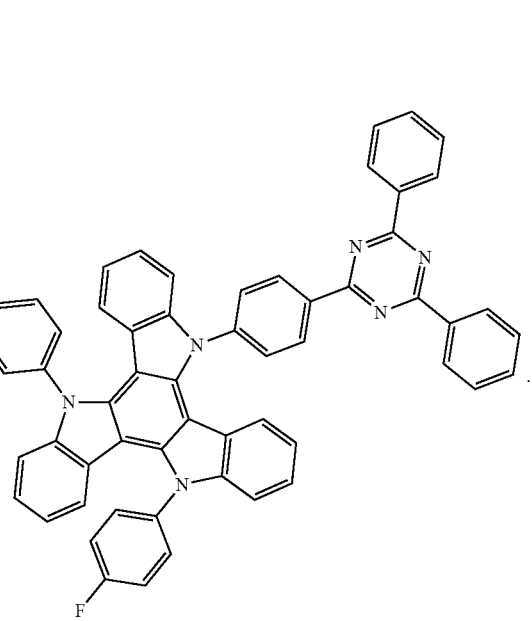

7

Another reaction was carried out under substantially the same conditions as described above to provide Compound 7 (5.12 g, yield 79%). The molecular weight measured by FAB-MS is m/z=841 (M$^+$+1).

Synthesis of Compounds 12, 13, 14, and 15

Reaction 5-1

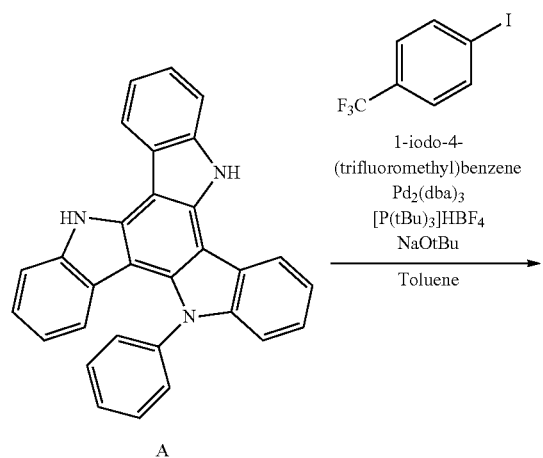

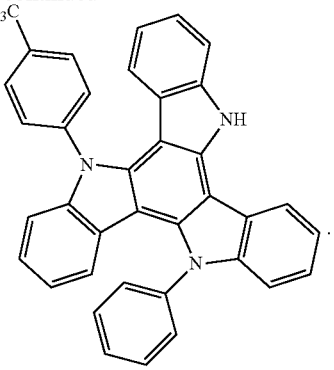

Intermediate 5

Compound A (20.0 g, 47.5 mmol), 1-iodo-4-(trifluoromethyl)benzene (14.2 g, 52.2 mmol), bis(dibenzylidene acetone) palladium(0) (Pd(dba)$_2$, 0.87 g, 0.95 mmol), tri-tert-butyl phosphonium tetrafluoroborate (P(t-Bu)$_3$HBF$_4$, 1.10 g, 3.80 mmol), and sodium tert-butoxide (NaOt-Bu, 6.85 g, 71.3 mmol) were added to toluene (1.2 L), and the mixture was heated and stirred at 80° C. for 2 hours. Then, water was added, the mixture was separated by filtration through Celite, and then the organic layer was concentrated and purified by silica gel column chromatography to obtain Intermediate Compound 5 (20.1 g, yield 78%). The molecular weight measured by FAB-MS is m/z=566 (M$^+$+1).

Reaction 5-2

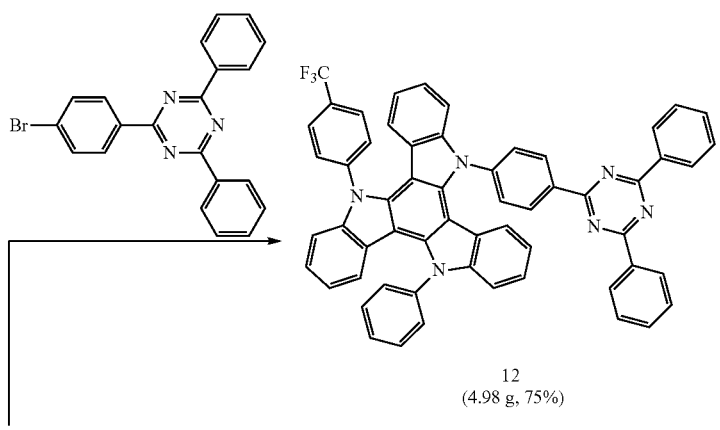

12
(4.98 g, 75%)

-continued
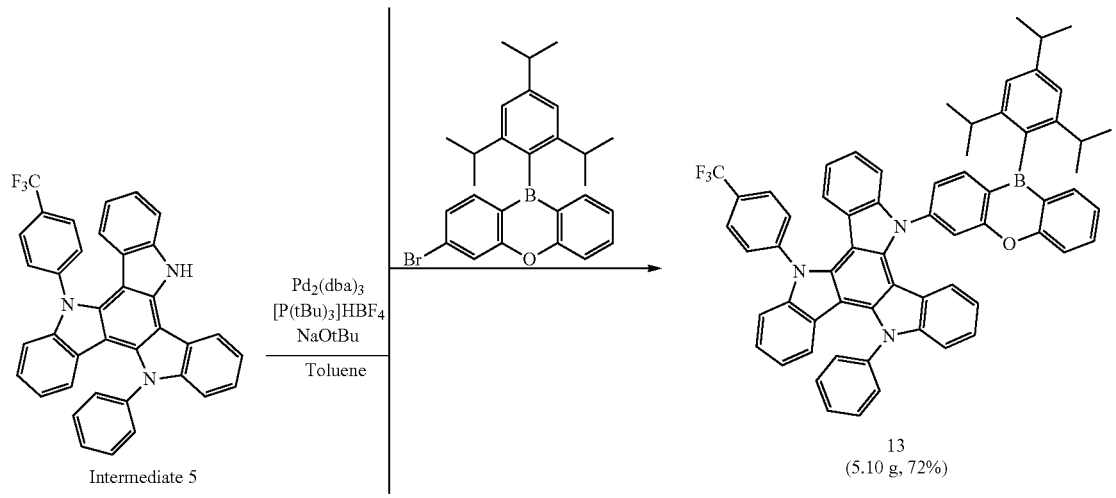
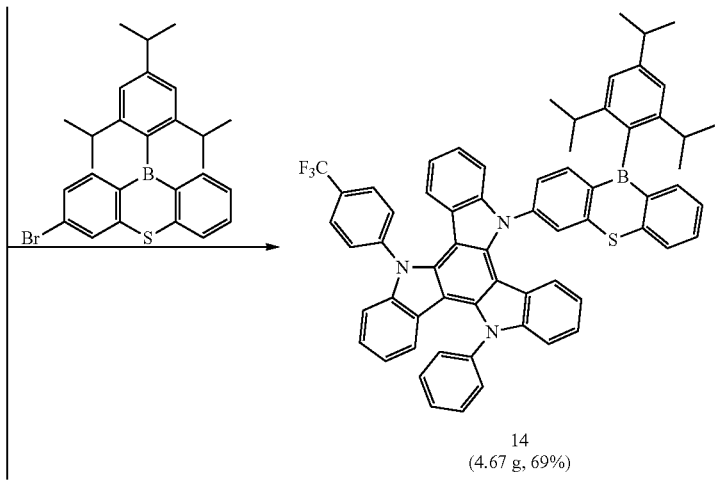
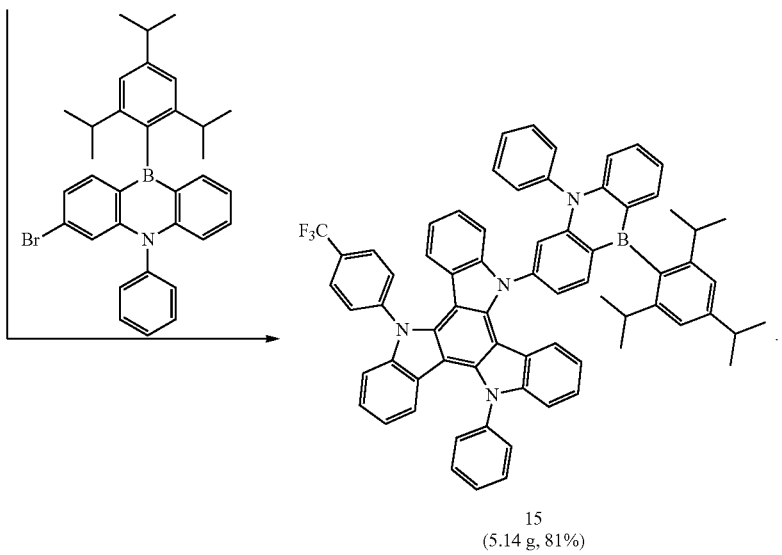

Additional reactions were carried out under substantially the same conditions as described above to provide Compounds 12, 13, 14, and 15. The yields and weights of the synthesized compounds are described in the synthetic scheme disclosed in the Reaction 5-2 above.

Synthesis of Compound 11

Reaction 6-1

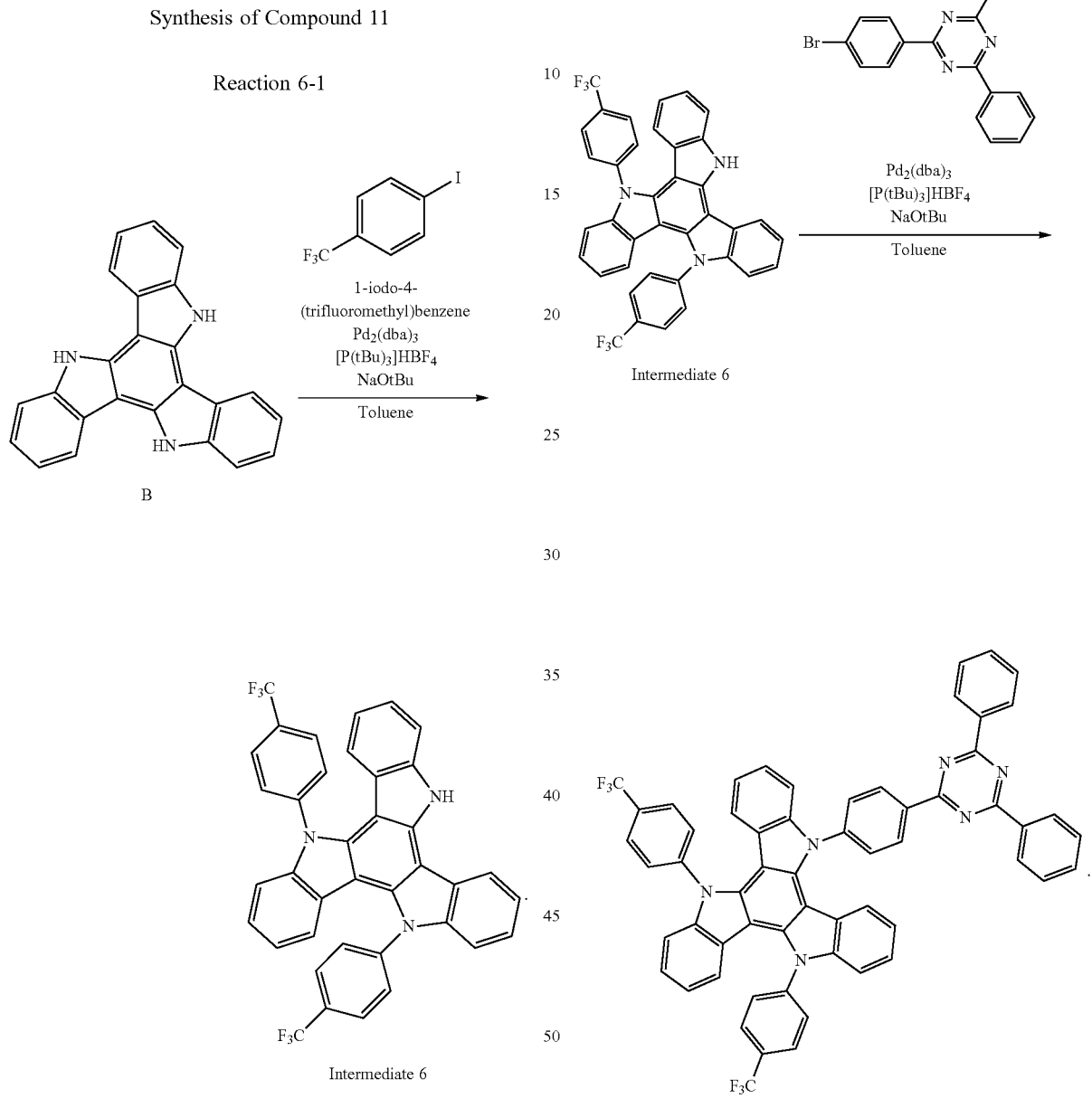

Compound B (5.00 g, 14.5 mmol), 1-iodo-4-(trifluoromethyl)benzene (8.67 g, 31.9 mmol), bis(dibenzylidene acetone) palladium(0) (Pd(dba)$_2$, 0.87 g, 0.95 mmol), tri-tert-butyl phosphonium tetrafluoroborate (P(t-Bu)$_3$HBF$_4$), 1.10 g, 3.80 mmol), and sodium tert-butoxide (NaOt-Bu, 6.85 g, 71.3 mmol) were added to toluene (1.2 L), and the mixture was heated and stirred at 80° C. for 2 hours. Then, water was added, the mixture was separated by filtration through Celite, and then the organic layer was concentrated and purified by silica gel column chromatography to obtain Intermediate Compound 6 (6.88 g, yield 80%). The molecular weight measured by FAB-MS is m/z=634 (M$^+$+1).

Reaction 6-2

Another reaction was carried out under substantially the same conditions as described above, and Compound 11 (6.12 g, yield 81%). The molecular weight measured by FAB-MS is m/z=942 (M$^+$+1).

2. Evaluation of Polycyclic Compound

Luminescence properties of the polycyclic compounds of the Examples and the compounds of the Comparative Examples were evaluated. The compounds of the Examples and the Comparative Examples used in the evaluation of luminescence properties are as follows.

Compounds of Examples
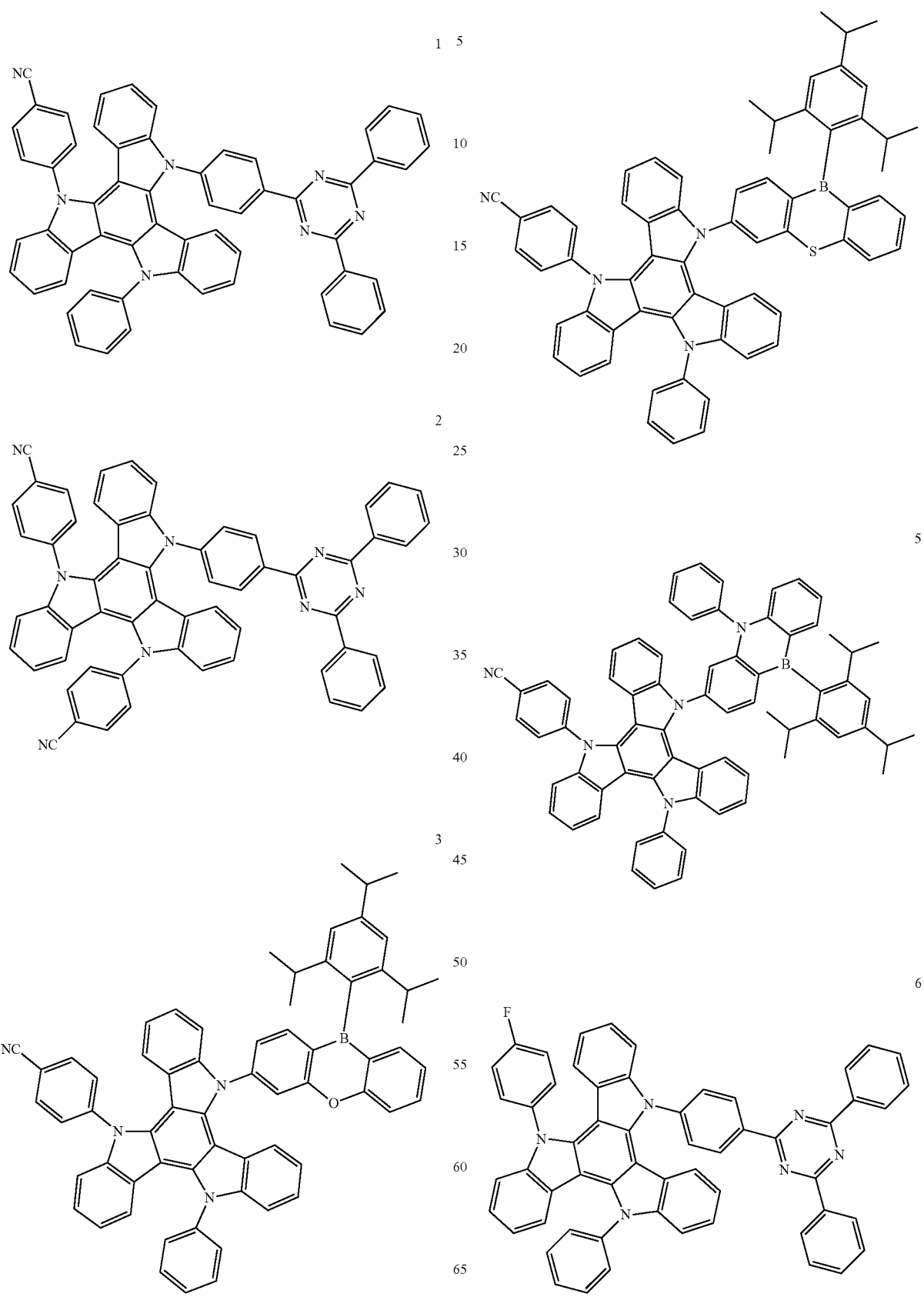

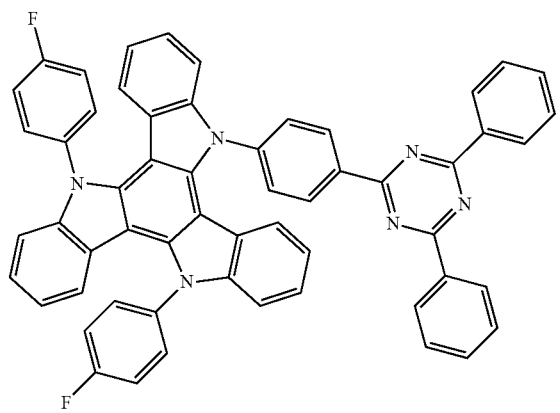
7
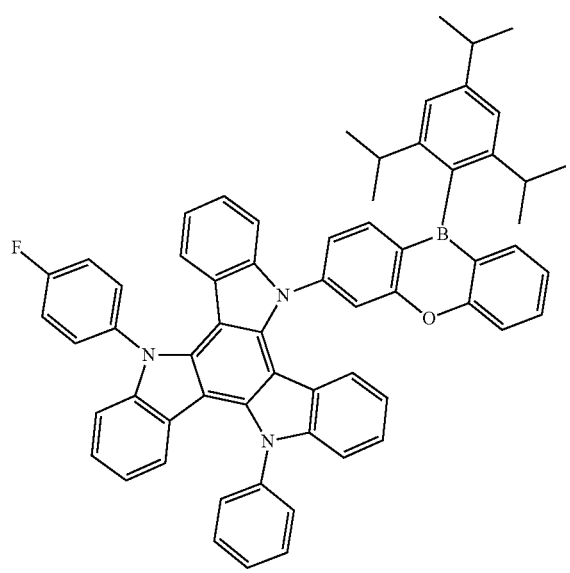
8
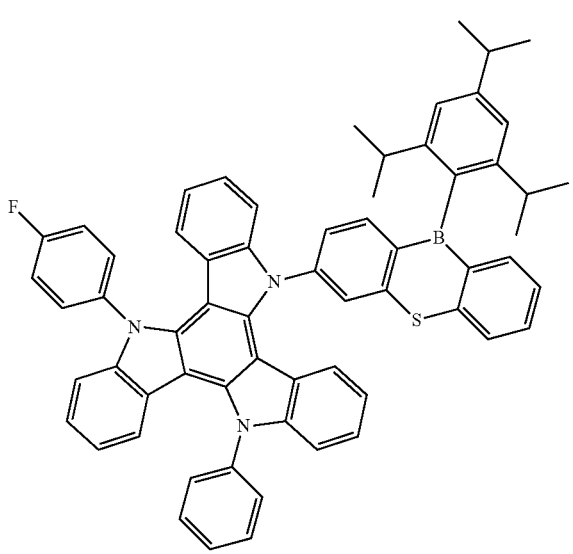
9
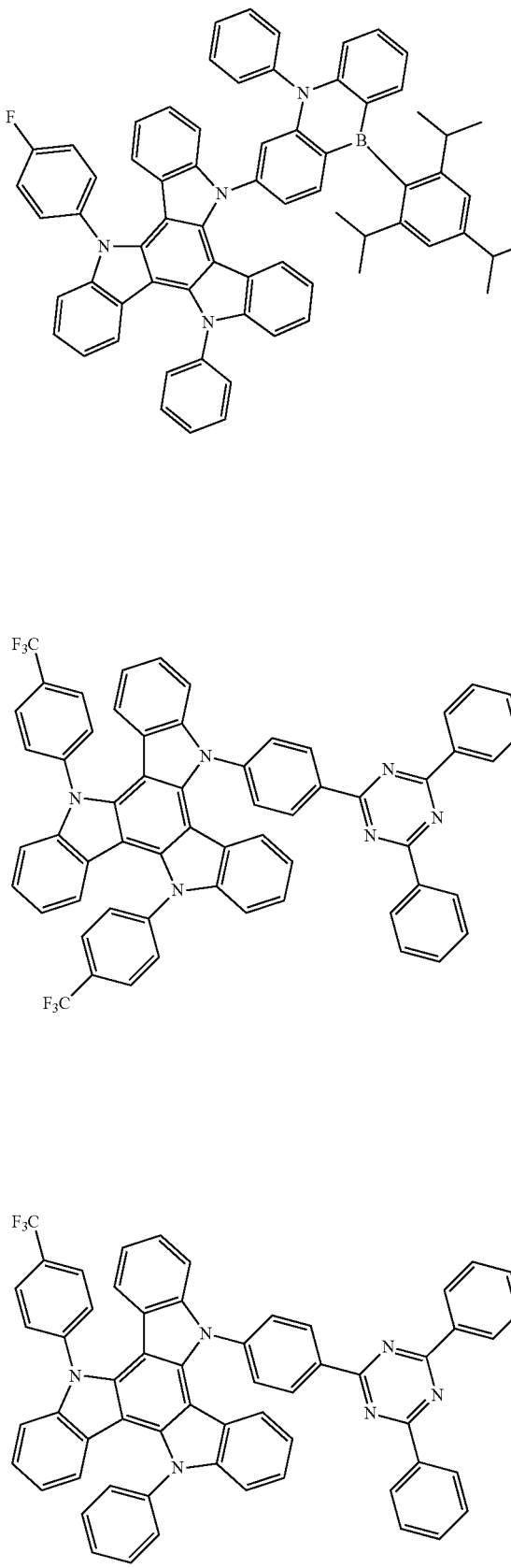

-continued
13
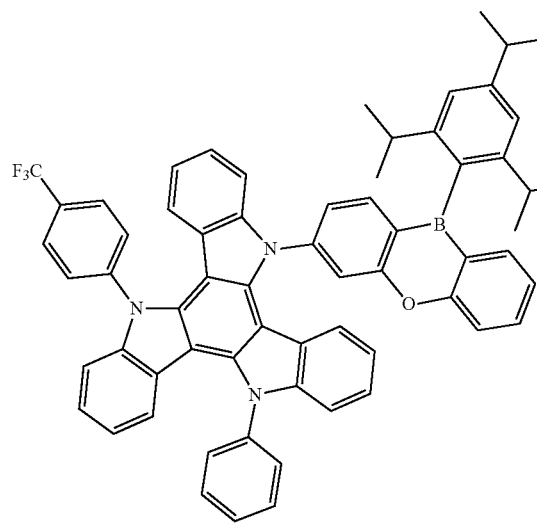
14
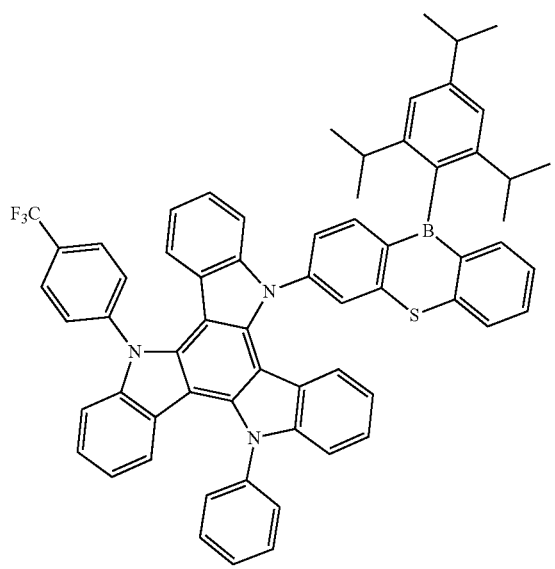
15
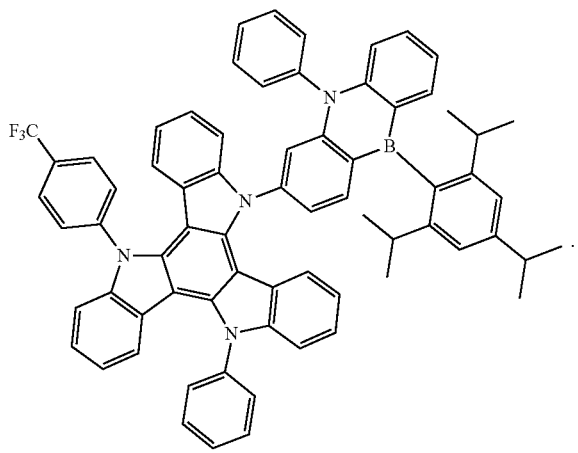
Compounds of Comparative Examples
X-1
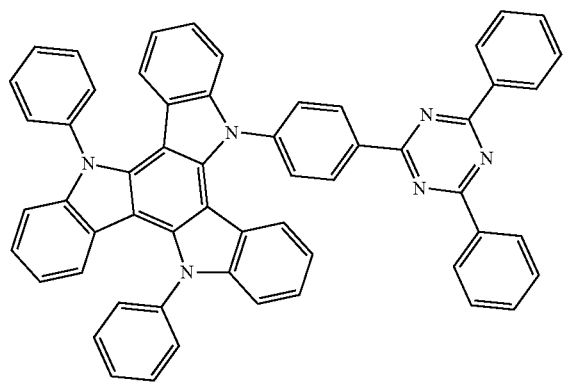
X-2
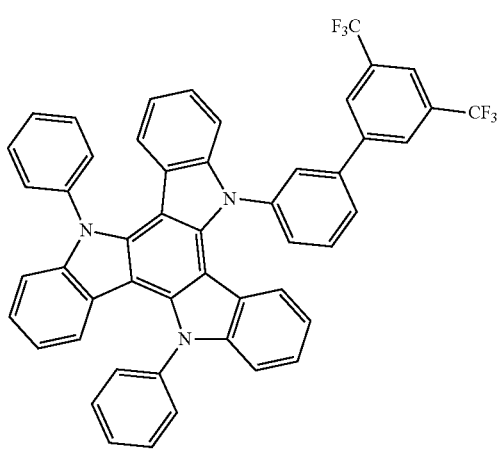
X-3
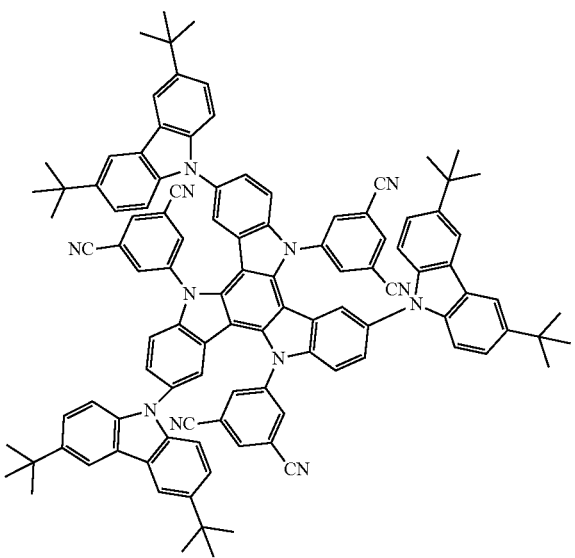

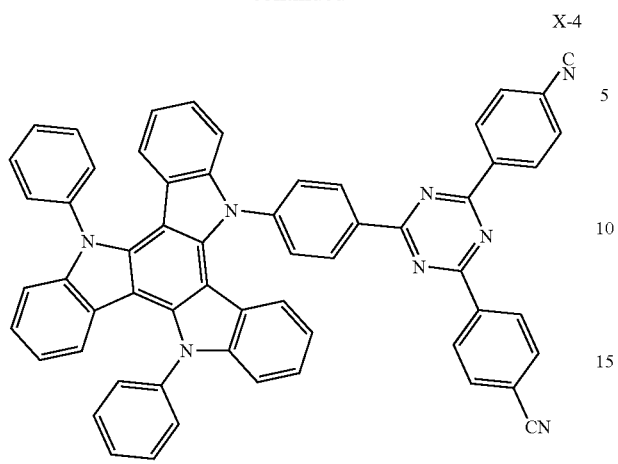

X-4

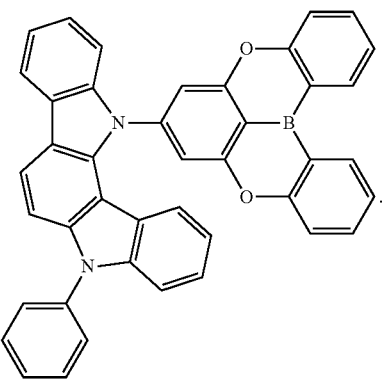

X-8

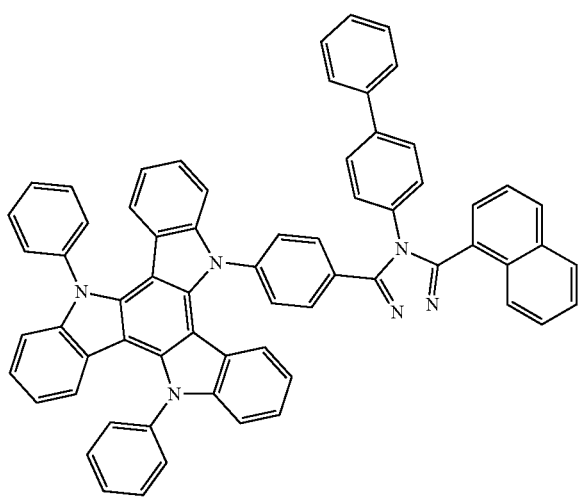

X-5

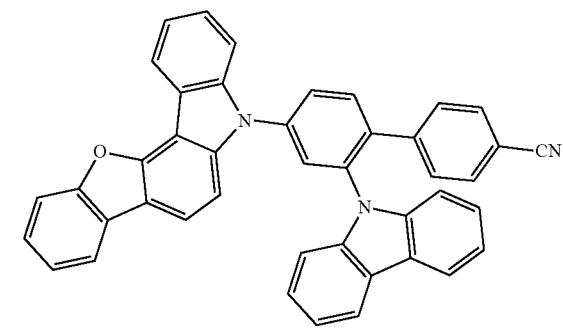

X-6

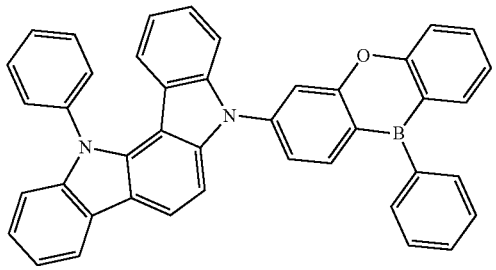

X-7

Evaluation of Luminescence Properties of Compounds

Toluene solutions of 5.0 mM were prepared as compounds of Examples and Comparative Examples, and luminescence properties were evaluated using a JASCO V-670 spectrometer. The luminescence spectrum at room temperature (e.g., about 298K) and 77K were measured. Table 1 shows the maximum emission wavelength $\lambda_{max}$ in the emission spectrum measured at room temperature and the full width at half maximum (FWHM) in the emission spectrum. In addition, the photoluminescent quantum yield (PLQY) of 5.0 mM toluene solutions were measured using a HAMAMATSU Quantaurus-QY.

TABLE 1

| Compound | $\lambda_{max}$ (nm) | FWHM (nm) | PLQY (%) |
|---|---|---|---|
| Compound 1 | 465 | 70 | 85 |
| Compound 2 | 460 | 65 | 79 |
| Compound 3 | 450 | 59 | 82 |
| Compound 4 | 455 | 55 | 83 |
| Compound 5 | 460 | 63 | 78 |
| Compound 6 | 464 | 65 | 79 |
| Compound 7 | 459 | 62 | 78 |
| Compound 8 | 449 | 55 | 80 |
| Compound 9 | 453 | 60 | 79 |
| Compound 10 | 450 | 56 | 82 |
| Compound 11 | 449 | 55 | 83 |
| Compound 12 | 450 | 58 | 78 |
| Compound 13 | 440 | 59 | 79 |
| Compound 14 | 445 | 60 | 78 |
| Compound 15 | 450 | 58 | 75 |
| Comparative Compound X-1 | 522 | 78 | 89 |
| Comparative Compound X-2 | 472 | 72 | 60 |
| Comparative Compound X-3 | 630 | 82 | 80 |
| Comparative Compound X-4 | 550 | 78 | 81 |
| Comparative Compound X-5 | 490 | 72 | 61 |
| Comparative Compound X-6 | 472 | 70 | 80 |
| Comparative Compound X-7 | 440 | 69 | 82 |
| Comparative Compound X-8 | 450 | 68 | 78 |

Referring to the results in Table 1, it can be seen that the Example polycyclic Compounds 1 to 15 each exhibit a maximum emission wavelength of 470 nm or less and therefore emit deep blue light. In comparison, the Comparative Compounds emit light having a relatively long wavelength compared to the Example Compounds. It can be seen from the evaluation of the luminescence properties of the compounds shown in Table 1 that the polycyclic compounds of the Examples of the present invention emit light in a short wavelength region of 470 nm or less and exhibit good quantum efficiency properties.

3. Manufacture and Evaluation of Organic Electroluminescence Device

Manufacture of Organic Electroluminescence Device

On a glass substrate, ITO with a thickness of about 1,500 Å was patterned and washed with ultra-pure water, cleaned with ultrasonic waves, exposed to UV for about 30 minutes, and treated with ozone. Then, HAT-CN was deposited to a thickness of about 100 Å, α-NPD was deposited to about 800 Å, and mCP was deposited to a thickness of about 50 Å to form a hole transport region.

Then, the polycyclic compound of an embodiment or the Comparative Compound and a host material were co-deposited in a ratio of 1:99 to form an emission layer having a thickness of about 200 Å. The emission layer formed by the co-deposition was conducted by mixing Compound 1 to 15 with mCBP and depositing the mixture in the device of Example 1 to Example 15, respectively, or by mixing Comparative Compounds X-1 to X-8 with mCBP and depositing the mixture in the device of Comparative Example 1 to Comparative Example 8, respectively.

After that, on the emission layer, a layer with a thickness of about 300 Å was formed using TPBi, and a layer with a thickness of about 50 Å was formed using LiF to form an electron transport region. Then, a second electrode with a thickness of about 1,000 Å was formed using aluminum (Al).

The hole transport region, the emission layer, the electron transport region, and the second electrode were formed using a vacuum deposition apparatus.

Evaluation of Properties of Organic Electroluminescence Device

Table 2 shows the evaluation results for the organic electroluminescence devices of Example 1 to Example 15, and Comparative Example to Comparative Example 8. In the evaluation results of the Examples and Comparative Examples shown in Table 2, the maximum emission wavelength ($\lambda_{max}$) indicates the wavelength representing the maximum value in the emission spectrum, the external quantum efficiency ($EQE_{max}$) indicates the maximum value of the external quantum efficiency, and the $EQE_{max}$ (1000 nit) indicates the external quantum efficiency when a luminance of 1000 cd/m² is displayed.

TABLE 2

| Device Manufacturing Examples | Emission Layer Material | $\lambda_{max}$ (nm) | $EQE_{max}$ (%) | $EQE_{max}$ (1000 nit) (%) |
|---|---|---|---|---|
| Example 1 | Compound 1 | 466 | 23.5 | 22.9 |
| Example 2 | Compound 2 | 462 | 22.9 | 22.3 |
| Example 3 | Compound 3 | 452 | 22.0 | 21.4 |
| Example 4 | Compound 4 | 457 | 23.2 | 22.6 |
| Example 5 | Compound 5 | 462 | 23.4 | 22.8 |
| Example 6 | Compound 6 | 465 | 23.9 | 23.3 |
| Example 7 | Compound 7 | 460 | 23.2 | 22.6 |
| Example 8 | Compound 8 | 450 | 21.0 | 20.4 |
| Example 9 | Compound 9 | 454 | 22.0 | 21.4 |
| Example 10 | Compound 10 | 452 | 22.9 | 22.3 |
| Example 11 | Compound 11 | 450 | 20.9 | 20.2 |
| Example 12 | Compound 12 | 452 | 19.2 | 18.7 |
| Example 13 | Compound 13 | 441 | 16.7 | 16.3 |
| Example 14 | Compound 14 | 446 | 16.0 | 15.6 |
| Example 15 | Compound 15 | 452 | 20.9 | 20.1 |
| Comparative Example 1 | Comparative Compound X-1 | 523 | 15.3 | 14.7 |
| Comparative Example 2 | Comparative Compound X-2 | 474 | 11.2 | 10.5 |
| Comparative Example 3 | Comparative Compound X-3 | 630 | 5.2 | 3.2 |
| Comparative Example 4 | Comparative Compound X-4 | 552 | 15.0 | 13.8 |
| Comparative Example 5 | Comparative Compound X-5 | 492 | 5.1 | 3.8 |
| Comparative Example 6 | Comparative Compound X-6 | 474 | 8.9 | 7.2 |
| Comparative Example 7 | Comparative Compound X-7 | 445 | 9.8 | 7.8 |
| Comparative Example 8 | Comparative Compound X-8 | 453 | 8.9 | 7.2 |

Referring to the results in Table 2, it can be seen that the organic electroluminescence devices of Examples 1 to 15 emit short-wavelength deep blue light and exhibit high efficiency characteristics, compared to the organic electroluminescence devices of Comparative Examples 1 to 8.

The polycyclic compounds of the Examples each include at least one electron accepting group (such as a cyano group, a fluoro group, and/or a trifluoromethyl group) substituted on the core of a diindenocarbazole that is an electron donor, while the Comparative Example compounds do not. Without being bound by the correctness of any theory or explanation, it is believed that this enables the Examples to exhibit comparatively excellent luminous efficiency characteristics in a short wavelength region of 470 nm or less.

Examples 1 to 15 emit light in a short wavelength region and show improved luminous efficiency characteristics compared to Comparative Examples 1-6. For example, in the case of Comparative Examples 4 and 5, diindenocarbazole is included as in the electron donor of the Example Compounds, but the electron accepting group is not substituted and the Comparative compounds thus emit light in a long wavelength region compared to the Examples.

Comparative Examples 7 and 8 emit light in a short wavelength region of 470 nm or less, but exhibit decreased luminous efficiency compared to Examples 1 to 15.

Therefore, the organic electroluminescence device including the polycyclic compound of an embodiment may exhibit excellent luminous efficiency in a short wavelength region of 470 nm or less. The polycyclic compound of an embodiment includes a diindenocarbazole core as an electron donor, which includes an electron accepting group (such as a cyano group, a fluoro group, and/or a trifluoromethyl group) as at least one substituent.

In addition, the polycyclic compound of an embodiment may exhibit good quantum efficiency in a short wavelength region by having a structure including an electron donor and an electron accepting group (such as a cyano group, a fluoro group, and/or a trifluoromethyl group) as at least one substituent. The polycyclic compound includes a diindenocarbazole core as the electron donor. The polycyclic compound of an embodiment may be used as a thermally activated delayed fluorescent material.

Although example embodiments of the present invention have been described, it is understood that the present invention should not be limited to these example embodiments, and that various changes and modifications can be made by

What is claimed is:

1. An organic electroluminescence device, comprising:
a first electrode;
a second electrode on the first electrode; and
a plurality of functional layers between the first electrode and the second electrode,
wherein at least one functional layer of the plurality of functional layers comprises a polycyclic compound represented by Formula 1, and
wherein the first electrode and the second electrode each independently comprises at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, or an oxide thereof:

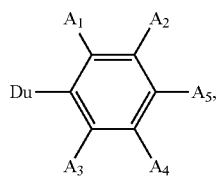

Formula 1 wherein in Formula 1,
$A_1$ to $A_5$ are each independently a hydrogen atom, a deuterium atom, a substituted or unsubstituted oxy group, a substituted or unsubstituted thio group, a substituted or unsubstituted thiocarbonyl group, a substituted or unsubstituted boryl group, a substituted or unsubstituted carbonyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or are combined with an adjacent group to form a fused heterocycle,
at least one of $A_1$ to $A_5$ or the fused heterocycle comprises an electron accepting group, and
"Du" is represented by Formula 2:

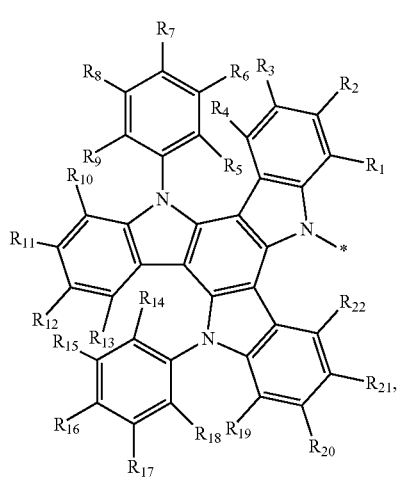

Formula 2 wherein in Formula 2,
at least one of $R_1$ to $R_{22}$ is a cyano group, a fluoro group, or a trifluoromethyl group, and the remainder are each independently a hydrogen atom, a deuterium atom, a substituted or unsubstituted oxy group, a substituted or unsubstituted thio group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

2. The organic electroluminescence device of claim 1, wherein the functional layers comprises:
a hole transport region;
an emission layer on the hole transport region; and
an electron transport region on the emission layer,
wherein the emission layer includes the polycyclic compound.

3. The organic electroluminescence device of claim 2, wherein the emission layer is to emit delayed fluorescence.

4. The organic electroluminescence device of claim 2, wherein the emission layer is to emit light having a maximum emission wavelength of about 470 nanometer or less.

5. The organic electroluminescence device of claim 1, wherein Formula 1 is represented by any one among Formula 1-A to Formula 1-D:

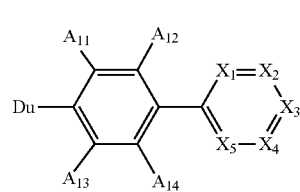

Formula 1-A

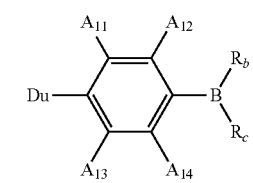

Formula 1-B

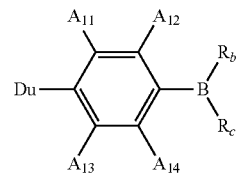

Formula 1-C

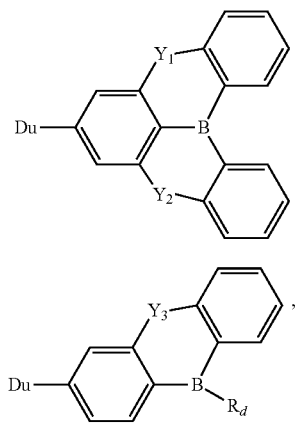

Formula 1-D wherein in Formula 1-A, at least one among $X_1$ to $X_5$ is N, and the remainder are each $CR_a$,
in Formula 1-C and Formula 1-D, $Y_1$ to $Y_3$ are each independently O, S, $NR_e$, or C(=O),
in Formula 1-A and 1-B, $A_{11}$ to $A_{14}$ are each independently a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, in Formula 1-A to 1-D, $R_a$ to $R_e$ are each independently a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and "Du" is the same as defined in Formula 2.

6. The organic electroluminescence device of claim 1, wherein Formula 1 is represented by any one among Formula 1-1 to Formula 1-23:

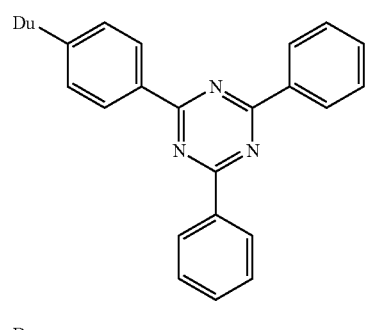

1-1

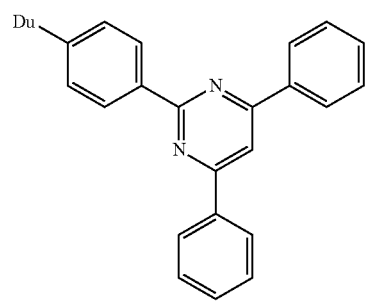

1-2

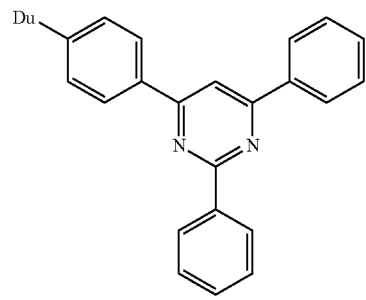

1-3

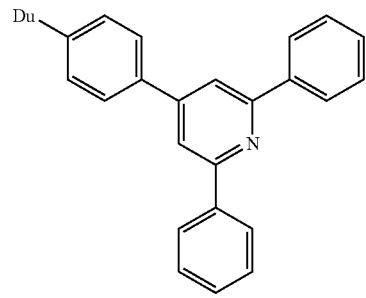

1-4

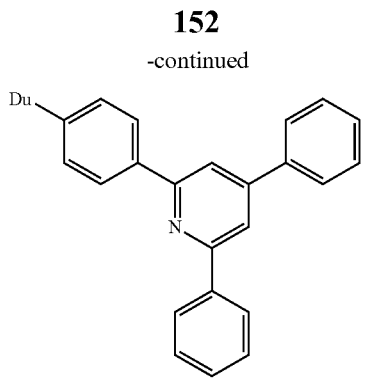

1-5

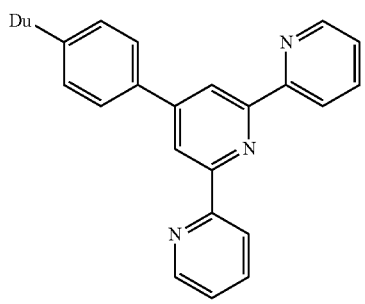

1-6

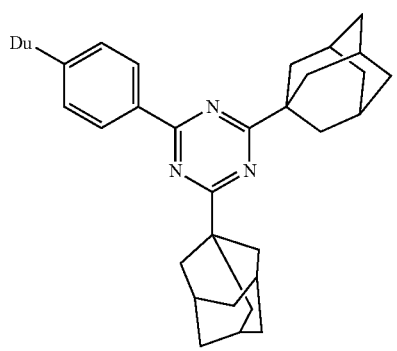

1-7

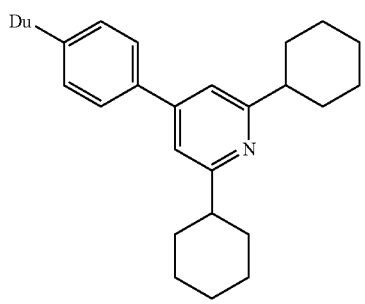

1-8

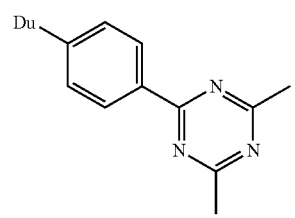

1-9

1-10 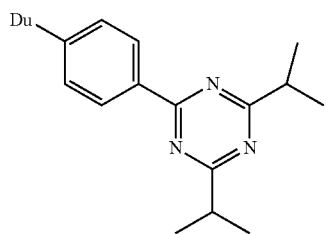
1-11 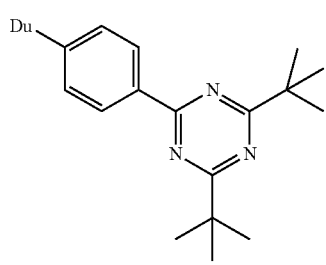
1-12 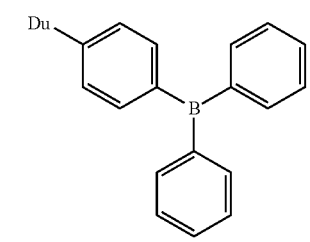
1-13 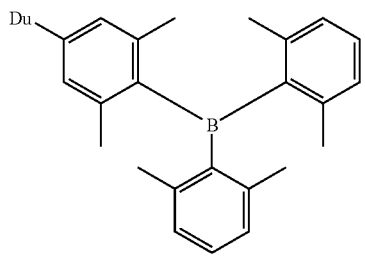
1-14 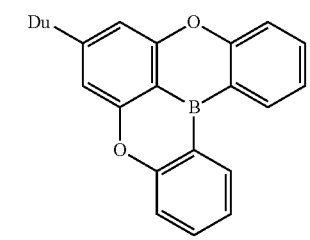
1-15 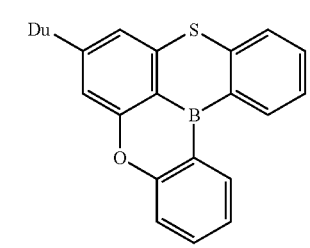
1-16 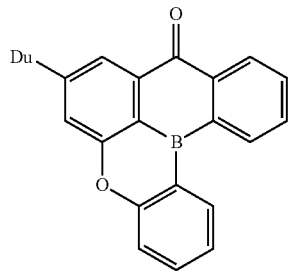
1-17 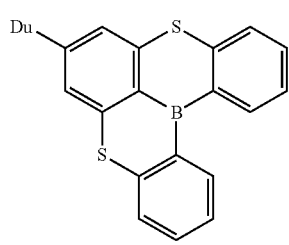
1-18 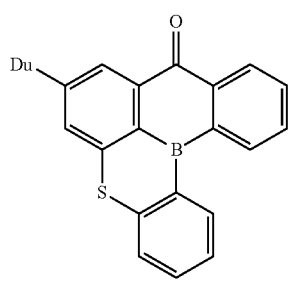
1-19 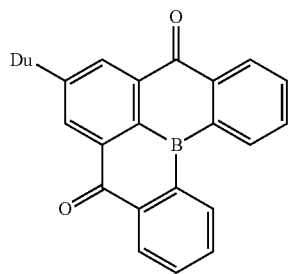
1-20 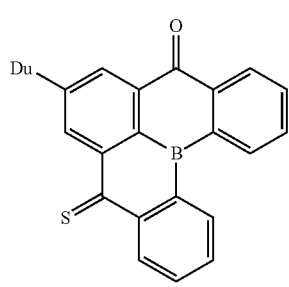

-continued

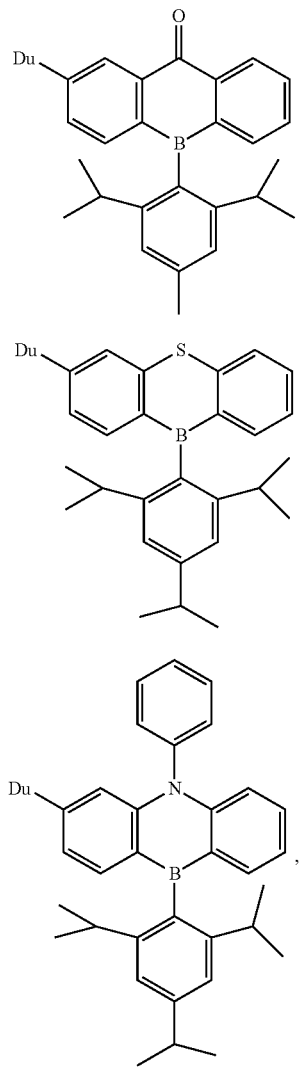

1-21

1-22

1-23 wherein in Formula 1-1 to Formula 1-23, "Du" is the same as defined in Formula 2.

7. The organic electroluminescence device of claim 1, wherein the electron accepting group is a substituted or unsubstituted heterocycle having at least one nitrogen atom as a ring forming atom, or a substituted or unsubstituted boryl group.

8. The organic electroluminescence device of claim 1, wherein the fused heterocycle is a substituted or unsubstituted heterocycle having a boron atom as a ring forming atom.

9. The organic electroluminescence device of claim 1, wherein in Formula 2, at least one of $R_1$ to $R_{22}$ is a cyano group, a fluoro group, or a trifluoromethyl group, and the remainder are each a hydrogen atom.

10. The organic electroluminescence device of claim 1, wherein in Formula 2, at least two or three selected from $R_1$ to $R_{22}$ are each a cyano group, a fluoro group, or a trifluoromethyl group, and the remainder are each a hydrogen atom.

11. The organic electroluminescence device of claim 1, wherein the polycyclic compound is represented by at least one polycyclic compound in Compound Group 1:

Compound Group 1

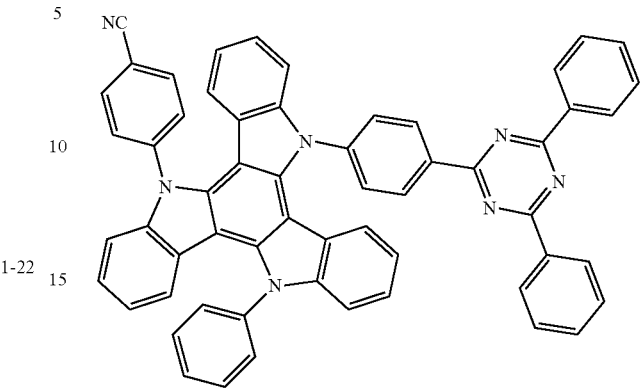

1

2

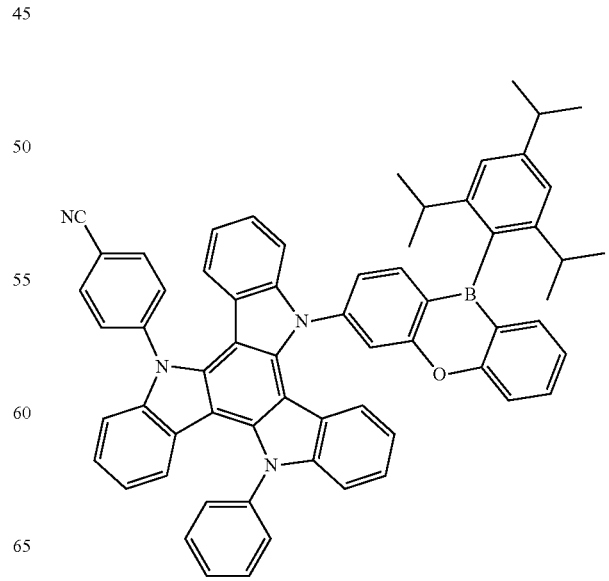

3

4
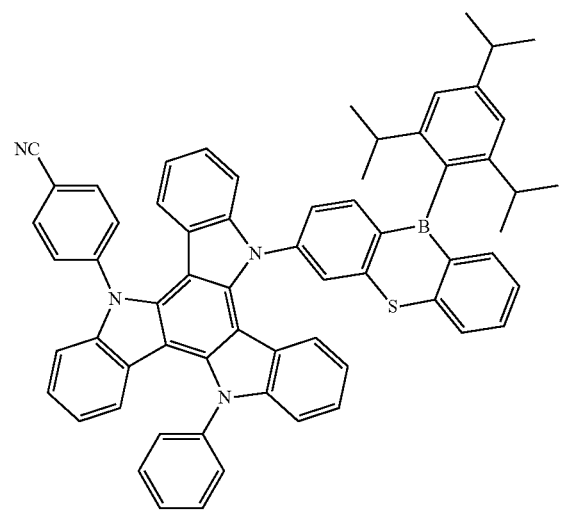
5
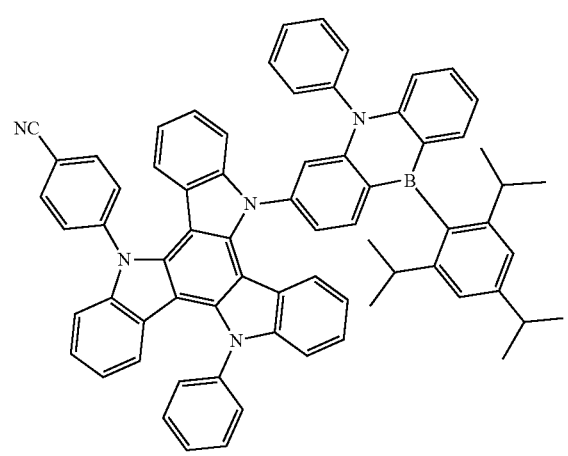
6
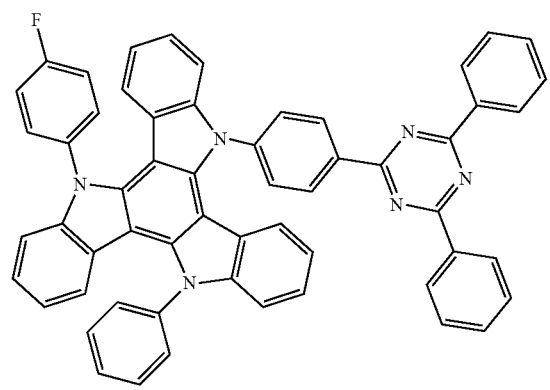
7
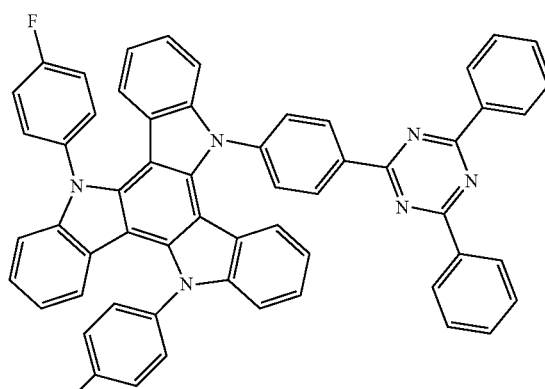
8
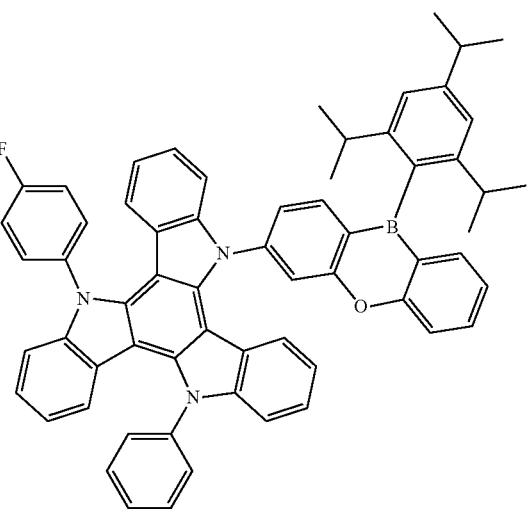
9
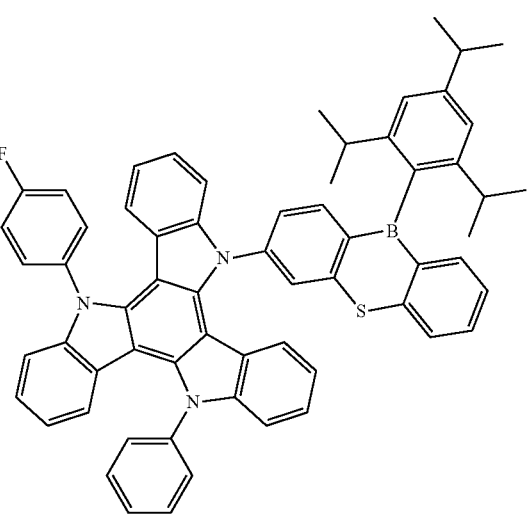

159
-continued
10
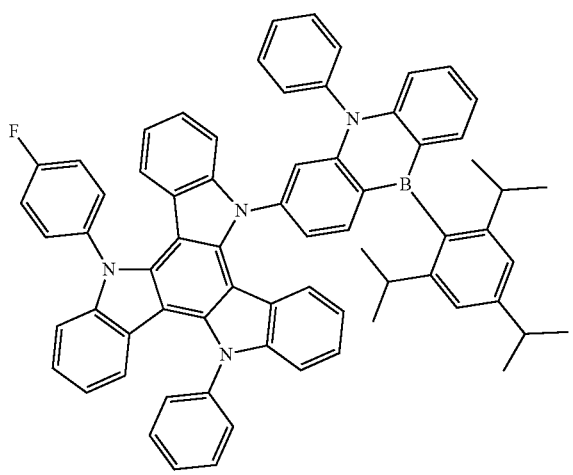
11
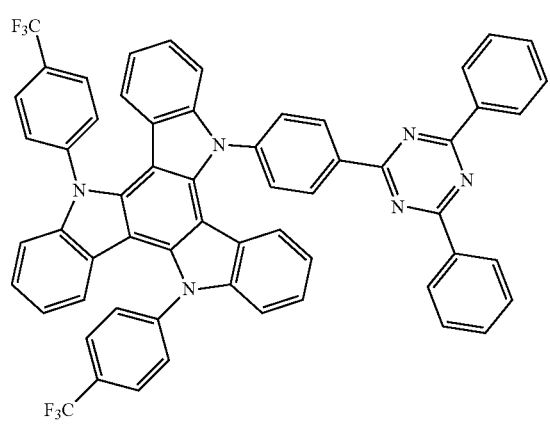
12
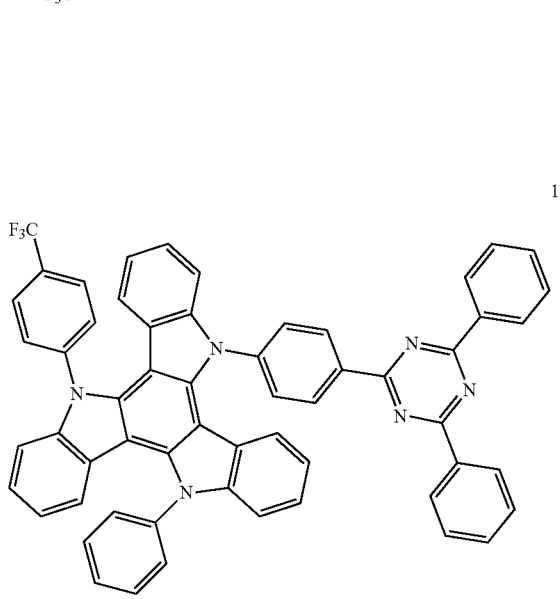
160
-continued
13
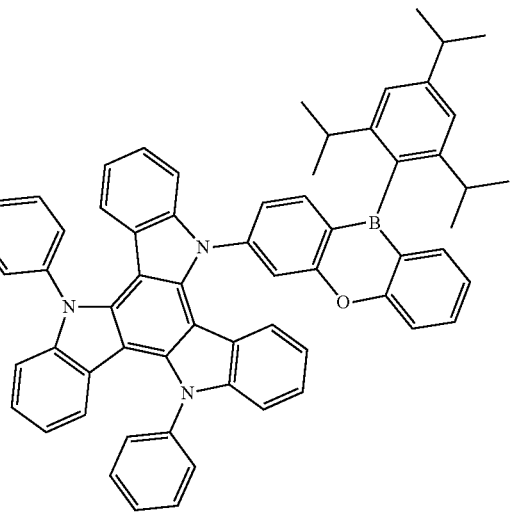
14
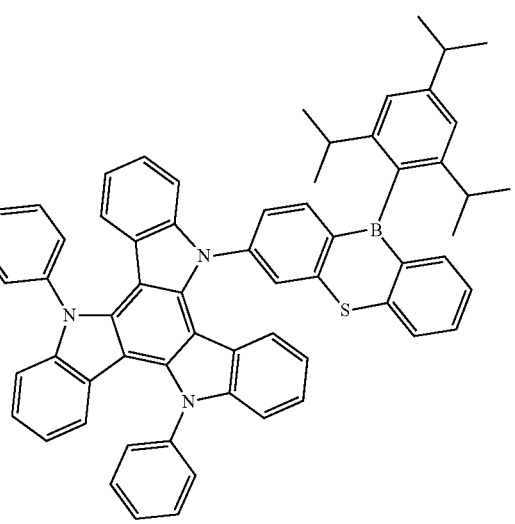
15
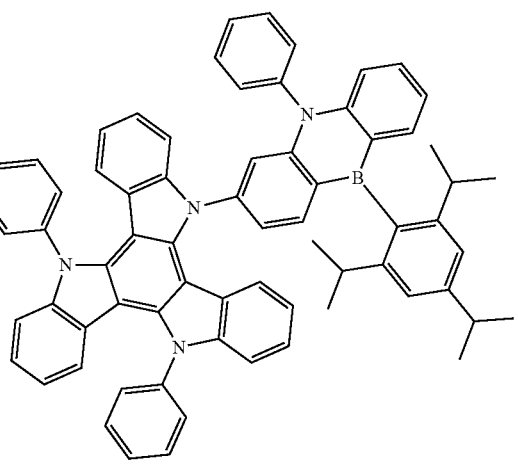

16
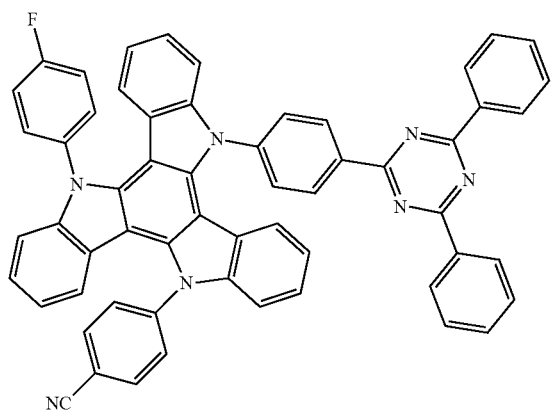
17
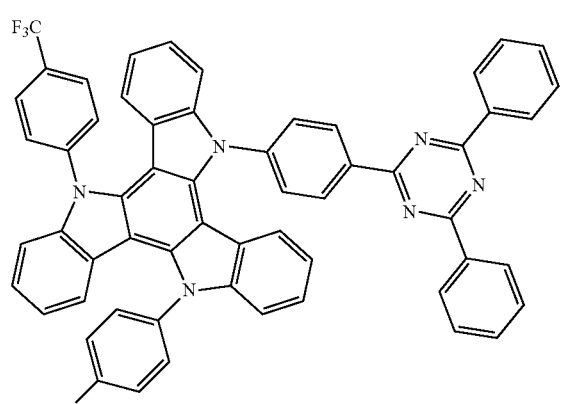
18
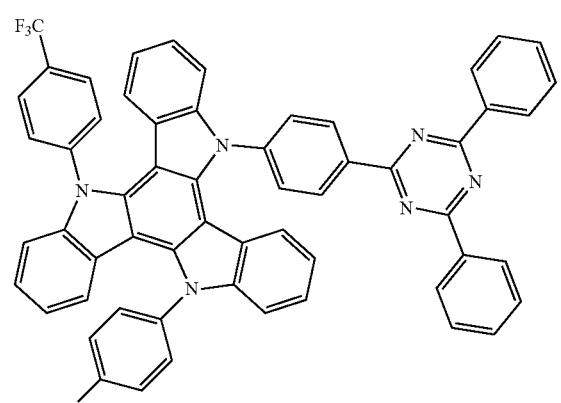
19
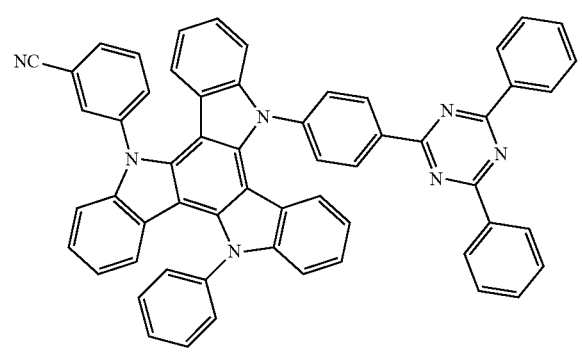
20
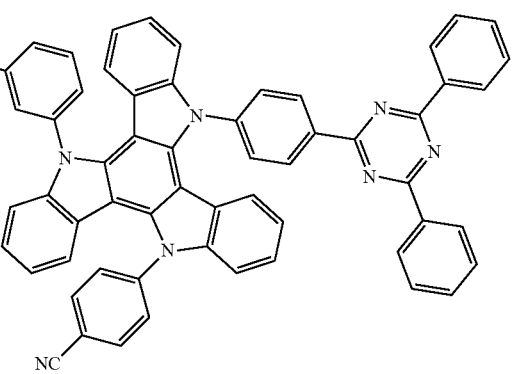
21
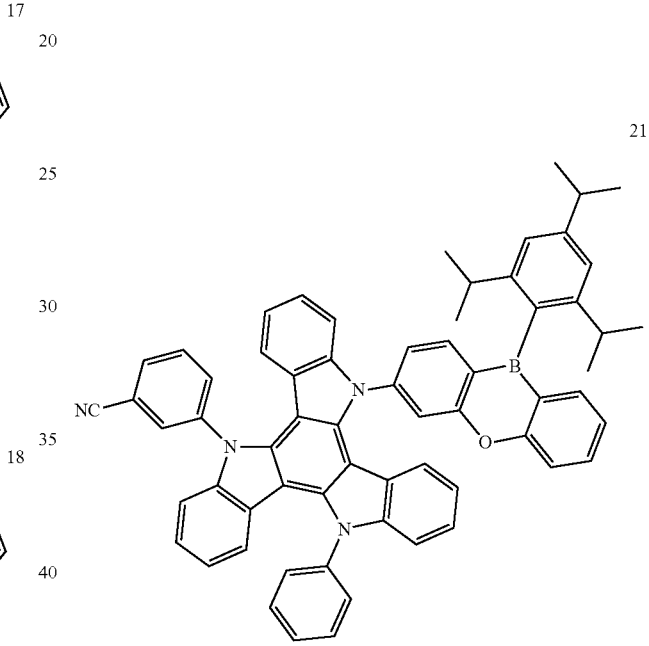
22
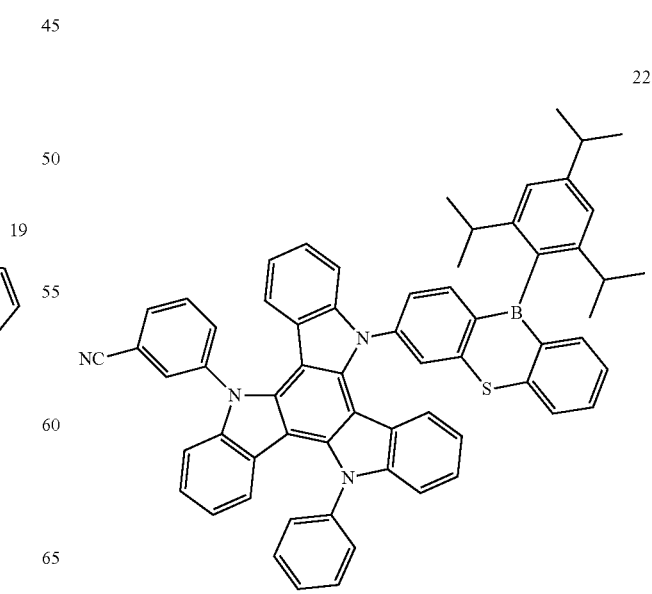

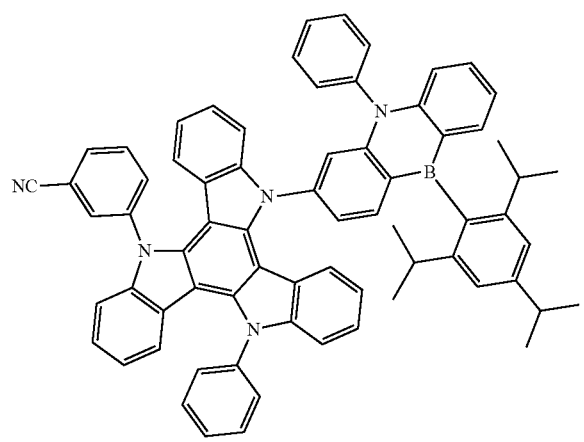
23
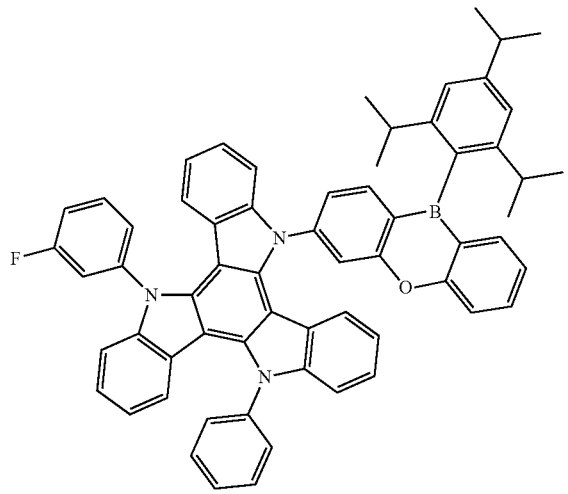
26
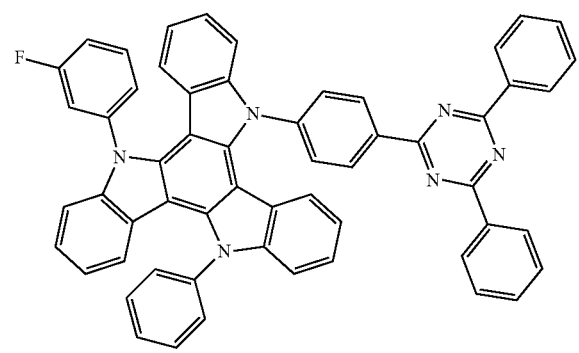
24
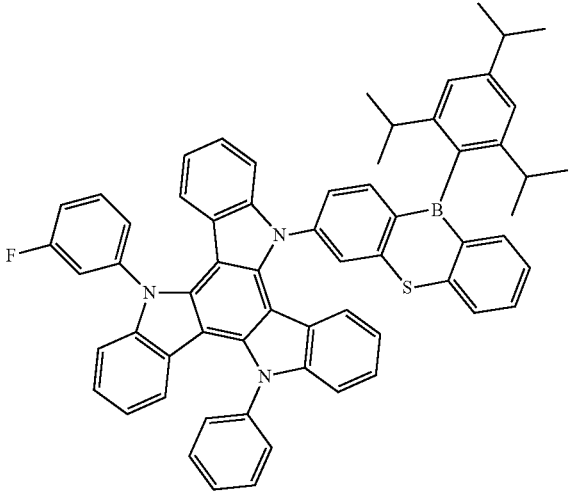
27
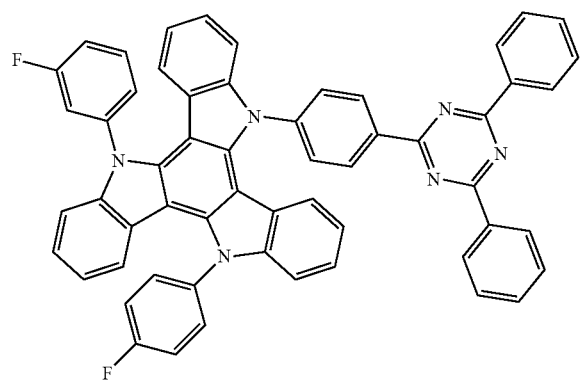
25
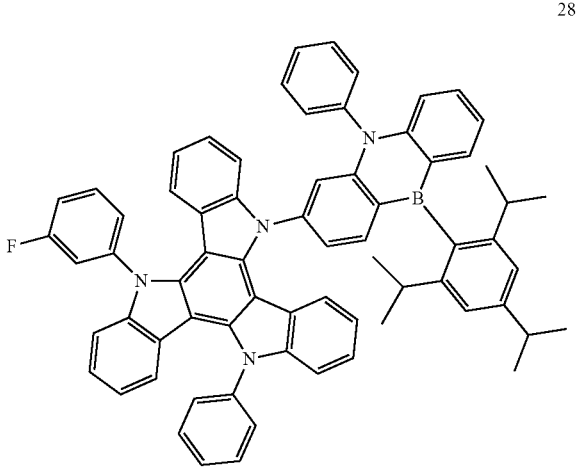
28

29
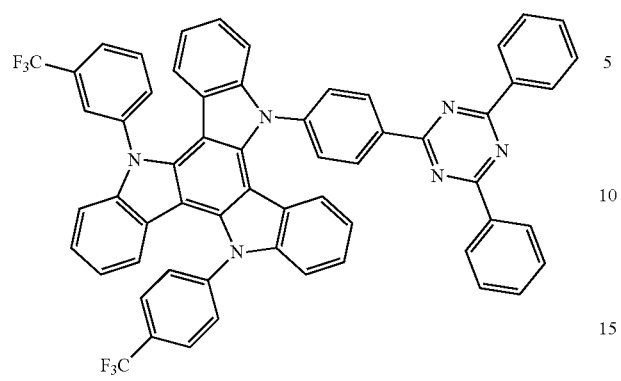
30
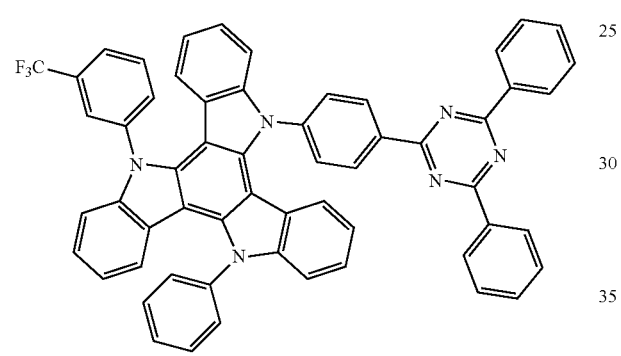
31
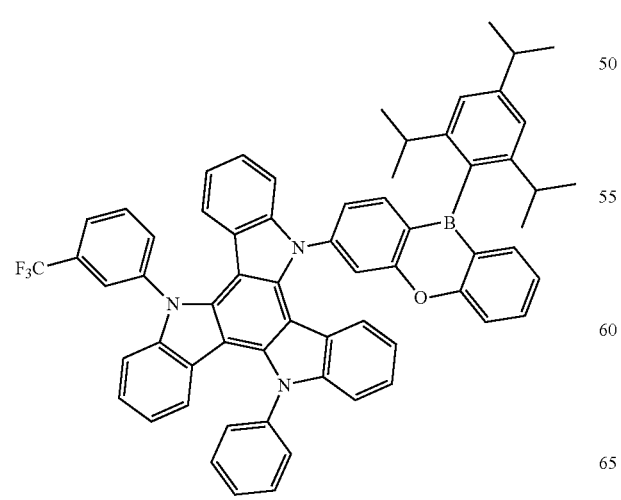
32
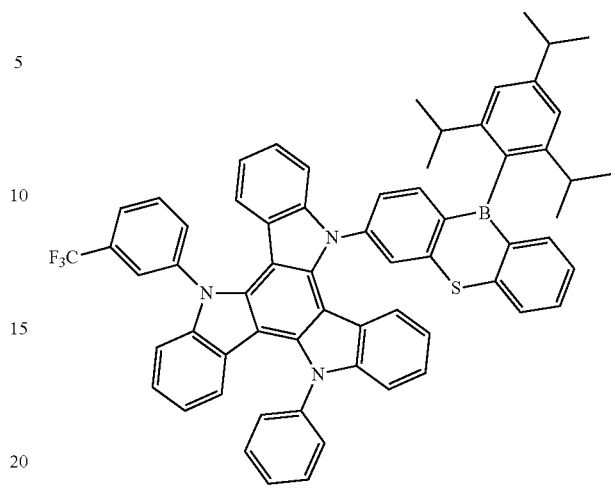
33
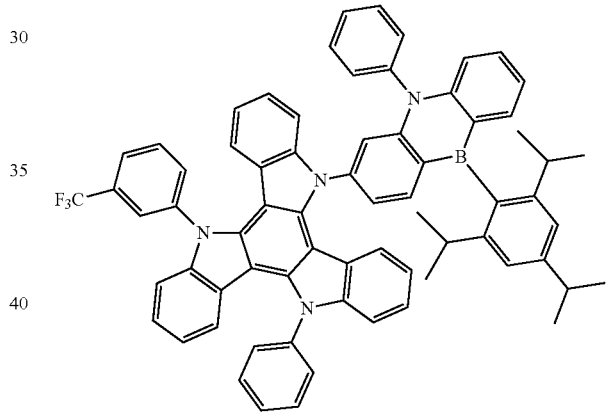
34
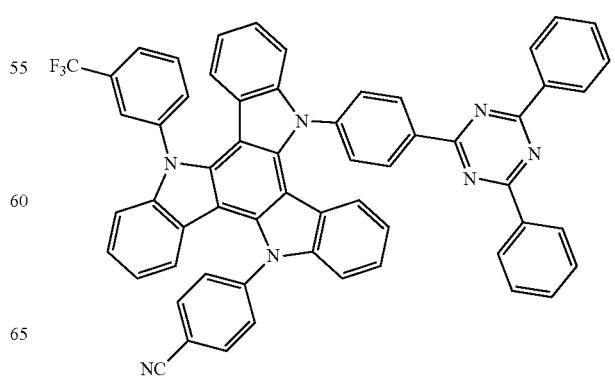

36
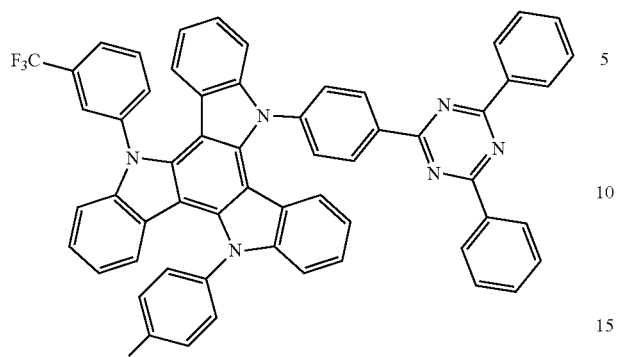
39
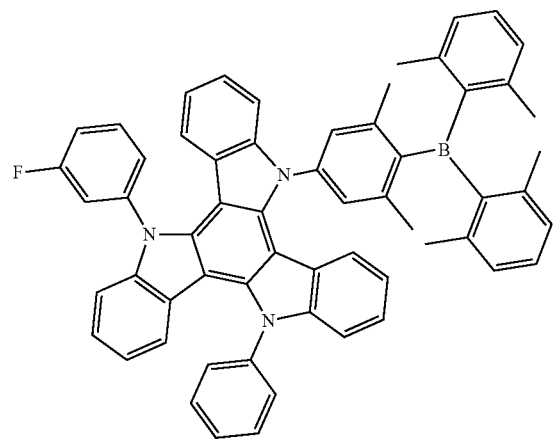
37
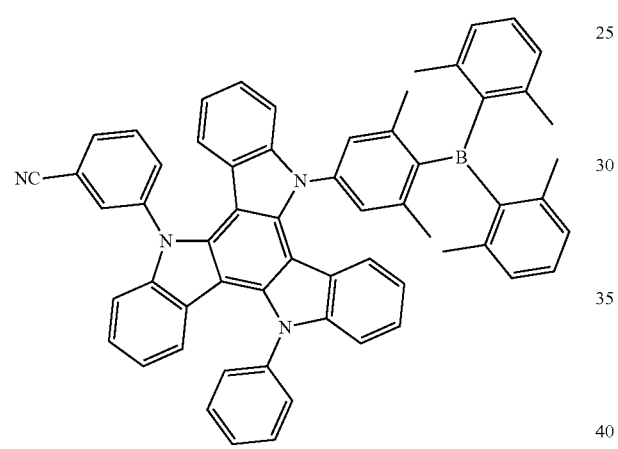
40
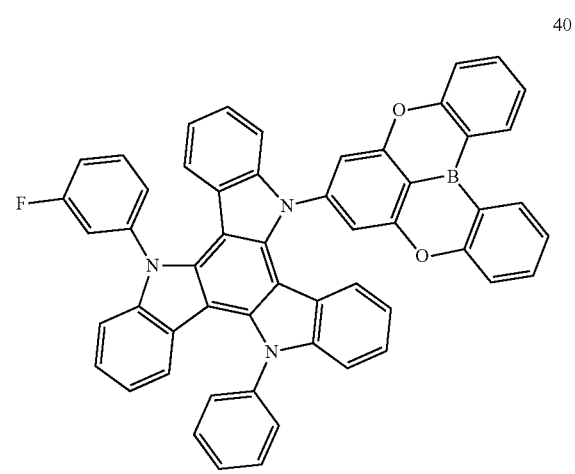
38
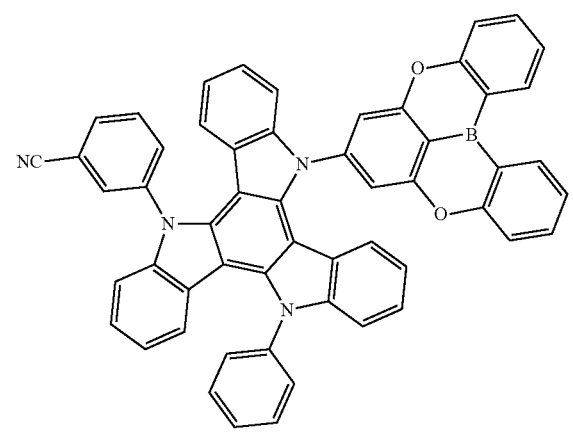
41
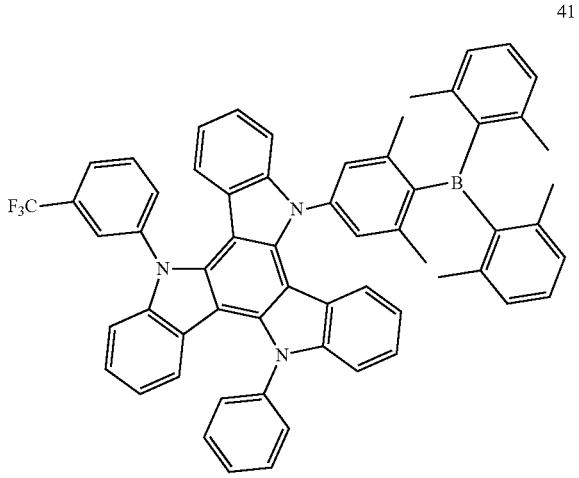

-continued

42

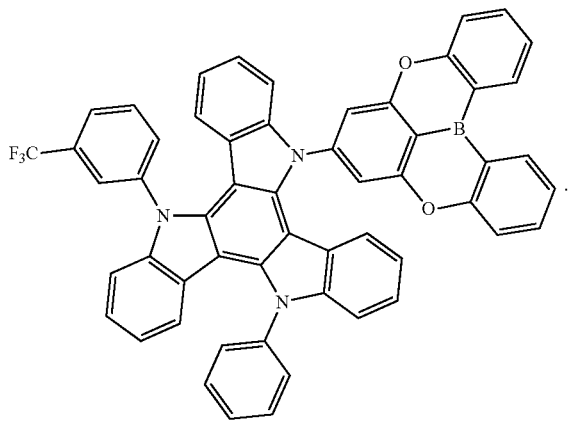

12. A polycyclic compound represented by Formula 1:

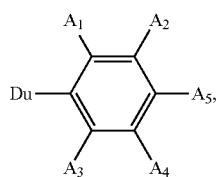
Formula 1 wherein in Formula 1,

A$_1$ to A$_5$ are each independently a hydrogen atom, a deuterium atom, a substituted or unsubstituted oxy group, a substituted or unsubstituted thio group, a substituted or unsubstituted thiocarbonyl group, a substituted or unsubstituted boryl group, a substituted or unsubstituted carbonyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or are combined with an adjacent group to form a fused heterocycle, at least one of A$_1$ to A$_5$ or the fused heterocycle comprises an electron accepting group, and "Du" is represented by Formula 2:

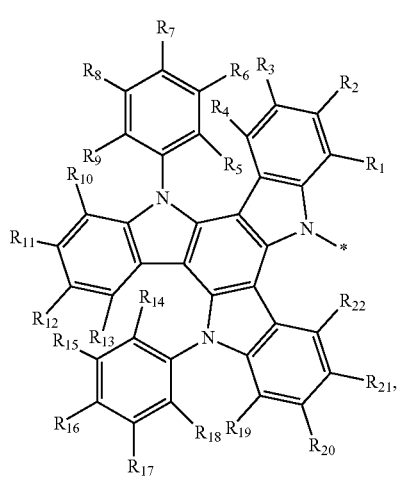
Formula 2 wherein in Formula 2, at least one of R$_1$ to R$_{22}$ is a cyano group, a fluoro group, or a trifluoromethyl group, and the remainder are each independently a hydrogen atom, a deuterium atom a substituted or unsubstituted oxy group, a substituted or unsubstituted thio group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

13. The polycyclic compound of claim 1, wherein Formula 1 is represented by any one among Formula 1-A to Formula 1-D:

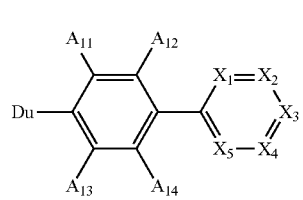
Formula 1-A

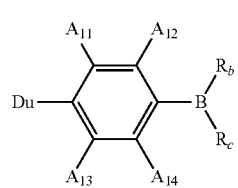
Formula 1-B

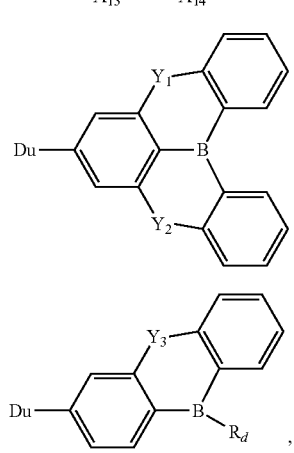
Formula 1-C

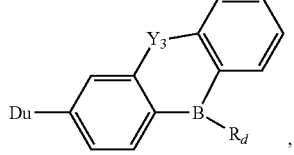
Formula 1-D wherein in Formula 1-A, at least one among X$_1$ to X$_5$ is N, and the remainder are each CR$_a$, in Formula 1-C and Formula 1-D, Y$_1$ to Y$_3$ are each independently O, S, NR$_e$, or C(=O), in Formula 1-A and 1-B, A$_{11}$ to A$_{14}$ are each independently a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, in Formula 1-A to 1-D, R$_a$ to R$_e$ are each independently a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and "Du" is the same as defined in Formula 2.

14. The polycyclic compound of claim 12, wherein Formula 1 is represented by any one among Formula 1-1 to Formula 1-23:
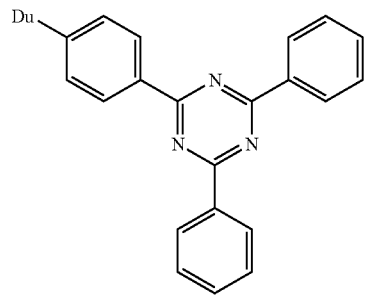
1-1
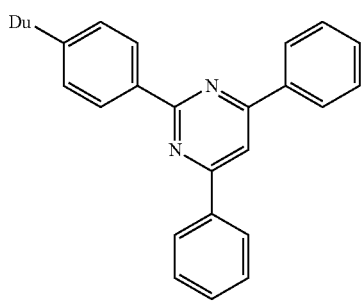
1-2
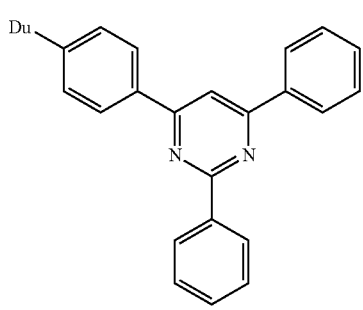
1-3
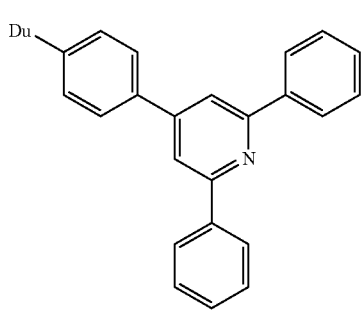
1-4
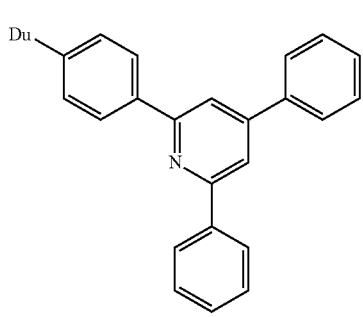
1-5
-continued
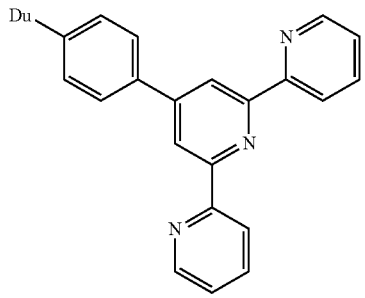
1-6
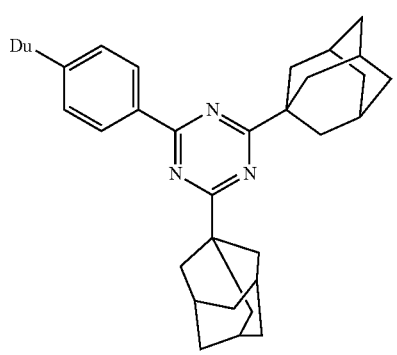
1-7
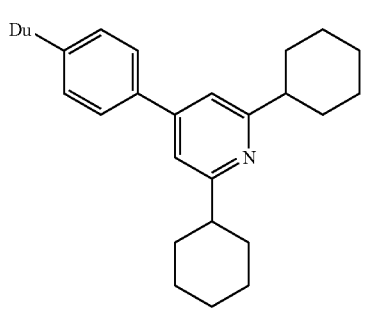
1-8
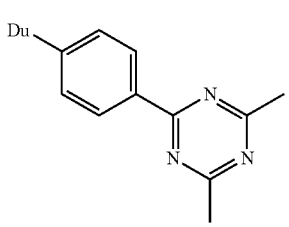
1-9
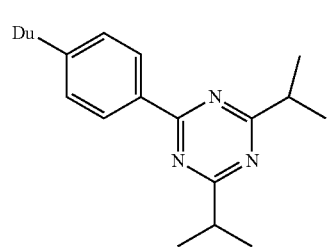
1-10

1-11 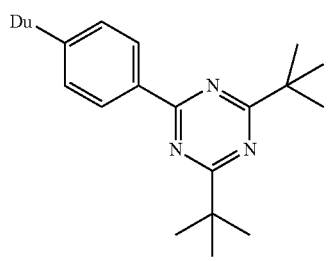
1-12 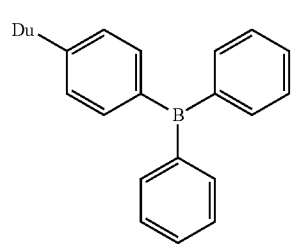
1-13 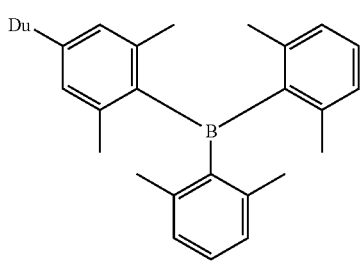
1-14 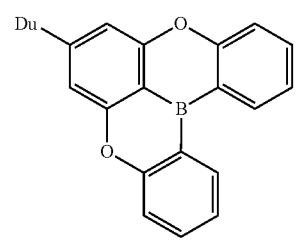
1-15 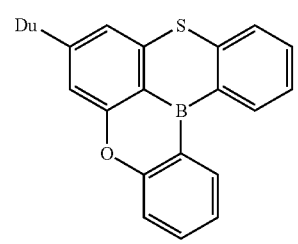
1-16 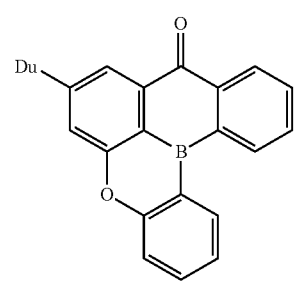
1-17 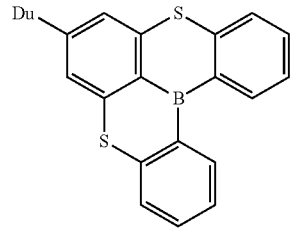
1-18 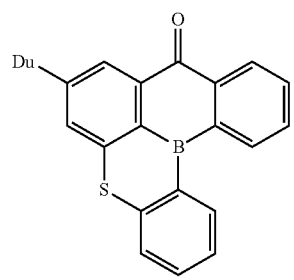
1-19 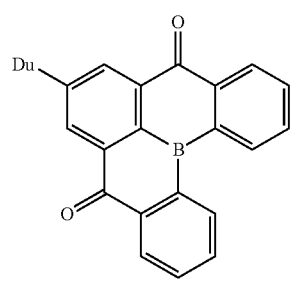
1-20 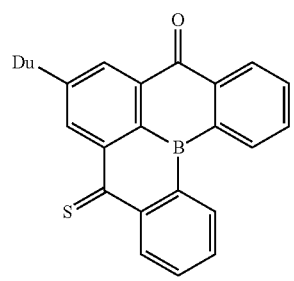
1-21 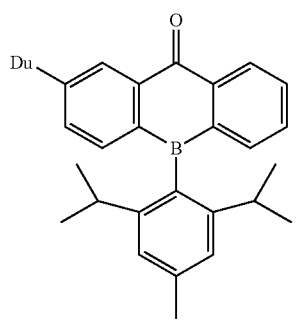

1-22

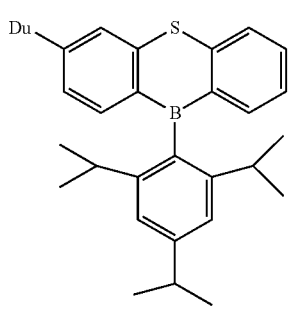

1-23

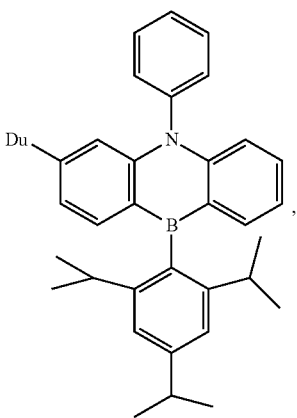

wherein in Formula 1-1 to Formula 1-23, "Du" is the same as defined in Formula 2.

15. The polycyclic compound of claim 12, wherein the electron accepting group is a substituted or unsubstituted heterocycle having at least one nitrogen atom as a ring forming atom, or a substituted or unsubstituted boryl group.

16. The polycyclic compound of claim 12, wherein the fused heterocycle is a substituted or unsubstituted heterocycle having a boron atom as a ring forming atom.

17. The polycyclic compound of claim 12, wherein the electron accepting group includes a cyano group, a fluoro group, a carbonyl group, or a sulfonyl group.

18. The polycyclic compound of claim 12, wherein in Formula 2, at least one of $R_1$ to $R_{22}$ is a cyano group, a fluoro group, or a trifluoromethyl group, and the remainder are each a hydrogen atom.

19. The polycyclic compound of claim 12, wherein in Formula 2, at least two or three selected from among $R_1$ to $R_{22}$ are each independently a cyano group, a fluoro group, or trifluoromethyl group, and the remainder are each a hydrogen atom.

20. The polycyclic compound of claim 12, wherein the polycyclic compound represented by Formula 1 is a material to emit thermally activated delayed fluorescence.

21. The polycyclic compound of claim 12, wherein the polycyclic compound represented by Formula 1 is a material to emit blue light having a central wavelength of about 470 nanometer or less.

22. The polycyclic compound of claim 12, wherein Formula 1 is any compound represented in Compound Group 1:

Compound Group 1

1

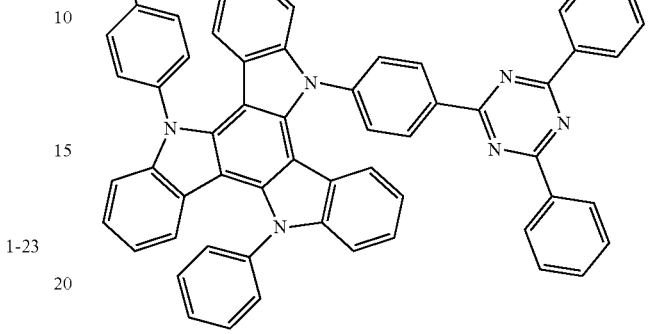

2

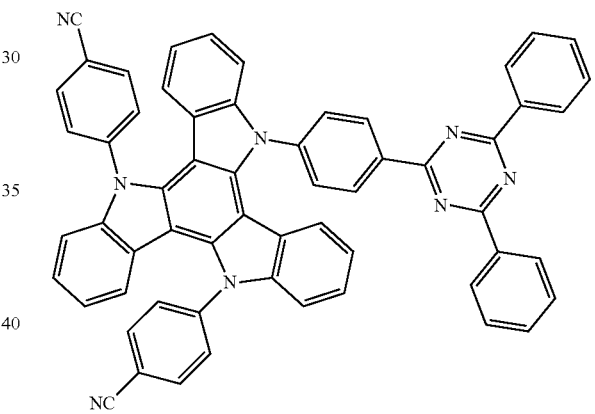

3

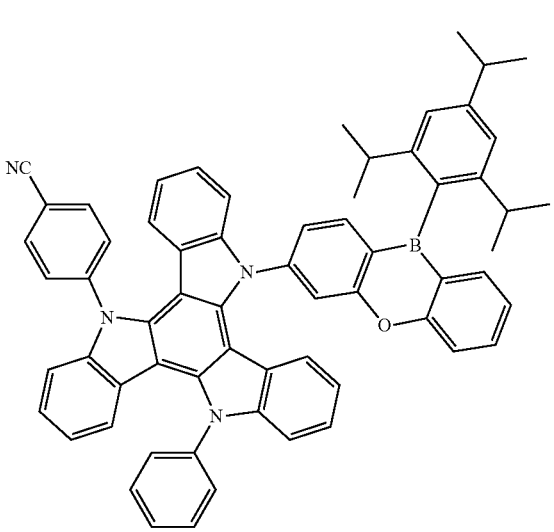

4
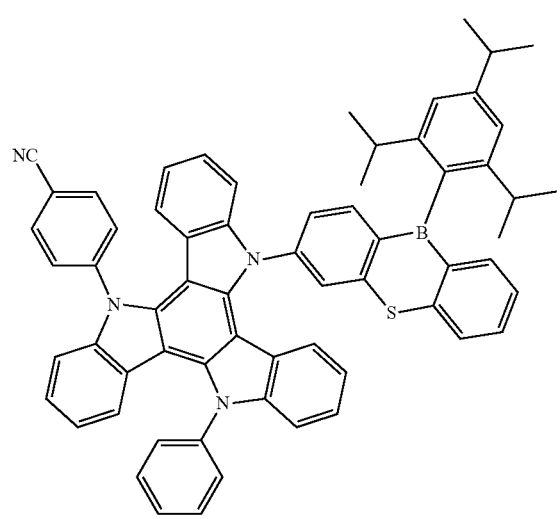
5
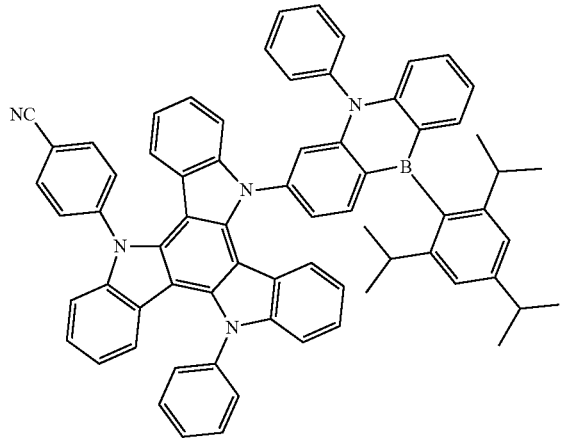
6
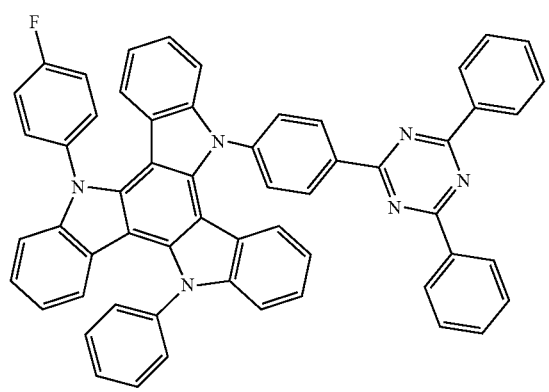
7
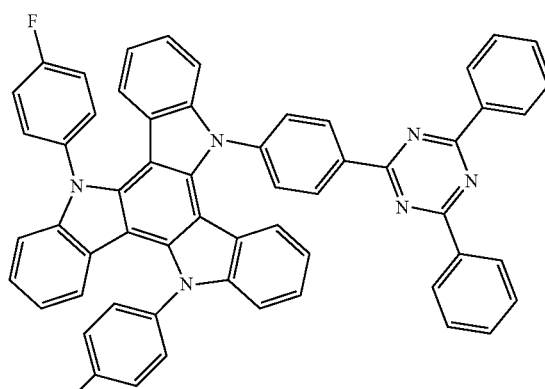
8
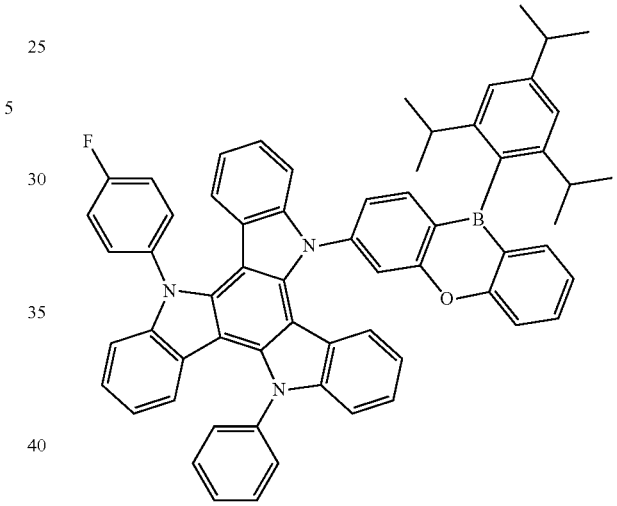
9
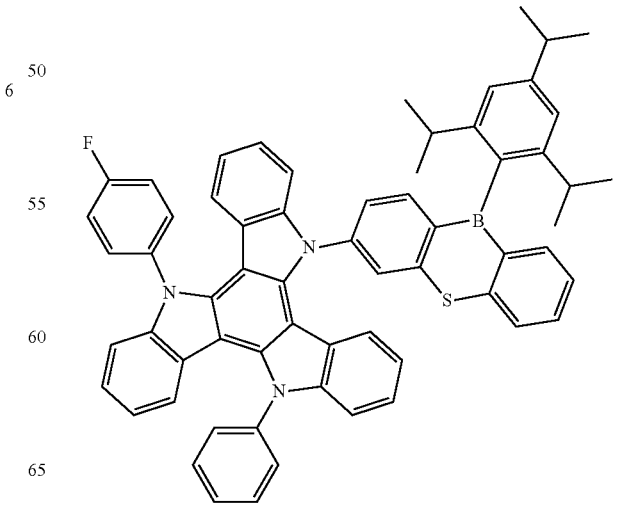

10
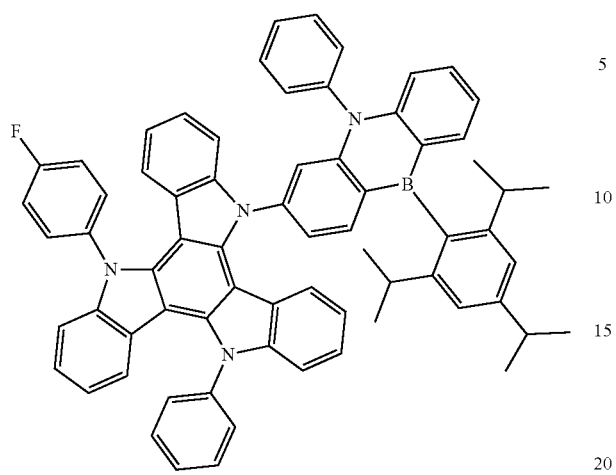
11
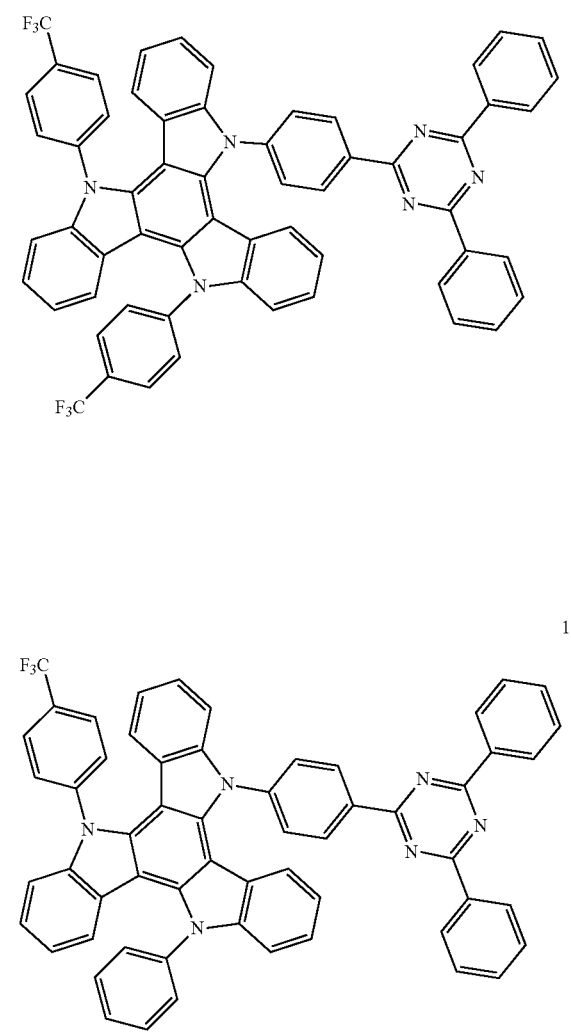
12
13
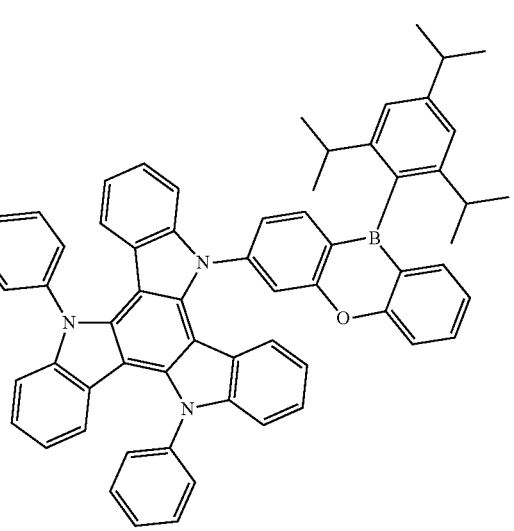
14
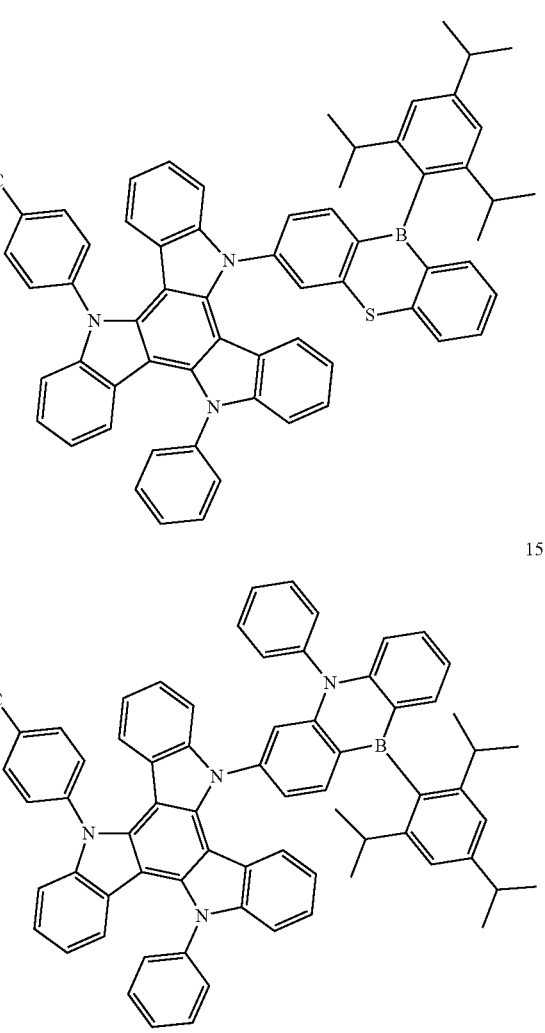
15

16
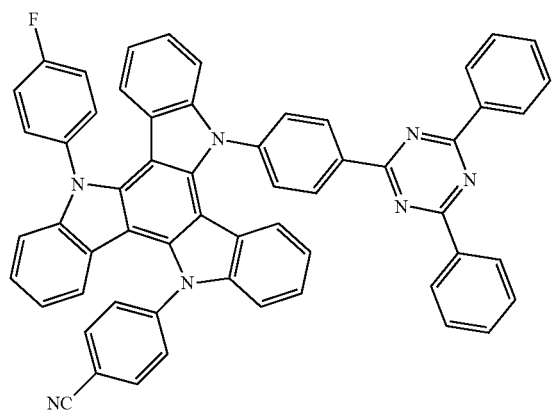
17
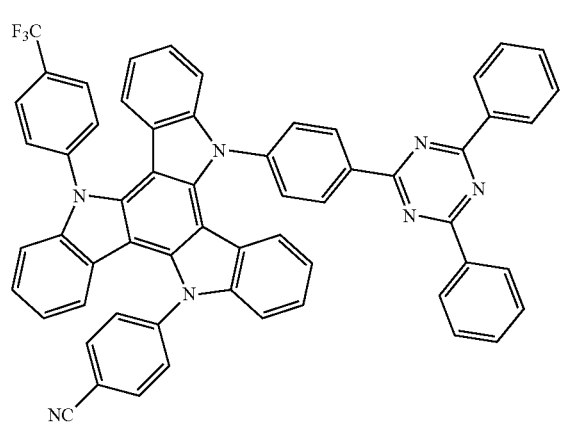
18
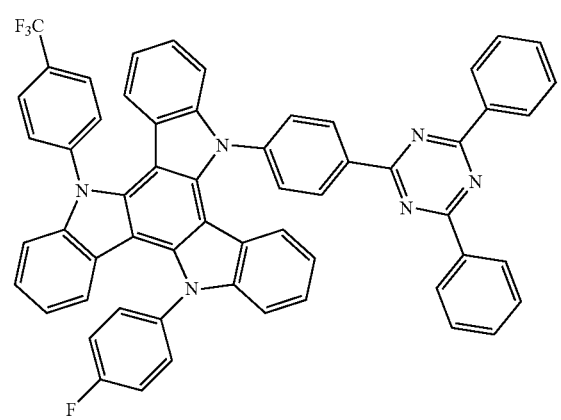
19
20
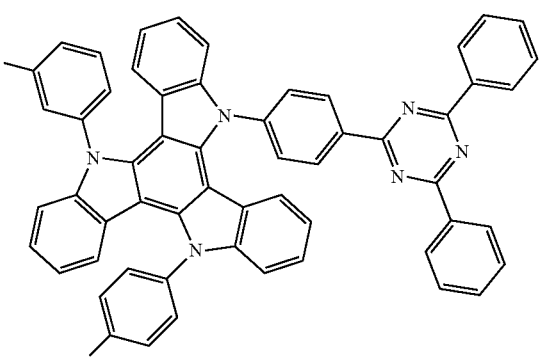
21
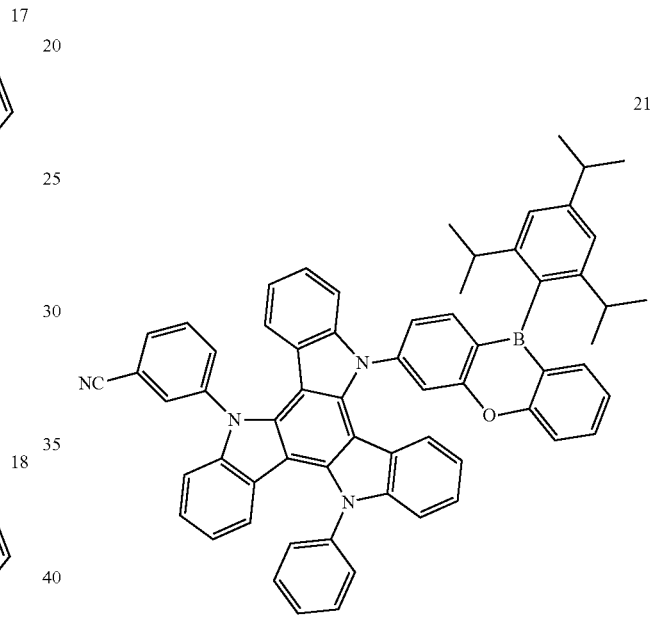
22
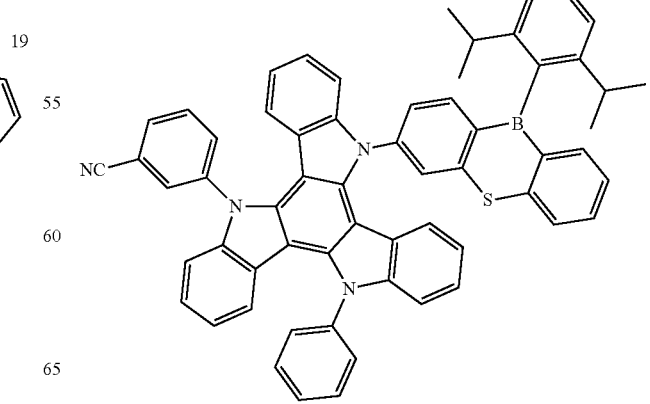

23
-continued
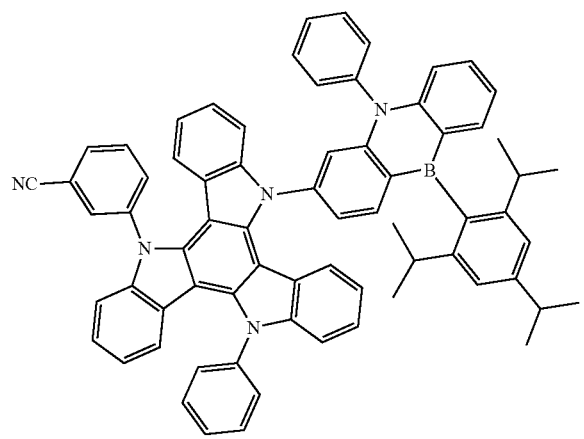
24
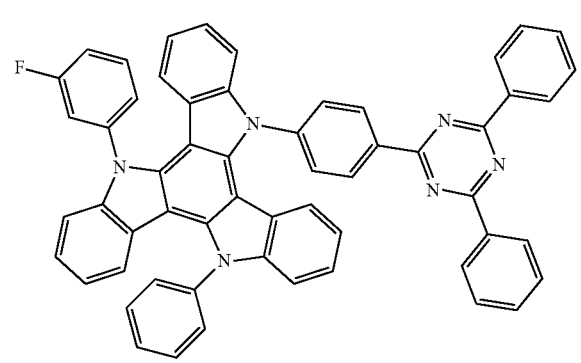
25
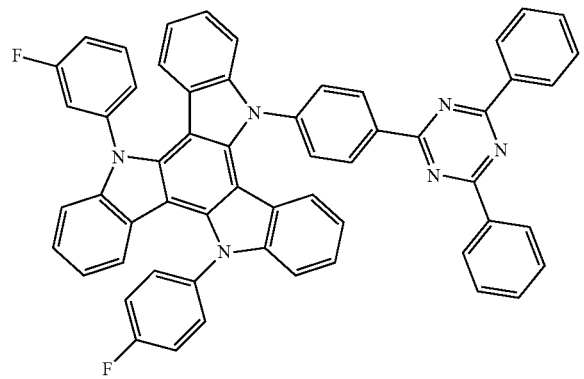
24
-continued
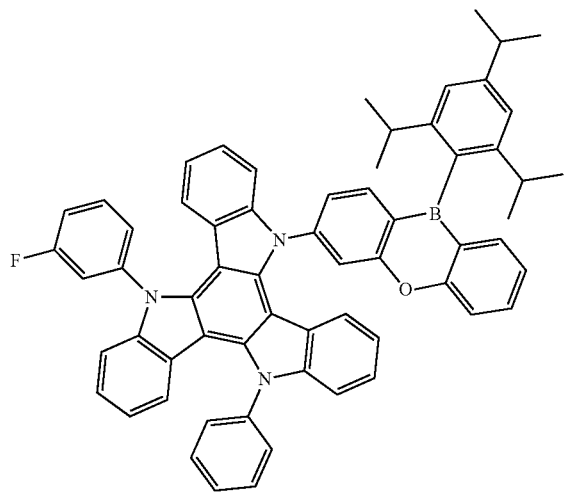
26
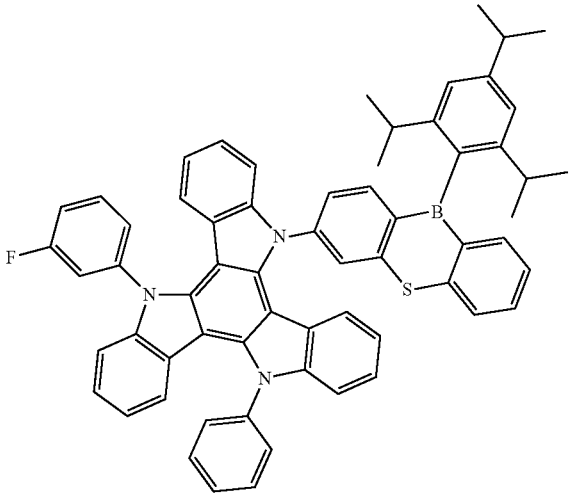
27
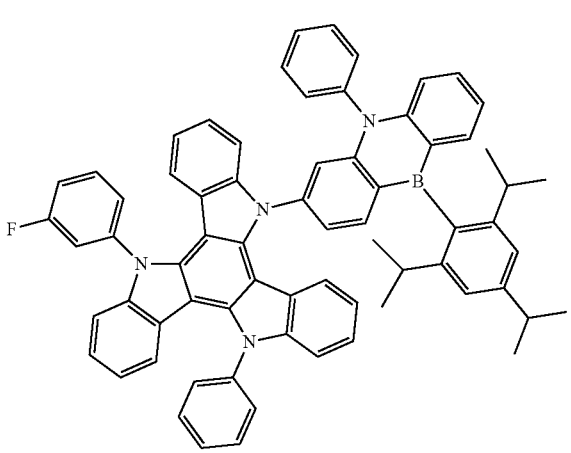
28

29
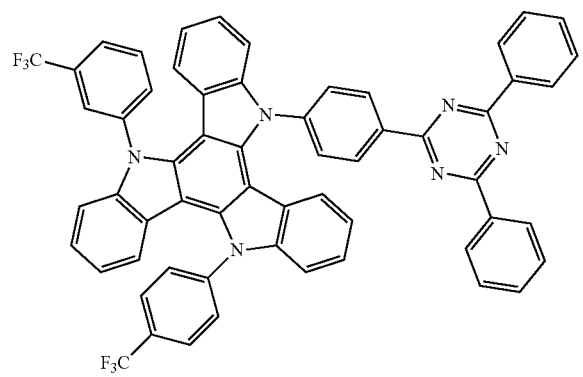
30
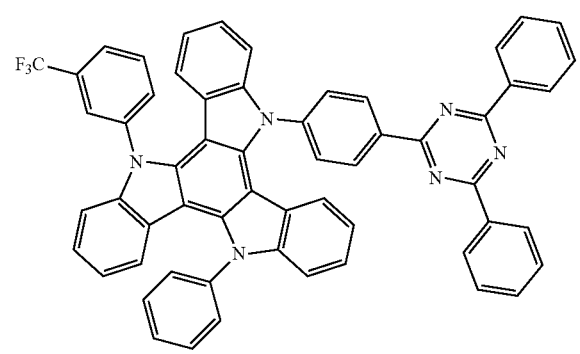
31
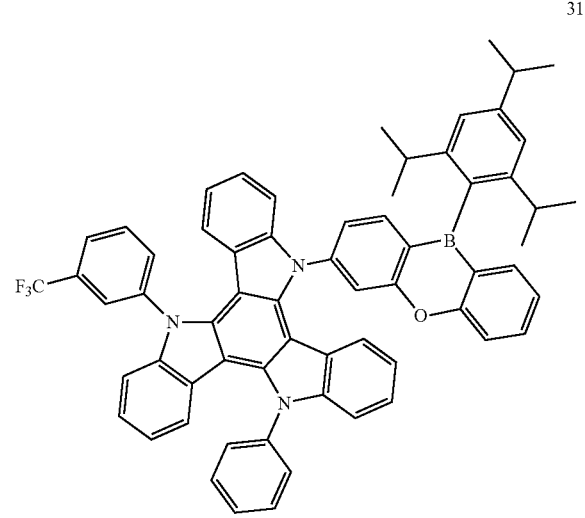
32
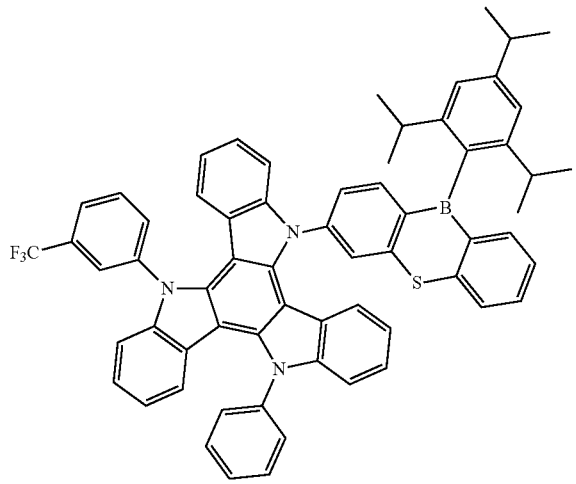
33
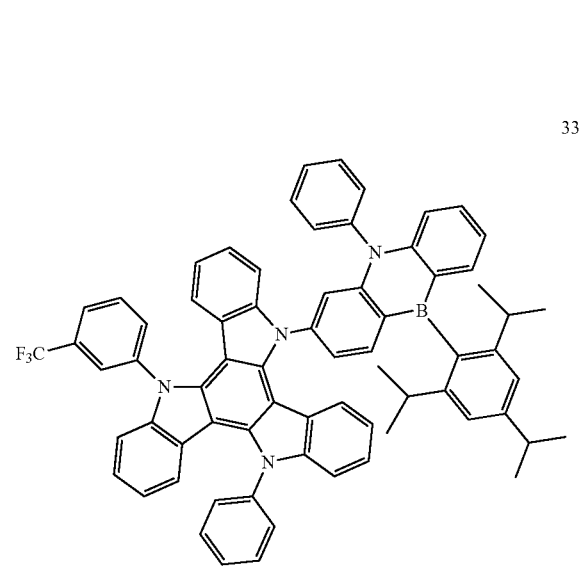 [SMILES: CC(C)c1cc(C(C)C)c(B2c3ccccc3N(c3ccccc3)c3cc(-n4c5ccccc5c5c6c(c7ccccc7n6-c6cccc(C(F)(F)F)c6)c6c(c7ccccc7n6-c6ccccc6)c54)ccc32)c(C(C)C)c1]
34
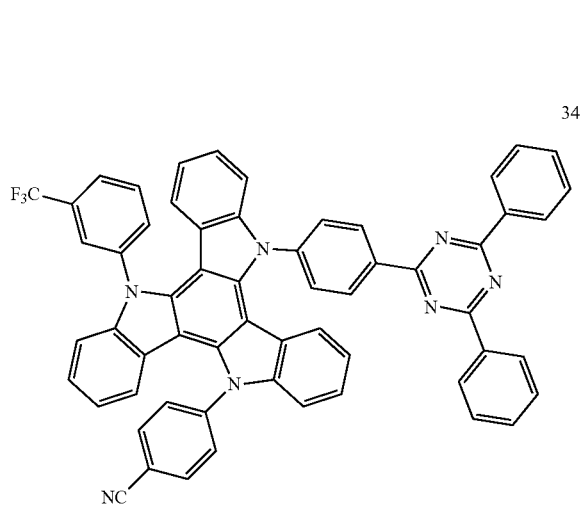

-continued
36
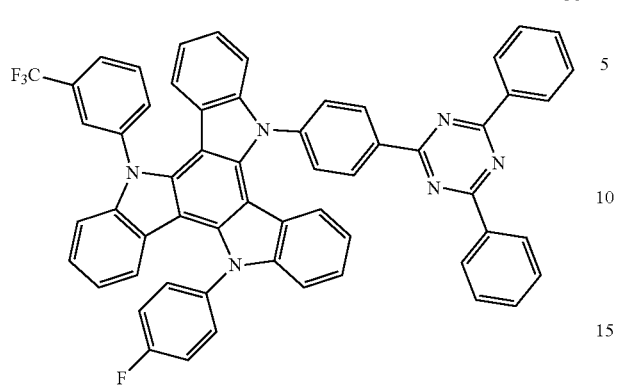
37
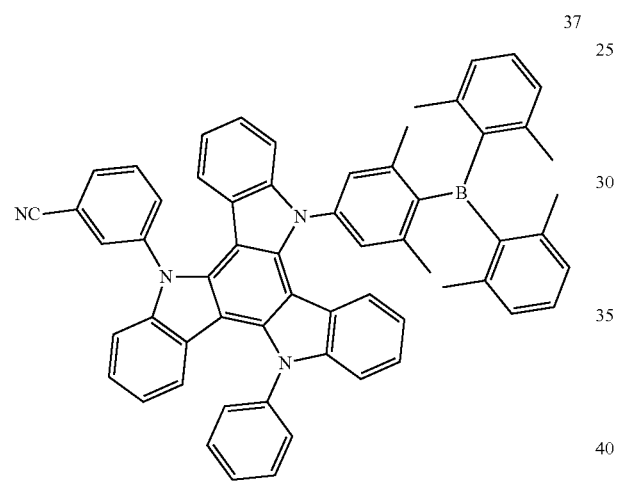
38
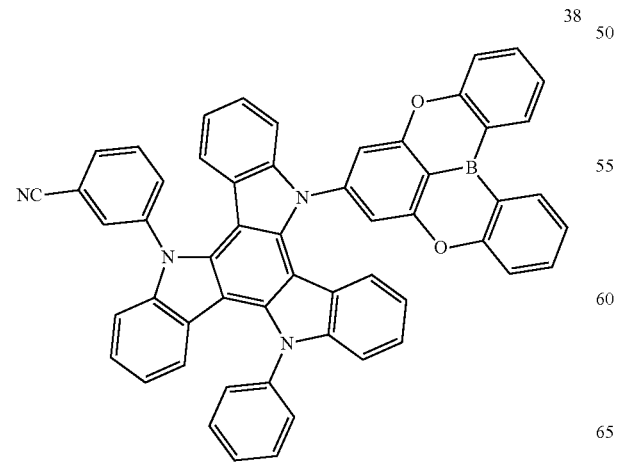
-continued
39
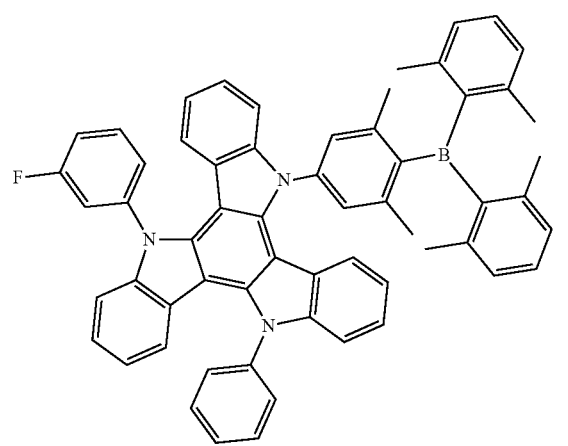
40
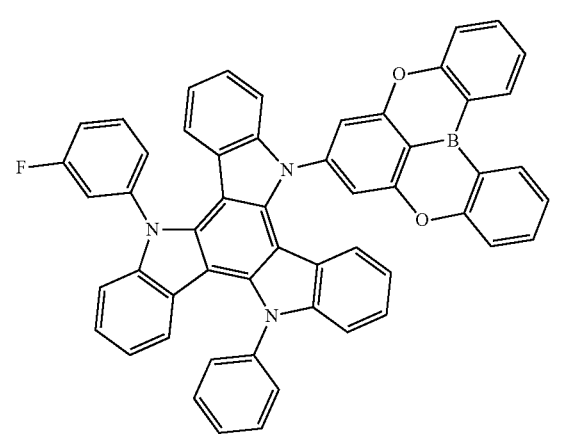
41
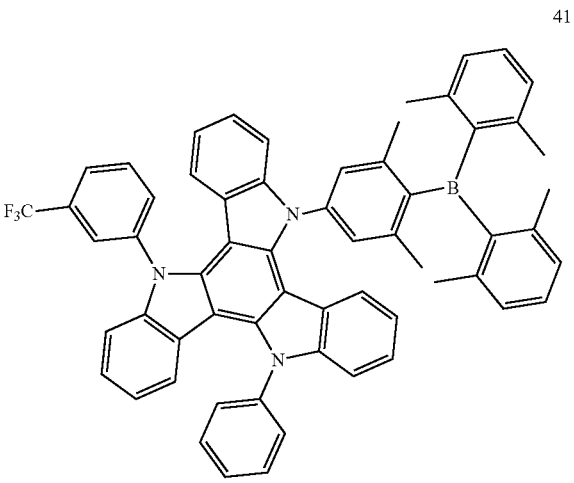

-continued
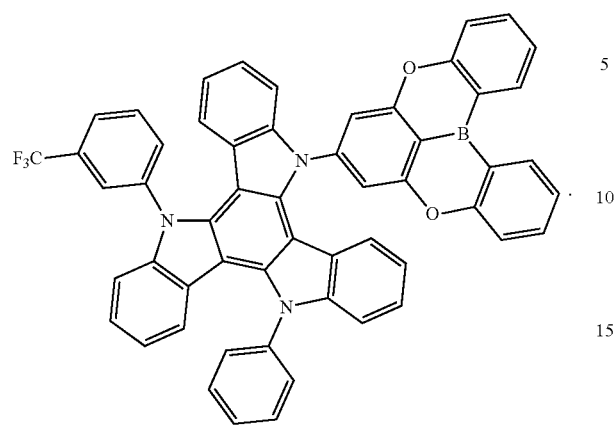
42
* * * * *